(12) United States Patent
Harrison et al.

(10) Patent No.: US 11,389,156 B2
(45) Date of Patent: Jul. 19, 2022

(54) SUTURE PASSING INSTRUMENTATION AND METHODS OF USE THEREOF

(71) Applicant: Anchor Orthopedics XT Inc., Mississauga (CA)

(72) Inventors: Robert Harrison, Milton (CA); Neil Godara, Milton (CA); Jeffery Arnett, Gilbert, AZ (US); Laura Man Yee Yu, Markham (CA)

(73) Assignee: Anchor Orthopedics XT Inc., Mississauga (CA)

( * ) Notice: Subject to any disclaimer, the term of this patent is extended or adjusted under 35 U.S.C. 154(b) by 281 days.

(21) Appl. No.: 16/545,518

(22) Filed: Aug. 20, 2019

(65) Prior Publication Data

US 2019/0365379 A1    Dec. 5, 2019

Related U.S. Application Data

(66) Continuation of application No. 14/238,945, filed as application No. PCT/IB2012/054204 on Aug. 17, (Continued)

(51) Int. Cl.
*A61B 17/04*      (2006.01)
*A61B 17/062*     (2006.01)
(Continued)

(52) U.S. Cl.
CPC ...... *A61B 17/0469* (2013.01); *A61B 17/0482* (2013.01); *A61B 17/062* (2013.01);
(Continued)

(58) Field of Classification Search
CPC ... A61B 17/04; A61B 17/062; A61B 17/0482; A61B 2017/0475; A61B 2017/0496; A61B 2090/0811
(Continued)

(56) References Cited

U.S. PATENT DOCUMENTS 3,630,261 A * 12/1971 Gley ..................... F16B 5/0208
                                                411/315
5,534,032 A *  7/1996 Hodorek ............. A61F 2/30721
                                                411/537
(Continued)

*Primary Examiner* — George J Ulsh
(74) *Attorney, Agent, or Firm* — Nir Lifshitz

(57) ABSTRACT

The instant disclosure is directed to methods and devices for passing suture bi-directionally using a hybrid approach. Embodiments of a method described herein include steps of advancing a suture at least partially through tissue; and retrieving the suture; wherein one of the steps of advancing and retrieving comprises manipulating the suture directly, and wherein the other step of advancing and retrieving comprises manipulating a suture trap to which the suture is coupled. Embodiments of a device that may be used to practice the method embodiments include a bi-directional suture passer having a proximal portion for holding a portion of a suture therein; a distal tip coupled to the proximal portion and defining a tissue receiving gap there-between; a reciprocally moveable suture passing member housed within the proximal portion for translating the suture portion between the proximal portion and the distal tip; and a suture trap operable to be detachably coupled to the distal tip for capturing the suture passed by the suture passing member.

15 Claims, 95 Drawing Sheets

Starting position

Needle penetrates tissue (stylet and suture within needle)

Stylet advances and pushes suture knot thru trap

Stylet retracts within needle

Needle and stylet retract from tissue, suture end remains thru trap

Related U.S. Application Data 2012, now Pat. No. 10,383,620, Substitute for application No. 61/524,766, filed on Aug. 18, 2011.

(60) Provisional application No. 61/597,449, filed on Feb. 10, 2012, provisional application No. 61/593,843, filed on Feb. 1, 2012, provisional application No. 61/586,287, filed on Jan. 13, 2012, provisional application No. 61/582,464, filed on Jan. 2, 2012, provisional application No. 61/561,486, filed on Nov. 18, 2011, provisional application No. 61/524,765, filed on Aug. 18, 2011.

(51) Int. Cl.
 *A61B 90/00* (2016.01)
 *A61B 17/00* (2006.01)
 *A61B 17/06* (2006.01)

(52) U.S. Cl.
 CPC ............ *A61B 2017/00455* (2013.01); *A61B 2017/0475* (2013.01); *A61B 2017/0496* (2013.01); *A61B 2017/06052* (2013.01); *A61B 2090/0811* (2016.02)

(58) Field of Classification Search
 USPC ........................................ 606/145
 See application file for complete search history.

(56) References Cited

U.S. PATENT DOCUMENTS

| | | | | |
|---|---|---|---|---|
| 5,697,979 | A * | 12/1997 | Pignataro | A61B 17/8605 606/187 |
| 6,551,330 | B1 * | 4/2003 | Bain | A61B 17/0469 606/144 |
| 6,770,084 | B1 * | 8/2004 | Bain | A61B 17/0469 606/144 |
| 7,601,161 | B1 * | 10/2009 | Nobles | A61B 17/0491 606/139 |
| 2006/0235390 | A1 * | 10/2006 | Zhang | A61B 17/701 606/264 |
| 2007/0096480 | A1 * | 5/2007 | Arneson | E05B 15/0205 292/340 |
| 2007/0250118 | A1 * | 10/2007 | Masini | A61B 17/0643 606/220 |
| 2011/0028998 | A1 * | 2/2011 | Adams | A61B 17/0482 606/145 |
| 2011/0066165 | A1 * | 3/2011 | Skinlo | A61B 17/0483 606/222 |
| 2011/0112555 | A1 * | 5/2011 | Overes | A61B 17/0491 606/145 |

\* cited by examiner

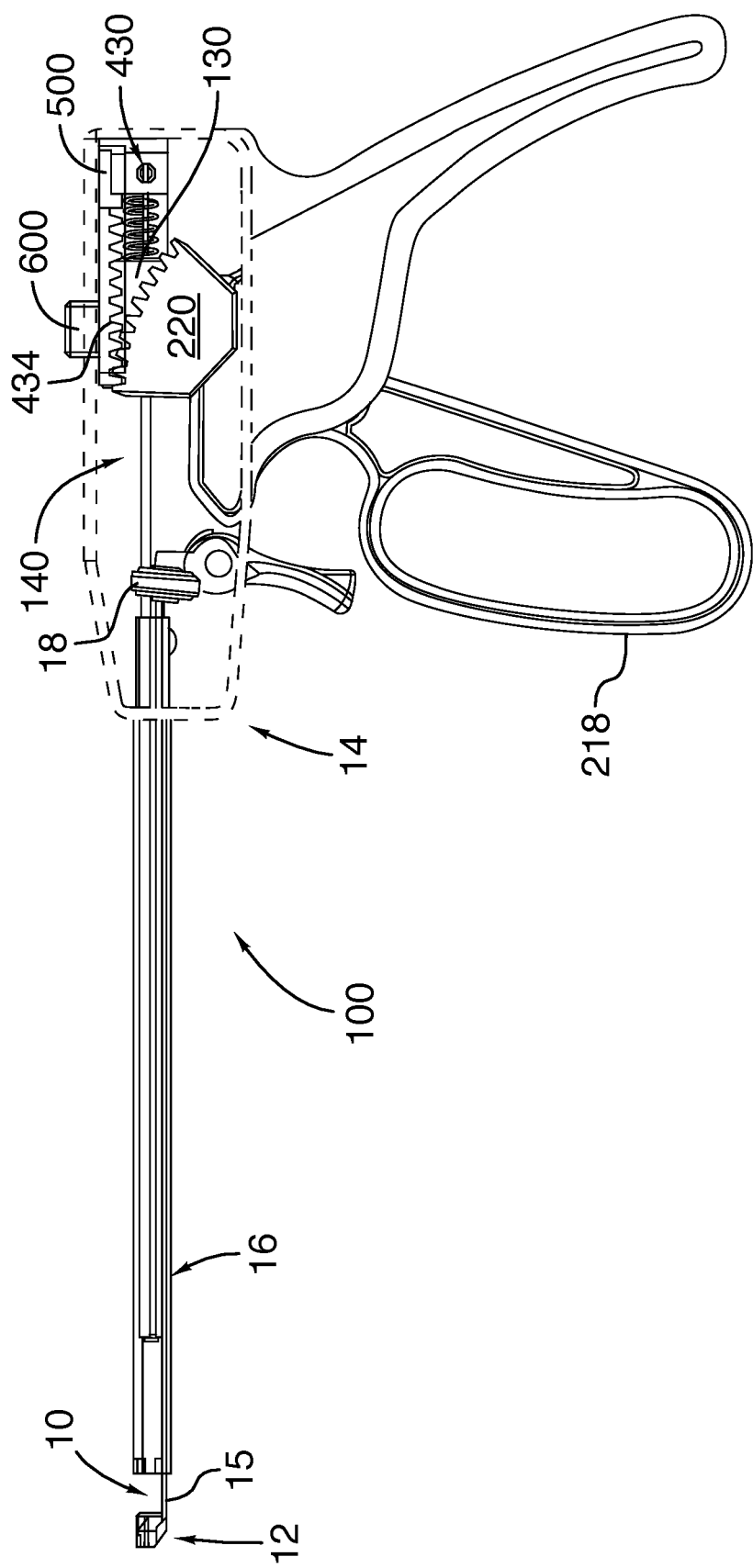

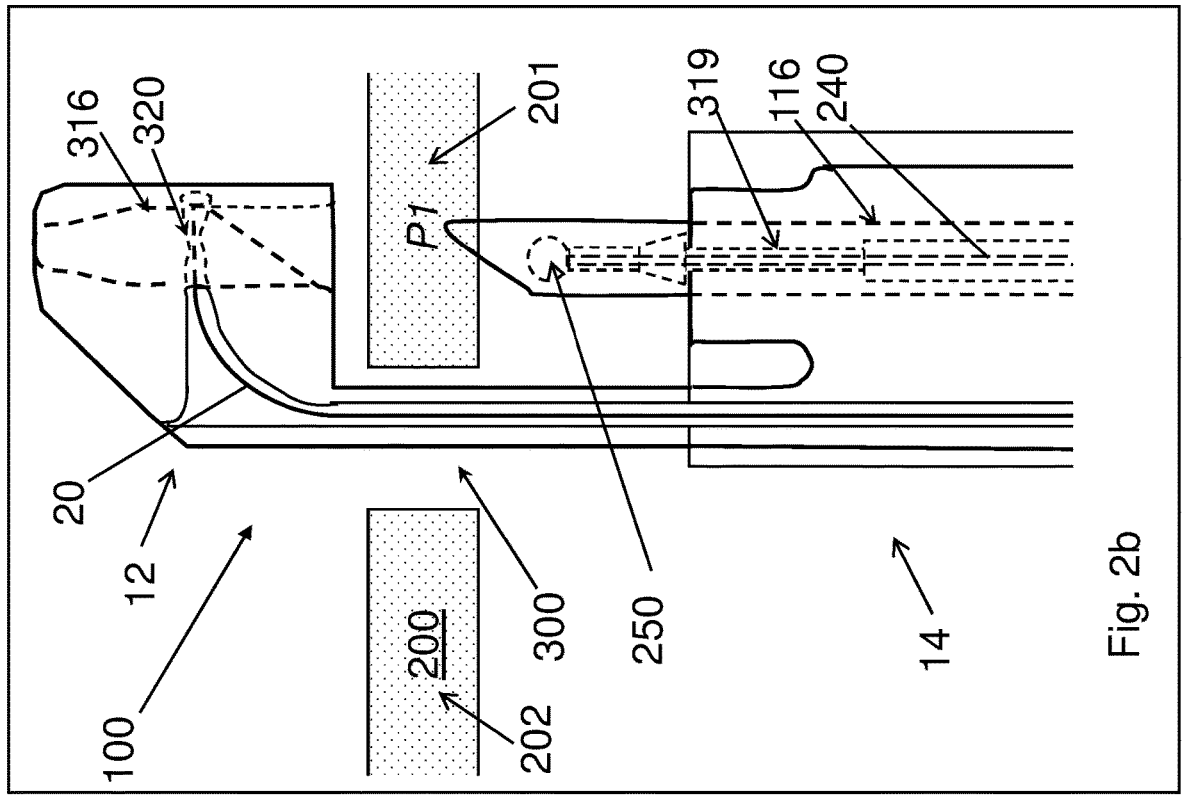
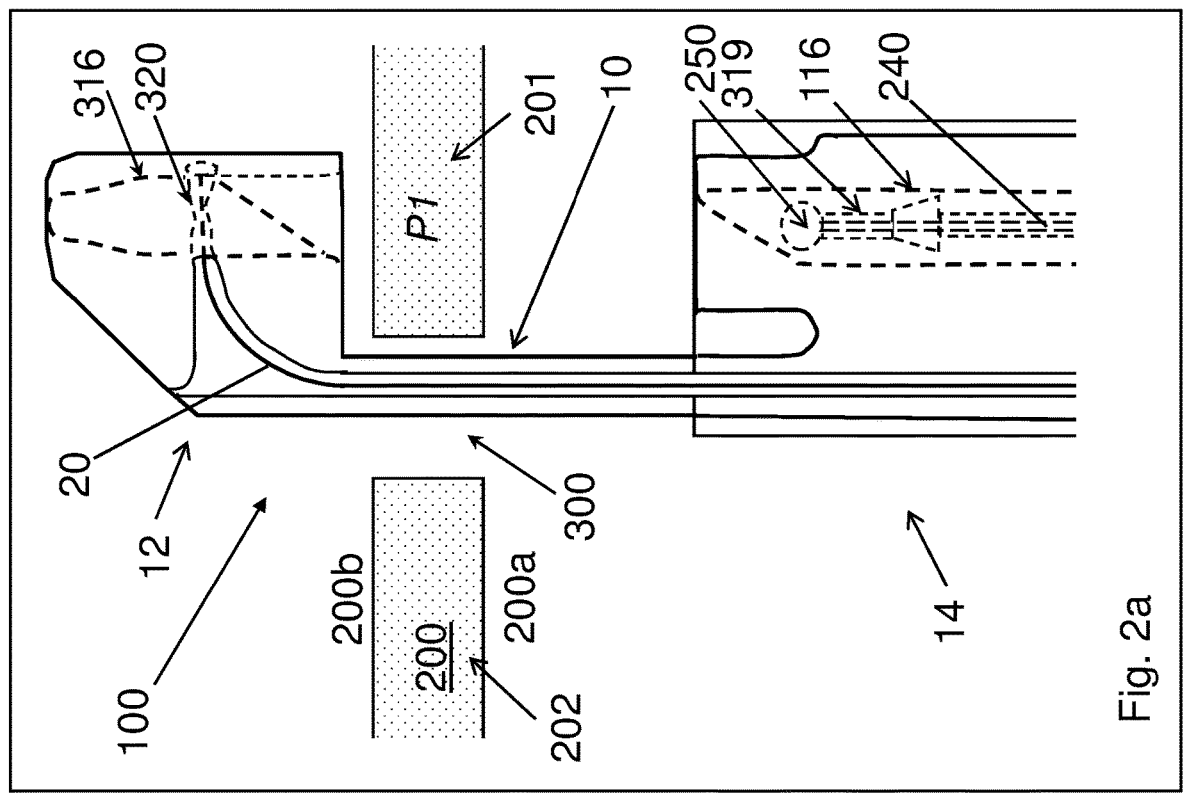

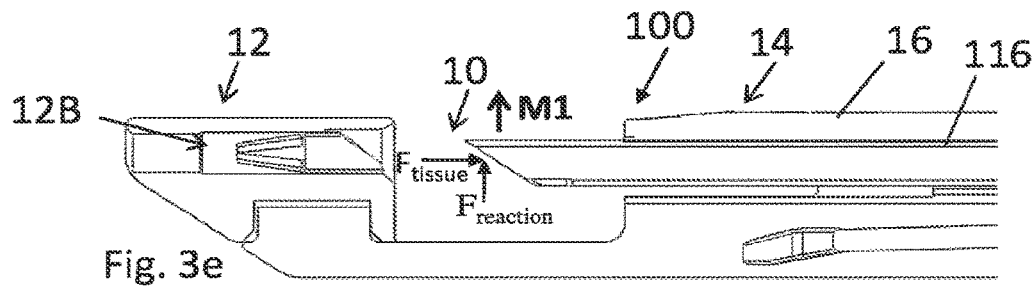
Fig. 3e
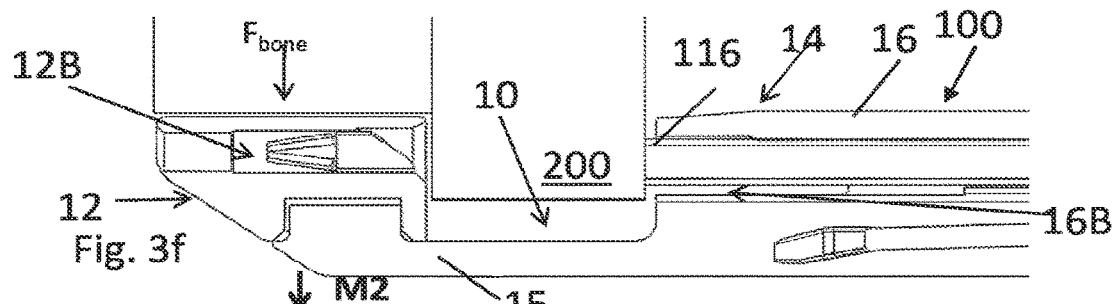
Fig. 3f
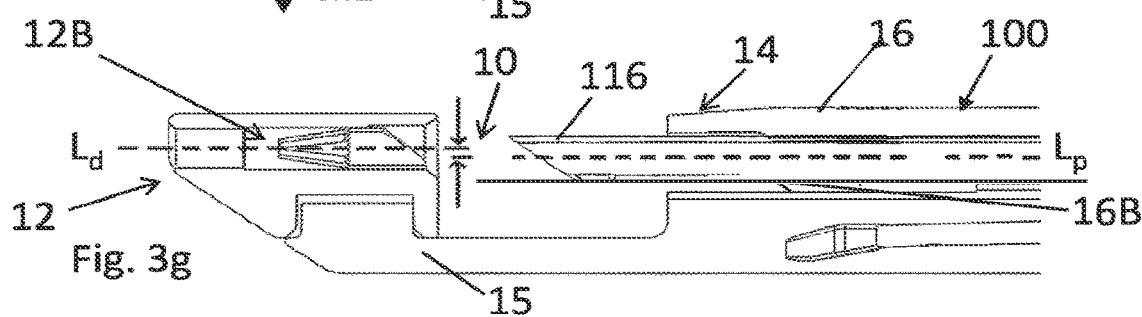
Fig. 3g
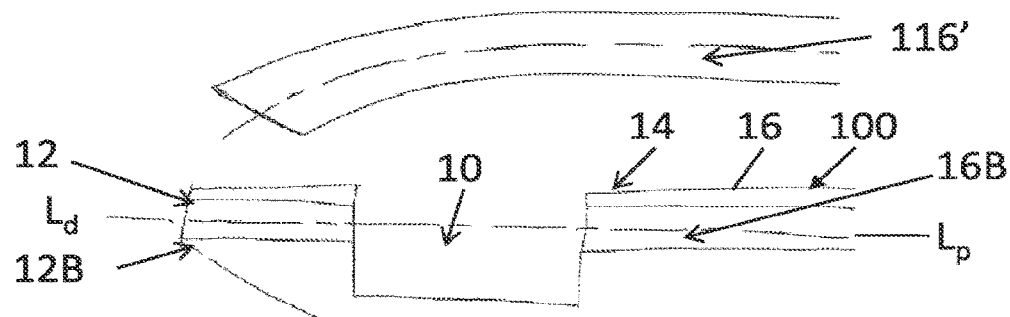
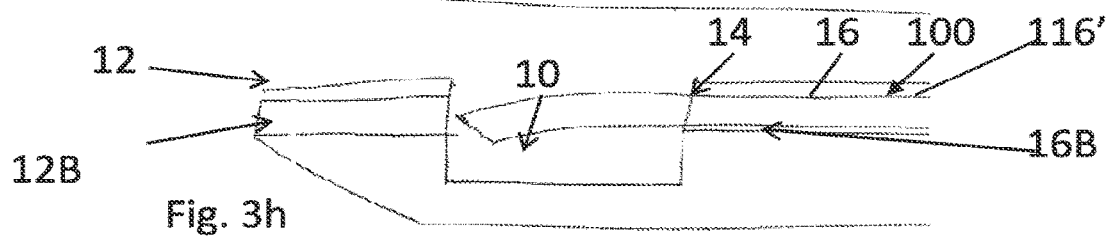
Fig. 3h

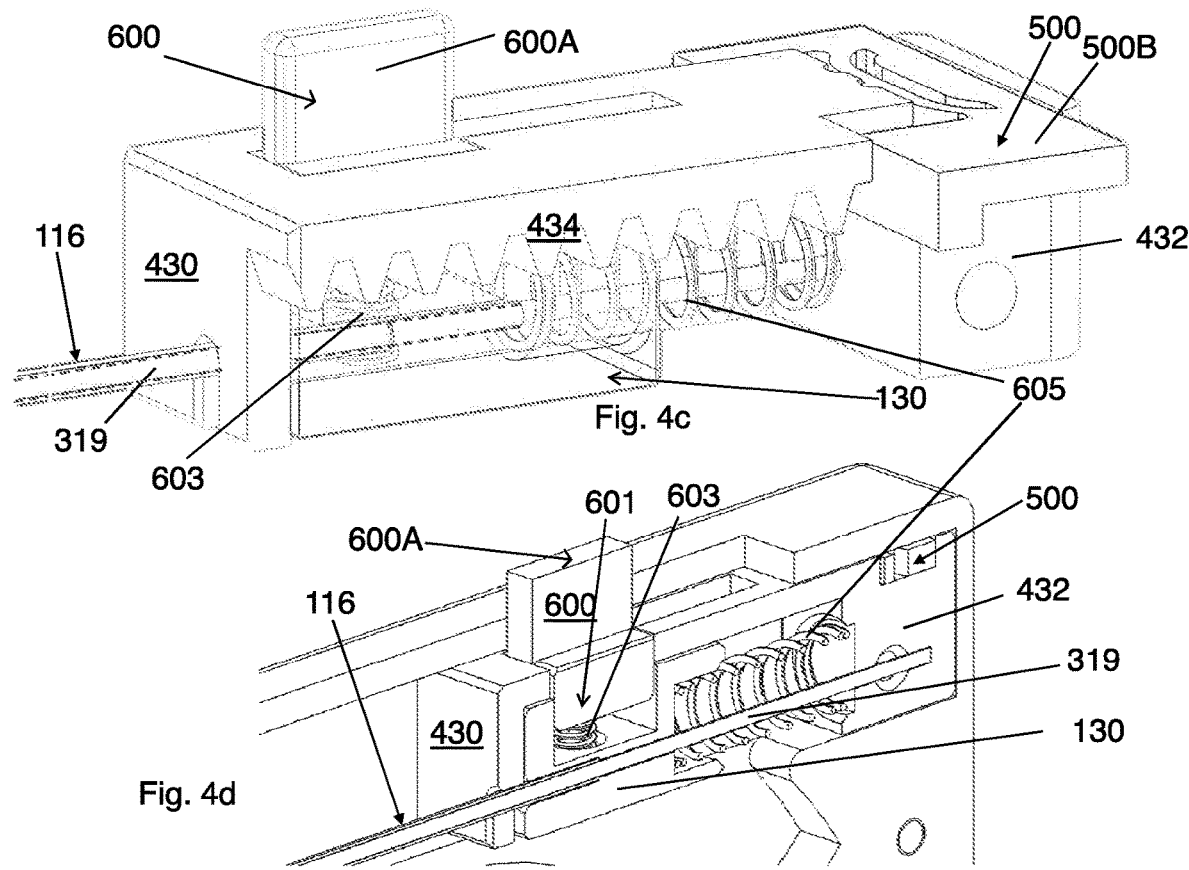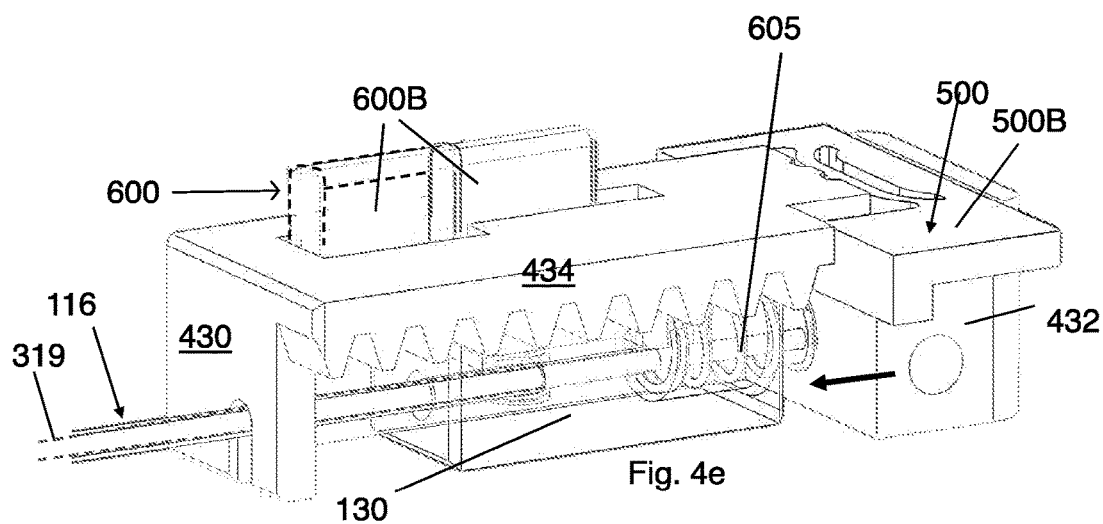

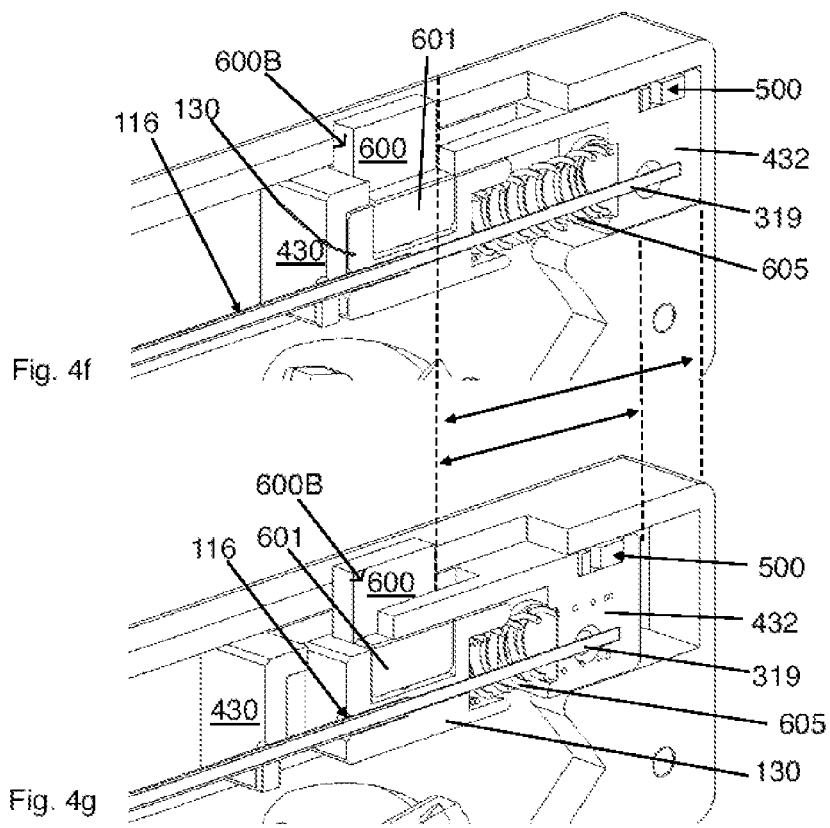
Fig. 4f
Fig. 4g
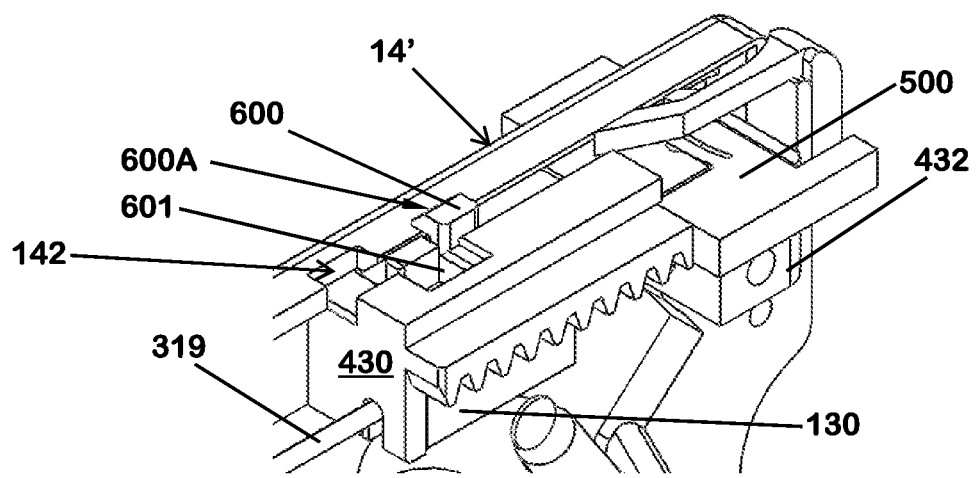
Fig. 4h
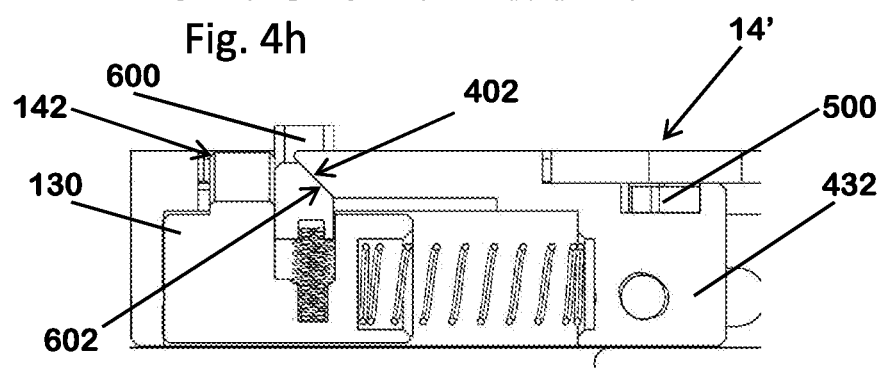
Fig. 4i

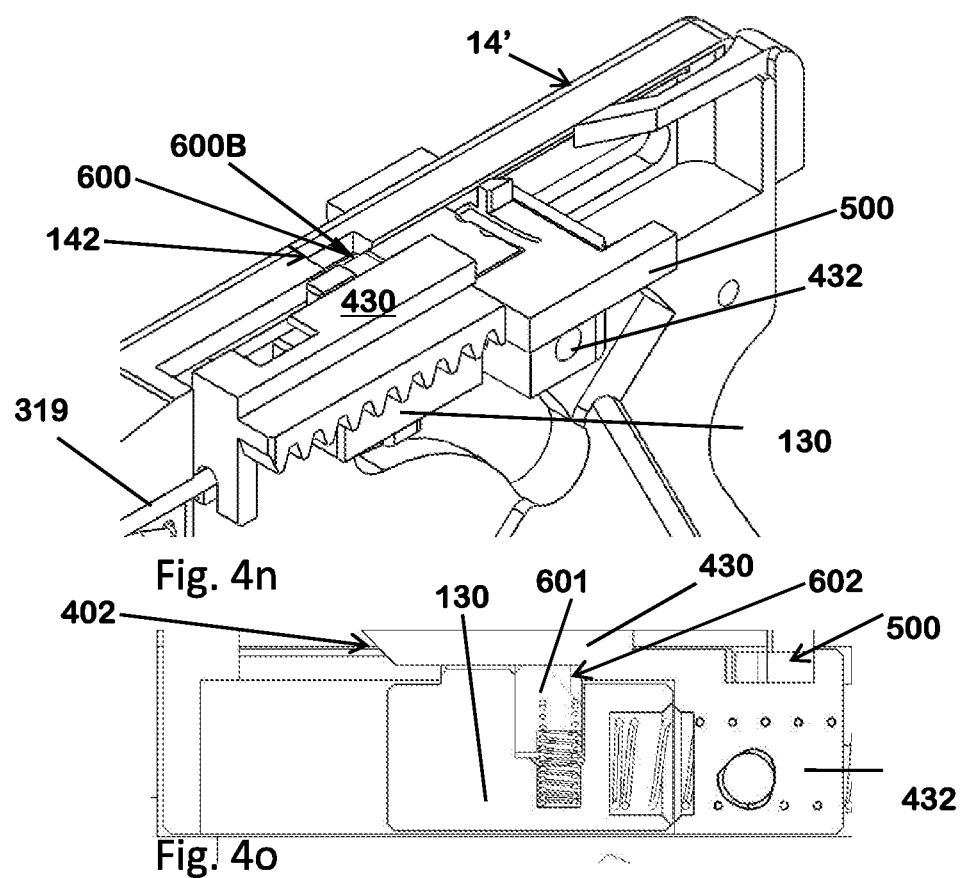

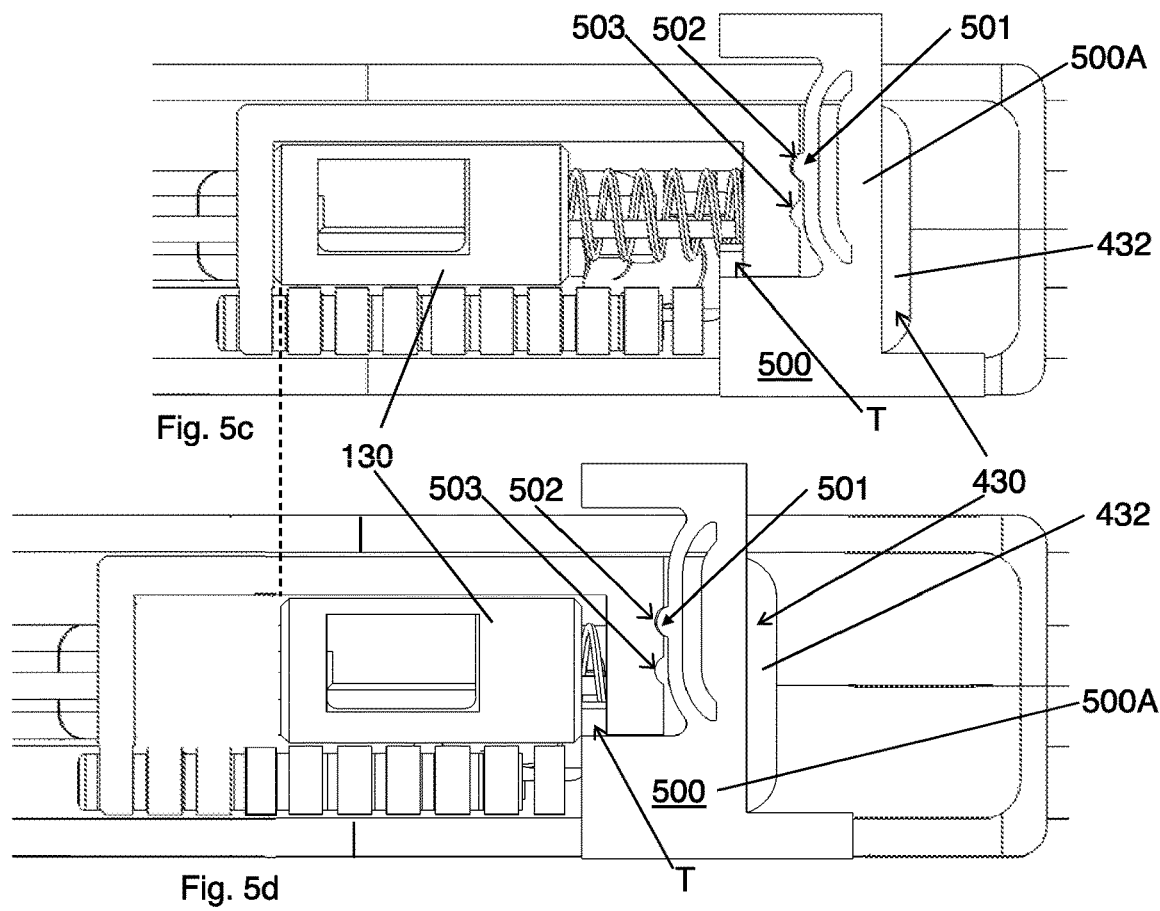
Fig. 5c
Fig. 5d
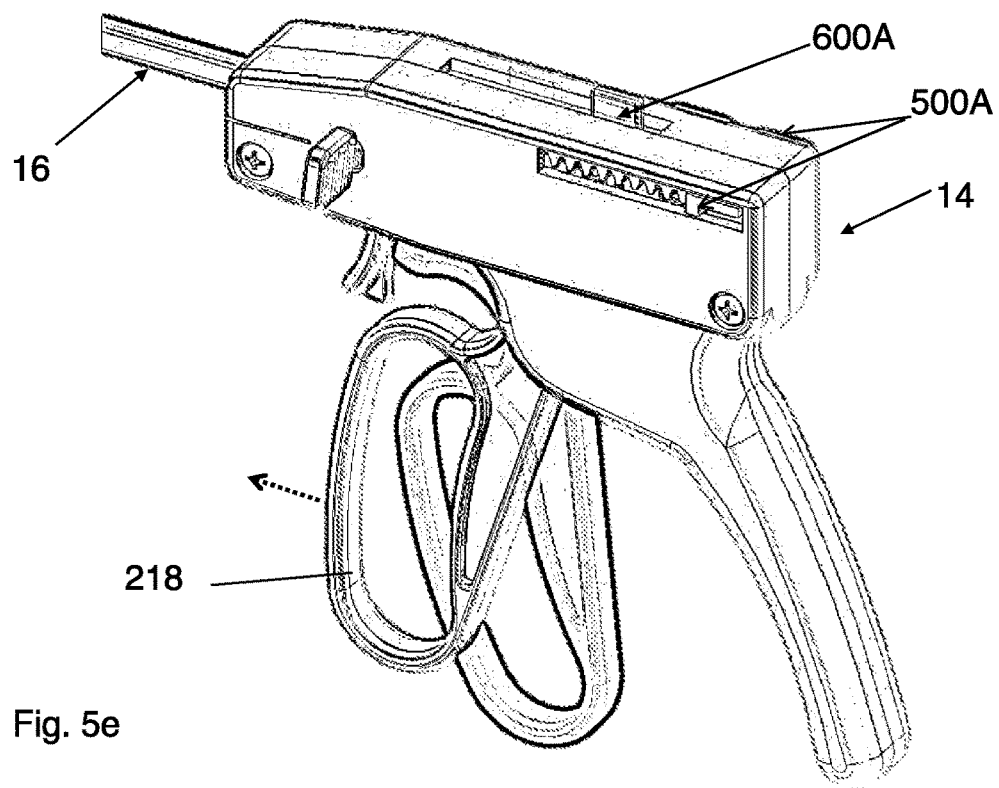
Fig. 5e

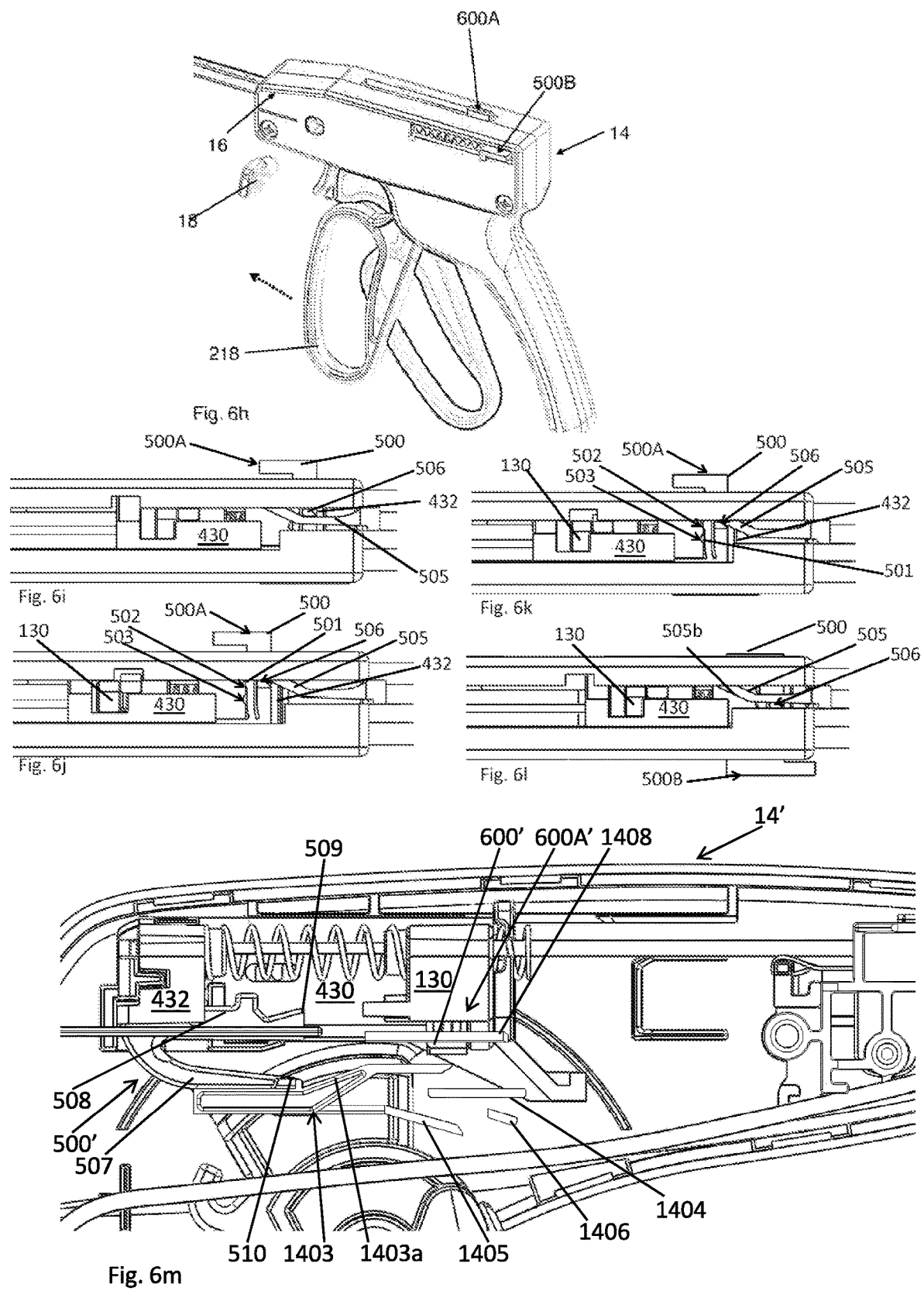

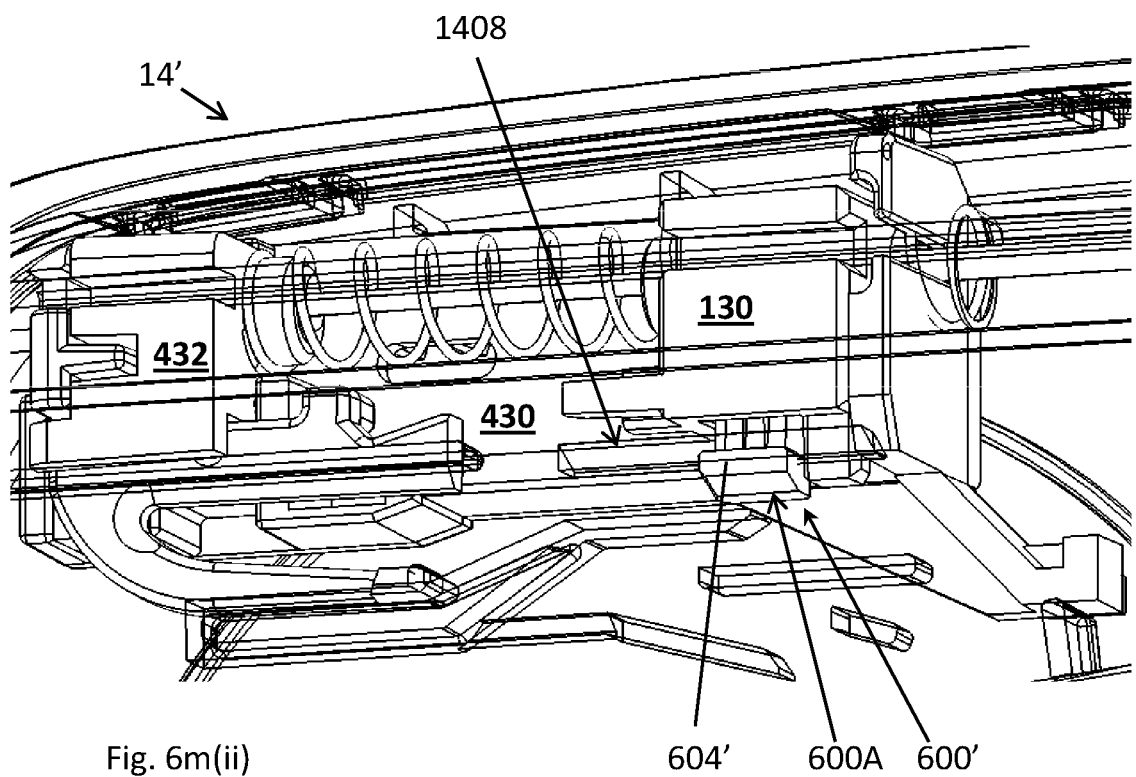
Fig. 6m(ii)
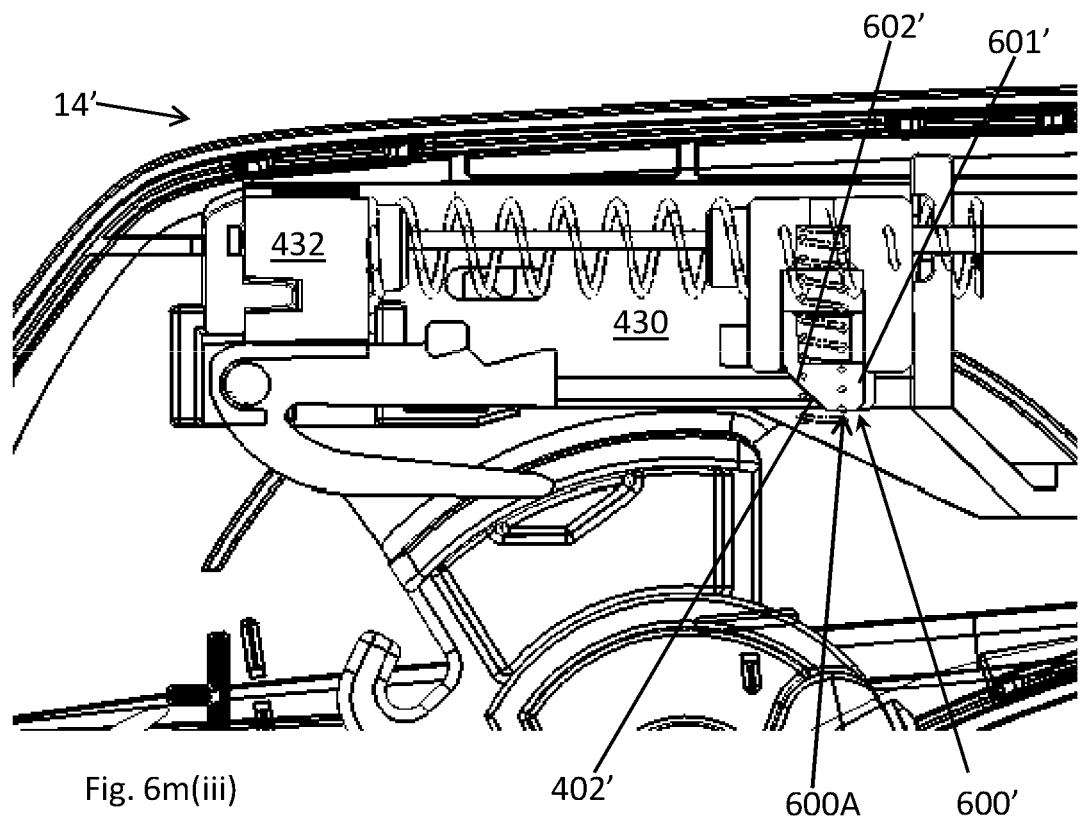
Fig. 6m(iii)

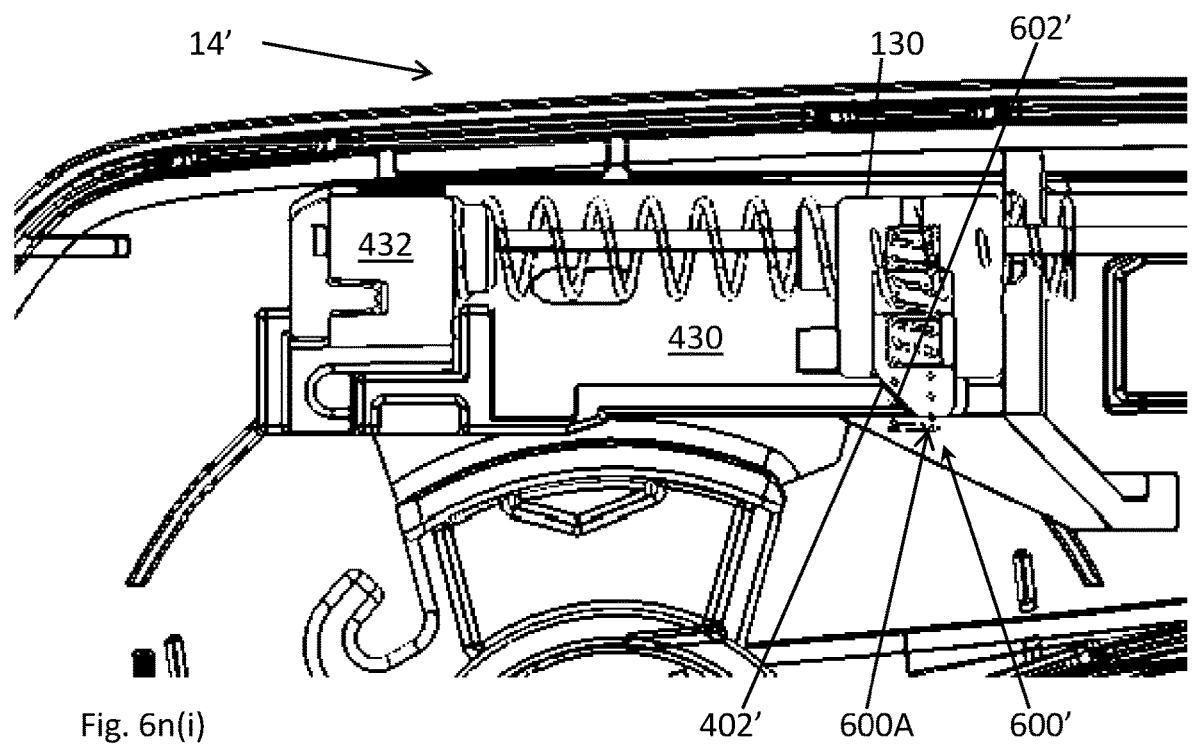
Fig. 6n(i)
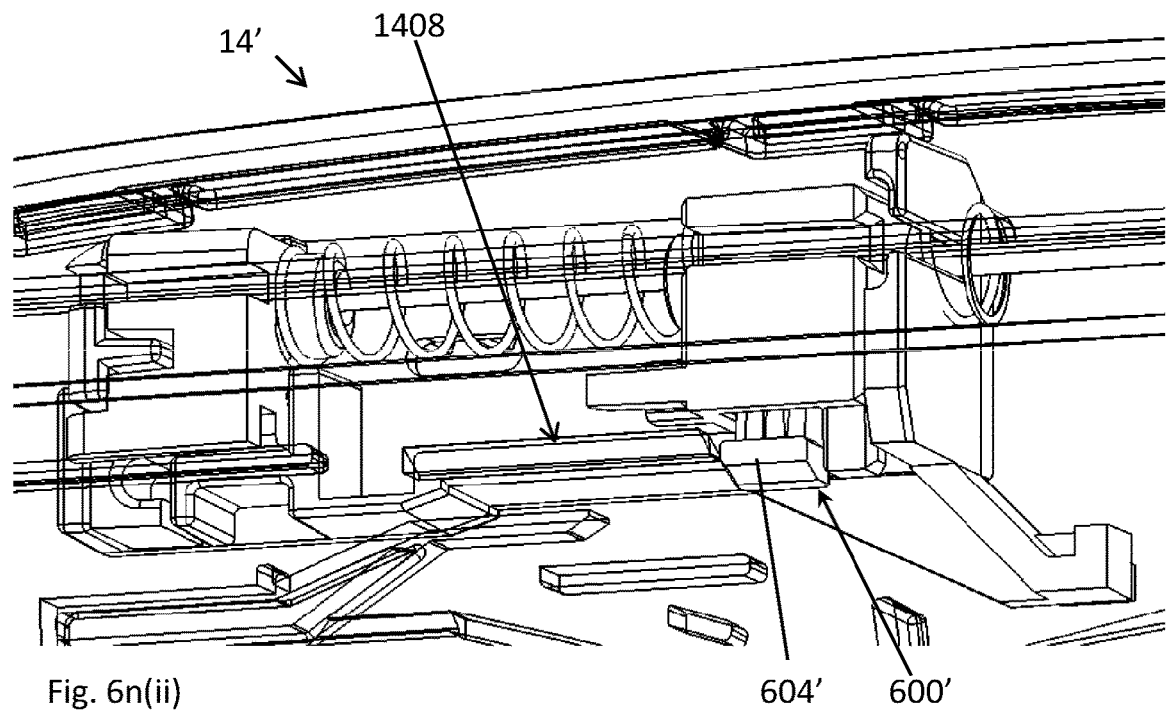
Fig. 6n(ii)

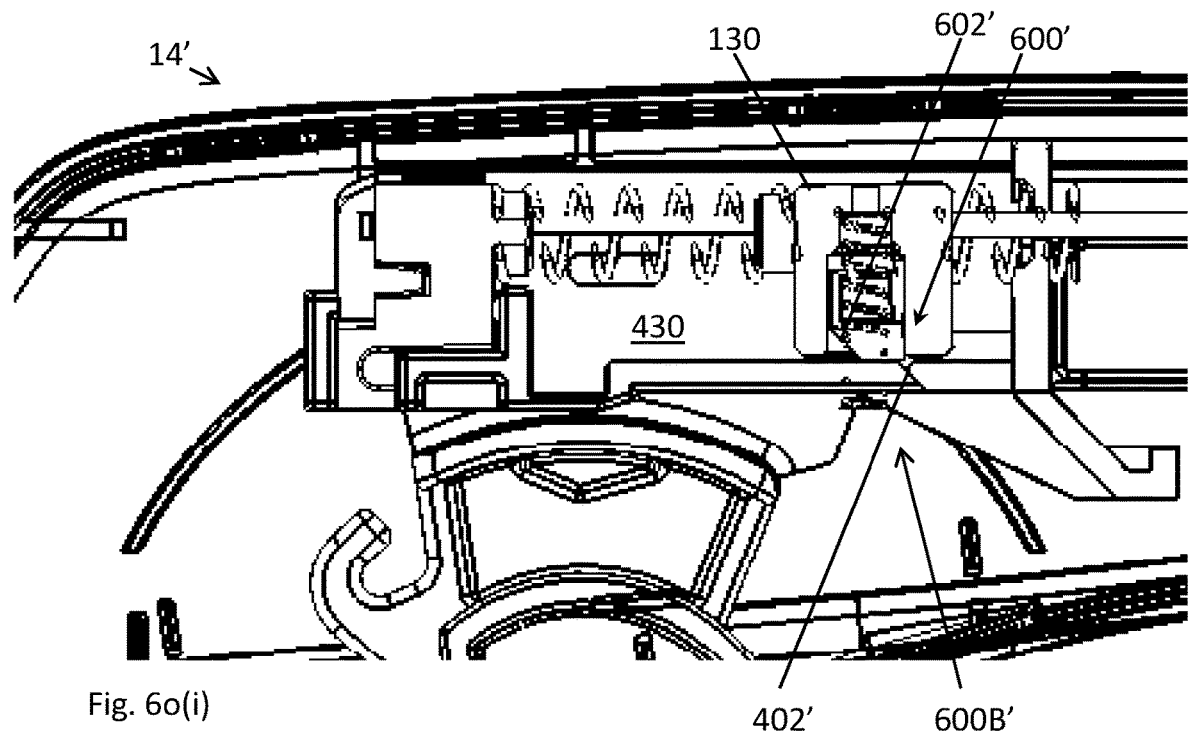
Fig. 6o(i)
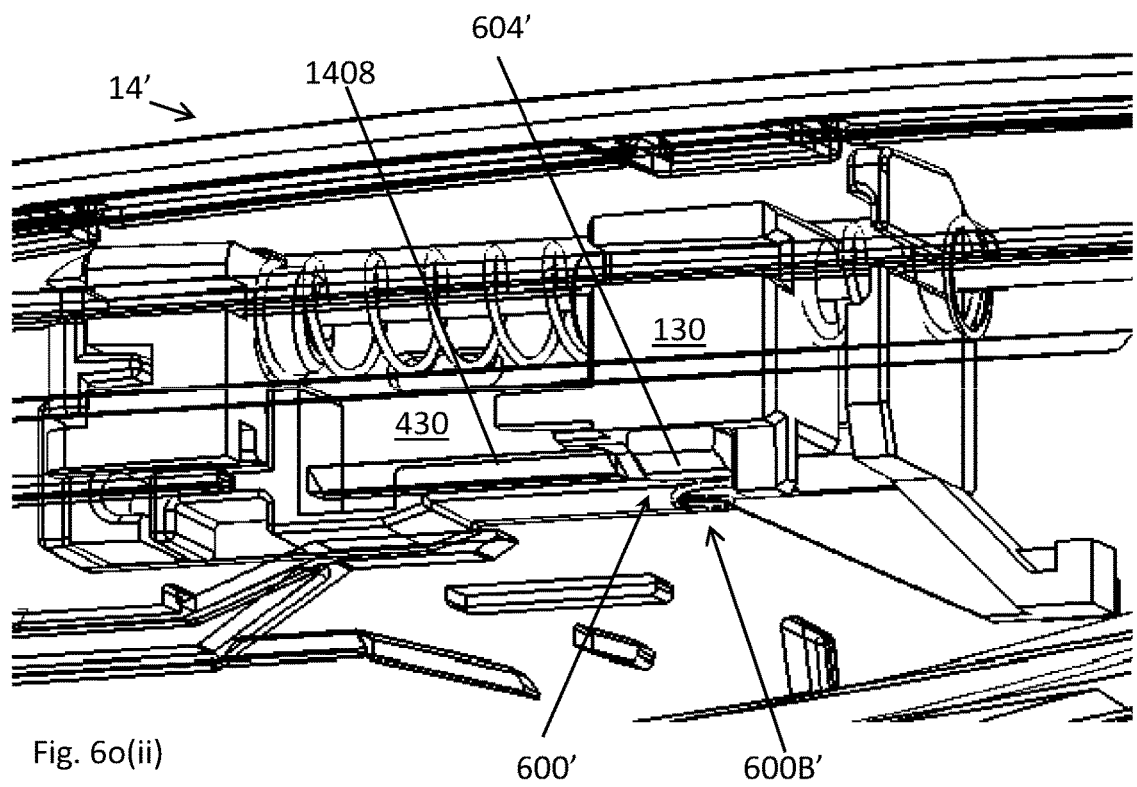
Fig. 6o(ii)

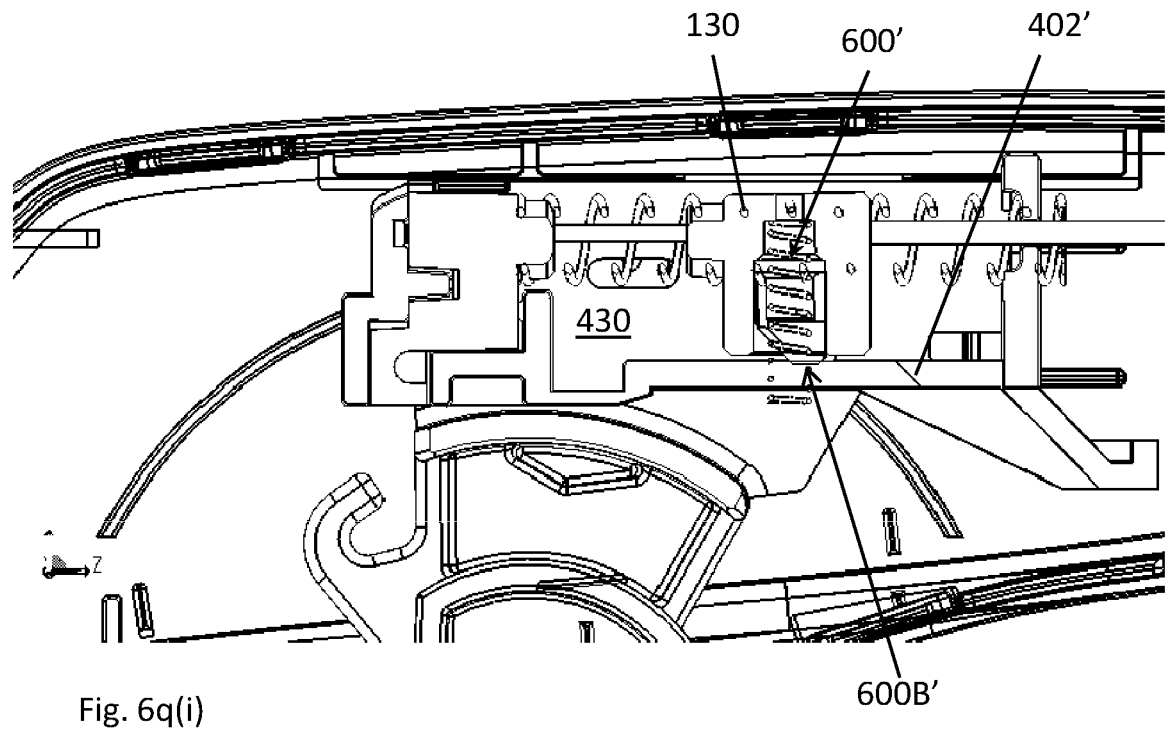
Fig. 6q(i)
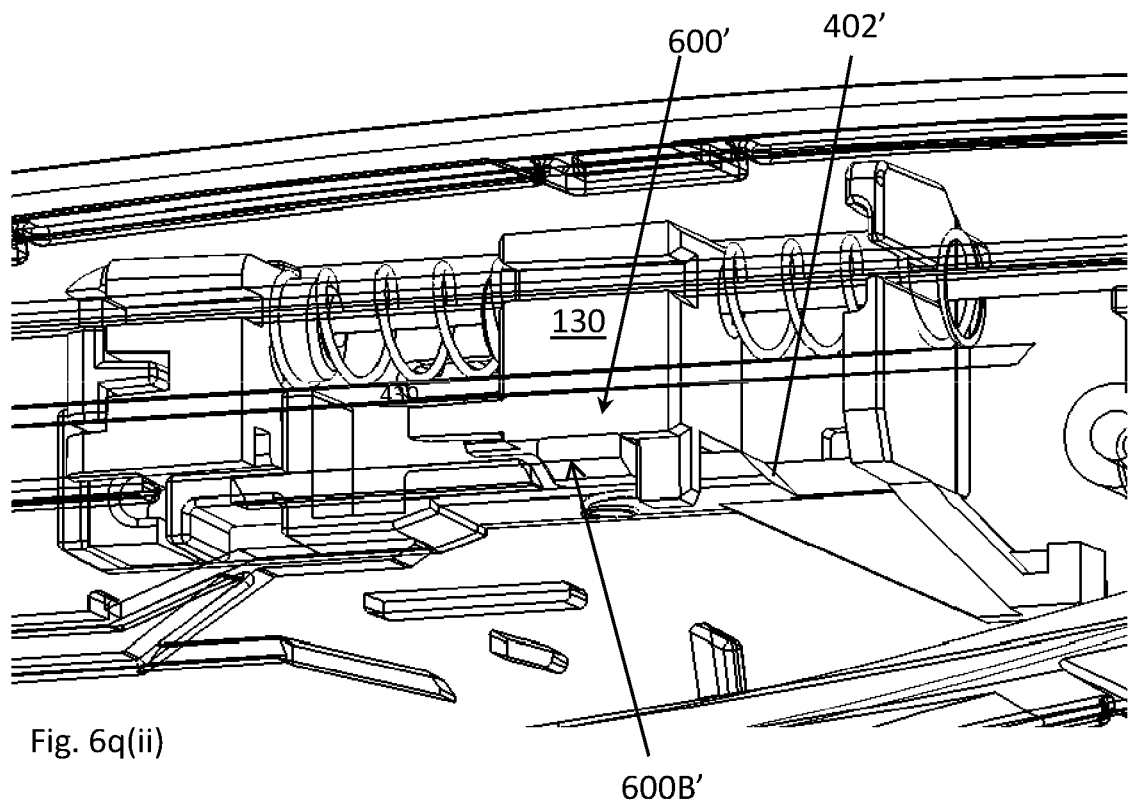
Fig. 6q(ii)

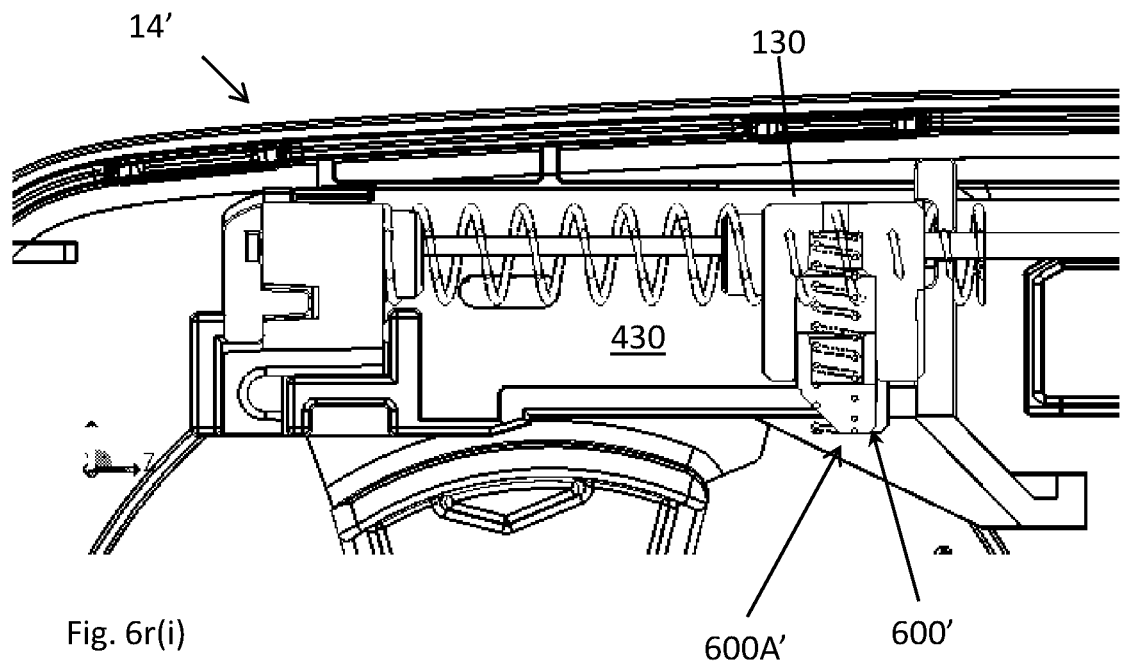
Fig. 6r(i)
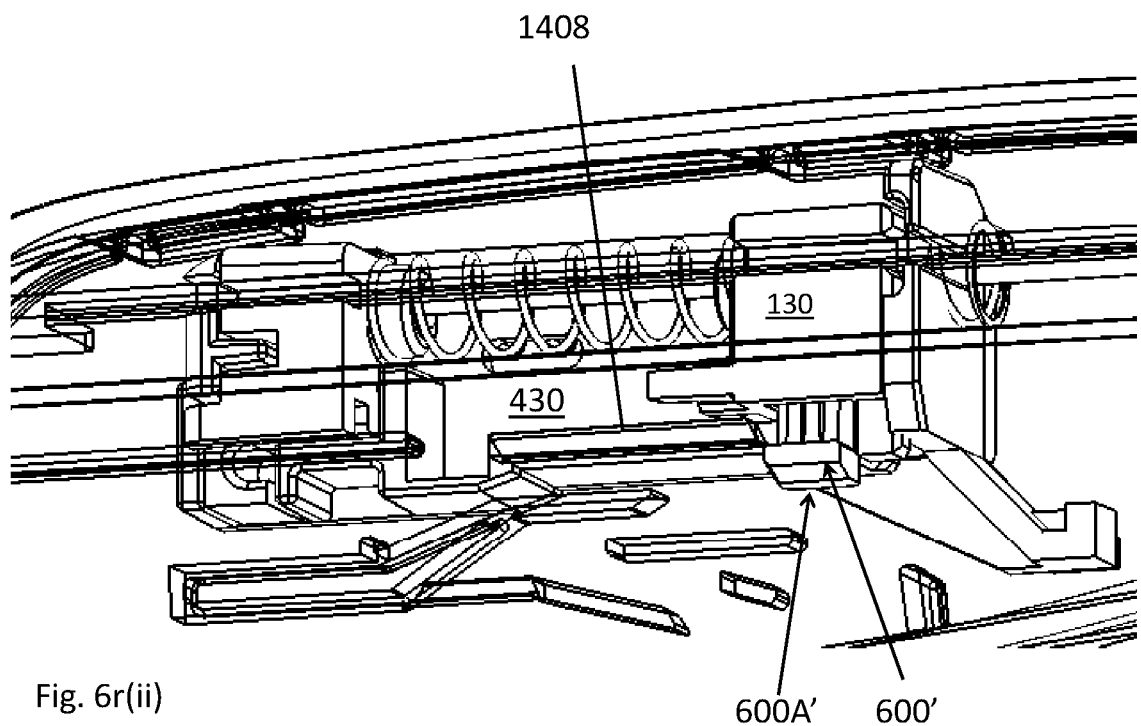
Fig. 6r(ii)

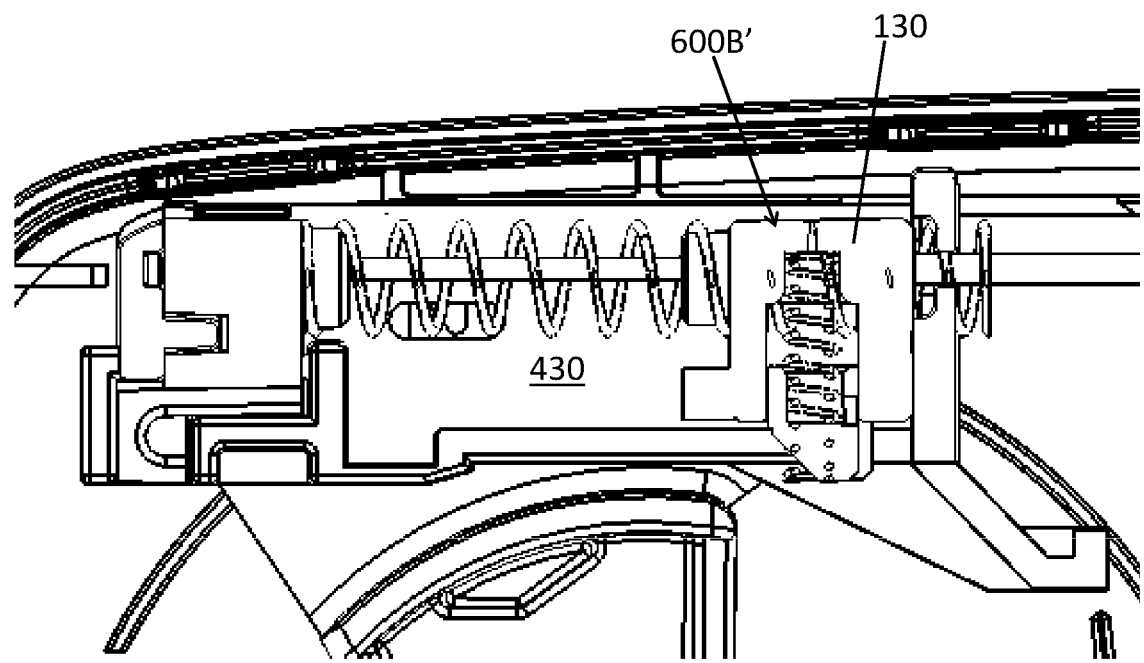
Fig. 6s(i)
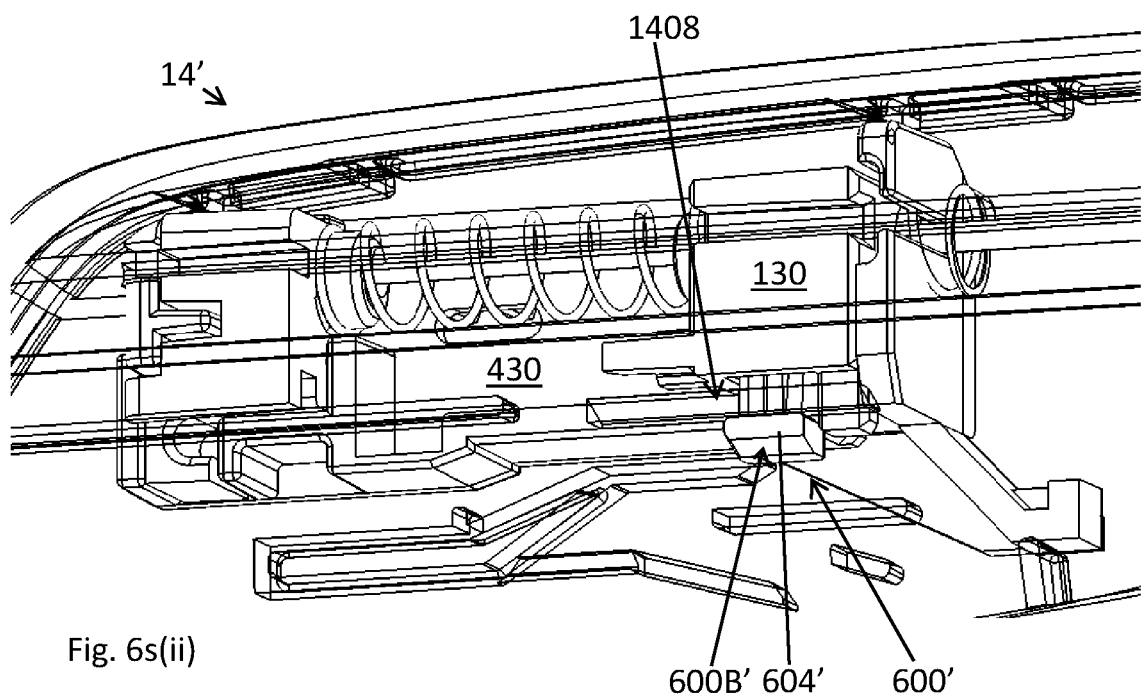
Fig. 6s(ii)

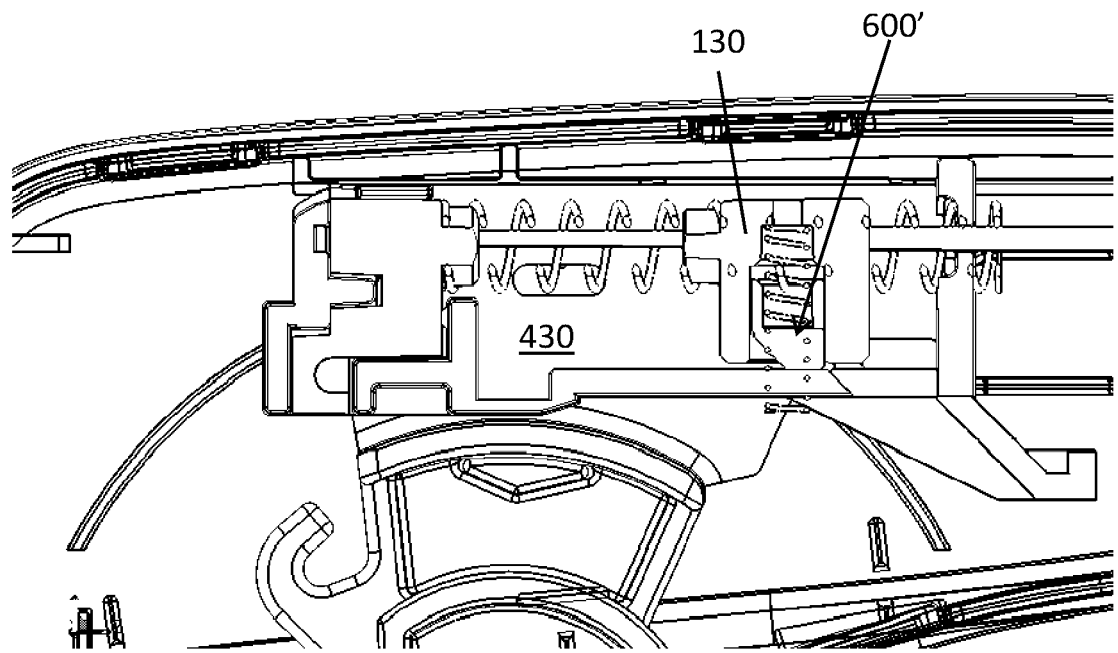
Fig. 6t(i)
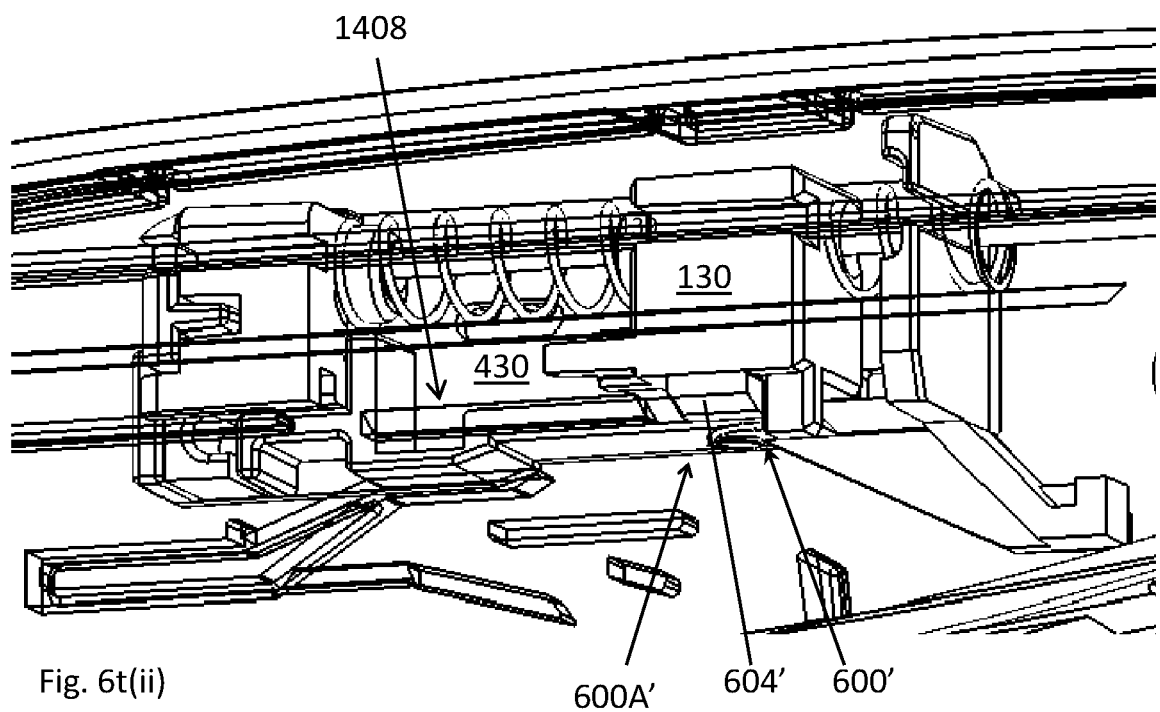
Fig. 6t(ii)

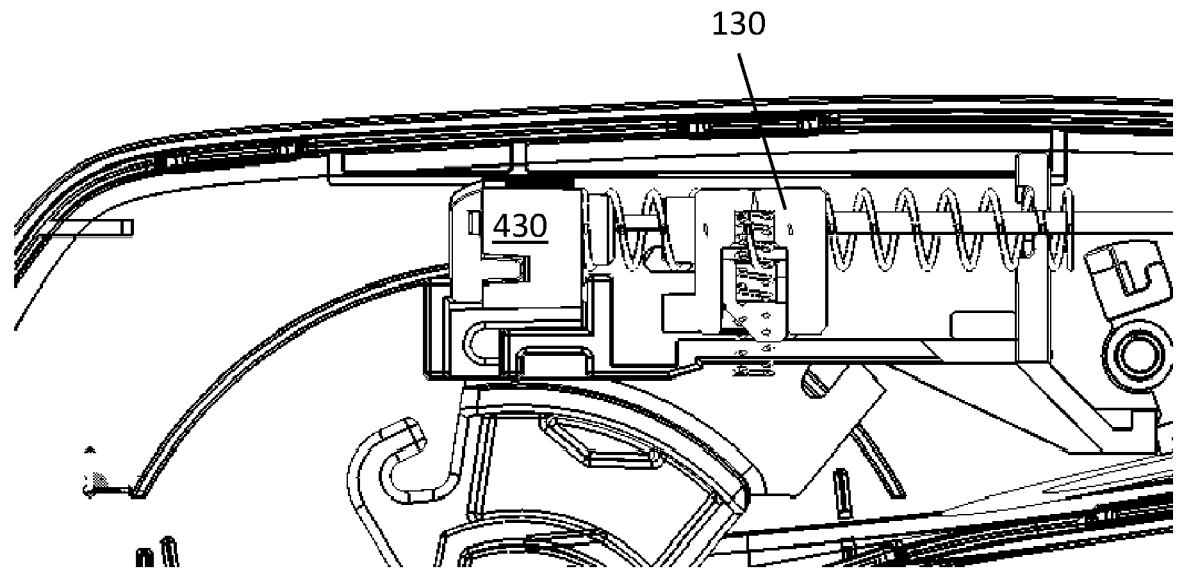
Fig. 6v(i)
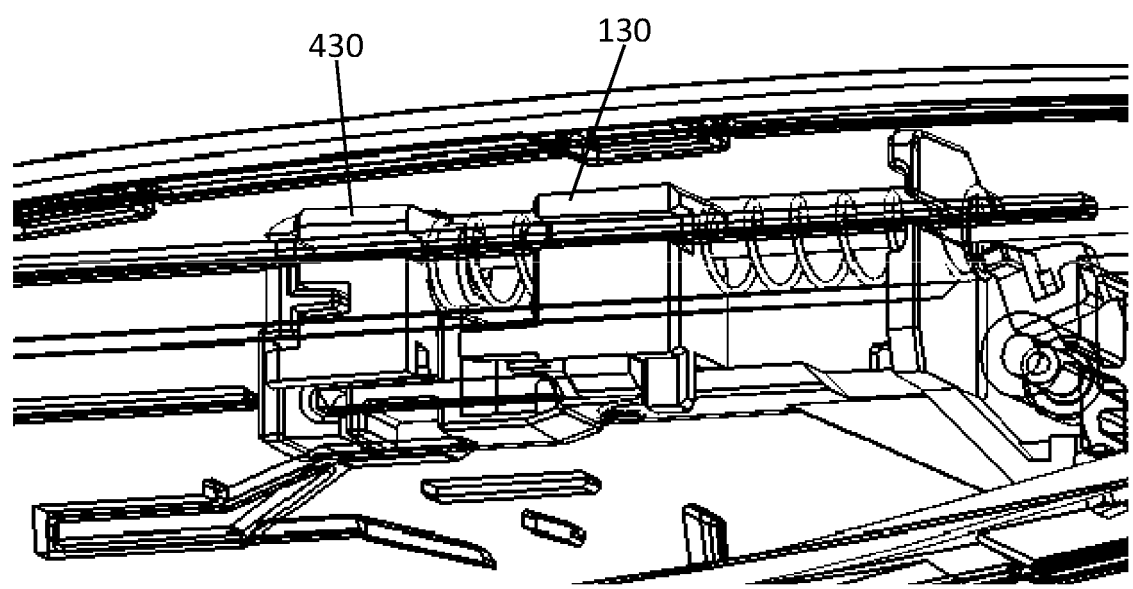
Fig. 6v(ii)

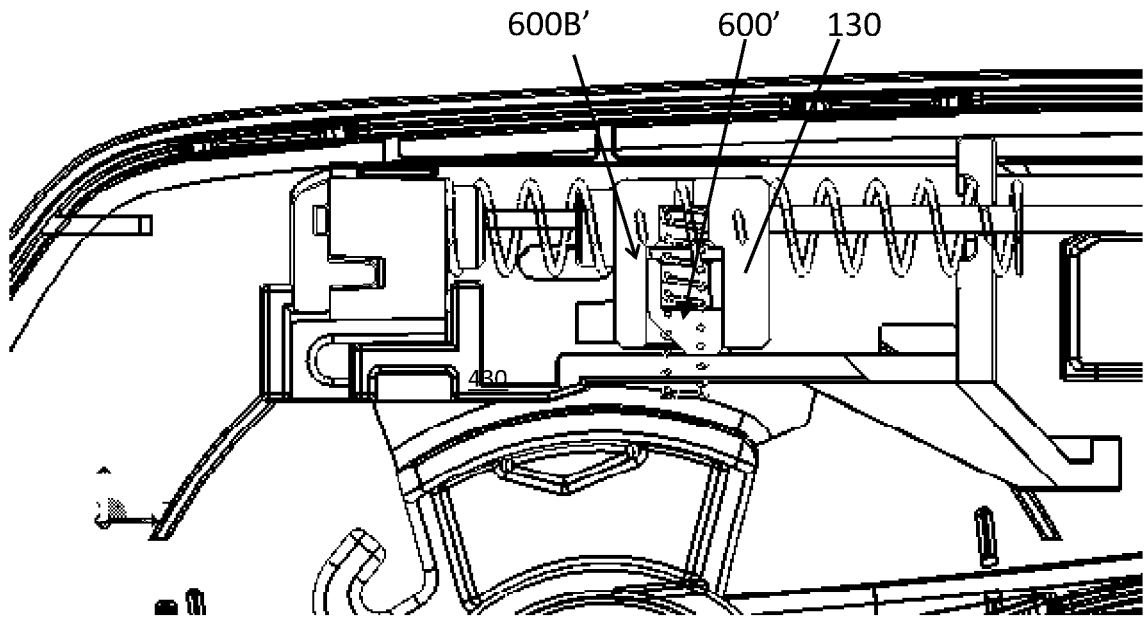
Fig. 6w(i)
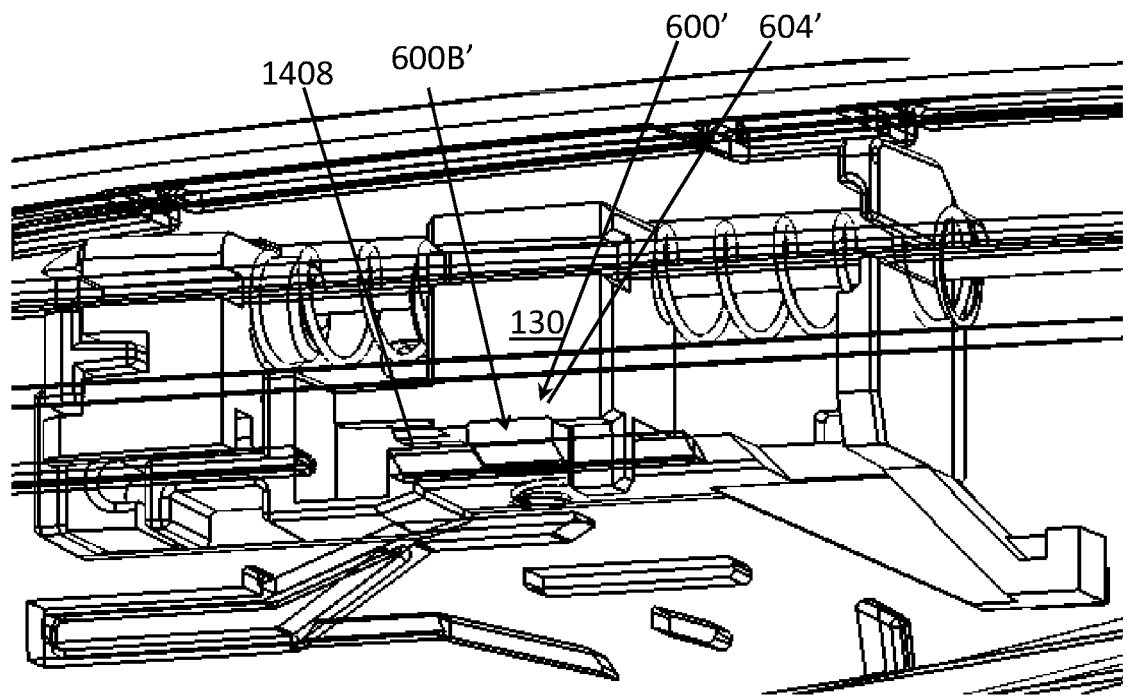
Fig. 6w(ii)

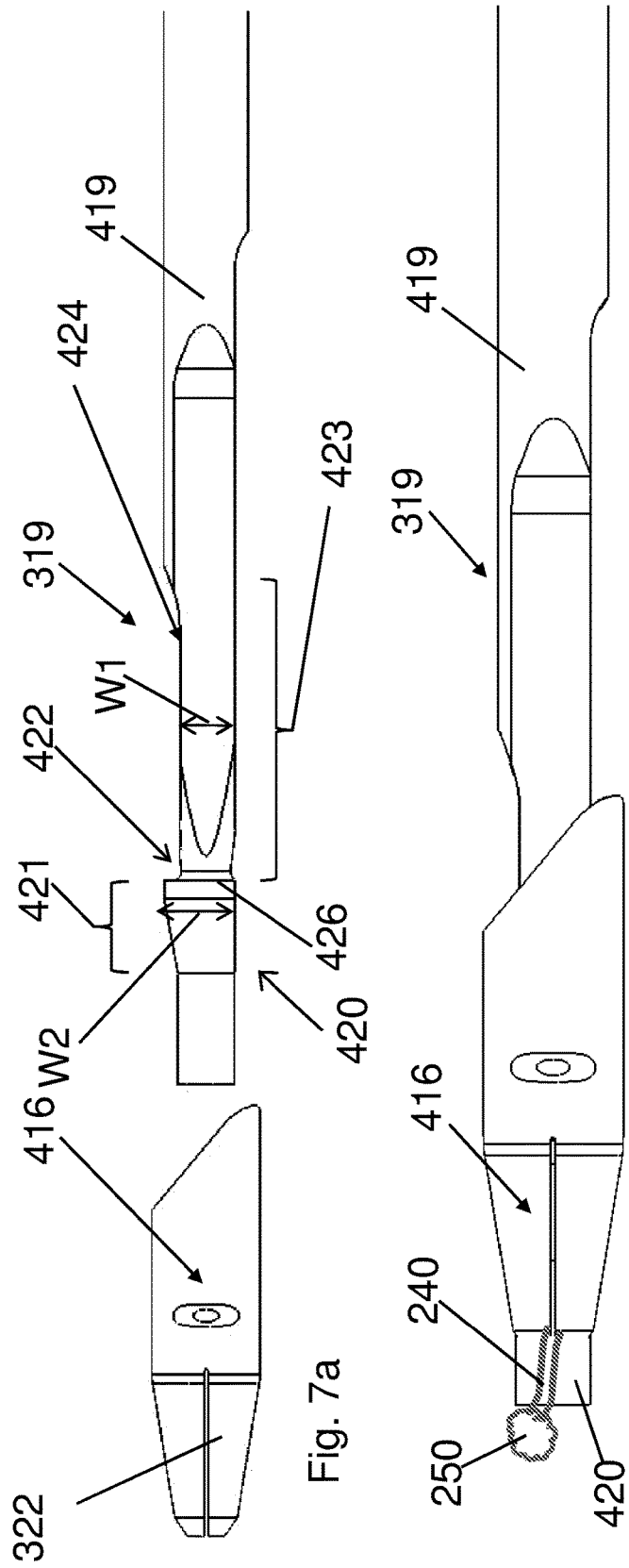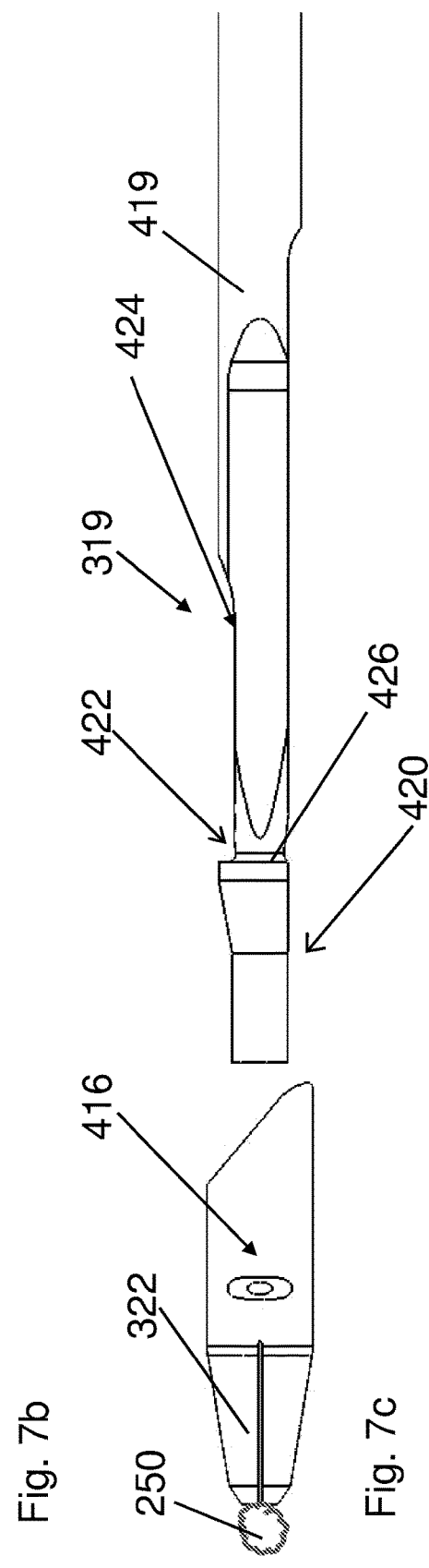
Fig. 7a  Fig. 7b  Fig. 7c

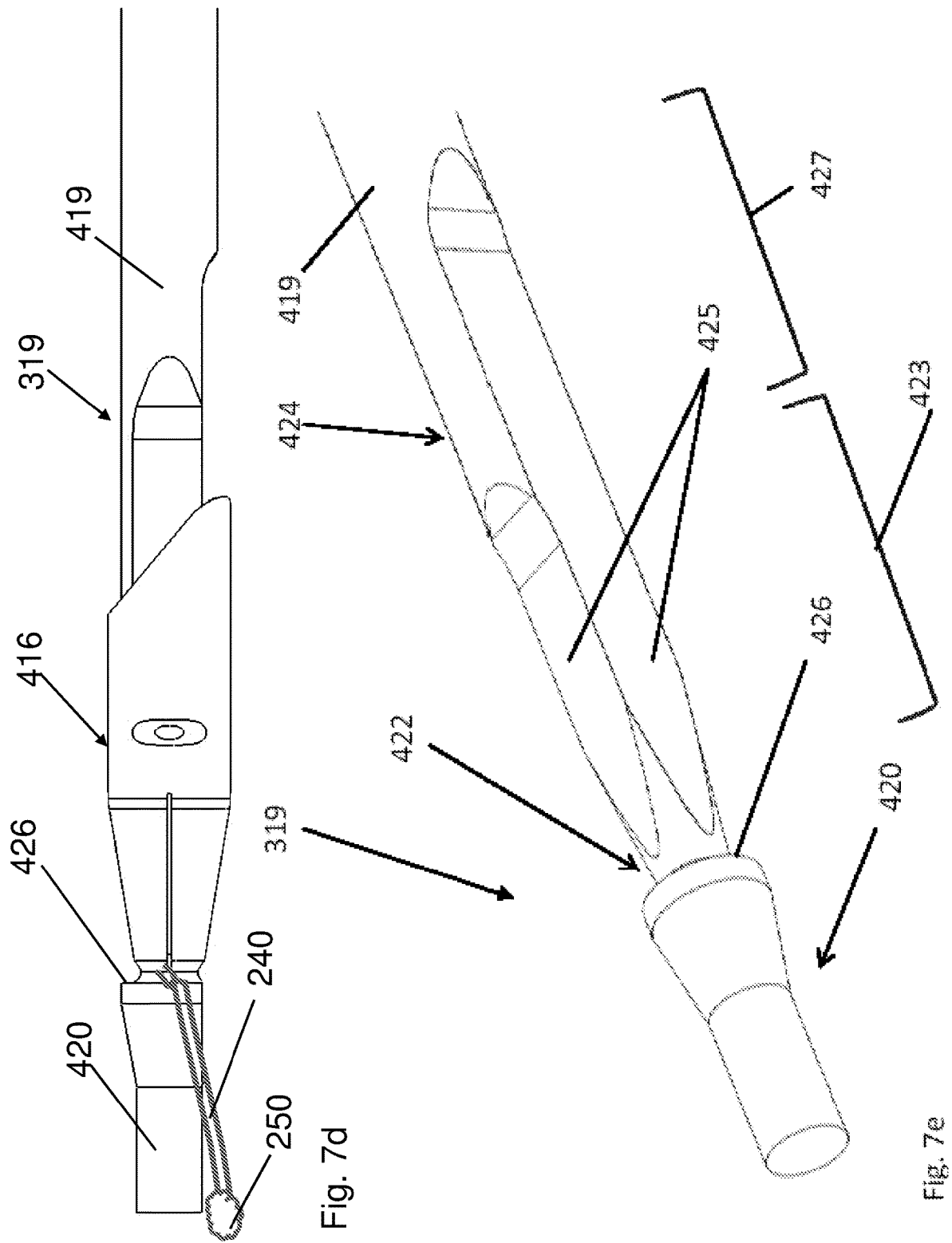

Starting position

Needle penetrates tissue (stylet and suture within needle)

Stylet advances and pushes suture knot thru trap

Stylet retracts within needle

Needle and stylet retract from tissue, suture end remains thru trap

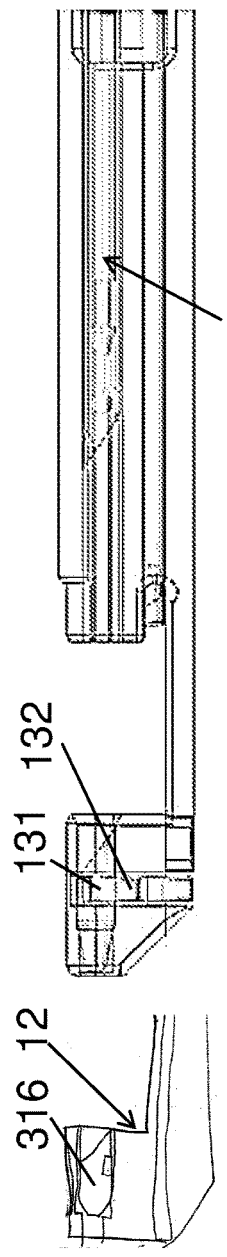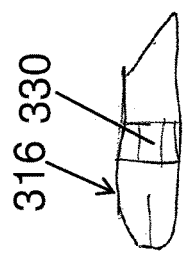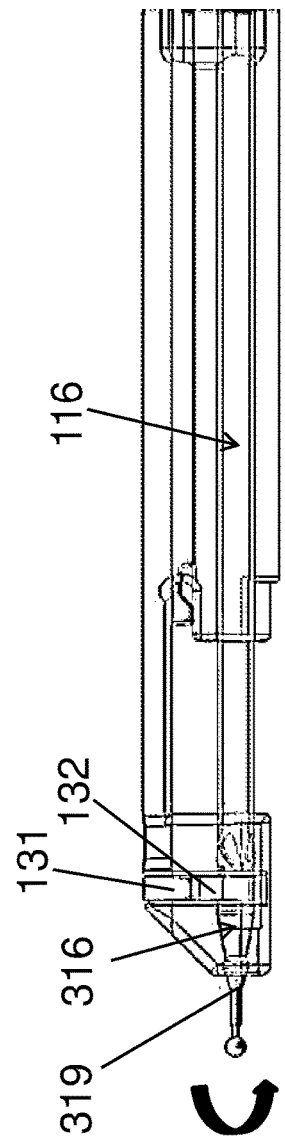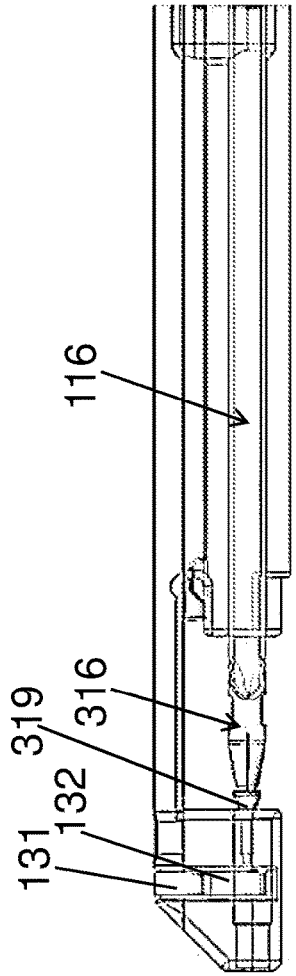
Fig. 11a
Fig. 11b
Fig. 11c
Fig. 11d

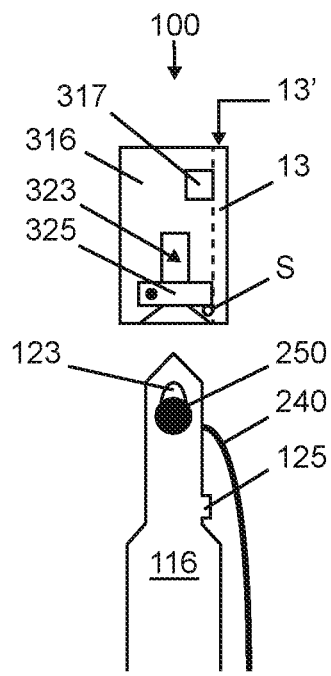
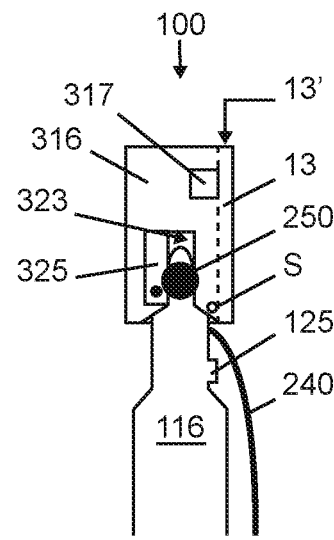
Fig. 13a
Fig. 13b
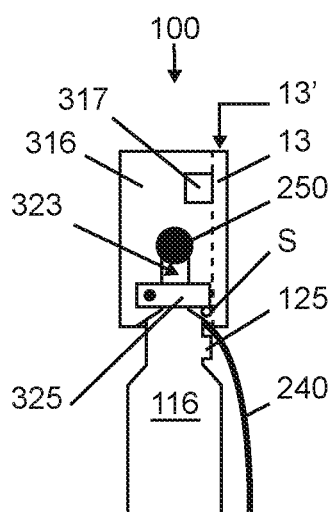
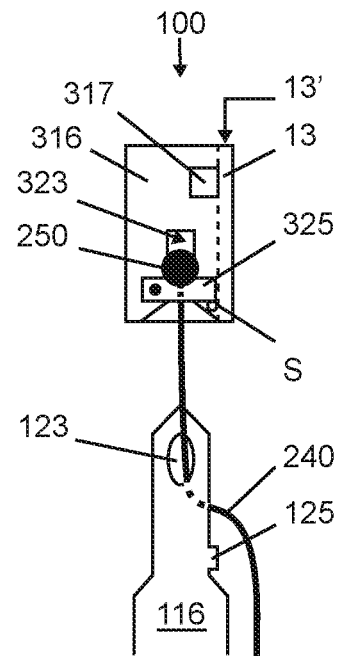
Fig. 13c
Fig. 13d

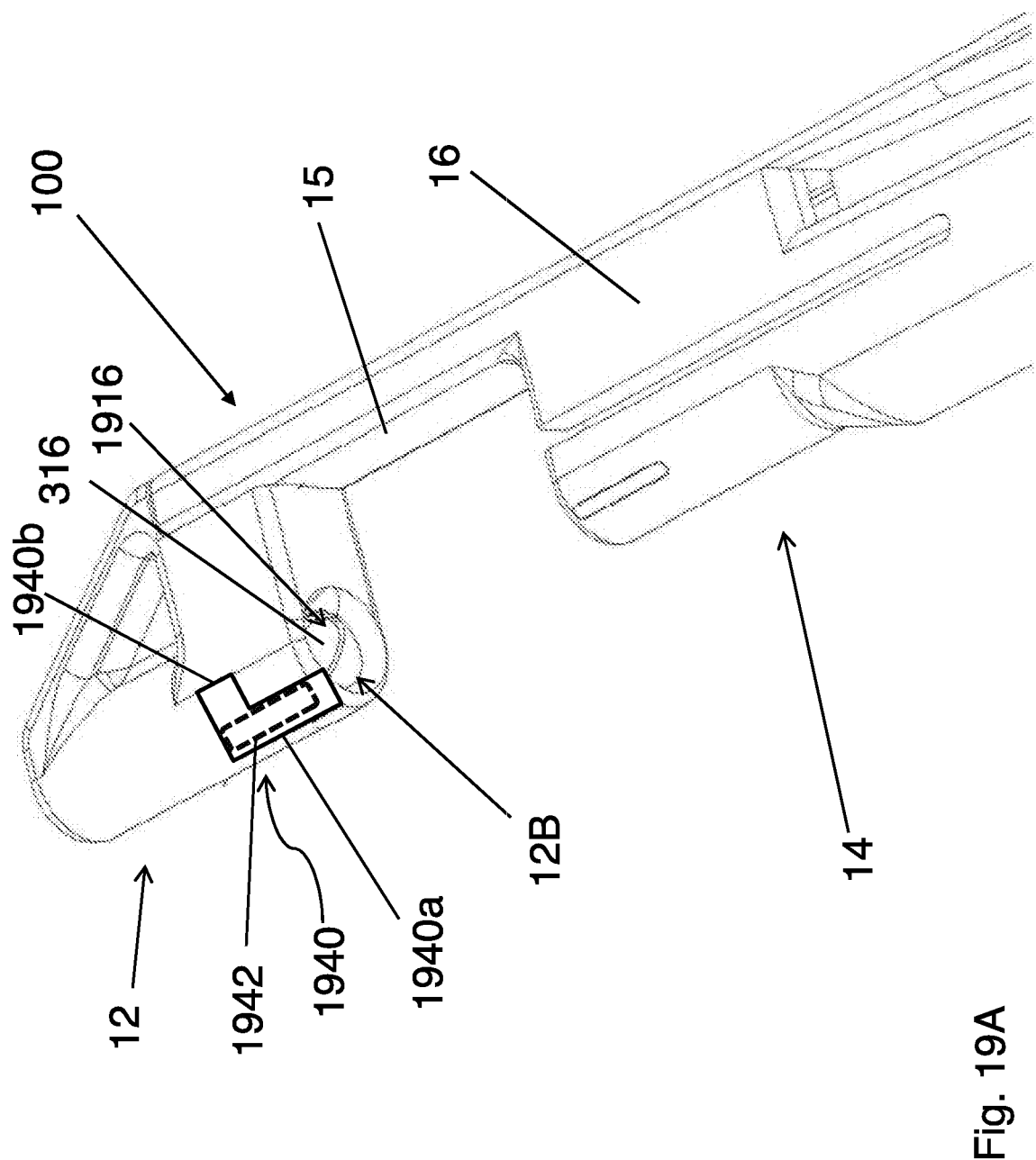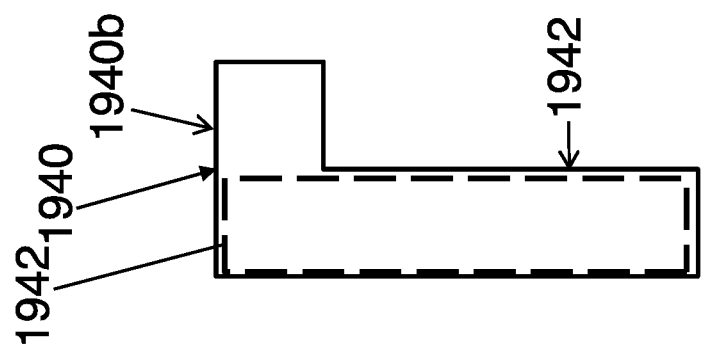
Fig. 19A

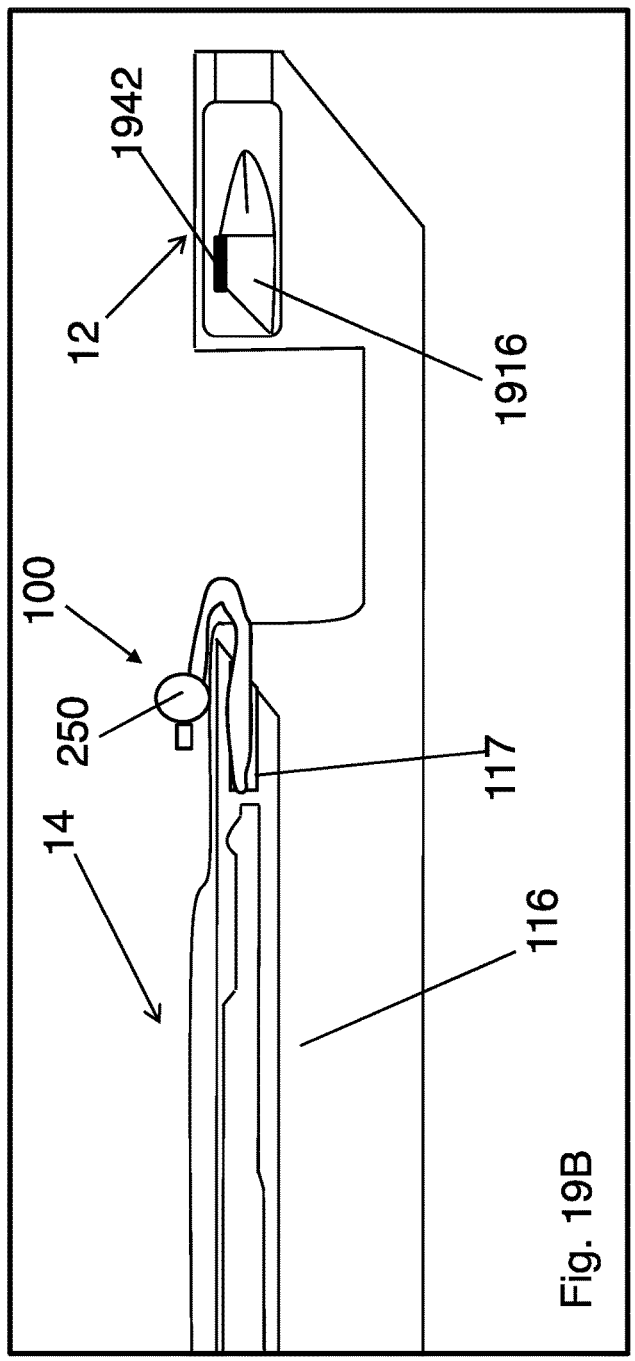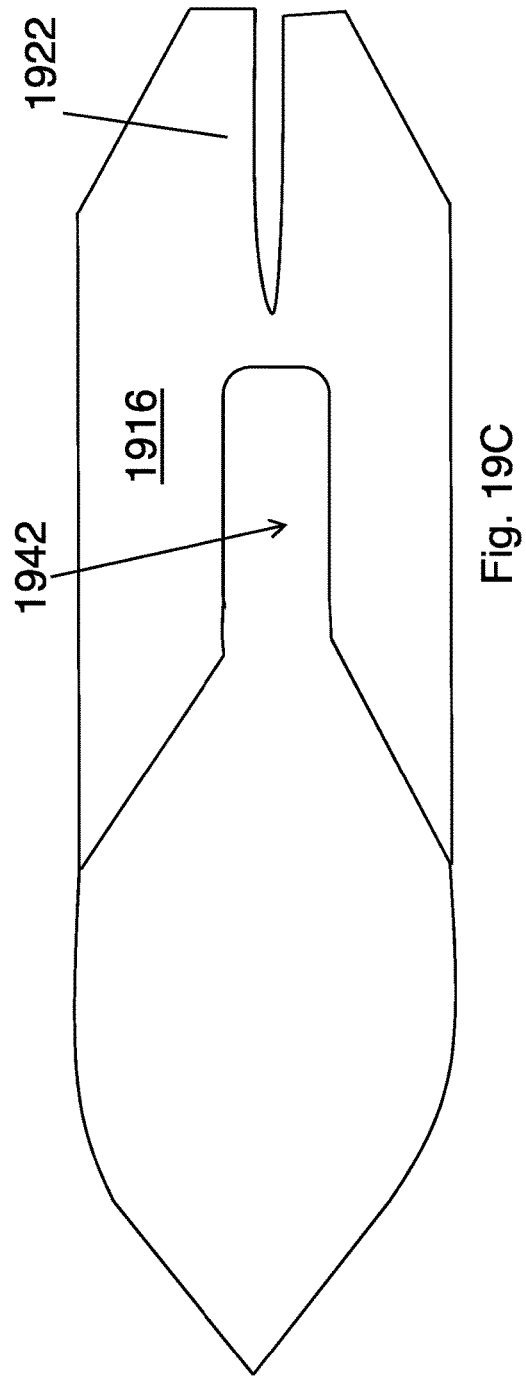

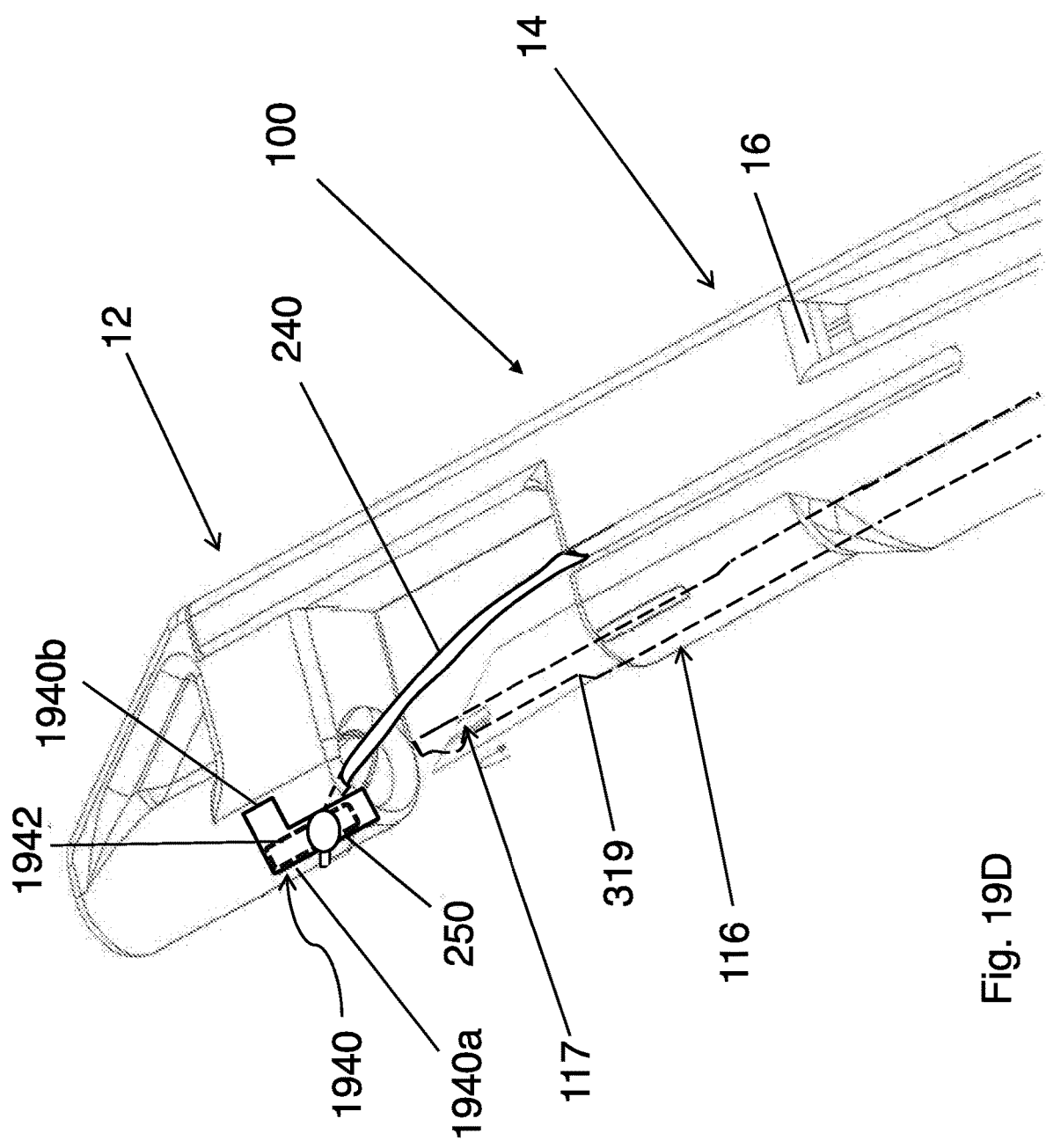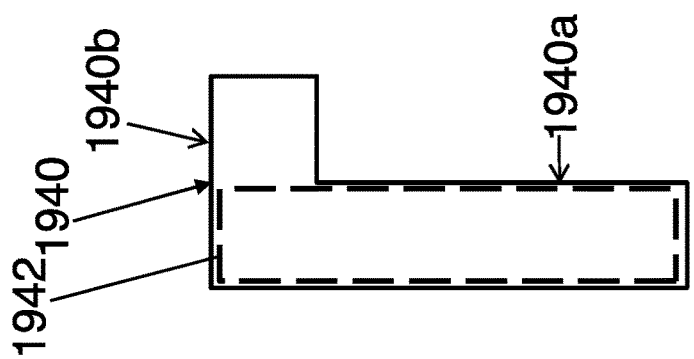
Fig. 19D

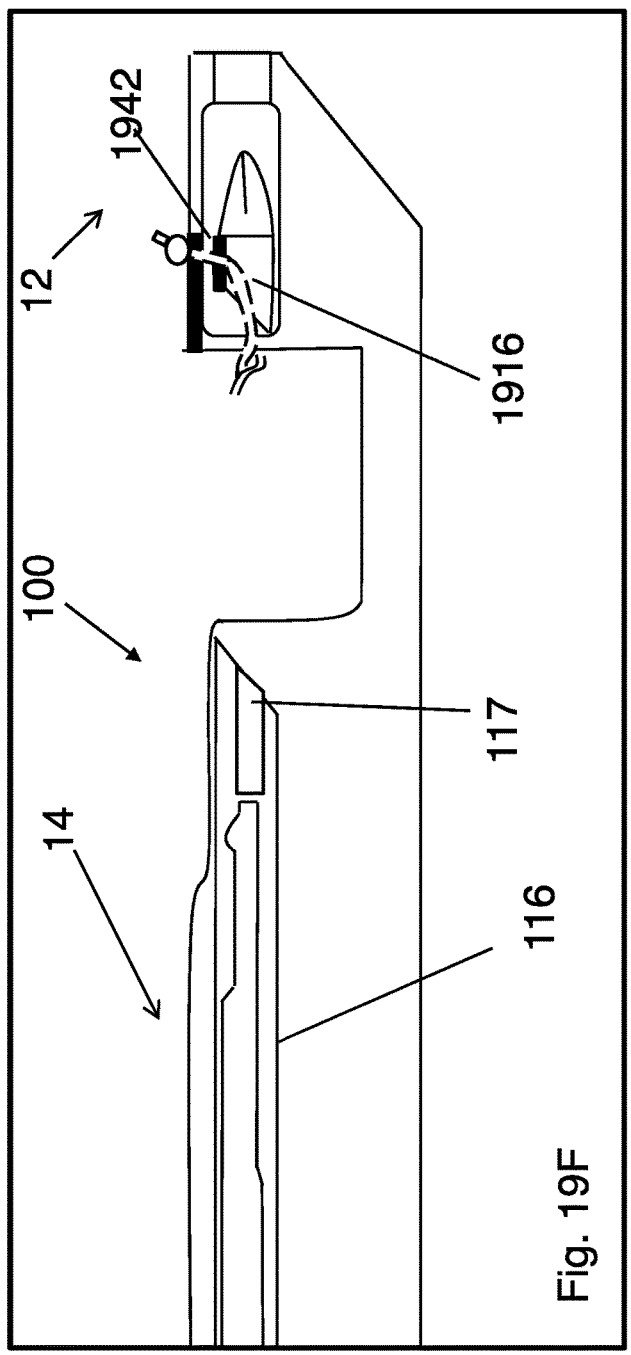
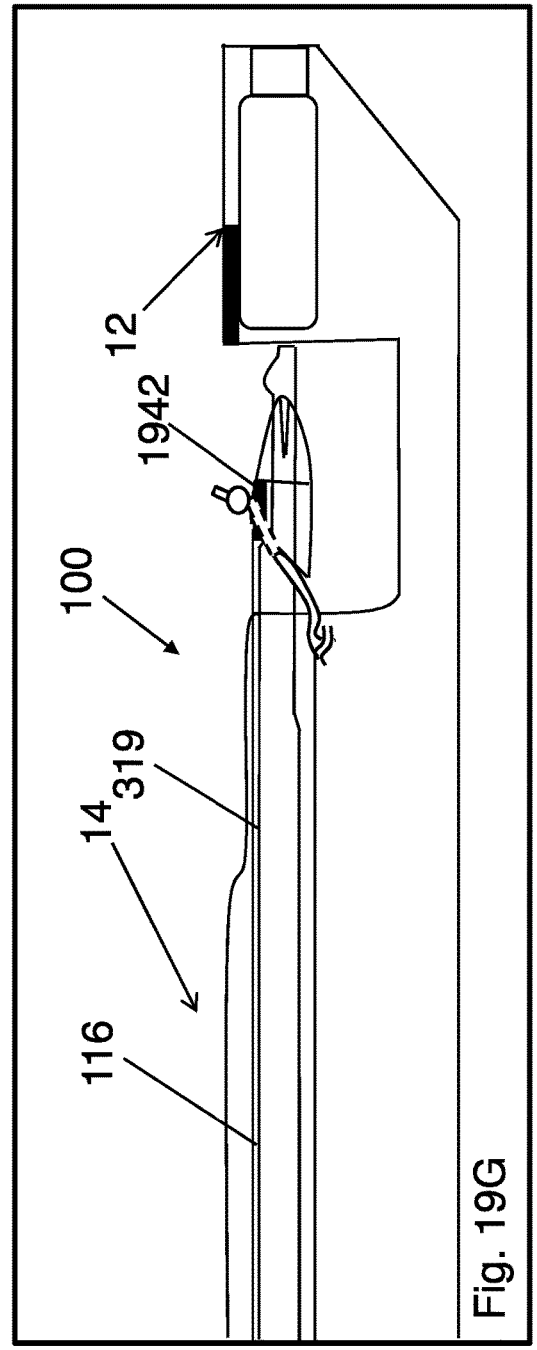

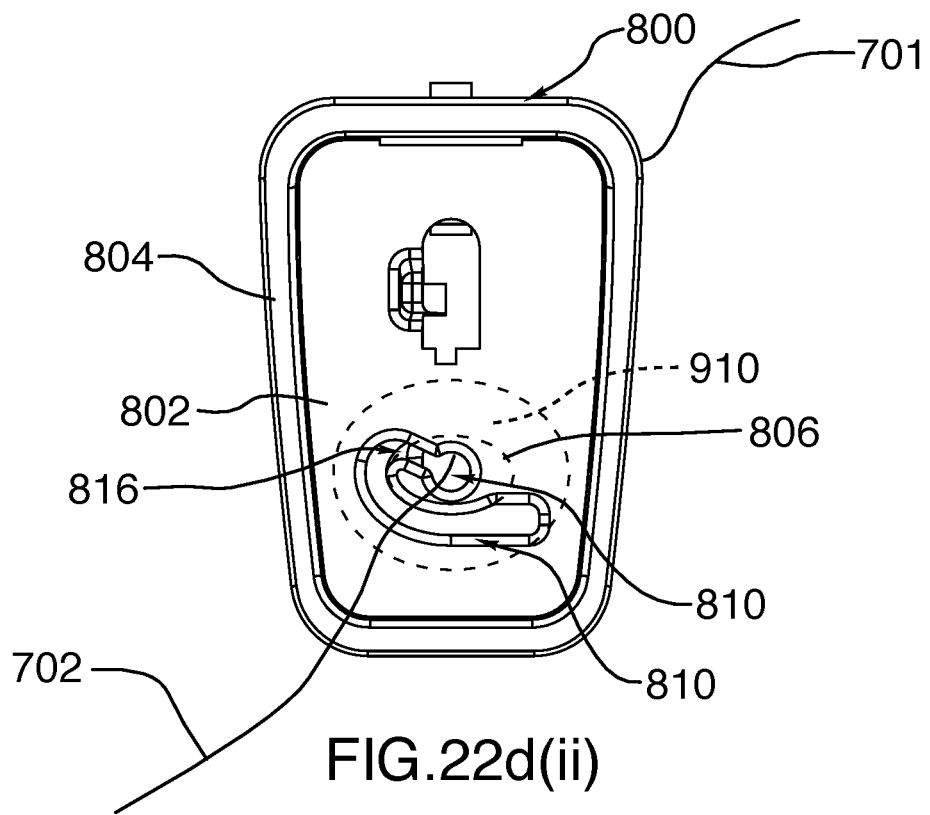
FIG.22d(ii)
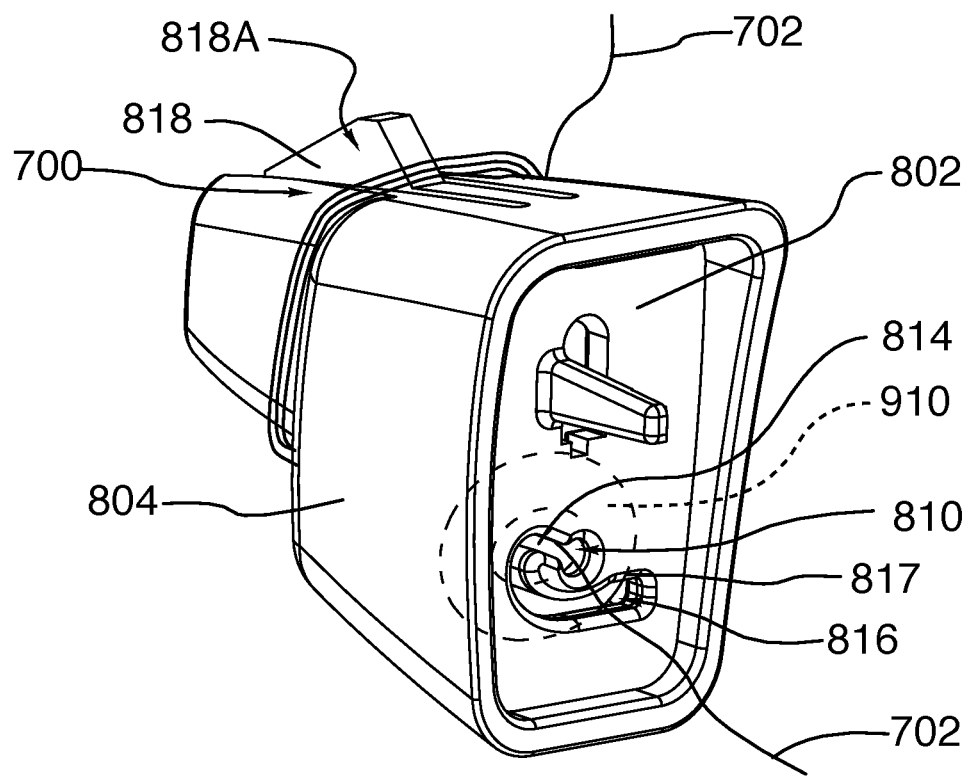
FIG.22d(iii)

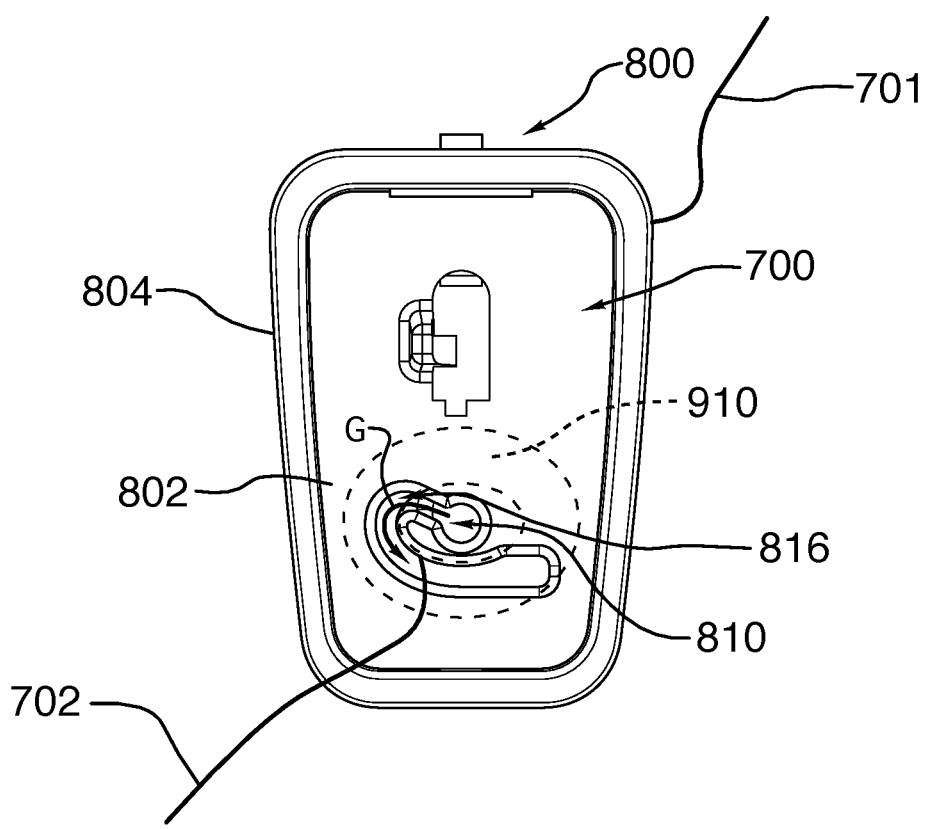
FIG.22d(iv)

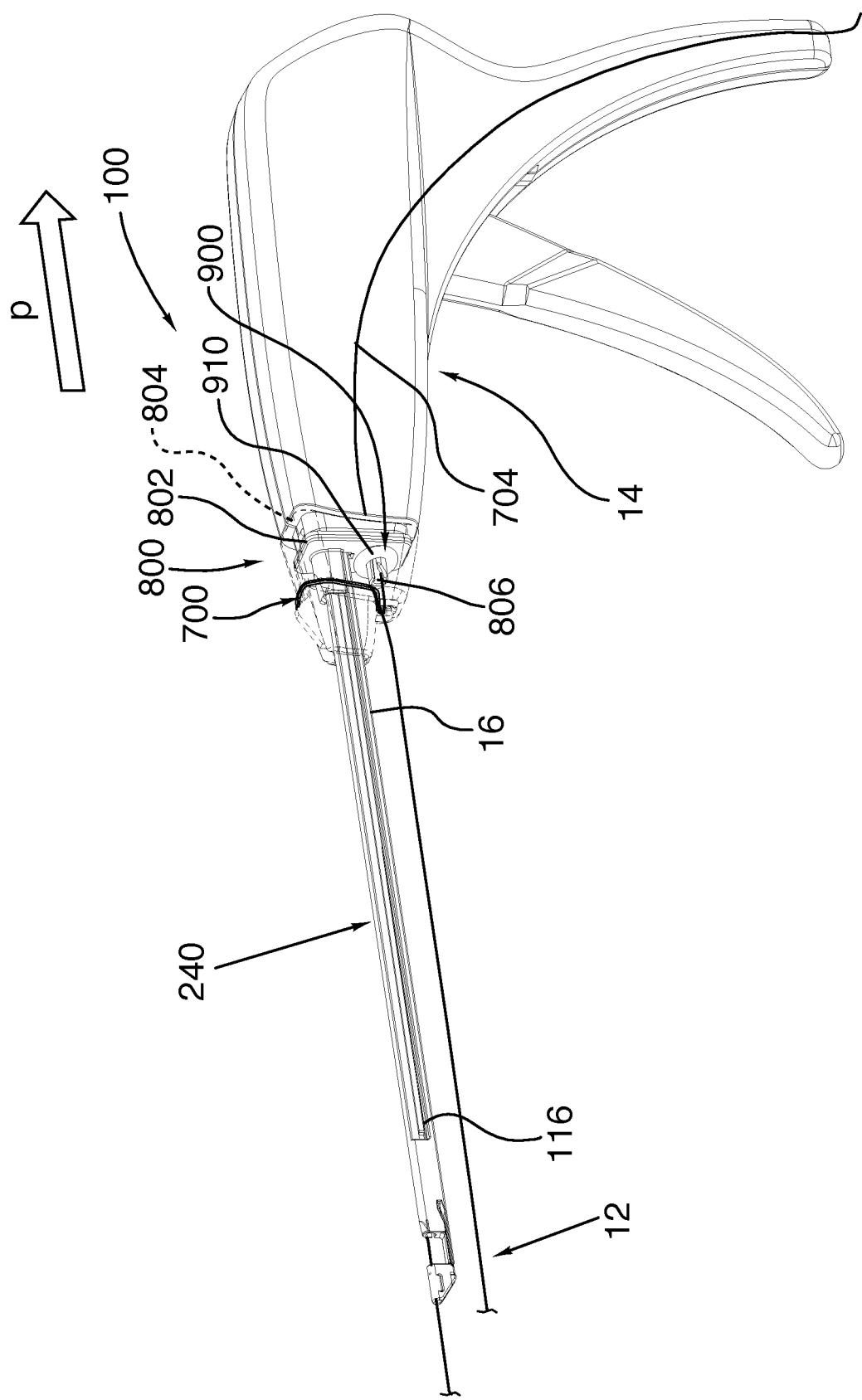

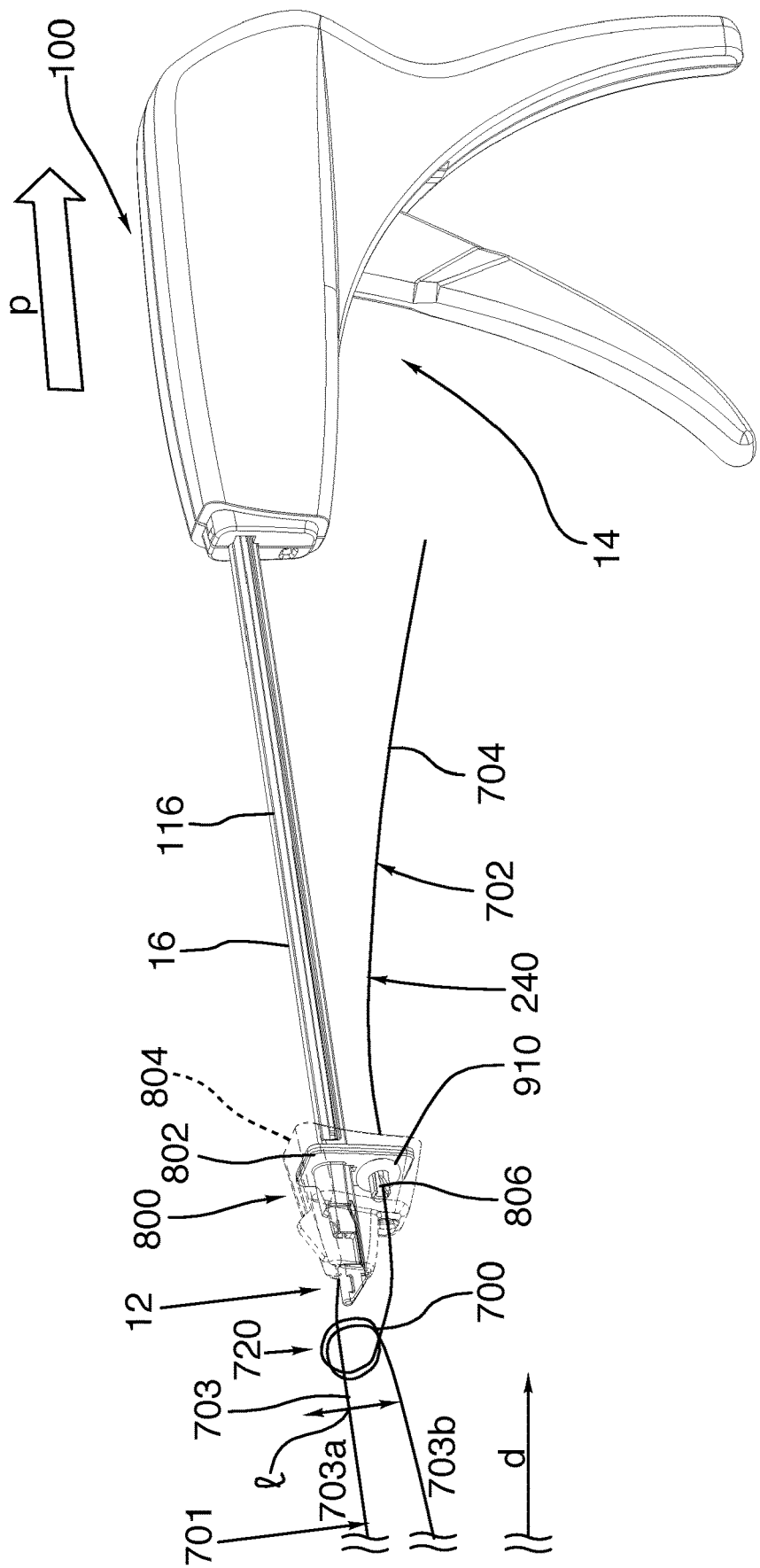

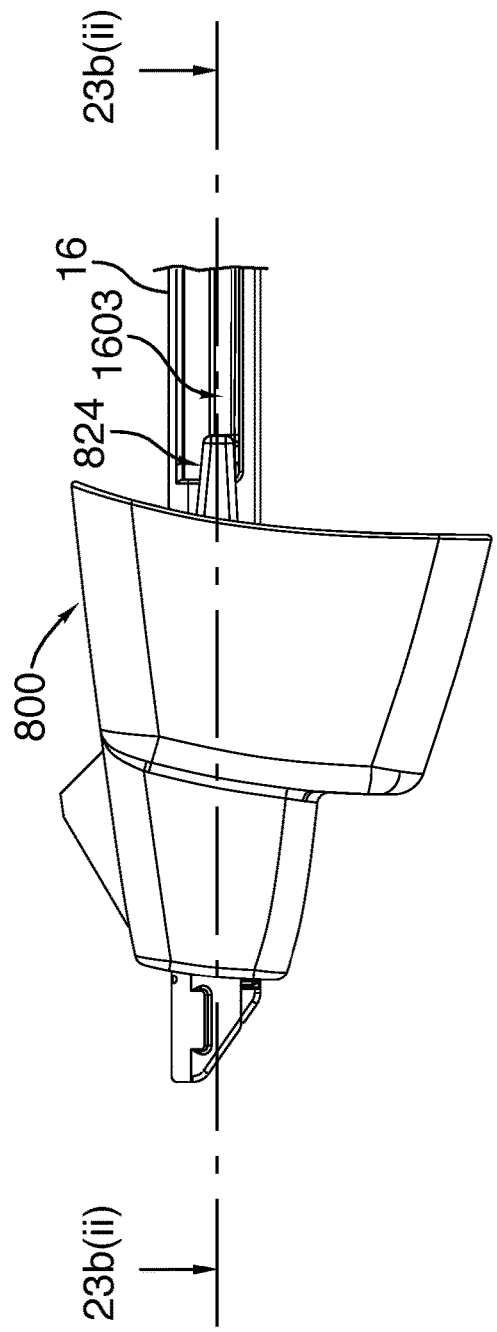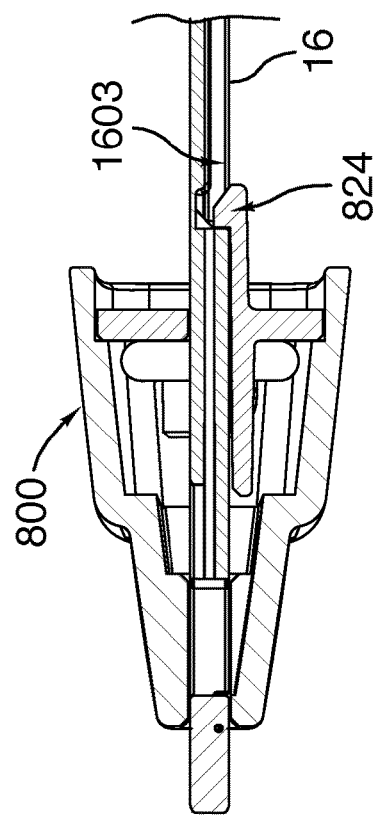

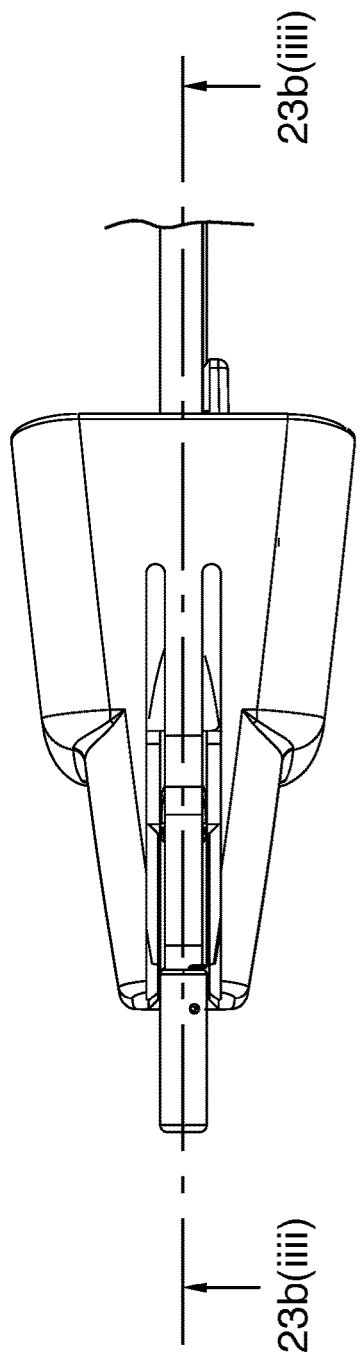
FIG.23b(iii)
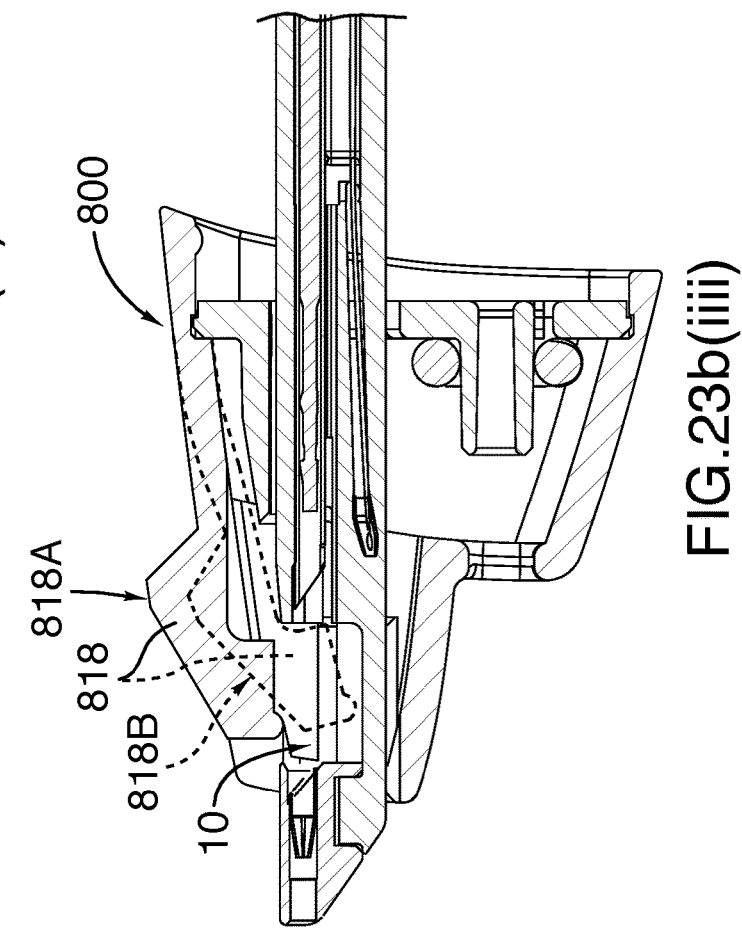
FIG.23b(iiii)

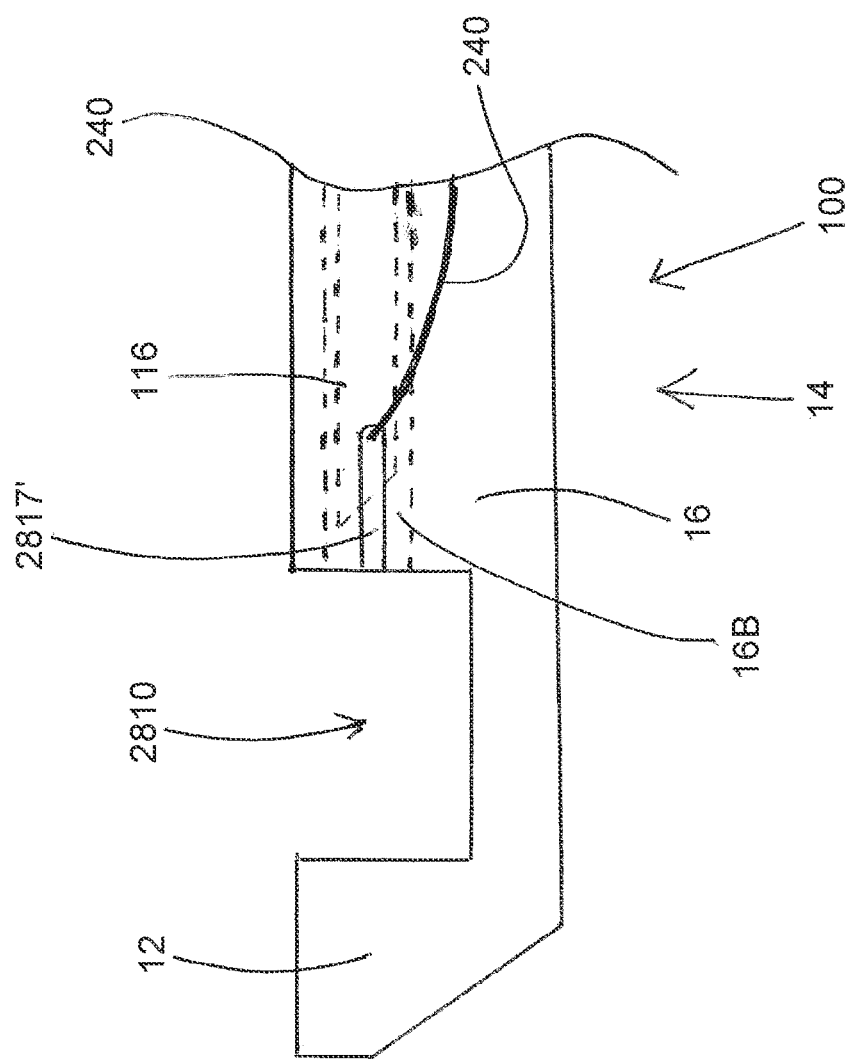

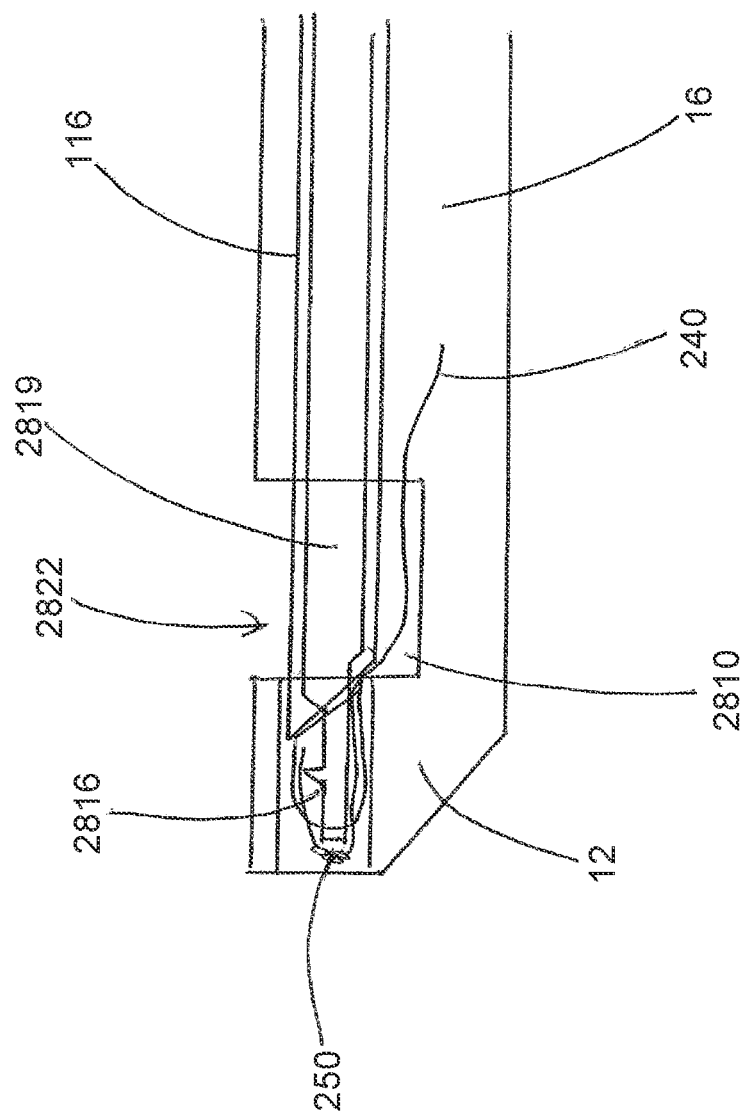

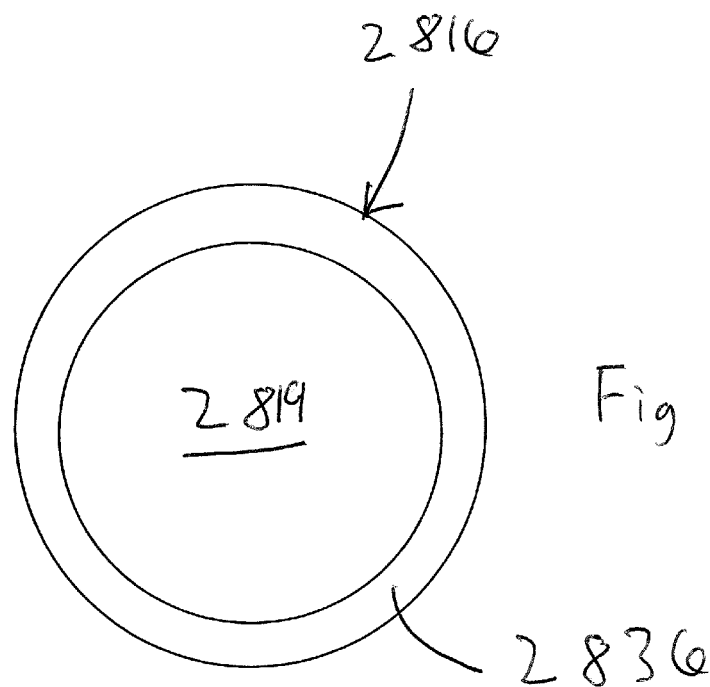
Fig 28 d(ii)
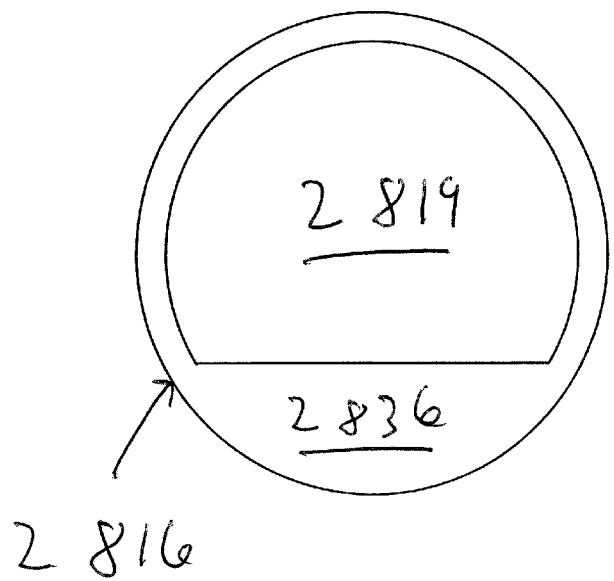
Fig. 28 d(i)

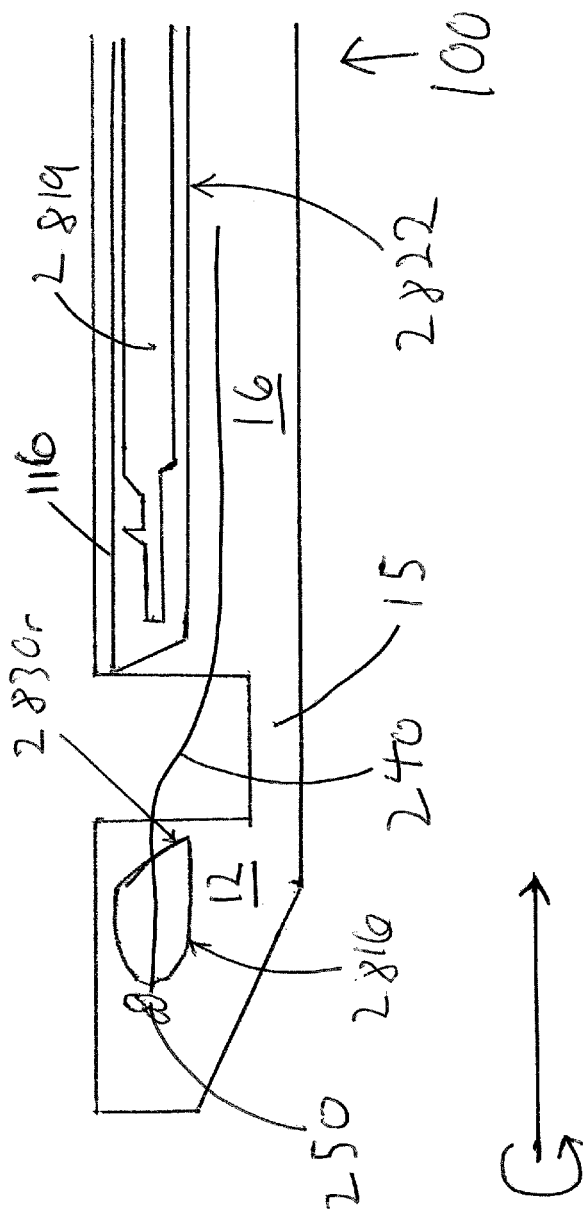
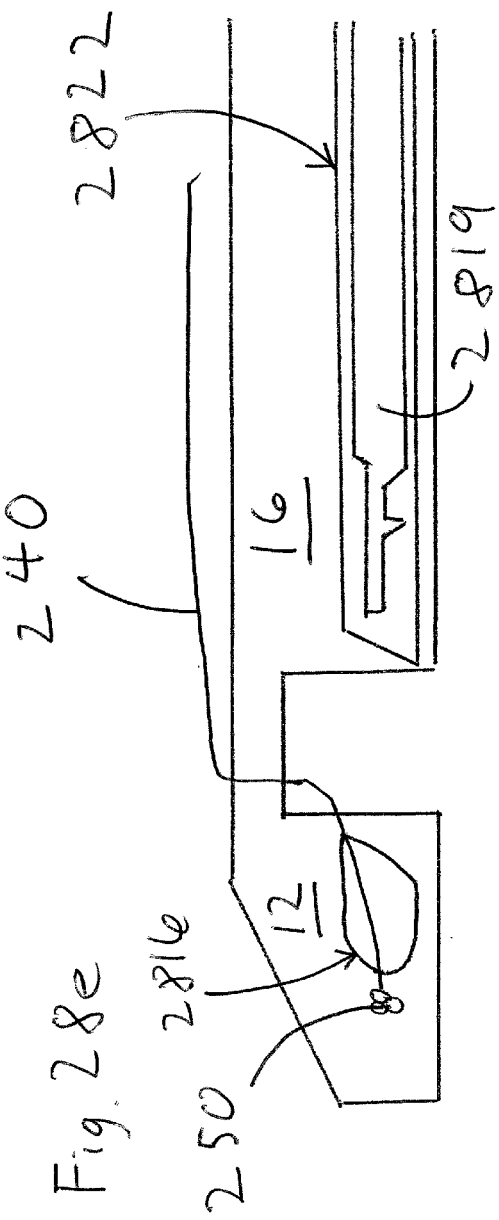
Fig. 28e

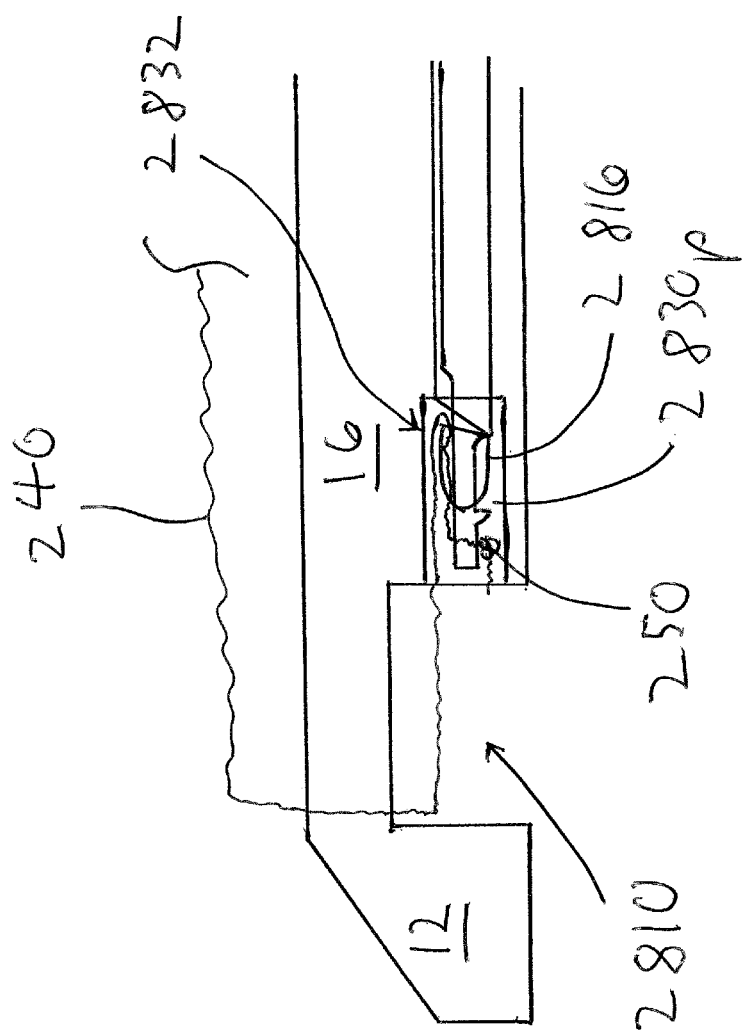

SUTURE PASSING INSTRUMENTATION AND METHODS OF USE THEREOF

TECHNICAL FIELD

The disclosure relates to a method for passing a suture through tissue. More specifically, the disclosure relates to a method for passing suture through tissue bi-directionally.

SUMMARY

The instant disclosure is directed to methods and devices for passing suture bi-directionally using a hybrid approach. Such an approach involves translating a suture strand in one direction directly, that is without requiring the suture to be coupled to a shuttle or ferrule, while translation of the suture in the other direction is accomplished by using a suture trap to capture the suture and translating the suture trap along with the suture.

A hybrid method such as is described hereinbelow provides several heretofore unknown and unrecognized advantages. These include, but are not limited to, the following: In designs utilizing a shuttle or ferrule to carry the suture both to and from the distal tip, the first pass of the shuttle to the tip requires the shuttle to be coupled to the distal tip in some manner. This coupling can, in certain instances, be compromised by tissues or bodily fluids entering the device, or damage by the user, whereby the security and integrity of the trap is lessened. Furthermore, unintended severing of the suture during the first pass results in a free-floating shuttle or ferrule within the patient's body, whereas a hybrid approach, whereby one pass of suture is done without requiring a shuttle or ferrule, leaves only a comparatively insignificant section of suture for the same failure mode. Furthermore, in designs passing suture in both directions without utilizing a shuttle or ferrule, the ability to securely grasp a suture once it has entered the body is difficult to implement in a consistent and reproducible manner. A hybrid approach, whereby suture is captured by a suture trap prior to being translated in a second pass, provides an advantage since retrieving a suture trap is significantly more achievable.

Employing a suture trap, that is a component configured to capture or retain a suture once it is passed through the material to be sutured, provides a unique and unanticipated advantage over shuttles and ferrules to which the suture is pre-attached, as it facilitates certain methods utilizing a hybrid approach as discussed hereinabove.

In one broad aspect, embodiments of a method described herein include steps of advancing a suture at least partially through tissue; and retrieving the suture; wherein one of the steps of advancing and retrieving comprises manipulating the suture directly, and wherein the other step of advancing and retrieving comprises manipulating a suture trap to which the suture is coupled.

In another broad aspect, embodiments of a device that may be used to practice the method embodiments include a bi-directional suture passer having a proximal portion for holding a portion of a suture therein; a distal tip coupled to the proximal portion and defining a tissue receiving gap there-between; a reciprocally moveable suture passing member housed within the proximal portion for translating the suture portion between the proximal portion and the distal tip; and a suture trap operable to be detachably coupled to the distal tip for capturing the suture passed by the suture passing member.

Various features of this aspect are described as well, including but not limited to depth selection mechanisms, interlocking features for coupling and de-coupling components and suture routing features to minimize risk of suture damage during a suture passing procedure.

In an additional broad aspect of the present invention, devices and methods are disclosed for controlled deployment of a knot, such as a pre-tied knot, from a device such as a medical instrument. Features of this aspect include a knot carrier or slider, a retaining element for maintaining tension on a portion of a suture strand as well as means for routing suture for controlled knot deployment.

BRIEF DESCRIPTION OF THE DRAWINGS

In order that the invention may be readily understood, embodiments of the invention are illustrated by way of examples in the accompanying drawings, in which:

FIGS. 1a, 1b are an illustration of a device for practicing a method in accordance with an embodiment of the present invention;

FIGS. 2a-2f illustrate steps of a method in accordance with an embodiment of the present invention;

FIGS. 3e-3h illustrate alternative embodiments of a device and method in accordance with the present invention;

FIGS. 4c-4g illustrate various components of a device in accordance with an embodiment of the present invention;

FIGS. 4h-4o illustrate a device in accordance with an alternate embodiment of the present invention;

FIG. 5a-5e illustrate steps of a method in accordance with an embodiment of the present invention;

FIGS. 6a-6h show a device and method in accordance with an embodiment of the present invention;

FIGS. 6i-6l illustrate a device and method in accordance with an alternative embodiment of the present invention;

FIGS. 6m(i)-6w(ii) illustrate a device and method in accordance with yet another alternative embodiment of the present invention;

FIGS. 7a-7e illustrate a suture holder and a stylet, in accordance with an embodiment of the present invention;

FIGS. 11a-11d illustrate steps of a method in accordance with an alternate embodiment of the present invention.

FIGS. 13a-13d illustrate steps of a method in accordance with an alternate embodiment of the present invention;

FIGS. 19*a*-19*g* illustrate a device and method in accordance with an alternate embodiment of the present invention;

FIGS. 22*a* and 22*c*-22*k* illustrate a device and method in accordance with embodiments of the present invention;

FIGS. 23*a*-23*e* illustrate a device and method in accordance with another embodiment of the present invention;

FIGS. 28*a*-28*h* illustrate a device and method in accordance with still another embodiment of the present invention.

DETAILED DESCRIPTION

Figure 1B:
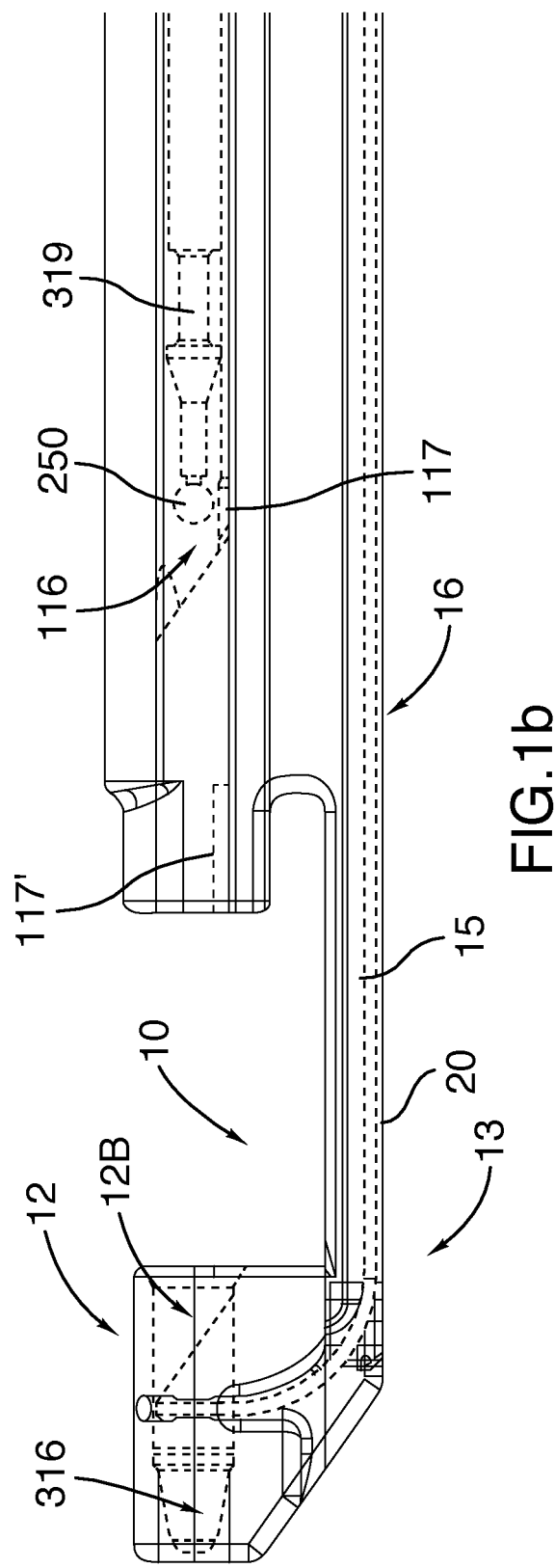

According to one broad aspect embodiment of the present invention there is provided a method for treating a defect within a region of tissue. The method is effected by positioning a suture holder on a distal side of a tissue and passing a suture through the tissue from the proximal side and coupling the suture to the suture holder. The suture holder is then retrieved through the tissue towards the proximal side of the tissue.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Overall Device Structure
Suture Passing Device

FIGS. 1*a*-*b* illustrate one aspect of a device for treating a defect in a tissue which is referred to herein as device 100. Device 100 may be configured for accessing tissue (e.g. disc annulus fibrosus tissue) having a defect and delivering an element such as a suture 240 through the tissue to treat the defect. In some embodiments, the suture may be resorbable. Device 100 includes a proximal portion 14 (also referred to herein as "device proximal portion 14") and a distal portion 13 having a neck portion 15 and a distal tip 12 (also referred to herein as "device distal tip 12"). Distal tip 12 is longitudinally spaced apart from proximal portion 14 and is coupled thereto via the longitudinally extending neck portion 15. According to one embodiment, distal tip 12 is coupled to a shaft 16 of the proximal portion 14 defining a tissue receiving gap 10 therebetween. Device 100 can be positioned such that distal tip 12 is positioned on a distal side of the tissue being treated and proximal portion 14 is positioned on a proximal side of the tissue.

Device 100 may comprise an actuator, actuating member or actuating mechanism (such as a trigger 218 shown in FIG. 1*a*) for advancing the various components within the device such as needle 116 and stylet 319, as described herein below, from the proximal portion 14 towards distal tip 12 of device 100. The trigger 218 may be used for advancing both needle 116 and stylet 319 in a direction along the longitudinal axis of device 100. As trigger 218 is actuated, both needle 116 and stylet 319 translate longitudinally from the proximal portion 14 towards distal tip 12. The needle 116 and stylet 319 may be configured to retract proximally back towards proximal portion 14 of device 100 when trigger 118 is released. As described further hereinbelow, the actuating member allows for at least two degrees of manipulation for advancing various components of the device 100 by differing amounts.

Structures internal to the handle 100 are presently described with reference to FIGS. 1.*a* and 1*b*. As shown in FIG. 1*a*, the handle 100 comprises a handle body 14 that defines an inner chamber 140 (within which a stylet hub 430 and a needle hub 130 are located) where the stylet hub 430 is coupled to the stylet 319 and the needle hub 130 is coupled to the needle 116. The trigger 218 has a geared portion 220 that co-operatively engages with a gear rack 434 of the stylet hub 430 to allow the stylet hub 430 and the needle hub coupled thereto to slide within the chamber 140 defined by the handle of device 100.

Interlock or Needle Release Button

In some embodiments, a means for decoupling/coupling two coaxial members during translation, such as (i) a suture passing or suture holder retrieving member (e.g. stylet 319), and (ii) a tissue puncturing member (e.g. needle 116), is disclosed. The means for decoupling/coupling allows one member to travel further than the other, whereas translation of both members is affected by a single trigger. As shown in FIG. 1*a*, needle 116 and stylet 319 are coupled using a needle release button 600 which allows the needle hub 130 to co-operatively engage with the stylet hub 430 allowing the needle 116 and stylet 319 combination to be advanced together.

Depth Selection Mechanism

In some embodiments, an element for controlling the translation distance of a suture passing element/suture holder retrieving element such as a stylet 319 is provided, such that the translation distance of the stylet 319 at a first actuation of a trigger is different than the translation distance of the stylet 319 at a second actuation of the trigger. In order to allow for varying the distance to which a stylet 319 is advanced when the trigger 218 is actuated, certain embodiments of the present invention provide a depth selection mechanism (depth selector) 500, as shown in FIG. 1*a*. Thus, the depth selector 500 allows various degrees of advancement of the stylet 319 in terms of how far it can be translated relative to the needle 116. In some embodiments the depth selector 500 fits into the stylet hub 430, as shown.

Tissue Puncturing Member

In some embodiments, a tissue puncturing member, such as a needle 116 may be housed within the device proximal portion 14 may be used to puncture tissue to allow the suture passing member such as stylet 319 to be passed through the tissue. The needle 116 may be hollow and may define a lumen therethrough for housing a Stylet 319 and suture 240 therein. In one specific example, the needle 116 may be beveled at its distal end to allow engagement or interaction with the suture holder 316 to allow suture to be passed through a channel formed therebetween. In some embodiments, the suture passing member (e.g. stylet 319) may be coupled to the tissue puncturing member (e.g. a needle 116) for at least a part of the procedure.

Suture Passing Member

Device 100 has a suture passing mechanism capable of passing an element such as a suture 240 from proximal portion 14 to distal tip 12 (in order to pass the suture 240 from the proximal side of the tissue to the distal side of the tissue). Suture passing mechanism can include a moveable suture passing member, such as a stylet 319, which is housed within proximal portion 14. Stylet 319 is moveable between a proximal position and first or second predetermined distal positions. The stylet 319 is configured for passing suture knot 250 through tissue 200 and coupling suture knot 250 to suture holder 316 attached to the distal tip 12. This enables passing of suture 240 through tissue 200. Device 100 further includes a mechanism for retrieving suture holder 316 from distal tip 12 such that suture holder 316 (and the suture coupled thereto) is passed from the distal side to the proximal side through tissue 200. Such a mechanism can include a suture holder retrieving member such as a stylet 319. Thus, stylet 319 is further configured for retrieving suture holder 316 (and thus the suture knot 250 coupled thereto) from the distal tip 12. Suture holder retrieving member is longitudinally translatable between proximal portion 14 and distal tip 12 and is optionally capable of reciprocal movement. Thus, in some embodiments stylet 319 is capable of passing a portion of suture 240 (which may include a knot 250), from proximal portion 14 to suture holder 316 at distal tip 12 and for retrieving suture holder 316 from distal tip 12 to proximal portion 14.

Suture Portion

An element such as suture 240 is housed within proximal portion 14 of device 100. According to one example, a portion of the suture 240 such as a knot 250 is held within the device proximal portion 14 adjacent to a suture passing member such as stylet 319, so that it can be passed through tissue by the stylet 319 as it advances from the device proximal portion 14 to the distal tip 12. In other embodiments, the element passed by the suture passing member may be an anchor which may be operatively coupled to the suture passing member.

Slotted Needle and Shaft

In some embodiments as show in FIG. 1b, the device 100 described comprises a slot 117 within the needle 116 and a similar slot 117' within the shaft to allow the suture 240 to be routed to secure the suture in place. The suture 240 is guided through slot 117 to the exterior of the needle and exists through as similar slot formed within the shaft 16 as later shown in FIGS. 28a and 28b. The needle and shaft slots may be offset from one another. The knot 250 of the suture 240 is unable to pass through the slot within the needle, thus securing the knot 250 within the needle lumen.

Suture Holder/Suture Trap

Device 100 further includes a suture holder 316 that is removably attached to distal tip 12. The suture holder 316 is capable of receiving a portion of a suture 240 such a as a knot 250 from the proximal portion 14 of the device 100 from a suture passing member such as a stylet 319 and retaining it at the distal tip 12.

In one specific example, as shown in FIG. 1a, suture holder 316 is removably attached to the distal tip 12 of device 100 via a trap engagement feature such as wire 20 which interacts with a tip engagement feature of the trap (such as a window, slot or aperture) for allowing the suture holder 316 to be held within a receiving chamber 12B defined by the device distal tip 12 The wire 20 may be attached to a wire stop 18 which may allow removal of wire to decouple the suture holder 316 from the distal tip.

Detailed Device Structure

The structure of a device 100 is described in further detail herein below with reference to FIGS. 2a-7e.

Distal Tip

In embodiments described in FIGS. 2a-3d, the device comprises a distal tip 12. The distal tip 12 may comprise a chamber 12B (FIG. 3d) for receiving the suture holder 316. The chamber 12B may define a lumen therethrough and may be open at both of its longitudinally opposed ends. In one embodiment as additionally shown in FIGS. 1a-b the distal tip 12 may taper towards its distal end to facilitate positioning or advancement of the device 100 within a region of tissue. In some embodiments the device 100 includes a suture retaining element for retaining a portion of the suture 240 such as a suture knot 250 on a distal side of the tissue. In one embodiment, the suture retaining element may be a component of the distal tip 12. In some embodiments, as shown in FIG. 2d, the suture retaining element can be, for example a component of the suture holder, e.g. a distal opening thereof, with the suture holder being received within a the distal tip 12.

Figure 2C:
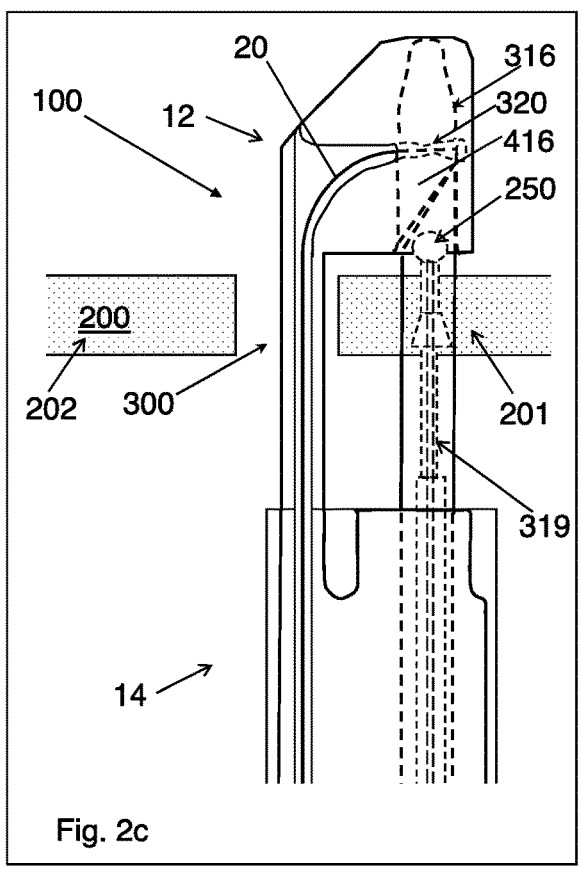

In one specific example, distal tip 12 of device 100 defines a receiving chamber 12B which holds suture holder 316 therein. As mentioned above, the suture holder 316 may be detachably coupled to the distal tip 12. Suture holder 316 comprises an engagement feature for detachably coupling the suture holder 316 to the distal tip 12. In one specific example, suture holder 316 is initially detachably coupled to the distal tip 12 within receiving chamber 12B using a wire 20 that is received within an opening or channel 320 of suture holder 316, as is further shown in FIGS. 2a-2f and FIGS. 3a-3c. The wire 20 is threaded through an opening or aperture in the distal tip 12 and into the receiving chamber 12B; it is received within the opening 320 of the suture holder 316 and secures the suture holder 316 within the receiving chamber 12B. The wire 20 may be attached to a wire stop which, when actuated, allows wire 20 to be removed. As shown in FIG. 3d, the wire 20 may be at least partially removed or retracted such that wire 20 is no longer coupled to suture holder 316, to allow disengagement of the suture holder 316 from the receiving chamber 12B of the distal tip 12. This enables retraction or retrieval of the suture holder 316 by the suture holder retrieving member which in this example comprises the stylet 319.

Mechanism for Enabling Differential Advancement of Needle and Stylet

Various embodiments or implementations of an engagement and release mechanism are provided to allow the stylet 319 to selectively engage with, and disengage from, the needle 116. In one example, a coupling/decoupling mechanism is provided (i) to couple the stylet hub 430 to the needle hub 130 in order to move the needle 116 and the stylet 319 together as an assembly, and (ii) to later decouple the needle hub 130 from the stylet hub 430 to allow the stylet 319 to advance on its own.

Manual Interlock or Needle Release Button for Coupling and Decoupling the Stylet and the Needle The coupling/de-coupling mechanism may be in the form of a needle release button 600 as shown in FIGS. 4a-4g. In its initial position the button 600 has both the needle hub 130 and the stylet hub 430 coupled. The button can be depressed manually for decoupling the two hubs. The needle release button 600 may be a spring-loaded button where the spring is biased away from the needle hub 130 in its first/initial position or the nominal position 600A. In one example, the button 600 may be connected to the needle hub 130 or may be a part of the needle hub 130. In its nominal position 600A, the button 600 provides an interference block 601 which obstructs the path the stylet hub 430 (and thus the stylet hub proximal portion 432), obstructing/impeding the movement of the stylet 319, as is further illustrated in FIG. 4d. More specifically, first the needle release button 600 in position 600A couples the needle hub 130 to the stylet hub 430 (which is driven by actuation of a trigger). By coupling the two hubs, the actuation of the trigger drives both the stylet 319, and the needle 116 forward. This forward translation stops when the needle 116 hits the suture holder 316. At this point, the interference block 601 of needle release button 600 is obstructing/impeding the stylet hub 430.

When the button 600 is depressed (compressing the spring 603), the button 600 moves from its first position 600A to its second position 600B as shown in FIGS. 4e and 4f. Depressing the button 600 removes the obstruction created by the interference block 601 and allows the stylet hub 430, and thus the stylet hub proximal portion 432 to translate relative to the needle hub 130 (as shown in FIG. 4g) with the stylet hub proximal portion 432 depressing spring 605 against the bias. This allows the stylet 319 to advance beyond the needle 116, as the trigger 218 is continued to be pressed (as shown earlier in FIGS. 2d and 3c). As the stylet hub 430 is advanced, it continues to press against the needle release button 600, keeping it in the second or depressed position 600B.

Automatic Interlock or Needle Release Button for Coupling and Decoupling the Stylet and the Needle In an alternate embodiment, as shown in FIGS. 4h-4i, an automated system for coupling and decoupling the needle 116 and the stylet 319 is disclosed. Similar to the embodiment of the needle release button 600 described above, in the initial position, the needle release button 600 couples the stylet hub 430 to the needle hub 130. The button 600 can be depressed automatically for decoupling the two hubs. More specifically, the interference block 601 of the button 600 engages with the stylet hub 430 when it is in its nominal or initial position 600A, as shown in FIG. 4h. to couple the needle hub 130 to the stylet hub 430 during forward translation. In some embodiments, the button 600 is coupled to the needle hub 130 or is a part of the needle hub 130. Thus, as the stylet hub 430 is advanced by actuation of the trigger, the needle hub 130 and the button 600 advance along with it. The button 600 comprises an overhang or hook 604 that rides over the handle body 14' of the device. In other words the hook 604 rests against the handle body that defines the inner chamber 140 (within which the stylet hub 430 and the needle hub 130 are located). The button 600 is retractable into the needle hub 130, but cannot retract until the hook 604 is positioned within a notch 142 defined within the handle body 14'.

Figure 4A:
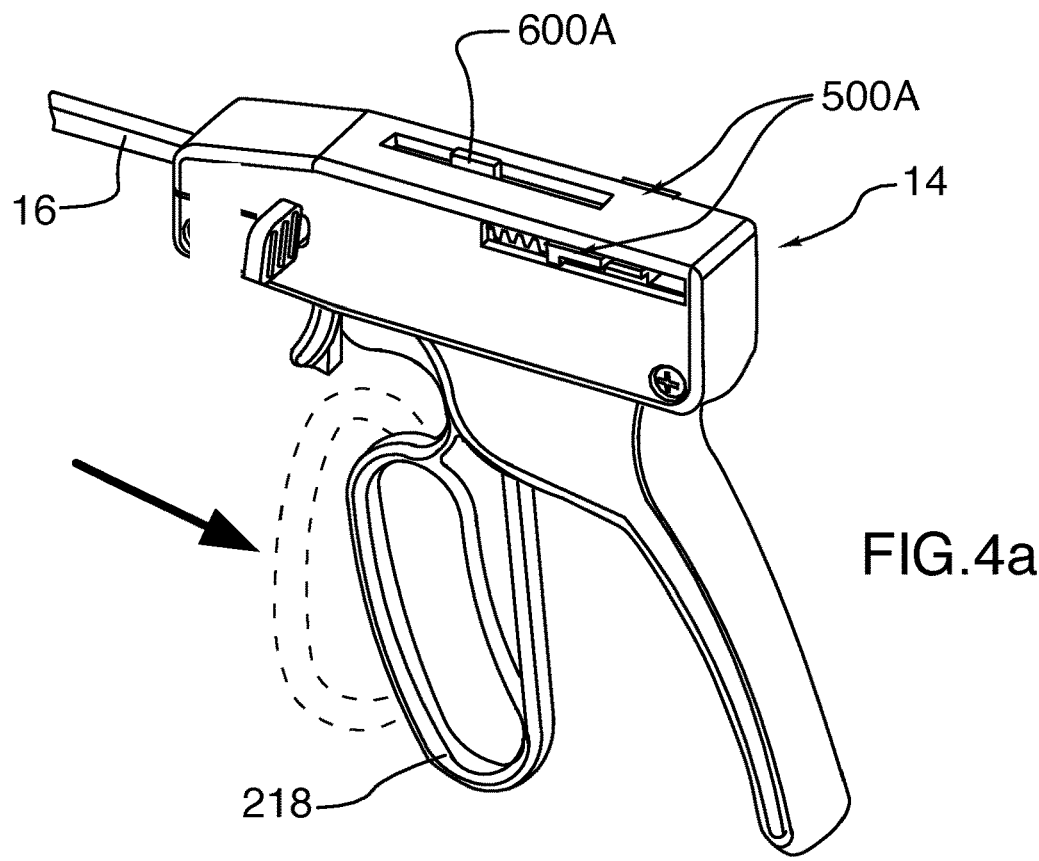
FIGS. 4a-4b illustrate steps of a method in accordance with an embodiment of the present invention.
Figure 4B:
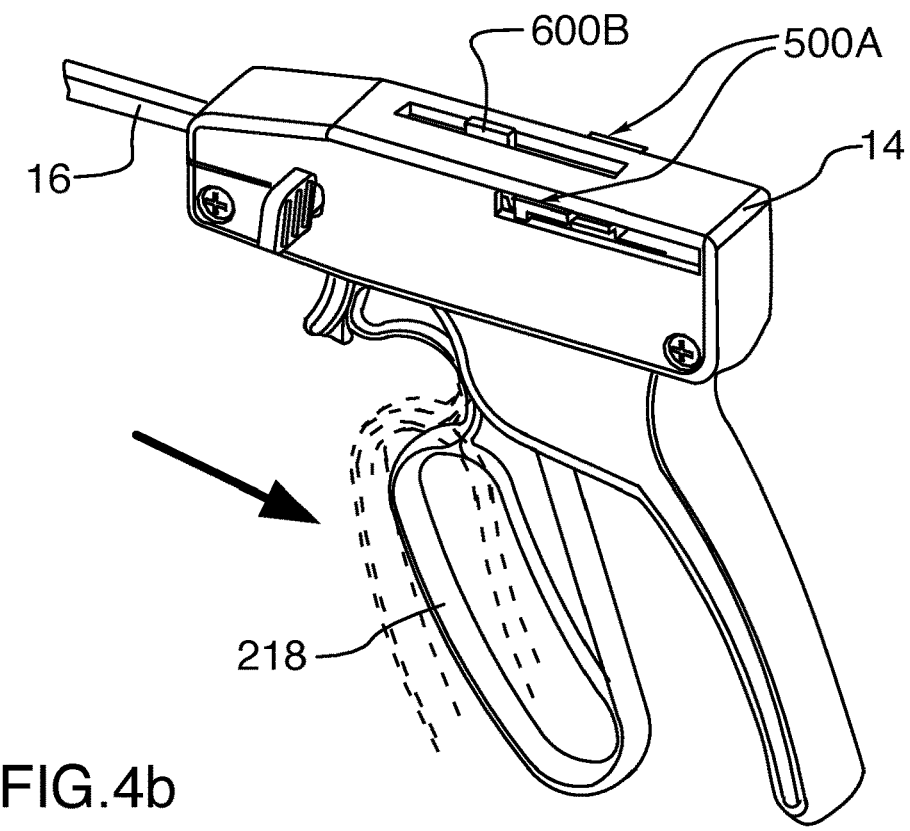
Figure 4J:
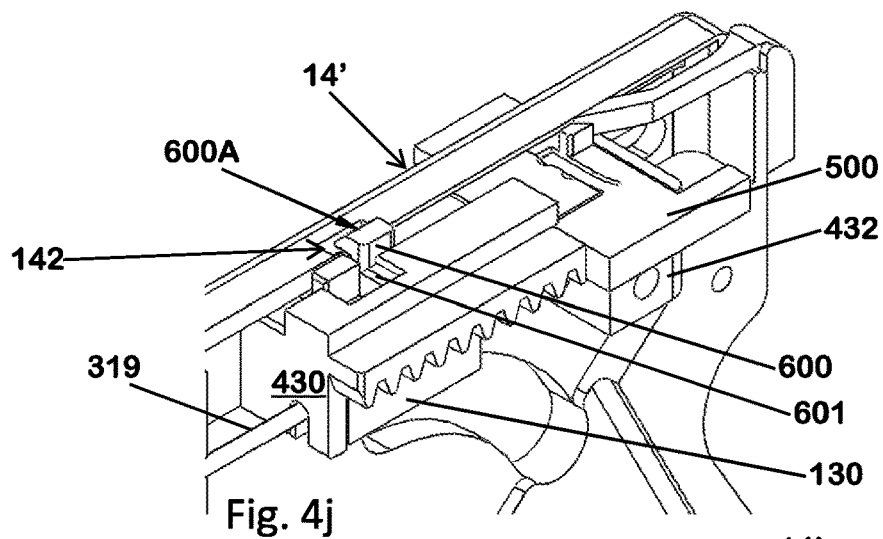
Figure 4K:
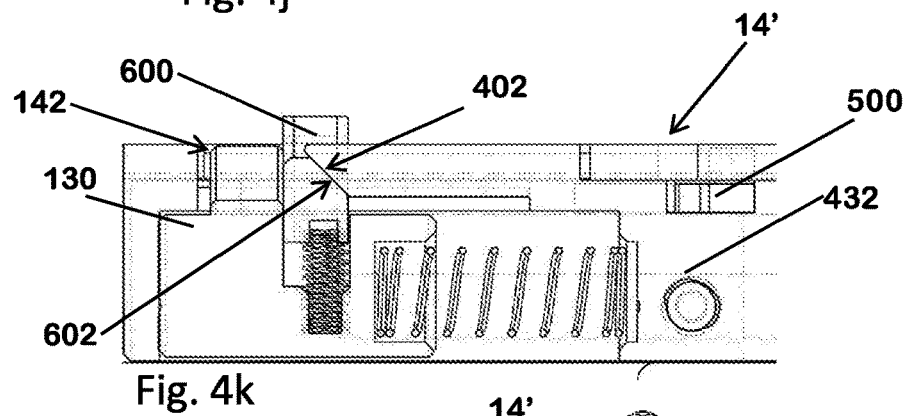
Figure 4L:
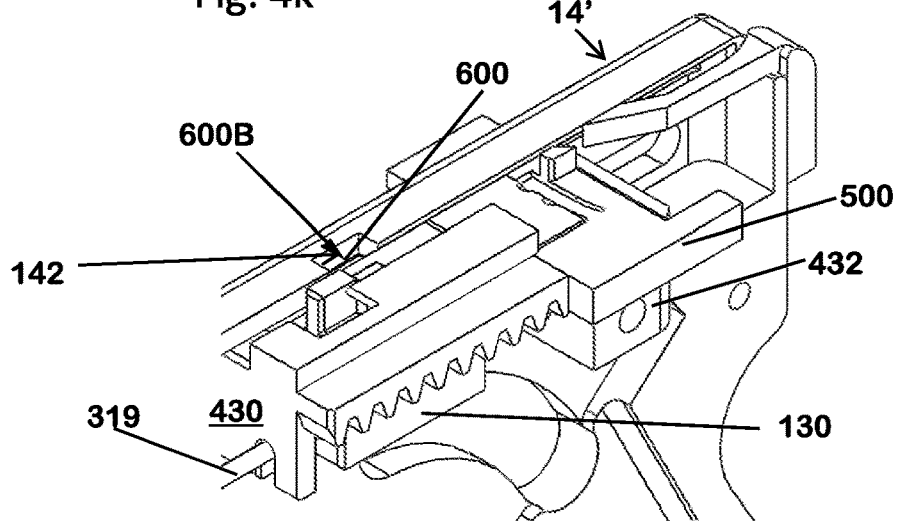
Figure 4M:
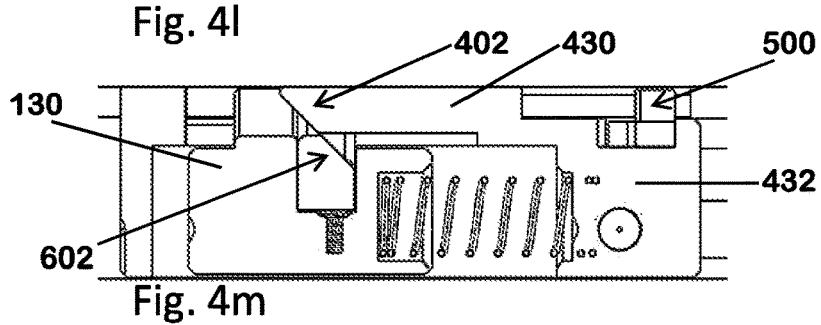

As shown, for example, in FIG. 4i, a ramp 602 is provided on the interference block 601 on its proximal face, and a corresponding ramp 402 is provided on a distal face of the stylet hub 430, that interacts with ramp 602 of the interference block 601. As the stylet hub 430 is advanced, for example, by pressing a trigger, ramp 402 of the stylet hub 430 engages ramp 602 of the interference block 601, allowing the button 600 (which includes interference block 601) to advance distally along with the stylet hub 430. The button 600 is advanced until the button 600 is aligned with the notch 142, as shown in FIGS. 4j and 4k. In other words, the needle hub 130 is pushed/advanced by the stylet hub 430/button 600 until the button 600 can retract out of the way into the needle hub 130. Once the interference block 601 is positioned within the notch 142, the interference block 601 is forced down by ramp 402 of the stylet hub 430, as it interacts with ramp 602 of the interference block 601. The button 600 now moves from its initial position 600A to its second position 600B. This allows the stylet hub 430 to be advanced further distally relative to the needle hub 130, as shown in FIGS. 4l and 4m. In other words, the portion of the stylet hub 430 that defines ramp 402, slides over the needle hub 130, thus decoupling the needle hub 130 from the stylet hub 430. As further shown in FIGS. 4n and 4o, the stylet hub 430 has advanced while the needle hub 130 has not.

Automatic Needle Release Button for Coupling and Decoupling the Stylet (Used in Conjunction with the Automatic Depth Selector with Audible Feedback as Described Herein Below)

Figure 6A:
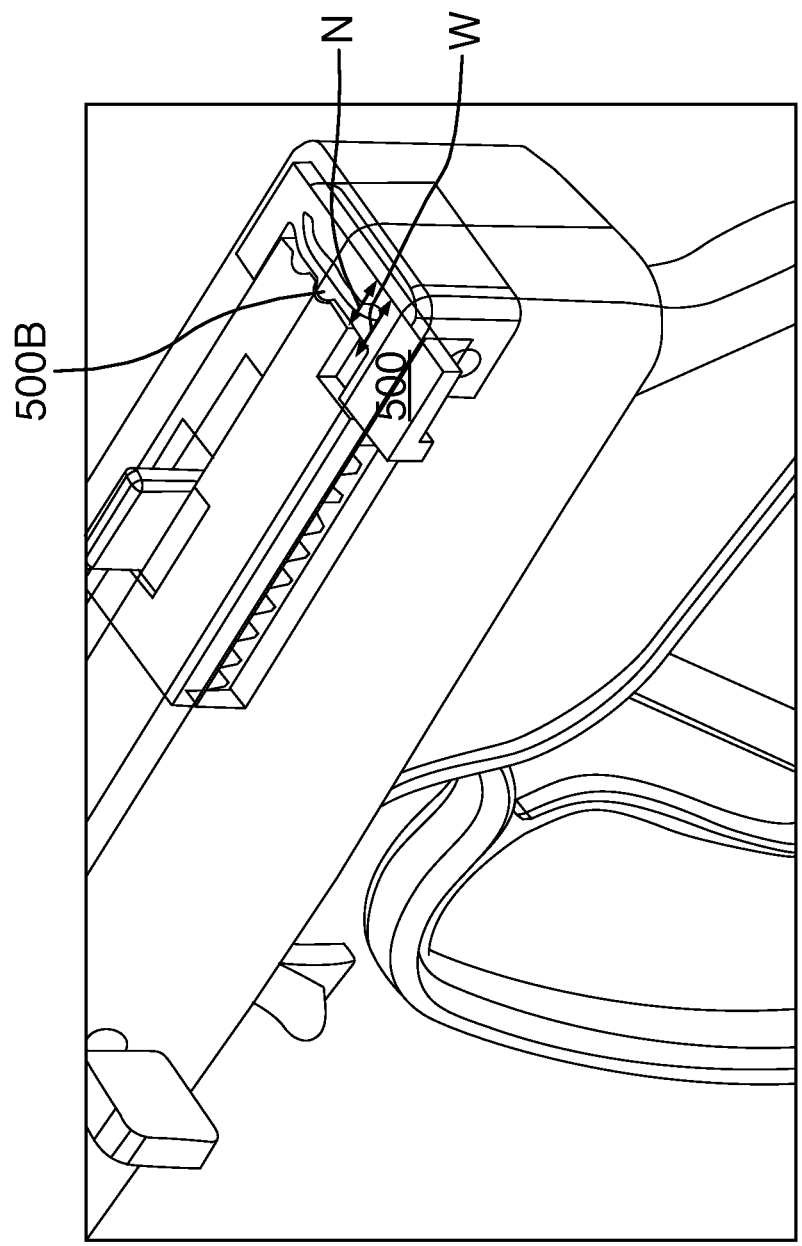

In some embodiments a needle release button 600' is provided internal to the handle body 14'. The needle release button 600' initially locks the needle hub 130 and the stylet hub 430 and is automatically depressed for disengaging the two hubs, allowing the stylet 319 to be advanced beyond the needle 116 (while the needle is blocked by the suture holder 316 (FIG. 2d)). The embodiment of the needle/stylet interlock or needle release button 600' is shown in FIGS. 6m-6x.'. Similar to embodiments described herein previously with respect to FIGS. 4j-4k actuation of the trigger allows the stylet hub 430 to advance, and in its initial or engaged position 600A' the interlock or needle release button 600' allows or forces the needle hub 130 to advance in unison with the stylet hub 430. As discussed previously, FIG. 6m illustrates the device 100 prior to a first actuation of the trigger and additionally shows the interlock 600' in its first position 600A'. Furthermore, FIGS. 6m (*i*), 6m (*ii*) and 6m (*iii*) show a side bottom view of the device 100 showing the needle release button 600' in its initial position 600A'. FIGS. 6m (*i*) and 6m(*iii*) show a cut-away view showing ramp 602' provided on a proximal face of an interference block 601', and a corresponding ramp 402' that is provided on a distal portion of the stylet hub 430, that interacts with ramp 602' of the interference block 601. In one embodiment, the proximal housing or handle body 14' comprises a tab 1408 that extends from the handle body 14' into the handle inner chamber 140 defined by the handle body 14'. When the needle release button 600' is in its initial position as shown in FIG. 6m (*ii*), an overhang portion or hook 604' of the button 600' is positioned below the tab 1408 of the handle body 14' of the device 100. The tab 1408 may prevent the needle release button 600' from being prematurely depressed upwards into its second position 600B' and allows the stylet hub 430 and needle hub 130 to be advanced together. In one example, the tab 1408 functions to prevent the button 600' from being released by allowing the hook 604' to abut against or engage with the tab 1408. The button 600' is coupled to the needle hub 130 and is retractable into the needle hub 130; however, the button 600' cannot retract until the hook 604 is positioned/translated past the tab 1408 defined within the handle body 14'. In some embodiments, the needle release button 600' is coupled to the needle hub 130. The needle release button 600' may be biased towards its initial position 600A' by a biasing means. In some examples, the biasing means for the needle release button 600' comprises a spring biased mechanism. In a particular example of this, the hook 604' of the needle release button 600' is biased towards its initial position 600A' using a spring. The needle release button 600' and particularly the hook 604' has the ability to retract, when the needle release button 600' is in its depressed or second position 600B', for example under application of a force. This allows the stylet hub 430 to be advanced further distally relative to the needle hub 130. Each of these embodiments of the needle release button are described in greater detail hereinbelow with reference to the device in use.

Mechanism for Controlling the Translation Distance of the Stylet

In some embodiments, an element for controlling the translation distance of a suture passing element/suture holder retrieving element such as a stylet 319 is provided, such that the translation distance of the suture passing element at the first actuation of a trigger is different than the translation distance of the suture holder retrieving element at a second actuation of the trigger. In order to allow for varying the distance to which a stylet 319 is advanced when the trigger 218 is actuated, certain embodiments of the present invention provide a depth selection mechanism (depth selector) 500, 500', as shown in FIGS. 5a-5e, 6a-h, FIGS. 6i-6l and FIGS. 6m-6x. Thus, the depth selector 500 allows various degrees of advancement of the stylet 319 in terms of how far it can be translated relative to the needle 116. In some embodiments the depth selector 500 fits into the stylet hub 430. The depth selector comprises a component that interferes with full advancement of the stylet 319, with the component capable of being positioned adjacent to the stylet hub 430, distal to the stylet hub 430. This interference component may be a tab (as shown in FIGS. 5a-e and 6a-h) and discussed further with respect to FIGS. 6i-6l. In other embodiments, the interference component may comprise an arm with a stop as shown in FIGS. 6m-6x. The depth selector may be actuated manually or automatically.

Manual Depth Selector for Controlling the Translation Distance of the Stylet—(the Manual Depth Selector being Operational in Conjunction with the Manual Needle Release Button Discussed Above)

Figure 5A:
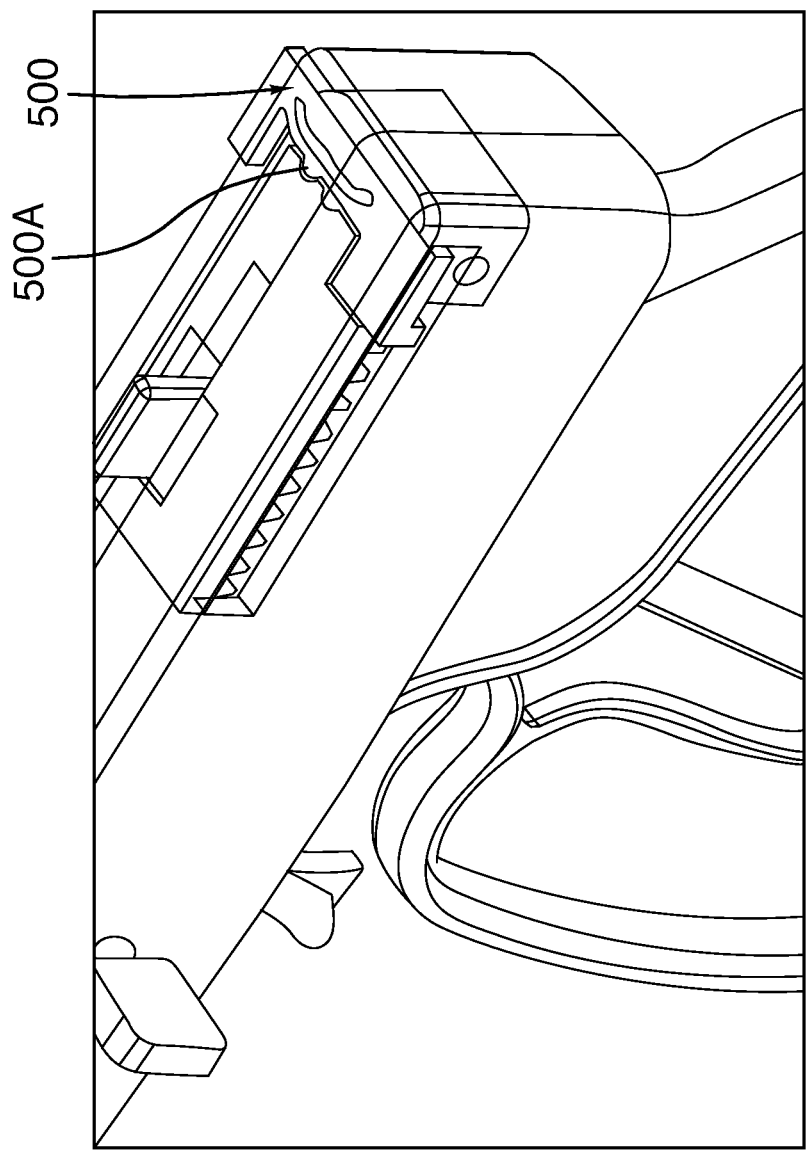
Figure 5B:
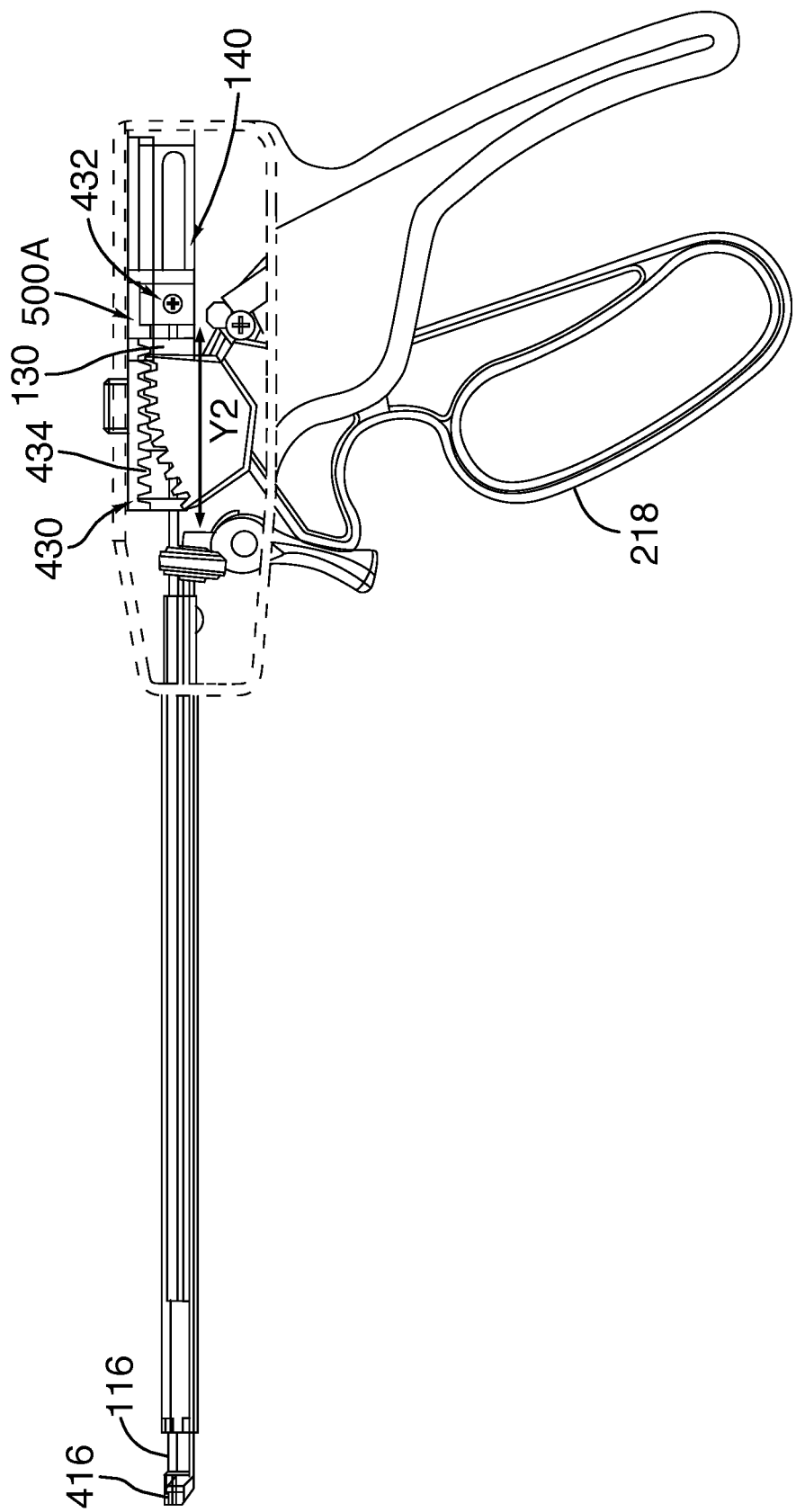

FIGS. 5a and 5b illustrate the depth selector 500 is in its first/initial or starting position or depth setting 500A and illustrate the starting and final (after trigger actuation) locations of the depth selection or adjustment mechanism 500 with respect to the handle housing. With reference to FIG. 5c, the depth selector 500 extends transversely with respect to the longitudinal axis of the device 100 and is coupled to the stylet hub 430. The depth selector 500 defines two positions, a first position 500A and a second position 500B. In the initial position 500A, an overhang or tab T of the depth selector 500 is positioned adjacent the proximal portion 432 of stylet hub 430 and abuts against a distal face of the proximal portion 432 of stylet hub 430. As shown in FIGS. 5c and 5d, In order to retain the depth selector 500 in its first position 500A, a projection 501 is provided on the depth selector that snaps into or otherwise engages with an indentation 502 within the stylet hub 430. The projection 501 is held within the indentation 502 until a transversally directed force is applied against the depth selector, to move the depth selector into its second position 500B.

With reference now to FIG. 5d, the depth selector 500 at its first position or initial depth setting 500A is positioned such that the tab T is positioned adjacent the stylet hub proximal portion 432. Thus, the tab T is positioned distal to the stylet hub proximal portion 432 between the distal surface of the stylet hub proximal portion 432 and the needle hub 130, and interferes with full advancement of the stylet in terms of how far it can be translated relative to the needle. This allows the stylet 319 to be advanced to a first predetermined distance to deposit the suture knot 250 within the suture holder 316 but not to engage therewith.—The depth selector 500 is moveable into its second position by application of a transversally directed force F against the depth selector 500, thereby moving the projection 501 of the depth selector into the second indentation 503 within the stylet hub, which allows the depth selector to remain in its second position 500B. With reference now to FIG. 6e, when the depth setting 500B of depth selector 500 is in its second position the tab T of the depth selector 500 is not located between the distal surface of the stylet hub proximal portion 432 and needle hub 130. In this position, the depth selector tab T does not interfere with the advancement of the stylet hub 430 relative to the needle hub 130 and allows the stylet 319 to be advanced to a second predetermined distance to engage the suture holder to retrieve the suture holder 316

Automatic Depth Selector for Controlling the Translation Distance of the Stylet—(the Automatic Depth Selector Being Operational in Conjunction with the Automatic Needle Release Button Discussed Above)

In some embodiments, as shown in FIGS. 6i-6l, the depth adjustment or selection mechanism may be automated. However, instead of requiring a manual transversally directed force to move the depth selector 500 from its initial position 500A to 500B, an automatic mechanism is provided to move the depth selector from its first position 500A to its second position 500B. As shown in FIG. 6i, a depth selector 500 is shown in its first position 500A, prior to the first trigger actuation of the trigger. The device proximal portion or housing 14 additionally comprises an arm 505 and a tab 506. When the depth selector is in its first position the tab 506 rests on a first side of the arm 505 and projection 501 of the depth selector is positioned within the first indentation 502 within the stylet hub 430. The tab 506 is moveable past the arm 505 upon actuation of the trigger to advance the stylet hub 430. The automatic depth selector 500 functions in a manner similar to the manual embodiment described above to limit the translation of stylet hub proximal portion 432 distally within the handle chamber 140, thus allowing the stylet 319 to be advanced to deposit the suture knot 240 within the suture holder 316. Upon release of the trigger, when the stylet hub 430 automatically retracts together with needle hub 130 to its initial position, the tab 506 is operable to hit the ramp 505b of the arm 505 forcing the depth selector 500 to move into its second position 500B, as shown in FIGS. 6k and 6l. The tab 506 is positioned on a second side of the arm 505. The projection 501 of the depth selector 500 engages with the second indentation within the stylet hub 430. The stylet hub proximal portion 432 may then be re-advanced with a second actuation of the trigger to allow the stylet 319 to be advanced further to engage the suture holder 316 so that it can be retracted therewith.

Automatic Depth Selector for Controlling the Translation Distance of the Stylet with an Audible Feedback—(the Automatic Depth Selector with Audible Feedback being Operational in Conjunction with the Automatic Needle Release Button Discussed Above)

In some embodiments a depth selector is shown with an additional mechanism for generating audible feedback is provided which indicates when the translation of each of the suture passing element and the suture holder retrieving elements (to their respective distances) is complete. The suture holder passing element and the suture holder retrieving element can both translate to different distances when actuated. In one embodiment, as shown in FIGS. 6m-6w, a U-shaped depth stop or depth selector 500' is shown. As shown in FIG. 6m, the depth selector 500' comprises a lower arm 507 and an upper arm 508, which further comprises a stop 509. In a specific example, the depth selector 500' is pivotally coupled to the stylet hub proximal portion 432, for example using a pin. Upward rotational movement of the depth selector 500' is prevented as it abuts against the stylet hub proximal portion 432. Downward rotation movement of the depth selector 500' may also be limited by providing a tab on the depth selector 500' that engages with the stylet hub 430. The handle body 14' of the device, comprises depth selector control or guide ribs 1403, 1405 and click ribs 1404, 1406 that face/project towards the interior of the chamber 140 defined by the handle body 14'. In the initial position a tab 510 of the deflectable arm rests against an upper surface 1403a of the control rib 1403.

In the initial position, the depth selector 500' is positioned such that arm 508 is positioned between the needle hub 130 and the stylet hub proximal portion 432. The stop 509 of arm 508 is operable to contact or abut against the needle hub 130 upon a first actuation of the trigger to prevent full translation of the stylet hub 430 with respect to the needle hub 130. This allows the stylet 319 to be advanced distally to a first predetermined position to deposit a suture knot 250 within the suture holder 316 at the distal tip 12. Additionally the depth selector 500' comprises a lower arm 507 having a tab 510 that is moveable into its deflected position during the first actuation of the trigger and is moveable thereafter into its undeflected position, to allow tab 510 to hit rib control 1404 of the handle body 14'. This allows the depth selector 500' to generate a "clicking" sound indicating the stylet advancement to its first desired distance is complete.

In its second position the depth selector 500' is pivoted downwards so that arm 508 is no longer positioned between the stylet hub proximal portion 432 and the needle hub 130, and does not interfere with full advancement of the stylet 430. This allows the stylet 319 to advance distally to a second position to engage with the suture holder. Additionally the lower arm 507 is further moveable into its deflected position during the second actuation of the trigger and is moveable thereafter into its undeflected position, to allow tab 510 to hit control rib 1406 of handle body 14'. This allows the depth selector to generate a "clicking" sound indicating the stylet advancement to its second desired distance is complete.

In some embodiments the stylet hub proximal portion 432 may be an integral part of stylet hub 430. In other embodiments, the stylet hub proximal portion 432 may be a separate component but is integrally coupled with the stylet hub 430. In some examples, the stylet hub proximal portion 432 may comprise a material that differs from the stylet hub 430. In a specific example, the stylet hub proximal portion 432 comprises stainless steel.

Each of these embodiments describing the depth selector 500 are described in greater detail hereinbelow with reference to the device in use.

Mechanism for Compensating for Deflection

The present device can include a mechanism for compensating for deflection when translating a suture passing element or a suture retrieving element through tissue from the device proximal portion 14 to the device distal tip 12. In some examples, the device may comprise a mechanism for compensating for deflection upon translation of a tissue puncturing member of the device, such as a needle 116. In other examples, the device 100 may provide a mechanism for compensating for deflection within another component, such as a longitudinally extending neck portion 15 of the device (which may be a part of shaft 16 of the device proximal portion) which may cause distal tip 12 to deflect.

The deflection may be a result of the tissue resisting advancement of the needle 116 or stylet 319 or the resistive force of the tissue acting at the distal tip 12. In some examples, deflection of needle 116 or the distal tip 12 may cause the needle 116 to become misaligned from chamber 12B which may, for example, prevent a suture passing element such as a stylet housed within the needle 116 to pass a suture into the distal tip 12.

In one embodiment a feature is provided for compensating for deflection of the tissue puncturing member. In one specific example, the tissue puncturing member comprises a needle 116 housed within shaft 16. The feature for compensating for deflection of the needle 116 comprises providing an offset between the needle 116 and chamber 12B. As shown in FIG. 3e, the needle 116 is advanced from the shaft 16 of the device proximal portion 14 to the distal tip 12 to puncture tissue positioned within the tissue receiving gap 10. As the needle 116 penetrates the tissue, the tissue applies a resistive force ($F_{tissue}$) the needle 116. In a specific example as shown, the needle 116 has a non-symmetric (For example, bevel) geometry. As a result a component of the applied resistive force ($F_{tissue}$) acts normal to the longitudinal axis or centerline of the needle ($F_{reaction}$). This normal force ($F_{reaction}$) deflects the needle 116 from its centerline. As a result the needle 116 may be bent as it is being used to puncture or penetrate the tissue and is thus may become aligned with chamber 12B of the distal tip 12. In some examples, the needle 116 is deflected away towards the top of the device as shown as shown by directional arrow M1. Thus, the needle 116 may then be aligned substantially collinearly with the chamber 12B. Alternatively the needle 116 is deflected such that the tip of the needle 116 engages the opening of the chamber 12B, and the continued advancement of the needle 116 substantially collinearly aligns the needle 116 with the chamber 12B as the bevel of the needle 116 results in deflection towards the top of the device as shown as shown by directional arrow M1.

In another embodiment, a means is provided for compensating for deflection of the device distal tip 12. Similar to the embodiment described above, the feature for compensating for deflection of the needle 116 comprises providing an offset between the needle 116 and chamber 12B. In another specific example, as shown in FIG. 3f, as the device 100 is positioned within tissue 200, the distal tip 12 may encounter resistance, such a resistive force that is encountered when the distal tip hits bone ($F_{bone}$). If a counter force is applied against this resistive force by the user using the device tip 12, a thin portion of the shaft 16, such as longitudinally extending neck portion 15, may bend. In some examples, the distal tip 12 may bend away or may be deflected towards the bottom of the device (as shown by directional arrow M2). As a result the distal housing or chamber 12B defined by distal tip 12, (which the needle 116 is targeting) may be moved. Thus, a force applied by the user using the distal tip 12 may bend a portion of the shaft 16, aligning chamber 12B of the distal tip 12 with the needle 116. In other words the needle 116 and chamber 12B may become substantially collinear.

In further detail, in accordance with an embodiment of the present invention as shown in FIG. 3g, a device 100 is provided that allows the needle 116 to be aligned with chamber 12B of distal tip 12 in its intended trajectory. More specifically, a device is provided wherein the distal tip 12 and the needle 116 are misaligned, in order to compensate for the misalignment created by deflection of either the distal tip 12 or the needle 116. More specifically, the device 100 provides a chamber or channel 16B defined by the shaft 16 of the proximal housing, chamber 16B having a longitudinal axis or centerline $L_p$. The device 100 further comprises a chamber 12B defined by the distal tip 12 of the distal housing, chamber 12B having a longitudinal axis or centerline $L_d$. According to an embodiment of the present invention, device 100 provides that the centerline $L_p$ of the shaft chamber 16B is offset from centerline $L_d$ of the distal tip chamber 12B. The chamber 12B is offset or misaligned in the direction of needle and shaft deflection as shown, so that the deflected needle 116 still targets within the chamber 12B within the distal tip 12.

In an alternate embodiment, other features may be provided to counter deflection of the tissue puncturing member or a portion of the shaft. In one specific example as shown in FIG. 3h, a pre-curved needle 116' is provided. The device 100 as shown in FIG. 3h, comprises a distal tip 12 defining chamber 12B and a shaft 16 defining chamber 16B, where the centerline $L_p$ of chamber 16B is aligned with or substantially collinear with centerline $L_d$ of chamber 12B. The curved needle 116' can accommodate or compensate for the deflection of either the distal tip 12 due bending of the neck portion 15, or deflection of the needle itself due to resistance force applied by the tissue. In one example, where the distal tip 12 is deflected downwardly, since the trajectory of the curved needle 116' is such that it deflects into the tissue receiving gap 10, the distal end of the curved needle 116' is aligned with the distal tip 12. In another example, where the curved needle 116' is deflected away from tissue receiving gap 10 due to tissue resistance, the resistive force applied by the tissue may straighten the curve of the needle 116', thus allowing the needle 116' to be aligned with the distal tip 12.

In some embodiments described above, once a distal end or tip of the needle 116 enter the chamber 12B within the distal tip 12, further distal translation force/slides the needle 116 into the chamber 12B. In some examples, a bevel provided on the needle end face allows the needle 116 to slide into chamber 12B, to allow the distal end the needle to be substantially collinear with chamber 12B. In some embodiments, the needle 116 assumes a slight curve or an s-shaped configuration as it is forced or slid into chamber 12B.

An Exemplary Suture Passing Member in Accordance with an Embodiment of the Present Invention An embodiment of the stylet 319 is described with reference to FIGS. 7a-7d, the stylet 319 comprising features for engaging the suture holder 316. The engagement between suture holder retrieving member such as the stylet 319 and the trap 416 may be further enhanced by the profile or configuration of stylet 319. In some embodiments, the suture holder retrieving element such as stylet 319 may comprise an engagement feature that co-operatively engages with the suture holder 316 such as the trap 416. The engagement feature may comprise a recess or groove that engages with fingers of the trap 416. In other embodiments the engagement feature may comprise a protrusion that engages with the fingers of the trap 416. In one example, a stylet 419 is provided as shown in FIGS. 7a-7e. The stylet 419 comprises a stylet tip 420 and a stylet shaft 424. A portion of the stylet tip 420 has a width W2. A portion of the stylet shaft 424 adjacent and proximal to the stylet tip 420 has a width W1. The width W2 along a portion of the stylet tip 420 being greater than width W1 along a portion of the stylet shaft 424. The portion of the stylet tip 420 having width W2 being defined as the stylet tip wider region 421. And the portion of the stylet shaft 424 having width W1 being defined as the shaft narrower region 423. A shoulder or edge 426 may form at the interface between the stylet tip wider region 421, and the stylet shaft narrower region 423.

In other words the stylet tip wider region 421 defines a shoulder or edge 426. As mentioned above, in some embodiments, a protrusion forms the engagement feature of stylet 419. As an example of this the protrusion is formed by the stylet tip wider region 421. In a specific example, the engagement feature comprises the shoulder or edge 426 defined by the stylet tip wider region 421. In one embodiment, wherein stylet 419 has a substantially circular cross-section, the stylet tip wider region 421 is of a substantially greater diameter than the stylet shaft narrower region 423.

In one example, wherein the stylet has a reduced profile substantially along the length of the stylet shaft 424 the stylet shaft may have a substantially rectangular cross-section or a partially rectangular cross-section along portions thereof. In a specific example of this as is further illustrated in FIG. 7e, the stylet shaft 424 has four flats or planar surfaces 425 that form the reduced rectangular cross-section along the distal portion of the shaft 424 along the shaft narrower region 423. Furthermore shaft 424 has a partially rectangular cross-section along the shaft portion 427, with a portion of the shaft cross-section being rounded or circular. In other embodiments, the shaft narrower region 423 may have any other cross-sectional shape which may non-limitingly include any one of a circular, oval or square cross-section or combinations thereof.

In operation, the stylet 419, functioning as the suture holder retrieving member is advanced to capture the trap 416. The stylet is advanced through the trap 416 such that the shoulder or edge 426 defined by the stylet tip wider region 421 advances past a distal opening of the trap 416 (FIG. 7d). The distal opening of the trap 416 is defined by fingers 322 that substantially converge at the distal end, the fingers 322 having a nominal shape and position. In some embodiments, the trap 416 is resilient and the fingers 322 flex as the stylet tip 420 is advanced past the distal opening of the trap 416, and return substantially to their nominal shape/position when the stylet tip 420 is positioned distal to the trap 416 (i.e. when the shoulder or edge 426 is positioned distal to the trap 416). When the trap 416 has returned substantially back to its nominal shape/position, the distal opening of the trap 416 has a smaller width than the width along the stylet tip wider region 421. Thus, when the stylet 419 is retracted, the shoulder or edge 426 of the stylet tip wider region 421 abuts against the narrow distal end of the trap 416, thereby preventing the stylet tip 420 from retracting back through the trap 416. The stylet 419 and the trap 416 are then retracted together as a unit, through tissue site P2 through the second segment of tissue 200. In alternate embodiments, the suture holder 316 may comprise a trap 416 having fingers 322 and the suture holder retrieving member such as stylet 319 may comprise an indent which engages with the fingers of the trap 416. Alternatively, the stylet 319 may comprise any other feature that allows the stylet 319 to engage a suture holder 316.

Put differently, an engagement mechanism may be provided between the stylet 319 and the trap 416 that enables the trap 416 to be retracted along with the stylet 319 as the stylet 319 is retracted, allowing for disengagement of the trap 416 from the distal tip 12, as shown in FIG. 3d. This allows the suture knot 250 to be withdrawn proximally through a second side of the tissue, for example through tissue site P2 using the trap 416. The suture 240 is passed from the distal side to the proximal side of the tissue through the second segment of the tissue. Thus, this allows the suture 240 to be passed through tissue on both sides of the defect to allow the two sides of the tissue to be approximated in order to substantially seal the defect.

An Exemplary Suture Trap in Accordance with an Embodiment of the Present Invention As illustrated and discussed in greater detail below, in some embodiments the suture holder 316 defines an opening on its distal side. The suture holder 316 is capable of receiving the stylet 319 that pushes the knot 250 through such that it exits through the opening thereof. In such an example, the opening on the distal side of the suture holder 316 is defined by the suture retaining means. In other words, the suture retaining means may be understood to be the portion of the suture holder defining the distal opening through which knot 250 is positioned. One specific embodiment of the suture holder 316 for receiving a knot 250 is described with reference to FIGS. 7a-7c. In one specific example, as shown in FIG. 7a, the suture holder 316 described herein above may comprise a trap 416. The trap 416 allows a suture holder retrieving member, such as the stylet 319 to engage the trap 416 when the stylet 319 is advanced to a second predetermined distance or in the second pass (FIGS. 3c-3d and FIG. 7d) to allow the trap 416 to be retracted with the stylet 319. The trap 416 is formed from a tubular hollow elongate member terminating in flexible tips or fingers 322. The tips or fingers 322 which may be elastic or resilient, form the suture retaining component of the trap 416. As mentioned above, in the first pass, the stylet 319 is advanced through tissue on a first side of the defect to pass the suture 240 there-through. As the stylet 319 is advanced through the trap 416, the flexible elastic fingers 322 of the trap 416 forming the suture retaining component flex to allow the stylet 319 to pass the knot 250 through the trap 416 (FIG. 7b). The fingers 322 subsequently return to their nominal position when the stylet 319 is retracted, to trap and retain the knot 250 in a position distal to the trap 416 (FIG. 7c), which in one example, may be beyond the device distal tip 12. Thus, the trap 416 allows the knot 250 to travel through the trap in one direction and retains the knot 250, preventing proximal movement of the knot 250 through the trap 416. In one embodiment, the suture retaining component of the trap 416 comprises at least four fingers 322. In an alternate embodiment, the suture retaining component of the trap 416 comprises at least three fingers 322. In one specific example, wherein the suture holder 316 includes a trap 416, trap 416 comprises a bevel at its proximal end face (a beveled proximal face) to allow engagement with the bevel at the distal end of the needle 116 (beveled distal face) according to one embodiment as described above,

Alternative Embodiments of the Suture Trap and Corresponding Engagement Features within the Distal Tip Alternative embodiments of the device of the present invention are shown below with respect to FIGS. 9-19. Each of these embodiments may be used in conjunction with the method described herein below with reference to FIGS. 2 and 3. The term "suture holder" as used throughout refers to a suture trap 316 operable to capture a suture passed therethrough by a suture passing member.

Figure 9A:
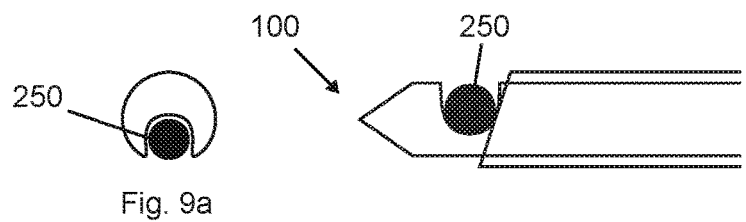
FIGS. 9a-9i illustrate steps of a method in accordance with alternative embodiments of the present invention.
Figure 9B:
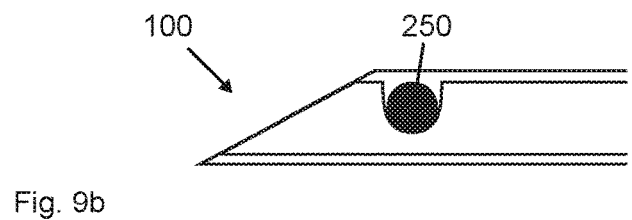
Figure 9C:
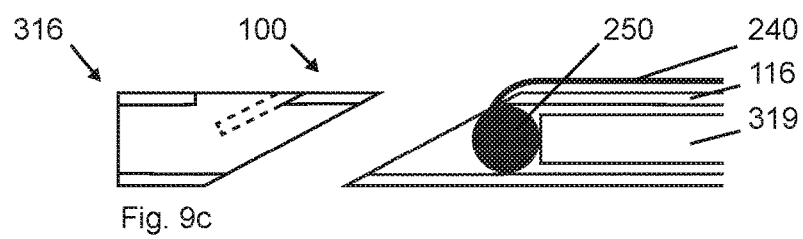

In a further embodiment, as shown in FIGS. 9a-9f, a device 100 is used to practice a method of the present invention to treat a defect. The device 100 comprises a suture holder 316 at a distal tip thereof. The suture holder 316 may be releasably coupled to the distal tip 12 using any of the member engagement features described herein. For example, the suture holder 316 may be coupled to the distal tip 12 using co-operative engagement between the suture holder 316 and distal tip 12 or using a wire that passes through the distal tip 12 into an aperture of the suture holder 316. The suture holder 316 may at least partially define a lumen there-through. In one embodiment the suture holder 316 has a suture retaining component for remotely capturing and/or retaining a portion of the suture. The suture portion may be captured remotely from the user during a medical procedure. In one example, the suture retaining/capturing component comprises one or more resilient fingers (or 'spring biased appendages') that are inwardly biased with respect to the suture holder. The suture retaining component comprises one or more resilient members or fingers that project from (a surface) of the suture holder to effect, direct or restrain motion when brought into contact with a second object. In another example, the one or more resilient fingers effect, direct or restrain motion of a portion of the suture. In a specific example of this, the fingers project sufficiently inwards to prevent retraction of the suture portion. In one example, the suture portion is taken from the group consisting of a suture knot, a suture ball, a metal tab or a plastic tab. The suture retaining component may comprise one finger. Alternatively, the suture retaining component may comprise more than one finger. In some examples, the suture retaining component may comprise two, three, or four fingers. In one embodiment, the inwardly biased fingers are located at a distal end of the suture holder. In an alternate embodiment, the one or more fingers are positioned at a location along the longitudinal length of the suture holder. In one example of this, as shown in FIGS. 9a-9b and 9c, the suture holder 316 has one or more resilient arms or finger 322 that may be bent or tapered towards the interior of the suture holder 316 at about a mid-length of the suture holder 316. In a specific example, the suture holder 316 has one arm or finger 322. In some embodiments, the fingers 322 may be referred to as protrusions, members or tips.

Figure 9D:
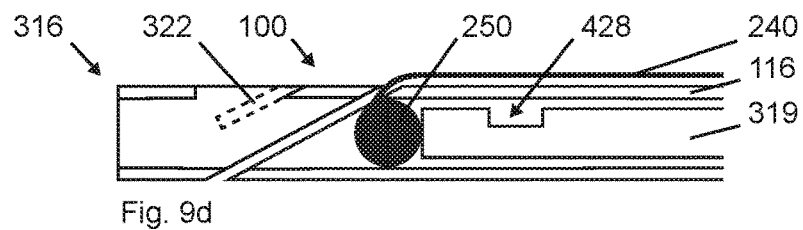
Figure 9E:
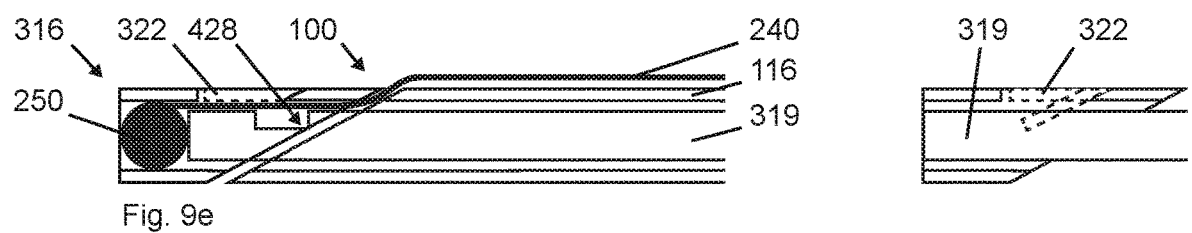
Figure 9F:
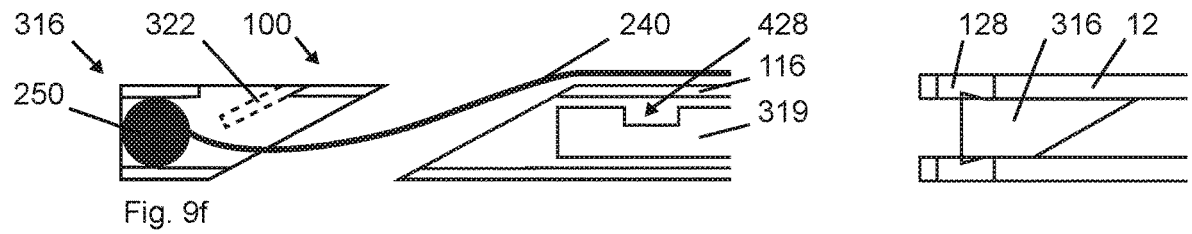
Figure 9G:
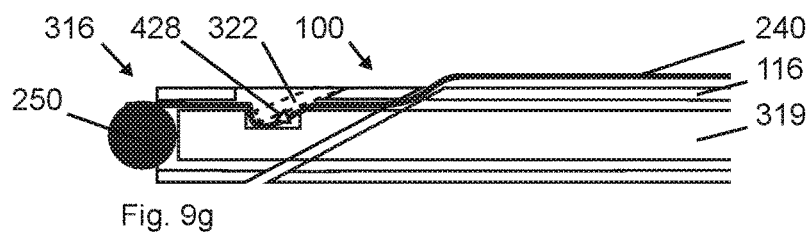

The device 100 further comprises a suture passing member in the form of a stylet 319 that has a groove 428 along its distal portion. The stylet 319 is housed within a hollow needle 116 that functions as a tissue puncturing member. A portion of the suture 240, such as knot 250 is held within the needle 116 in the device proximal portion, as shown in FIGS. 9a-9b, and 9c. The distal end of stylet 319 is equipped for pushing the suture knot 250 into suture holder 316 as shown in FIG. 9d upon advancement of the stylet 319 to a first predetermined distance. The resilient arm or finger 322 of the suture holder 316 is capable of flexing to allow passage of stylet 319 through the suture holder 316 as shown in FIG. 9e. Thus, the suture holder 316 may additionally function to restrict movement of the suture passing member such as stylet 319, such that it allows the suture passing member to advance till it allows the suture knot 250 to engage the suture retaining component and the suture passing member is free to retract there-from as shown in FIG. 9e. The suture holder 316 may additionally function to restrict movement of the suture holder retrieving member, such as stylet 319 such that it can engage stylet 319 upon readvancement of stylet 319 to a second distance. This allows the suture the stylet 319 to retract the suture holder 316 therewith as shown in FIG. 9f. The resilient arm or finger 322 of the suture holder 316 is received within and engages the groove 428 of stylet 319, allowing capture of the suture holder 316 by the stylet 319 (FIG. 9g). In this position the suture holder 316 restricts movement of the stylet 319 by allowing the groove 428 to engage with the finger 322 of the suture holder 316. In one embodiment as shown in FIG. 9f, the suture holder may comprise tabs that are held within a window 128 of the distal tip 12 to allow the suture holder to be coupled to the distal tip 12. In an alternative of the above described embodiment, the stylet 319 may be rotatable to change its orientation between first and second orientations.

Figure 9H:
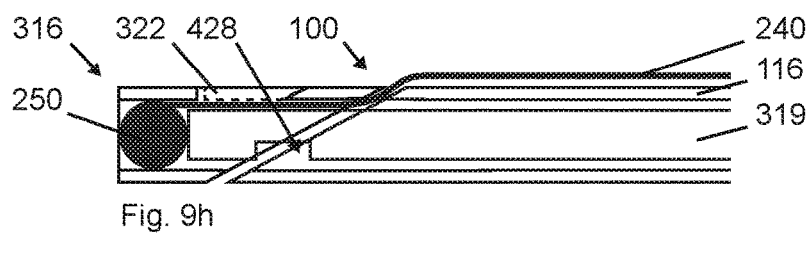
Figure 9I:
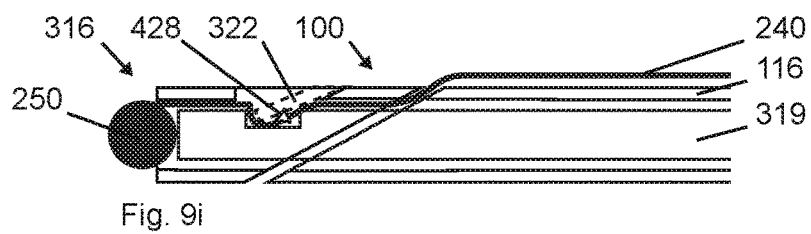

In its first orientation, such groove 428 of the stylet 319 faces away from the arm or finger 322, as shown in FIG. 9h. This may help prevent the groove 428 of the stylet 319 from engaging the arm or finger 322 during initial advancement of the stylet 319, thus ensuring that the stylet 319 can be retracted freely after the knot 250 is deposited at the suture holder 316. Thus, in its first orientation the stylet 319 is in its non-engaging orientation where it cannot engage the suture holder 316 as it is advanced. In its second orientation, the stylet 319 is in its suture holder engaging orientation where the groove 428 is positioned on the same side as the arm or finger 322 so the stylet 319 may engage the suture holder 316 upon re-advancement. The, the arm or finger 322 of the suture holder 316 is operable to fit into or engage the groove 428 of the stylet 319, which may allow the stylet to retrieve the suture holder 316 upon retraction, as shown in FIG. 9i. Thus, the arm or finger 322 of the suture holder 316 functions to restrict or restrain the motion of the stylet 319 and allows engagement of the stylet 319 with the suture holder 316.

In another example of an embodiment of the present invention as shown in FIGS. 10a-10f, the device 100 comprises a suture holder 316 that is disposed at the device distal tip 12. The suture holder 316 comprises a hollow tubular member defining a lumen there-through. The suture holder 316 comprises a suture retaining component such as one or more inwardly biased resilient fingers that project from a surface of the suture holder 316 at a distal end thereof. The fingers 322 function to effect, direct or restrain motion of a portion of the suture passed through the suture holder 316. The fingers 322 additionally also function to restrict motion of the suture passing member used to pass the suture portion through the suture holder 316, and further to engage the suture holder retrieving member that is passed thereafter through the suture holder 316 to retrieve the suture holder 316 with the suture portion coupled thereto.

Figure 10A:
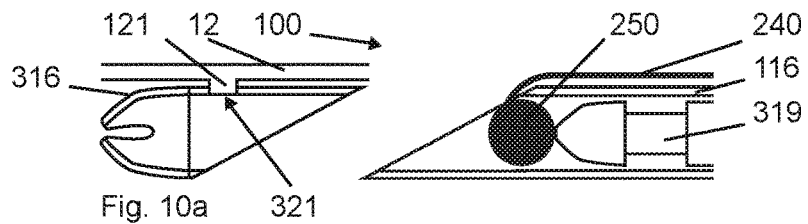
FIGS. 10a-10f illustrate steps of a method in accordance with an alternative embodiment of the present invention.
Figure 10B:
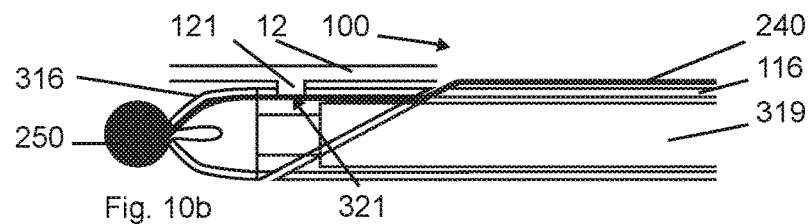
Figure 10C:
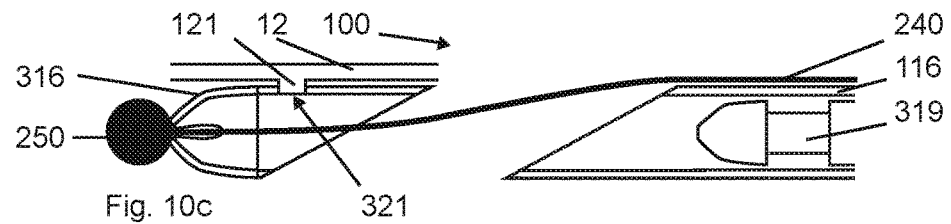
Figure 10D:
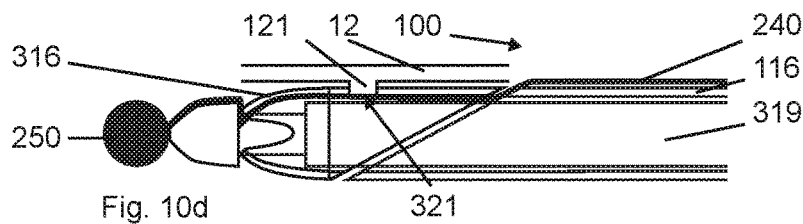
Figure 10E:
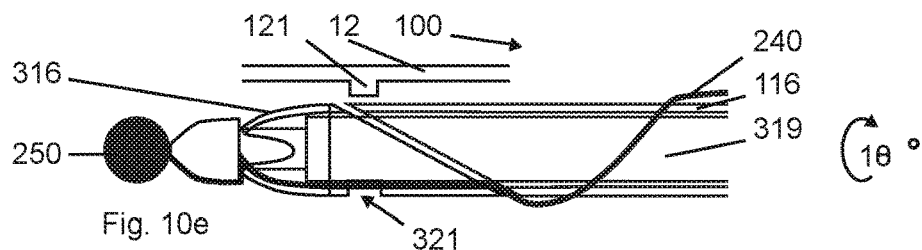
Figure 10F:
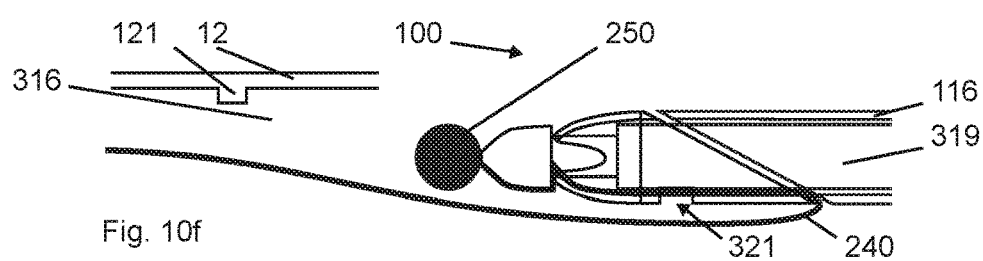

Additionally, the suture holder 316 comprises an engagement feature for releasably coupling the suture holder 316 to the device distal tip 12. The engagement feature comprises co-operative engagement between the suture holder 316 and the device distal tip 12. In one example, the suture holder 316 has an indent, a recess or groove 321 that co-operatively engages with a projection 121 of the distal tip 12, to allow the suture holder 316 to be releasably coupled to the distal tip 12, as shown in FIG. 10a. The engagement feature allows suture holder 316 to remain detachably engaged with the suture holder 316 during advancement of stylet 319 to pass suture 240 and retraction thereafter as shown in FIGS. 10b and 10c. The disengagement of the projection 121 of the distal tip 12 with the indent, recess or groove 321 of the suture holder 316 may be affected by rotation of the suture holder 316 using stylet 319 after it has been re-advanced through the suture holder 316 as shown in FIGS. 10d and 10e, thereby allowing suture holder 316 to be retracted through tissue on the opposing side of the defect using the suture holder retracting member such as stylet 319, as shown in FIG. 10f.

A further alternate embodiment is shown in FIG. 11a, with the suture holder 316 disposed at the device distal tip 12 and is received within a receiving chamber of the distal tip 12. The suture holder 316 comprises a suture retaining component in the form of one or more fingers 322, as described previously to retain a portion of the suture 240 that is passed by the suture passing member into the suture holder 316. The suture holder 316 further comprises an engagement feature allowing it to be detachably coupled to the device distal tip 12. The engagement feature comprises a notch or an engaging surface 330 that co-operatively engages with a projection at the distal tip 12, to retain the suture holder 316 within the receiving chamber of the distal tip 12. In one specific example, the projection at the distal tip 12 is a projection 131 of a spring clip 132, with the spring clip 132 being coupled to the distal tip 12, as shown in FIG. 11a. The suture holder 316 comprises a suture retaining member such as fingers 322, to capture and retain the suture knot 250 therein. Furthermore, the stylet 319 may comprise an engagement feature to order to allow the stylet 319 to engage the suture holder 316, as shown in FIG. 11b. For example similar to embodiments discussed previously, the stylet 319 may have a tip wider region that has a width that is greater than the width along the distal end of the suture holder 316 for engaging with the suture holder upon advancement of the stylet tip wider region through and distal to the suture holder 316. In order to enable retraction of the suture holder 316, a mechanism is provided to disengage the suture holder 316 from the distal tip 12. As shown in FIGS. 11c and 11d, in one example, the needle 116 that houses the stylet 319, may be rotatable (for example by 90 degrees) to allow the suture holder 316 to rotate with the needle 116 allowing the notch or engaging surface 330 to be rotated out of engagement with the projection of the spring clip 132, thus decoupling the suture holder 316 from the distal tip 12. This ensures that the notch or engaging surface 330 no longer faces the clip 132; instead, the spring clip 132 is adjacent and in contact with a non-engaging surface of the suture holder 316, (which in one particular example may be a smooth outer surface of the suture holder 316). This allows the stylet 319 (as the suture holder retrieving member), as well as the suture holder 316, to be retracted with limited, reduced or substantially no hindrance.

Figure 12A:
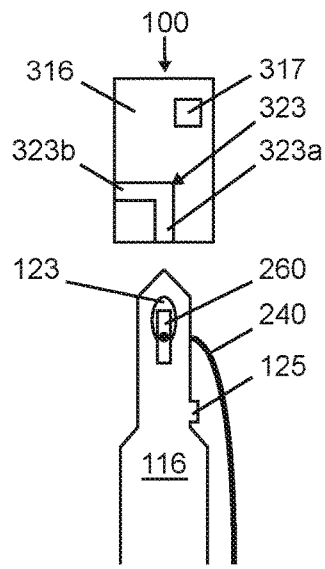
FIGS. 12a-12f illustrate steps of a method in accordance with an alternate embodiment of the present invention.

In accordance with an alternate embodiment of a method of the present invention, a device 100 shown in FIG. 12a may be used The suture holder 316 may be detachably coupled to the distal tip 12 using co-operative engagement. The suture holder 316 additionally comprises a suture retaining component where the suture retaining/capturing component comprises an element of the suture holder 316 that at least partially defines an aperture. In some embodiments the suture retaining component comprises a wall of the suture holder 316 that defines an aperture. In some embodiments, an edge 327b of the wall defines the aperture and forms a proximal boundary of the aperture. In alternate embodiments, the aperture may be any one of a rectangular aperture, an oblong aperture or a key-shaped aperture. In some embodiments, the aperture may be referred to as a slot, a window, an opening or a hole. In some embodiments, the suture holder 316 defines a hollow lumen at least partially there-through. In one example, the suture holder 316 defines a lumen that extends completely there-through. In some embodiments, the suture retaining component comprises a distal face of a wall of the suture holder 316, the distal face defining the aperture. In one example, the aperture extends transversally within the wall of the suture holder 316. In other examples, the aperture extends longitudinally within the wall of the suture holder 316. In some embodiments, the aperture extends both transversally and longitudinally. In one specific example, the aperture is an L-shaped slot 323 having a transversally extending portion 323b that is formed distally to longitudinally extending opening 323a. A portion of the suture 240 may be passed into the slot 323 through the longitudinally extending opening 323a. The suture portion may then be retained by the suture retaining component within the transversally extending portion 323b of the slot. In one particular example, the suture retaining component comprises an edge 327b of the suture holder wall that forms the proximal boundary of the slot 323.

As shown in FIGS. 12a-12d, in order to facilitate the transfer of the suture portion from the device proximal portion to the suture holder 316 at the distal tip 12, the device 100 further comprises a suture passing member. In one particular embodiment the suture passing member comprises an elongate needle 116 that defines an opening 123 for carrying a portion of the suture 240. In one example, the suture portion is a suture knot 250. In an alternate embodiment, the suture portion comprises a tab 260 which may be a metal or a plastic tab affixed to a free end of the suture.

Figure 12B:
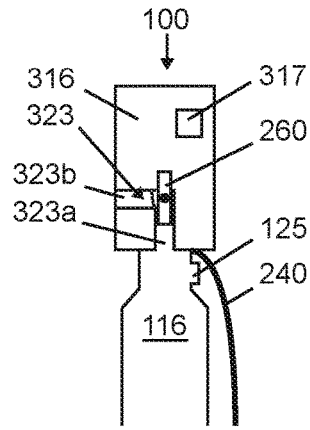
Figure 12C:
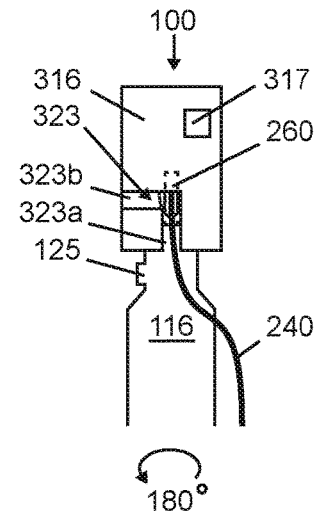
Figure 12D:
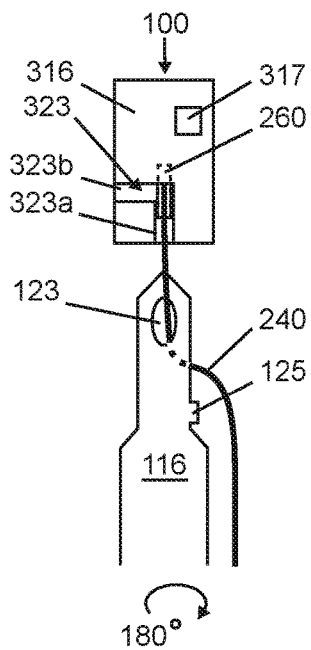

In operation, the device 100 is insertable through a defect within a region of tissue, such that the suture holder 316 (coupled to the device distal tip 12) is positioned on a distal side of a first segment of tissue (Not shown). The needle 116 (functioning as the suture passing member) may be advanced through the first segment of tissue to deposit the suture portion within the suture holder 316. As shown in FIG. 12b, the needle is advanceable to a first distance (which may be a predetermined distance) such that the suture tab 260 or knot 250 is received within the longitudinally extending opening 323a of slot 323 of the suture holder 316. The distal portion of the needle 116 is received into the suture holder 316 but the raised portion or projection 125 of the needle 116 does not engage with the suture holder 316. The needle 116 may then be rotated 180 degrees (e.g. counterclockwise) to translate the suture tab 260 or knot 250 within the slot portion 323b away from the slot opening 323a to secure the suture tab 260 within the suture holder 316, as shown in FIG. 12c. As shown in FIG. 12d, the needle 116 may then retracted and rotated by another 180 degrees (e.g. clockwise) after having passed suture 240 through the first segment of tissue on one side of the defect.

Figure 12E:
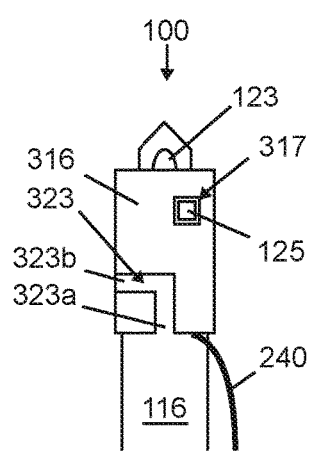
Figure 12F:
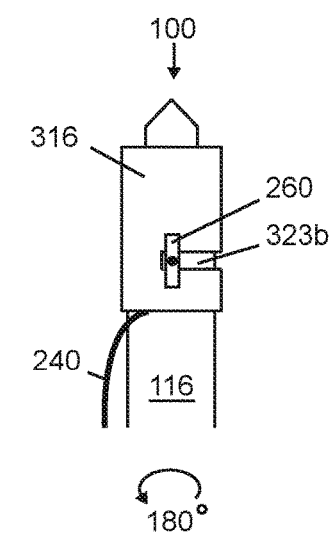

In operation, the device 100 may then be re-positioned on the other side of the defect. In other words the device 100 is re-positioned such that the suture holder 316 is now positioned on a distal side of a second segment of tissue. The needle 116 (now operating as the suture holder retrieving member) is then re-advanced and passed through the second segment of tissue. As shown in FIG. 12e, the needle 116 is advanceable to a second distance (which may be a predetermined distance). The needle 116 advanced further distally relative to the distance traveled by needle 116 in FIG. 12b. This allows the raised portion or projection 125 of the needle 116 to be positioned within the suture holder 316. The needle 116 may then be rotated 180 degrees (e.g. counterclockwise) to lock the needle 116 and suture holder 316 together. In this particular example, when the needle 116 is rotated the projection 125 of the needle 116 is received within/engages a portion of the suture holder 316, such as a recess or a groove or a window 317 as shown. The needle 116 is then retracted, disengaging the suture holder 316 from the distal tip 12. Both the needle 116 and the suture holder 316 can then be withdrawn together through the defect (FIG. 12G), thereby passing suture 240 coupled to the suture holder 316 through tissue on the second or opposing side of the defect. Thus, device 100 can allow suture 240 to be passed through both the first and second segments of tissue on opposing sides of the defect. FIGS. 13a-13d illustrate a device 100 in accordance with still another embodiment of the present invention for passing a suture through tissue using. Similar to embodiments discussed herein above, the device 100 comprises a suture holder 316 coupled to the device distal tip 12 (not shown). The device 100 additionally comprises a means for passing a portion of the suture from the device proximal portion to the suture holder 316 at the device distal tip 12. As discussed previously, the suture holder 316 comprises both an engagement feature for detachably coupling the suture holder 316 to the device distal tip 12, as well as a suture retaining component for receiving and retaining the suture portion. Generally, the suture retaining component of the suture holder 316 comprises an aperture defining element of the suture holder 316. In one embodiment, the suture retaining component comprises an aperture defining wall of the suture holder 316. As an example of this, the suture retaining component forms/defines an edge of the aperture.

In one particular embodiment, the suture retaining component comprises a door, i.e. a hinged, sliding or revolving barrier that forms an edge of the aperture. The barrier is positioned substantially perpendicularly between opposed edges of the aperture. Additionally, the barrier is moveable between an open position and a closed position, where the barrier in its open position allows access to the aperture for receipt of the suture portion therein. In a specific example of this, the barrier forms a side edge of the aperture. In another example, the barrier forms a proximal edge of the aperture. More specifically, the suture holder 316 defines a longitudinally extending slot 323 with the suture retaining component comprising a barrier or flap 325 at the proximal opening of the slot 323. In some embodiments, the barrier may be hinged or pivotable. As an example of this, the barrier is biased towards its closed position. Furthermore, the bias may be provided using a spring biased mechanism. In one example, the barrier 325 is coupled to the suture holder 316 using a spring that biases the barrier towards its closed position.

The operation of the device in use is discussed further herein below. As the needle 116 (carrying knot 250) is advanced through a first side of the tissue and into the suture holder 316, the knot 250 pushes against the hinged barrier 325, causing the hinged barrier 325 to open towards the interior of the slot 323 to receive the knot 250, as shown in FIG. 13b. As the knot 250 moves past the open hinged barrier 325, the hinged barrier 325 closes, and returns to its nominal closed position (FIG. 13c). In one example, a stopper S may be provided that prevents the barrier from opening towards the exterior of the trap and allows the barrier to remain in the closed position. When the needle 116 is retracted proximally, the suture knot 250 is retained in the slot 323 by the hinged barrier 325 (FIG. 13d). The suture holder 316, and subsequently the knot 250 retained therein, may then be retracted through tissue on an opposing side of the defect using a suture holder retrieving member as discussed for any of the embodiments described herein. In one specific example, the suture holder retrieving member comprises a needle 116. The needle 116 comprises a projection or tooth 125. The needle 116 is advanced to retrieve the suture holder 316. As the needle 116 is advanced into the suture holder 316, the tooth 125 is received within a lumen 13' of a longitudinally extending shaft 13 within the suture holder 316. The needle 116 is not free to rotate as the movement of the needle 116 is restricted to longitudinal advancement due to the interaction of the tooth 125 with lumen 13'. Once the needle 116 is fully advanced within the suture holder 316, the tooth 125 is positioned adjacent a groove or window 317 of the suture holder 316. As the needle 116 is then rotated, the tooth 125 is received within the groove or window 317 and engages therewith. This couples the needle 116 to the suture holder 316 enabling the needle 116 and the suture holder 316 to be retracted together.

Figure 13G:
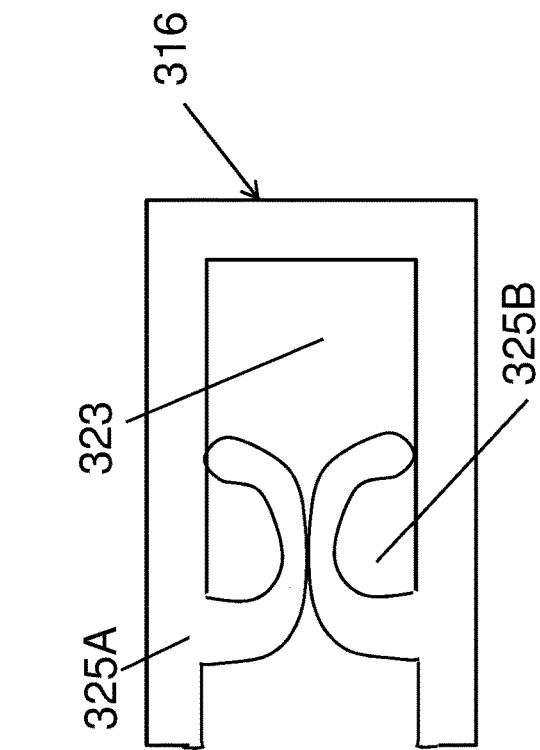
FIGS. 13e-13g illustrate a suture holder in accordance with an alternate embodiment of the present invention.
Figure 13E:
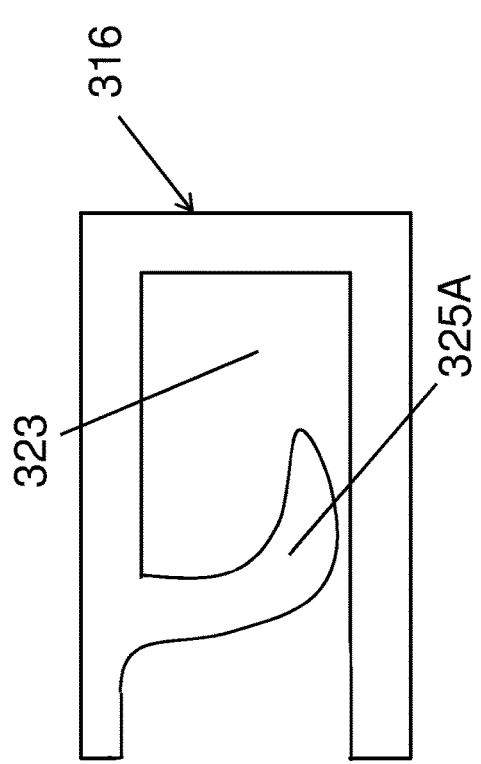
Figure 13F:
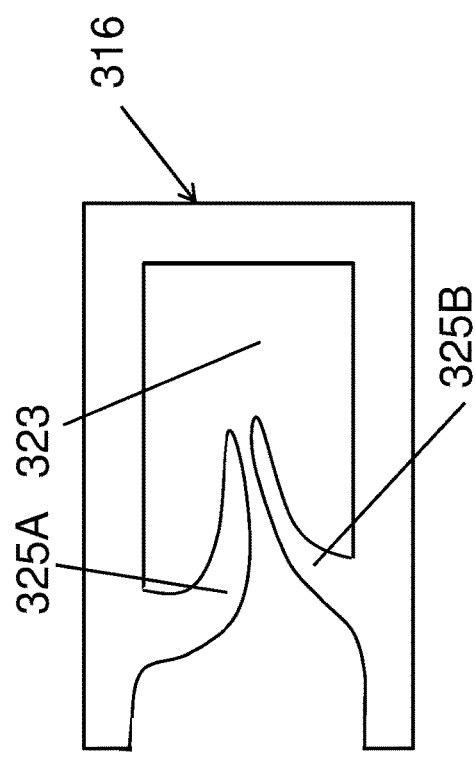

In an alternate embodiment, the hinged barrier 325 may be replaced by a resilient member or tab 1325A, as shown in FIG. 13e. The material properties of the tab 1325A may allow it to return substantially to its nominal or resting position. In some embodiments the tab 1325A may comprises an elastomer. In one specific example the tab 1325A comprises silicone. In some embodiments, suture holder 316 may comprise a plurality of tabs. In one specific example, suture holder 316 comprises two tabs such as tabs 1325A and 1325B, shown in FIG. 13f and FIG. 13g. In another example, the suture holder 316 comprises three tabs. In other embodiments, the suture holder 316 may comprise more than three tabs.

Figure 14A:
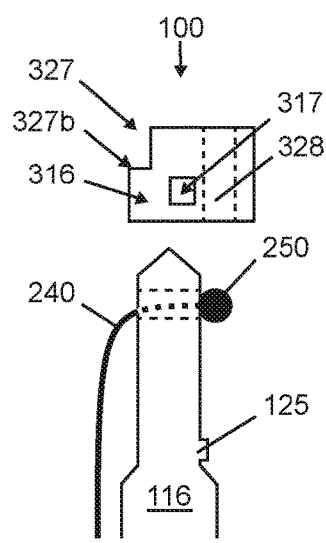
FIGS. 14a-14f illustrate steps of a method in accordance with an alternate embodiment of the present invention.

In still another embodiment as shown in FIGS. 14a-f, a device 100 is disclosed for passing suture for example to treat a defect, wherein the device comprises a suture holder 316 coupled to a distal tip of the device 100. The suture holder 316 in some embodiments may define a lumen at least partially there-through. The suture holder comprises a suture retaining component for capturing and retaining the suture. In some embodiments, the suture retaining component comprises a wall defining an aperture such as a slot 327, which in one example is positioned at or adjacent a distal end of the suture holder 316. The slot is defined by an edge 327b of the wall that is proximal to the slot 327 and forms the proximal boundary of the slot 327. In other words, the suture retaining component comprises a distal face of a wall of the suture holder 316 where the distal face defines the aperture. Furthermore, the suture holder 316 further comprises an engagement feature for coupling the suture holder 316 to the device distal tip 12 for example, through co-operative there-between. In some embodiments, the suture holder 316 comprises a projection that is received within a notch or a recess of the distal tip 12. As an example of this, the projection on the suture holder 316 comprises a fin 328. Thus, the suture holder 316 is retained within the device distal tip by the fin 328 being received within a slot or groove of the distal tip 12. The device 100 further comprises a needle 116 carrying a suture knot 250 of the suture strand 240, as shown in FIG. 14a.

Figure 14B:
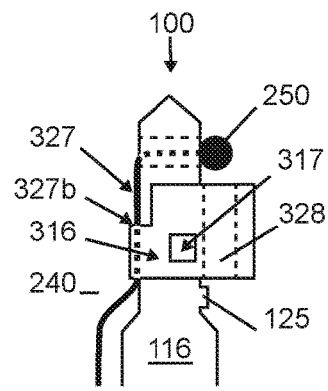
Figure 14C:
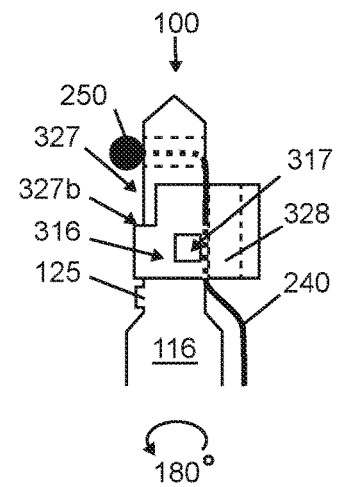
Figure 14D:
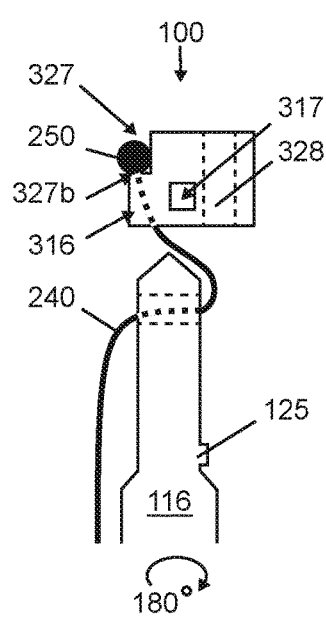
Figure 14E:
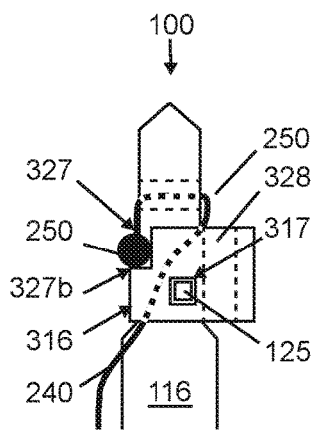
Figure 14F:
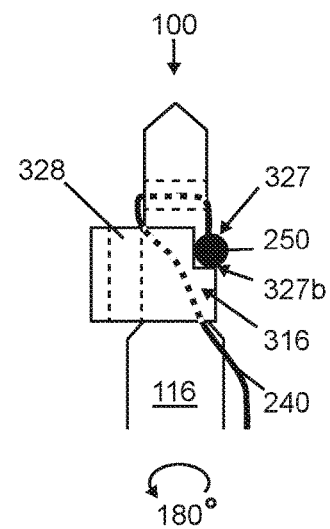

In operation, the device 100 is inserted through a defect within the tissue in order to treat it. The device distal tip 12 is positioned on a far side of the tissue and positioned such that a first segment of tissue 200 is received the tissue receiving gap 10 (not shown). As shown in FIG. 14b, the needle 116 is then advanced through the first segment of tissue on one side of the defect, to a first distance such that it is received within the suture holder 316 and the knot 250 is positioned distal to the suture holder 316, as shown in FIG. 14b. The needle 116 is then rotated by 180 degrees (e.g. counterclockwise) with respect to the suture holder 316 such that the knot 250 is longitudinally aligned with the slot 327, and then withdrawn, as shown in FIGS. 14c and 14d. As the needle 116 is retracted, the knot 250 abuts against the edge 327b forming the proximal boundary of slot 327 and is retained within the slot 327. The needle is then rotated, e.g. clockwise, by 180 degrees. The device 100 is then re-positioned at tissue on a second side of the defect. The device further comprises a suture holder retrieving member that is housed within the proximal portion and advanced distally to retrieve the suture holder 316. In one particular example, as shown in FIG. 14e, the needle 116 also functions as the suture holder retrieval member and is then re-advanced through tissue and into the suture holder 316 to a second location (which requires advancing a greater distance (distally) relative to the distance traveled by the needle 116 with respect to FIG. 14b). A raised portion or projection 125 of needle 116 is received within the suture holder 316 and the needle 116 is then rotated 180 degrees (e.g. counterclockwise) to allow the projection 125 to engage a window or aperture defined by a wall of the suture holder 316. This allows the needle 116 to engage the suture holder 316 while substantially simultaneously allowing the fin 328 of the suture holder 316 to disengage from the device distal tip. The needle 116 can then be withdrawn or retracted, thereby drawing the suture holder 316 and suture 240 through tissue on the second side of the defect.

In another embodiment of the present invention, a device 100 is disclosed having a suture holder 316 coupled to the device distal tip 12. The suture holder 316 may comprise a resilient material such as an elastomer, plastic or metal such as stainless steel. In some embodiments the suture holder 316 may comprise a resilient material that is capable of elastic deformation when force is applied to it and is capable of returning substantially to its original position when the force is removed. In some embodiments, the suture holder 316 comprises a valve 1516. In one example, passage of material/object through the valve 1516 in a first direction exerts an internal force which causes it to open. Whereas, retraction of material/object in the opposing direction exerts a force on the valve 1516 from the outside preventing the return passage of material/object therethrough. In one specific example the valve 1516 is formed of an elastomer such as silicone. In another specific example the valve 1516 is formed of a metal such as stainless steel.

FIG. 15a. is an illustration of a valve 1516 comprising resilient material. FIG. 15a shows the valve 1516 with fingers or flaps 1522a and 1522b at rest, when no force is applied. In some examples, when force is applied on the inside of the valve or internal pressure is applied, it causes the two fingers 1522a and 1522b to separate and may cause the two faces to stretch away from each other as shown in FIG. 15b. For example, as described previously, the two fingers 1522a and 1522b separate as the knot 250 is pushed through the valve 1516 for example, using a stylet 319. Once the knot 250 is passed through the valve 516, the fingers 1522a and 1522b return substantially back to their resting position. In some embodiments, as shown in FIG. 15c, the internal force may be removed allowing the valve to return substantially to its resting/nominal position. Additionally, in some embodiments, as further shown in FIG. 15c, an external force may be applied to fingers 1522a, 1522b which may assist in returning the fingers substantially to their nominal position. In one example, the valve 1516 may be closed using a pull wire. In other examples, alternative means may be used to close the valve 1516, such as an electromagnetic means or a mechanically driven means.

Figure 16:
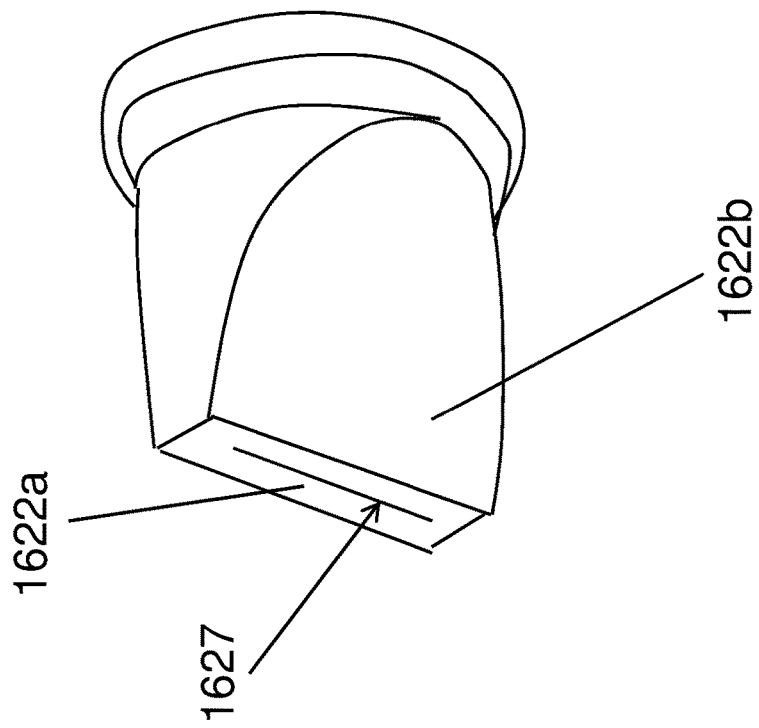
FIG. 16 illustrates a suture holder in accordance with an alternate embodiment of the present invention.
Figure 15:
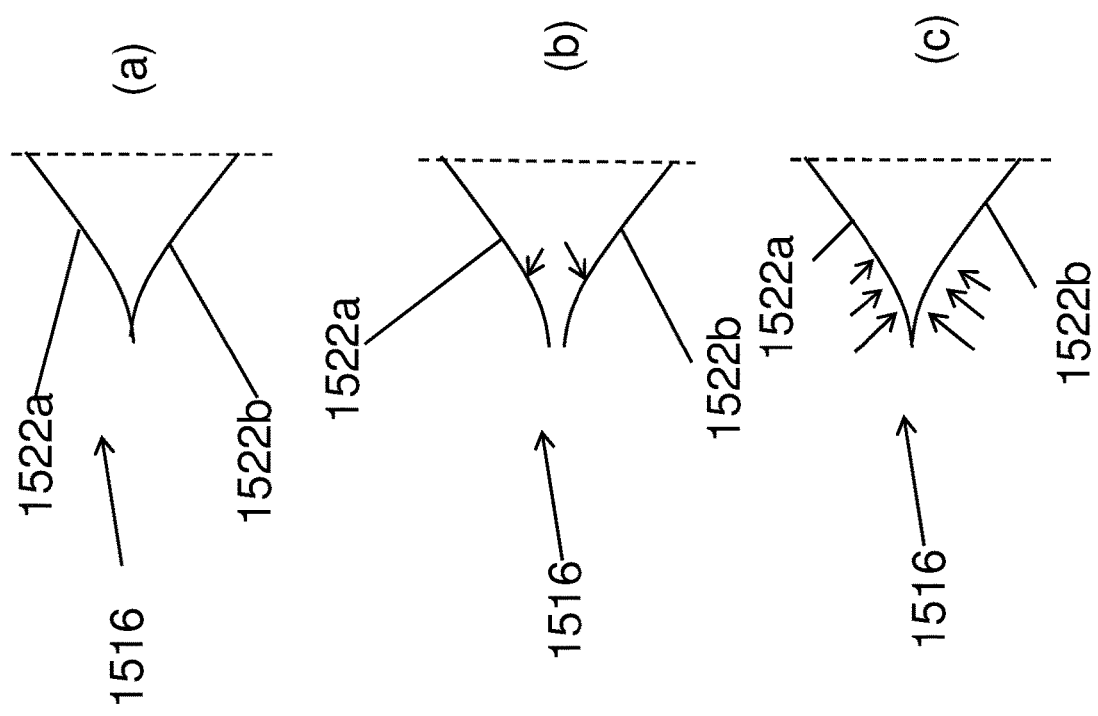
FIGS. 15(a)-(c) illustrate steps of a method in accordance with an alternate embodiment of the present invention.

In an alternate embodiment, the suture holder 316 may comprise a valve, For example, a duckbill valve 1616 as illustrated in FIG. 16. In some examples, a duckbill valve 1616 may generally comprise an elastomeric material. In other examples, the duckbill valve 1616 may comprise other materials such as plastics or metals such as stainless steel. In one example the duckbill valve comprises two fingers or flaps 1622a and 1622b that are joined together along their sides along the length of the duckbill valve 1616. A slit or opening 1627 is formed at the distal end of the valve 1616. The opening of slit 1627 is formed along the distal face of the valve, between the two fingers or flaps 1622a and 1622b.

Figure 17A:
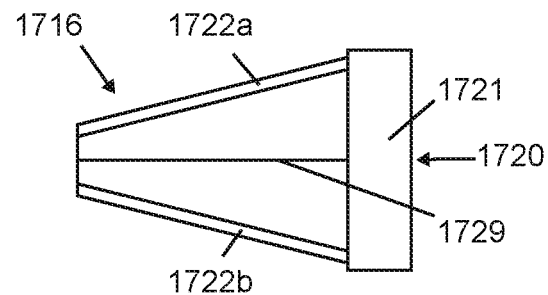
FIGS. 17a-17c illustrate steps of a method in accordance with an alternate embodiment of the present invention.
Figure 17B:
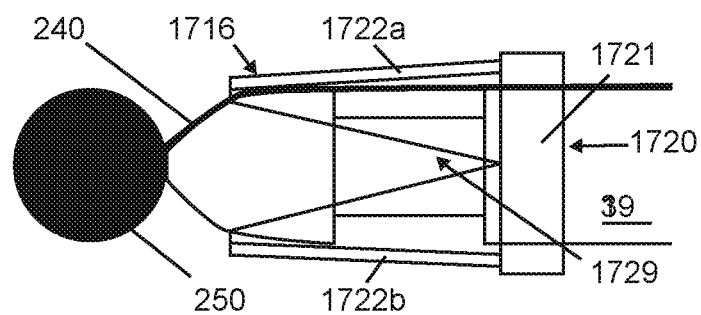
Figure 17C:
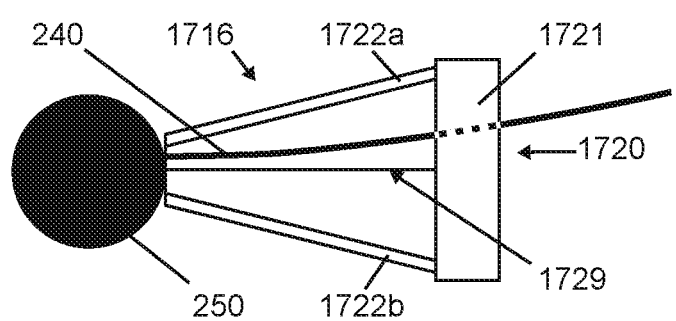

In some embodiments, the suture holder 316 comprises a valve 1716 comprising two fingers or flaps 1722a and 1722b, as shown in FIG. 17, with a longitudinally extending slot 1729 extending there-between along a portion of their length. The valve 1716 functions to allow passage of material or object there-through in a first direction, but prevents the movement or flow of the material or object there-through in a second direction substantially opposite to the first direction. In one example, the slot 1729 extends substantially along the length of the valve 1716. The two fingers 1722*a* and 1722*b* are coupled by the proximal portion 1720 of the valve 1716. In one example, the proximal portion 1720 comprises elastic properties. This allows the two fingers 1722*a* and 1722*b* to remain closed in their resting position, but allows them to open—for example to allow passage of a stylet 319 therethrough. In one specific example as shown in FIG. 17, the slot 1729 does not extend along the proximal portion 1720 of the valve 1716 and the proximal portion 1720 comprises a continuous cylindrical/tubular section that extends circumferentially about the two fingers 1722*a*, 1722*b*. In a specific example of this, the cylindrical/tubular section comprise metal and the continuous metallic cylinder that connects the first and second fingers 1722*a* and 1722*b* functions substantially like a spring. In other examples, the slot 1729 may extend substantially along the length of the valve 1716 until the proximal portion 1720. An additional component may be used at the proximal portion 1720 of the valve 1716 such as a metal ring to secure the two fingers 1722*a*, 1722*b*.

In some embodiments of the present invention, the valve 1716 may comprise a resilient material such as an elastomer, a plastic or a metal. In some embodiments, the valve 1716 may be formed from a combination of resilient and non-resilient materials. As an example of this, the valve 1716 has resilient fingers 1722*a*, 1722*b* that are coupled to a rigid metallic ring 1721 along the proximal portion 1720. The combination allows the resilient fingers 1722*a* and 1722*b* to flex, widening slot 1729 to allow passage of material/object there-through in a first direction. The rigid ring 1721 allows the fingers 1722*a* and 1722*b* to close thereafter to prevent the passage of the material/object there-through in a second direction. In an alternate example, the fingers 1722*a* and 1722*b* may comprise a rigid material and the proximal portion 1720 of the valve 1716 may comprise a resilient material. The proximal portion 1720 then functions to allow the fingers 1722*a* and 1722*b* to open to allow forward passage of material/object through the valve 1716 and to close thereafter substantially back to their resting position to prevent backward flow of the material/object there-through.

In operation the device 100 is positioned such that the valve 1716 is positioned on a distal side of the tissue. A suture passing member may then be used to pass a portion of the suture 240, such as a knot 250, from the device proximal portion to the device distal tip 12. In one specific example, the suture passing member comprises a stylet 319 that may be housed within the device proximal portion 14. In operation, the stylet 319 is advanced through a first segment of tissue and then advanced further through the valve 1716. The valve 1716 expands or opens up to allow the stylet 319 to push the knot through the valve 1716 (FIG. 15*b*). In other words a distal opening formed at the distal end of the valve enlarges as the stylet 319 is passed through. In one example, the entire body of the valve 1716 may flex to allow the stylet 319 to push the knot therethrough. As the stylet 319 is then retracted, the valve 1716 springs back substantially to its closed position as shown in FIG. 15*c*. The distal opening at the distal end of the valve closes back or in other words returns substantially back to its nominal size, thus preventing the knot 250 and suture 240 from translating proximally through the valve 1716. The nominal size is relative in scale to the size of the knot 250 and is substantially smaller that the knot 250 to prevent the knot from travelling proximally through the valve 1716.

The device 100 may then be repositioned or rotated such that a second segment of tissue is positioned within the tissue receiving gap 10. The valve 1716 may then be retrieved through the second segment of tissue that is on an opposing side of the defect using any of the embodiments as described herein above.

Figure 18A:
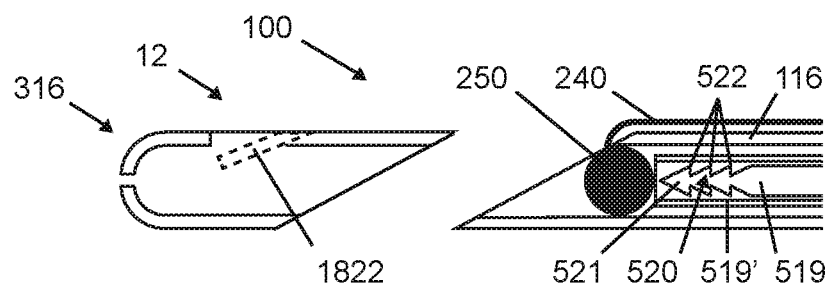
FIGS. 18*a*-18*c* illustrate steps of a method in accordance with an alternate embodiment of the present invention.
Figure 18B:
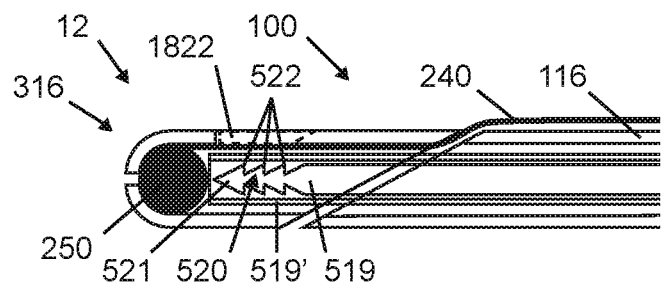
Figure 18C:
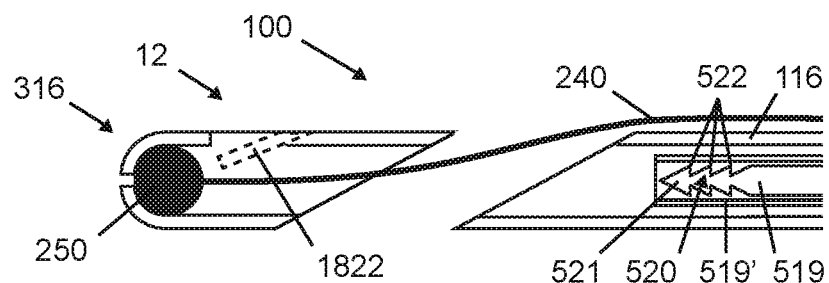

In another example as shown in FIGS. 18*a*-18*c*, a device 100 is shown for passing suture 240 through a region of tissue. The device comprises a suture holder 316 comprising a trap 1816 coupled to the device distal tip 12, the trap 1816 comprising a suture retaining component for receiving and retaining a portion of a suture 240. The portion of the suture 240 is passed from a proximal portion 14 of the device through the tissue to the device distal tip 12 using a suture passing member such as a stylet 519. The stylet 519 may be housed within the needle 116 within the device proximal portion. In one particular example the stylet 519 may be housed within an additional elongate member 519' within the hollow needle 116. The stylet 519 may be advanceable from the device proximal portion to the distal tip 12 with the elongate member 519'. The stylet 519 comprises a distal tip 520 for passing the suture portion and pushing it into the trap 1816. In some embodiments, the distal tip 520 of the stylet 519 has a sharpened tip or end 521 for carrying the suture portion. In a specific example of this, the stylet 519 is a barbed stylet additionally having one or more teeth 522 for engaging and carrying the suture portion. The sharpened end 521 and teeth 522 of the distal tip 520 allow the suture knot 250 to be translated from the device proximal portion 14 through the tissue (at a first location) to be deposited at the trap 1816 at the device distal tip 12. In some embodiments, the knot 250 may be removably secured to the stylet 319. In this particular example, the knot 250 is removably secured to the stylet 519 by spearing it using the sharpened end 521 of the stylet 519. The knot 250 may be passed from a proximal side of the tissue to a distal side of the tissue and may be held at the device distal tip 12 (FIG. 18*b*) by a suture retaining means such as suture retaining component of the trap 1816. In one example, the suture retaining component may comprise a finger 1822 within the trap 1816 which can flex to allow the stylet 519 to pass the knot 250 through the trap 1816. The finger 1822 subsequently returns to its nominal position when the stylet 519 is retracted, to trap and retain the knot 250 within the trap 1816 (FIG. 18*c*). The trap 1816 may then be retracted through tissue (at a second location different from the first location) and passed from the distal side of the tissue to the proximal side of the tissue. The trap 1816 may be retracted using a suture holder retrieving member of any of the embodiments described hereinabove to pass the suture 240 through the second tissue location. Once the suture 240 has been passed through the first and second tissue locations, the opposing free ends of the suture may be brought together and a closure knot may be provided to secure the two ends in place in order to approximate the defect.

In an alternate embodiment of the present invention a device 100 is disclosed as shown in FIG. 19A. Similar to embodiments described herein above, the device 100 has a shaft 16 that is coupled to a distal tip 12 via a longitudinally extending neck 15. The shaft 16 is a part of the device proximal portion 14. A tissue receiving gap 10 is formed between the distal tip 12 and the proximal portion 14. The distal tip 12 defines a chamber 12B for receiving a suture holder 316. Initially, the suture holder 316 is housed within the chamber 12B. The distal tip 12 defines a slot 1940. In one particular example, the slot 1940 within the distal tip 12 is an L-shaped slot that is axially and circumferentially disposed along an outer surface thereof. The L-shaped slot 1940 comprises a substantially rectangular slot 1940a that is longitudinally or axially disposed along the exterior of the distal tip 12. The rectangular slot 1940a is in communication with a substantially square slot 1940b which is disposed circumferentially along the exterior of the distal tip 12. In one particular example the suture holder 316 comprises a trap 1916 having two or more fingers 1922. In other examples a suture holder 316 may be of the type described in embodiments discussed previously herein. The trap 1916 also defines a substantially rectangular slot 1942 that is axially disposed along an outer surface of the trap 1916 as shown in FIGS. 19B and 19C. The trap 1916 is positioned such that slot 1942 of the trap is positioned substantially adjacent slot 1940a of the distal tip 12. In other words, rectangular slots 1940a, 1942 are aligned substantially co-axially with respect to each other. As shown in FIG. 19D, a needle 116 is disposed within a proximal portion 14 of the shaft 16.

Figure 19E:
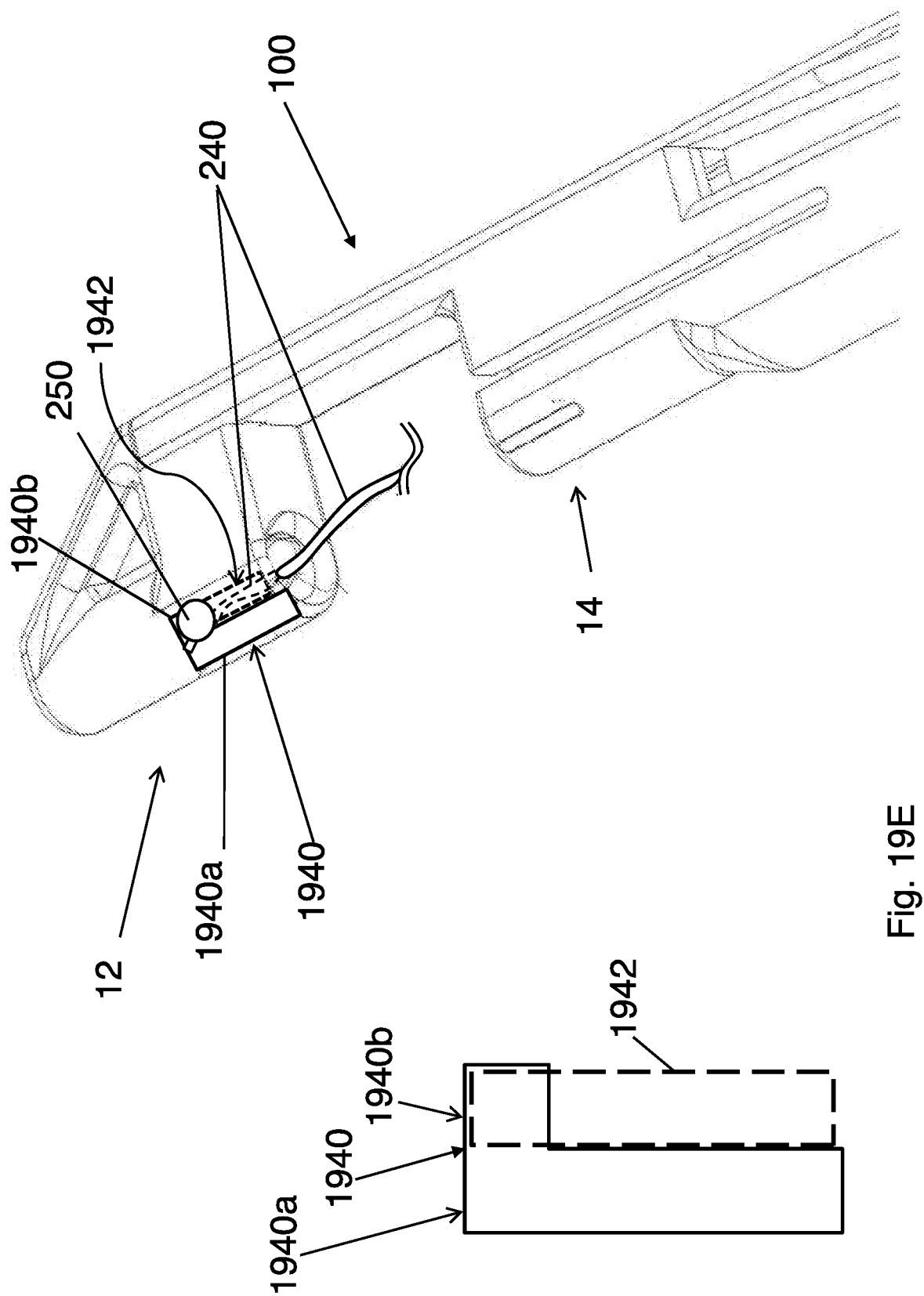

In operation, the device 100 is inserted into a region of tissue at the site of a defect. The device 100 is positioned such that a first segment of tissue on one side of the defect is positioned within the tissue receiving gap 10. The needle 116 is used to carry the suture 240 from the device proximal region 14 through the first segment of tissue to the device distal tip 12. In one particular example, the needle 116 comprises a notch or slot 117 in which the suture strand 240 is detachably secured, where the suture strand 240 comprises a knot 250 at its distal end. The needle 116 is advanced from the device proximal portion 14 to the distal tip 12. In some embodiments the needle 116 may be sized to be received within the trap 1916 and may be used to transfer the suture 240 held within notch 117 to be transferred to slots 1940, 1942. In other embodiments, the needle 116 carries the suture 240 through the first segment of tissue and is advanced further until it abuts the trap 1916. A stylet 319 is housed within the needle 116 and is used to deposit the suture 240 within the distal tip 12. The stylet 319 is translated distally until it is received within the trap 1916. The stylet 319 pushes the knot 250 such that it passes through slots 1940a, 1942 as shown in FIG. 19D. More specifically, the suture 240 is positioned within slot 117 within the needle 116 such that the knot is placed outside the needle 116. Slot 117 of the needle 116 is aligned with slots 1940, 1942 of the distal tip 12 and the suture holder respectively, such that when the needle 116 is advanced and abuts against the trap 1916, the stylet 319 advances the suture 240 into slots 1940,1942. Thus, the knot 250 of the suture 240 is carried by the needle 116 and then advanced into the trap 1916 and into slots 1940a, 1942 using the stylet 319, such that it rests on the outside of the distal tip 12. The stylet 319 is advanced further until the knot 250 is positioned at a distal end of each of the slots 1940a and 1942. The trap 1916 is then rotated clockwise for example using the stylet 319 or the needle 116 (similar to embodiments described herein previously). A mechanism may be provided within the device proximal portion 14 that that allows rotation of the needle 116 or the stylet 319. Clockwise rotation of the trap 1916 allows slot 1942 to be translated radially. This allows slot 1942 of the trap 1916 to now be aligned with the substantially square slot 1940b of the distal tip 12, trapping or locking the knot 250 within slot 1940b, as shown in FIGS. 19E and 19F. The knot is held within slot 1940b and rests against/abuts a proximal wall of the slot 1940b. This prevents knot 250 from translating proximally. The needle 116 and stylet 319 are then retracted.

The device 100 is then rotated and repositioned such that a second segment of tissue is positioned within the tissue receiving gap 10. The needle 116 and the stylet 319 are then re-advanced through the second segment of tissue until the needle 116 abuts against the trap 1916. The stylet 319 is then advanced further until the tip of the stylet 319 is positioned distal to the trap and the stylet 319 engages with the trap 1916. The stylet 319 is then rotated counterclockwise to transtate slot 1942 radially such that it is aligned again with slot 1940a of the distal tip 12. The knot 250 not longer abuts the proximal wall of slot 1940b and is free to move proximally within the slots 117,1942, of the needle and the trap respectively Thus, the stylet 319 is then retracted to withdraw the trap 1916 along with knot 250, as shown in FIG. 19G. This allows suture 240 to be passed through the second segment of tissue. The suture 240 can then be used to approximate the defect.

Embodiments of Devices for Deploying a Suture Knot

In another broad aspect of the present invention, device 100 includes features for deploying a suture knot, such as a partially pre-tied suture knot, as illustrated in various embodiments shown in FIG. 21-27. Some embodiments of device 100 comprise a retaining element that is coupled to the device 100 for retaining a portion of the suture during at least a part of the knot deployment procedure.

Features for Directly Coupling a Partially Pre-Tied Knot onto the Device

Figure 21A:
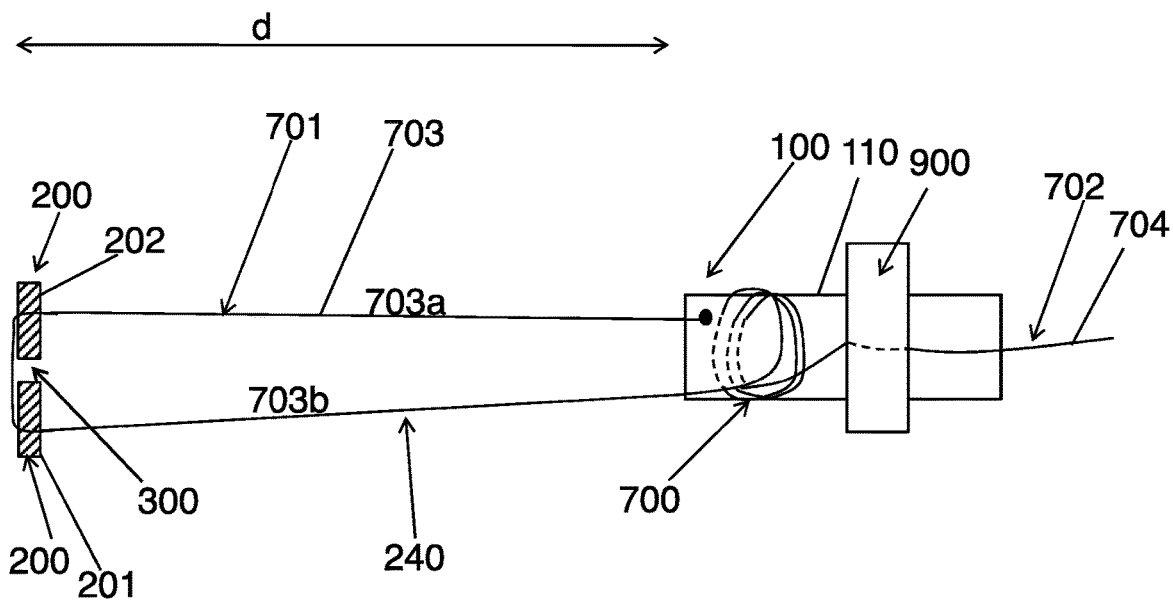
FIGS. 21*a*-21*e* illustrate a device and method in accordance with an embodiment of the present invention.

In particular as shown in FIG. 21a, in some embodiments, the device comprises an elongate member 110 having a retaining or tensioning element 900 disposed thereon. In some embodiments, in addition to deploying a suture knot, the device 100 may also be used to pass a suture 240 through a region of tissue 200 prior to deploying the knot. For example, device 100 may be used to pass suture through first and second segments, 201, 202 of a region of tissue 200 having a defect 300, as described herein. In other embodiments, another device may be used to pass the suture 240 through the region of tissue 200 and device 100 is used to deploy a suture knot.

In the illustrated embodiment, a suture 240 is formed into one or more loops 700 around the elongate member 110. In one particular example, the retaining or tensioning element 900 may be coupled to the device 100 proximal (relative to a user) to a location of the one or more suture loops 700. A first portion 701 of the suture 240 extending from the one or more loops 700 is coupled to a distal end of the device 100. In one particular example, the first portion 701 defines a post 703. Segment 703a of the post 703 generally extends from the tissue 200, specifically segment 202 of the tissue, to the device 100 where it is coupled. Whereas, segment 703b extends from the tissue 200, specifically segment 201 of the tissue, to the loops 700 of the suture 240. During use, the lengths of each of the segments 703a, 703b may vary at various points during the procedure. A second portion 702 of the suture 240 extends from the one or more loops 700 and interacts with the retaining or tensioning element 900, the second portion 702 being substantially longitudinally opposed (i.e. if the suture were to be released from the device and, for example, straightened out, portion 702 would be substantially longitudinally opposed to portion 701) to the first portion 701. In one specific example, the second portion 702 of the suture 240 forms a locker 704. In one specific example, the second portion 702 is passed under the retaining or tensioning element 900 and is held in frictional engagement between the retaining or tensioning element 900 and the elongate member 110. In other embodiments, the suture 240 may be routed and retained in other ways through the retaining or tensioning element 900. In alternate embodiments shown in FIGS. 24 and 26, the loops 700 of the partially pre-tied knot may be formed onto a portion of the shaft 16.

Figure 24:
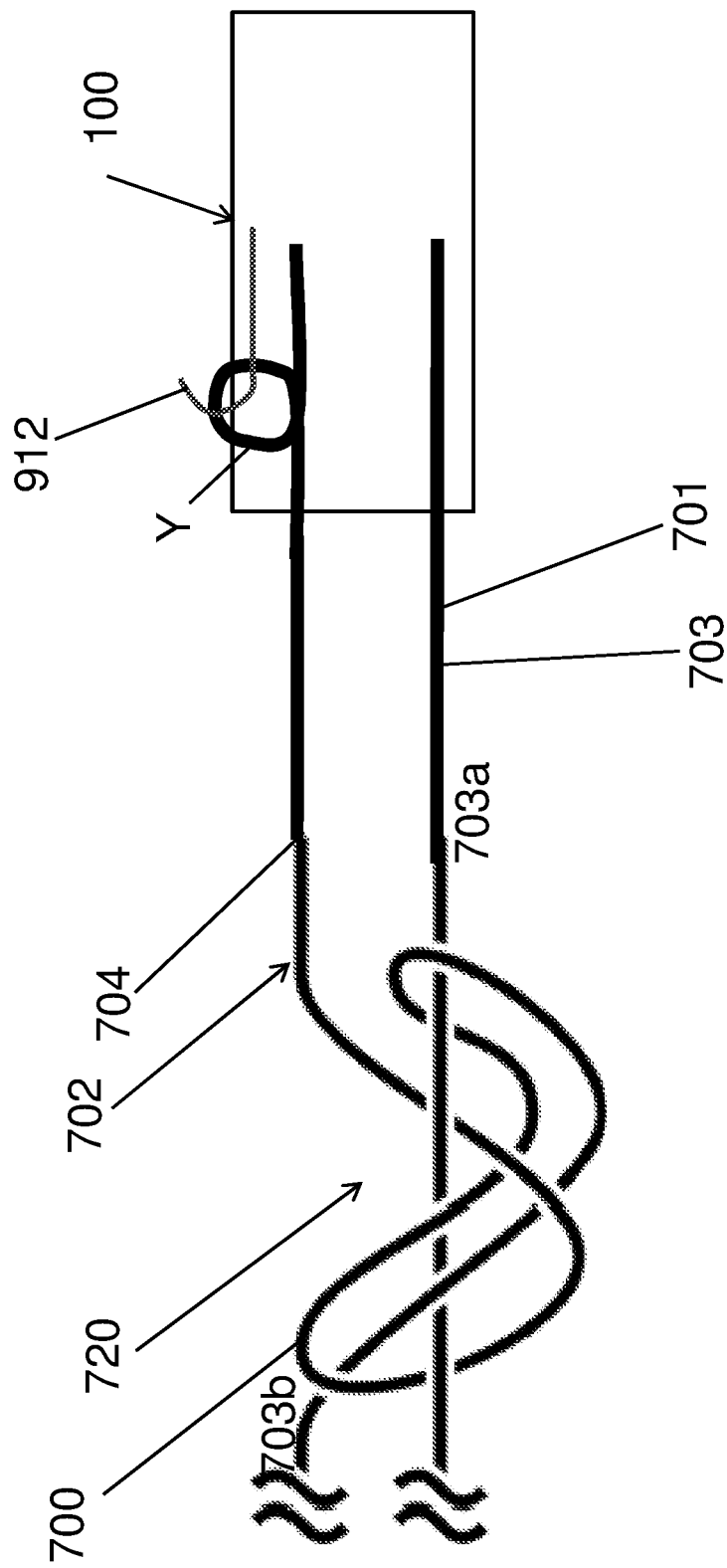
FIG. 24 illustrates a device and method in accordance with an alternate embodiment of the present invention.

Alternative Embodiment of a Device for Deploying a Knot, the Device Comprising a Retaining or Tensioning Element in the Form of a Resilient Spring Member In an alternate embodiment the retaining or tensioning element may comprise a resilient spring member 912 as shown in FIG. 24. The device 100 is illustrated after loops 700 of the pre-tied knot have been deployed from the device 100 onto the post 703 of the suture 240 forming a Dines knot 720 as the post 703 is pulled through the loops 700. Similar to embodiments discussed previously, the first portion 701 of the suture 240 forms the post 703 and the second portion 702 of the suture 240 forms the locker 704 with the post comprising segments 703a and 703b. The locker 704 is held in tension by the resilient spring member 912 that is coupled to the device 100. In one specific example, the resilient spring member 912 may be hook-shaped. The locker maybe formed into a loop Y, and the loop Y may held in engagement by the resilient hook-shaped member 912 that passes through the loop Y.

In an alternate embodiment, the retaining or tensioning element 900 for holding the second portion 702 of the suture such as the locker 704, may include interlocking mechanical pieces. In one example the retaining or tensioning element 900 may comprise two interlocking mechanical pieces, whereby a first mechanical piece is coupled to the locker 704 and maintains tension on it. In other words, the retaining or tensioning element 900 provides resistance against the movement of the locker 704. The retaining or tensioning element may provide a frictional force against the locker 704. The first mechanical piece interacts with the second mechanical piece (i.e. the two pieces are co-operatively engaged with each other).

Features for Indirectly Coupling a Partially Pre-Tied Knot on the Device

Figure 22A:
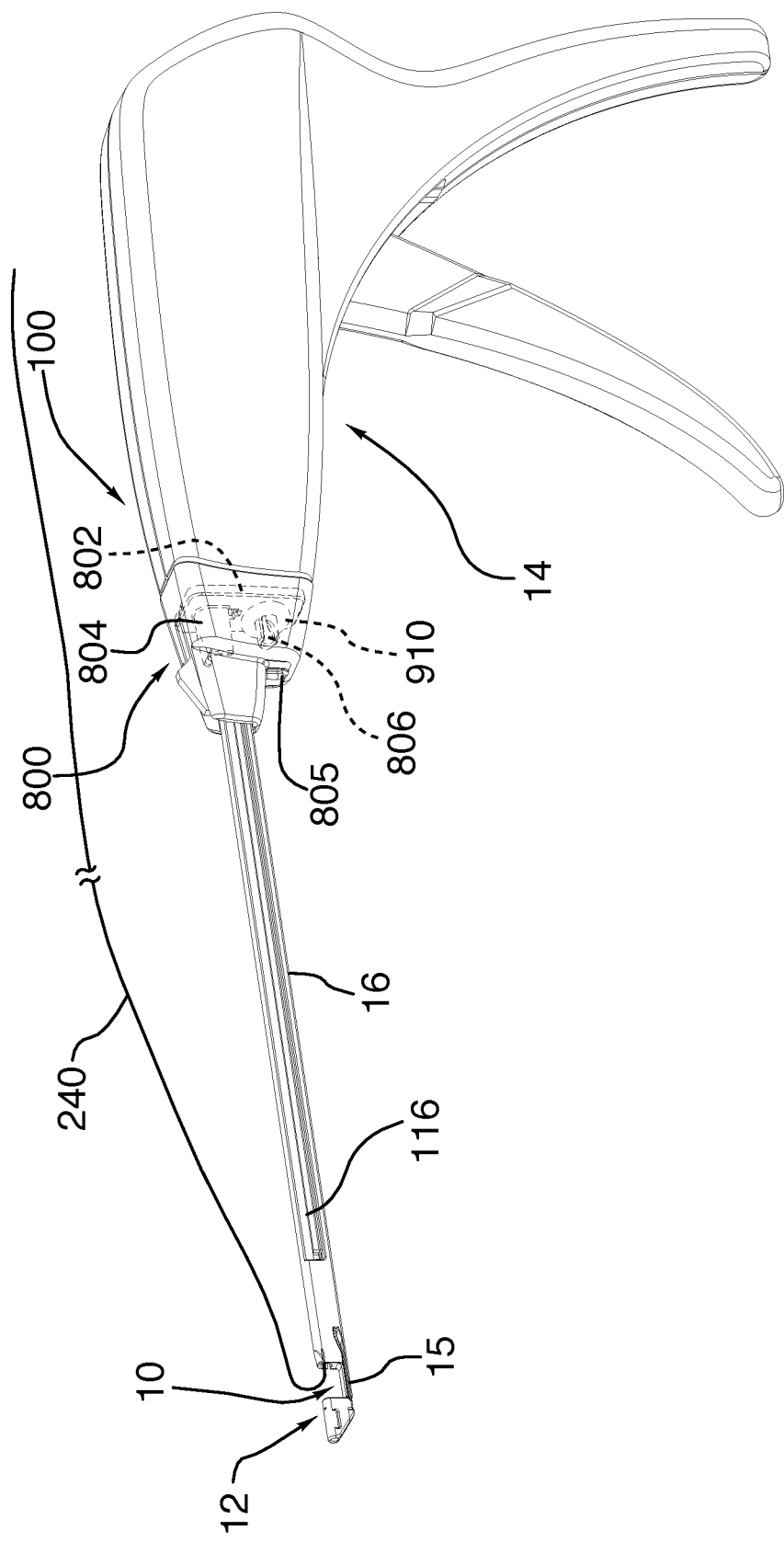

Features outlined herein below will be described with respect to a device 100 is disclosed as shown in FIG. 22a which of the type described hereinabove with respect to FIGS. 1, 4-6. The device 100 has a shaft 16 that is coupled to a distal tip 12 via a longitudinally extending neck 15. The shaft 16 is a part of the device proximal portion 14. A tissue receiving gap 10 is formed between the distal tip 12 and the shaft 16. A needle 116 is housed within the device proximal region 14 and one portion of a suture or a suture strand 240 is coupled to the device 100, for example to the needle 116. In some embodiments, the suture 240 may be secured within the needle 116 for example in proximity to the needle tip. In a specific example of this, the suture 240 may be formed into a knot and retained within a slot within the needle tip.

The suture 240 may be formed/arranged into one or more loops 700 wrapped around a portion of the shaft 16. In other words the suture 240 may be formed into a partial or fully pre-tied knot. In one broad aspect, embodiments of the present invention provide a means is provided for indirectly coupling the loops 700 of the partially or fully pre-tied knot onto the device 100. In other words, a partially or fully pre-tied knot is provided without coupling or tying the loops 700 of the partially pre-tied knot directly onto the device 100. In one such example, as shown in FIGS. 22a-22g the one or more loops 700 of the partially or fully pre-tied knot are formed around a knot slider 800 that is mounted on the shaft 16 and detachably coupled thereto. In one specific example, the loops 700 are wrapped around the exterior of the knot slider proximal to a flexible arm 818 of the knot slider 800. The arm 818 is shown in its initial position in FIGS. 22c and 22d (*iii*). In its first position 818A, the arm 818 prevents the loops 700 from sliding off the knot slider 800 and thus serves as an obstructing member 818.

Figure 22C:
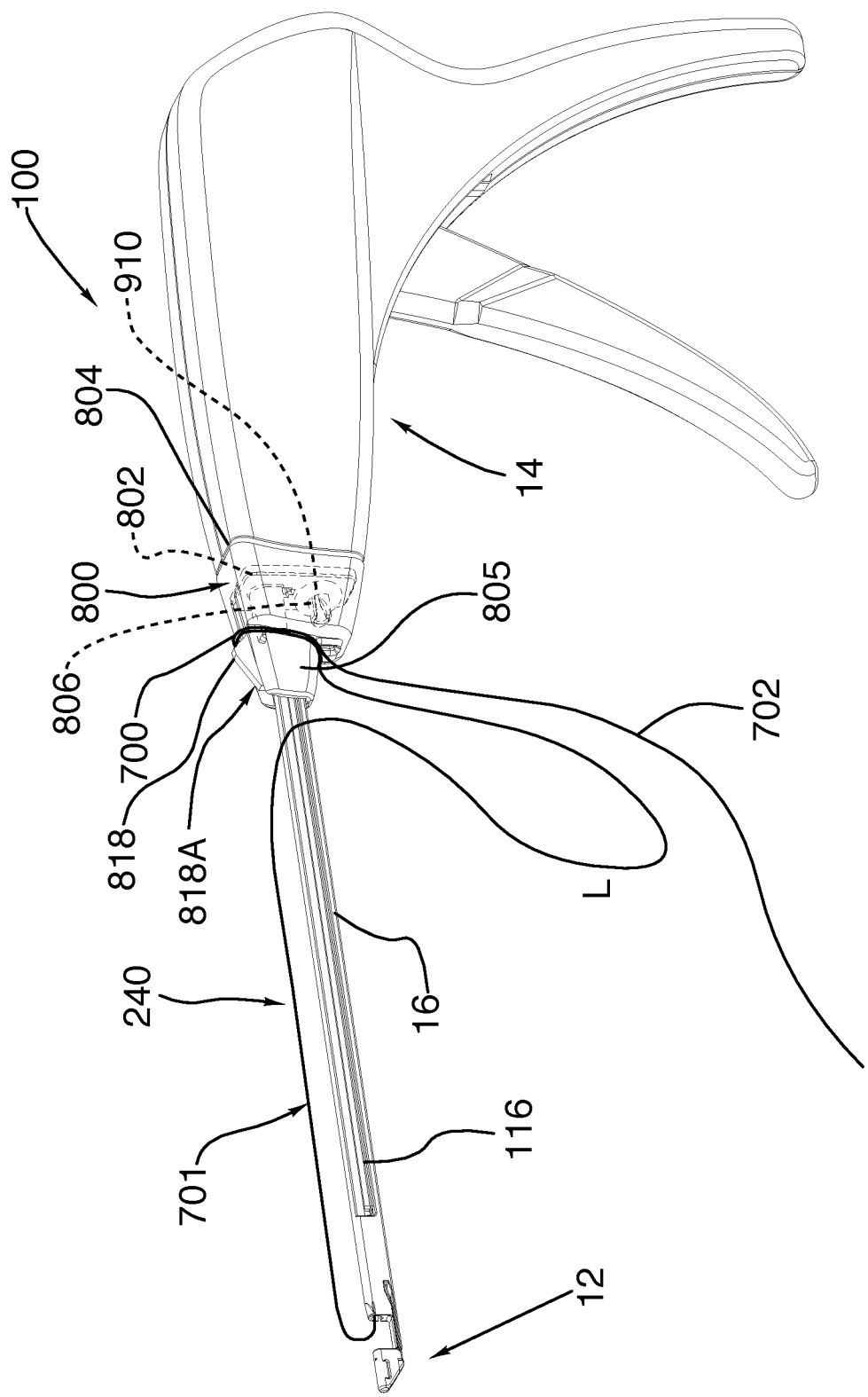

With respect to FIG. 22c, the suture 240 exits the needle 116, extends proximally and forms a service loop L. The suture 240 is then arranged into the one or more loops 700 around a portion of the knot slider 800. The portion of the suture 240 coupled to the needle 116 distal to the loops 700 may be termed a first portion 701 of the suture 240. A substantially longitudinally opposed second portion 702 of the suture 240 extends proximally from the suture loops 700. In one specific example, the second portion 702 of the suture 240 forms a locker, or knot locker. In one specific example the first portion 701 of the suture 240 defines a post.

Figure 22D:
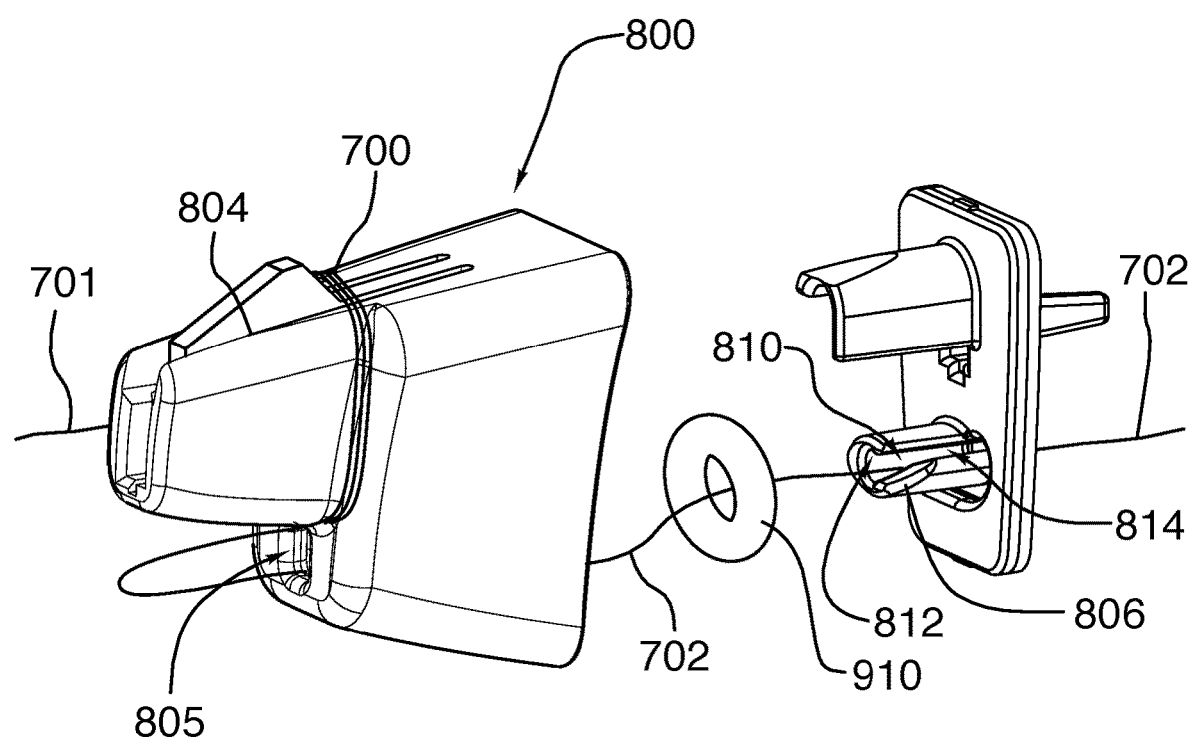

In a specific example, as shown in FIG. 22d (*i*) the knot slider 800 comprises an inner slider body 802 and an outer slider body (or external knot slider) 804. The inner slider body 802 comprises a substantially cylindrical projection 806. The projection 806 defines a lumen 810 and a distal opening 812. A longitudinally extending slot 814 runs substantially along the length of the projection 806 and is in communication with distal opening 812 and lumen 810. Additionally, a partially circular slot 816 is formed into the inner slider body 802 at the base of the projection 806 and partially surrounds projection 806 as shown in FIG. 22d(*ii*), showing a rear view of the knot slider 800. A boundary or edge 817 defines the slot 816. The slot 816 is in communication with slot 814 as well the device lumen 810 also shown in FIG. 22d(*iii*), showing a rear perspective view of the knot slider 800. In some embodiments, a retaining or tensioning element is mounted onto the projection 806. In some examples the retaining or tensioning element comprises a resilient material such as an O-ring (an "elastomeric ring") or a short section of tubing. In the particular embodiment shown in FIGS. 22a-22h, the retaining or tensioning element comprises an O-ring 910. In one particular example, a retention force applied by the O-ring 910 may comprise the force of friction. In some embodiments the retention force may be varied by changing the normal force and by changing the coefficient of friction (which may be altered by changing material properties or surface roughness).

As mentioned previously, the loops 700 are formed onto the knot slider 800, and the first and second portions 701, 702 of the suture 240 extend from the loops 700, as shown in FIG. 22c. In some embodiments a segment of the second portion 702 of the suture 240 may be restrained or substantially held in place by the retaining or tensioning element (such as the O-ring 910). In other embodiments the retaining or tensioning element, (such as the O-ring 910) may be used to secure both the first and second portions, 701, 702 of the suture 240. In the exemplary embodiment, shown in FIGS. 22d (*i*)-(*iii*), the second portion 702 of suture 240 is passed through an opening 805 within the external knot slider 804 and into the opening 812 formed within the projection 806 of the inner slider body 802. The suture 240 is then passed through lumen 810 of the projection 806. In order to secure the suture portion 702 using the O-ring, the suture 240 may then be guided in the direction G along slot 816 as shown in FIG. 22d (*iv*) such that it is held by the O-ring 910 and is pinched between the projection 806 and the O-ring 910.

Figure 22E:
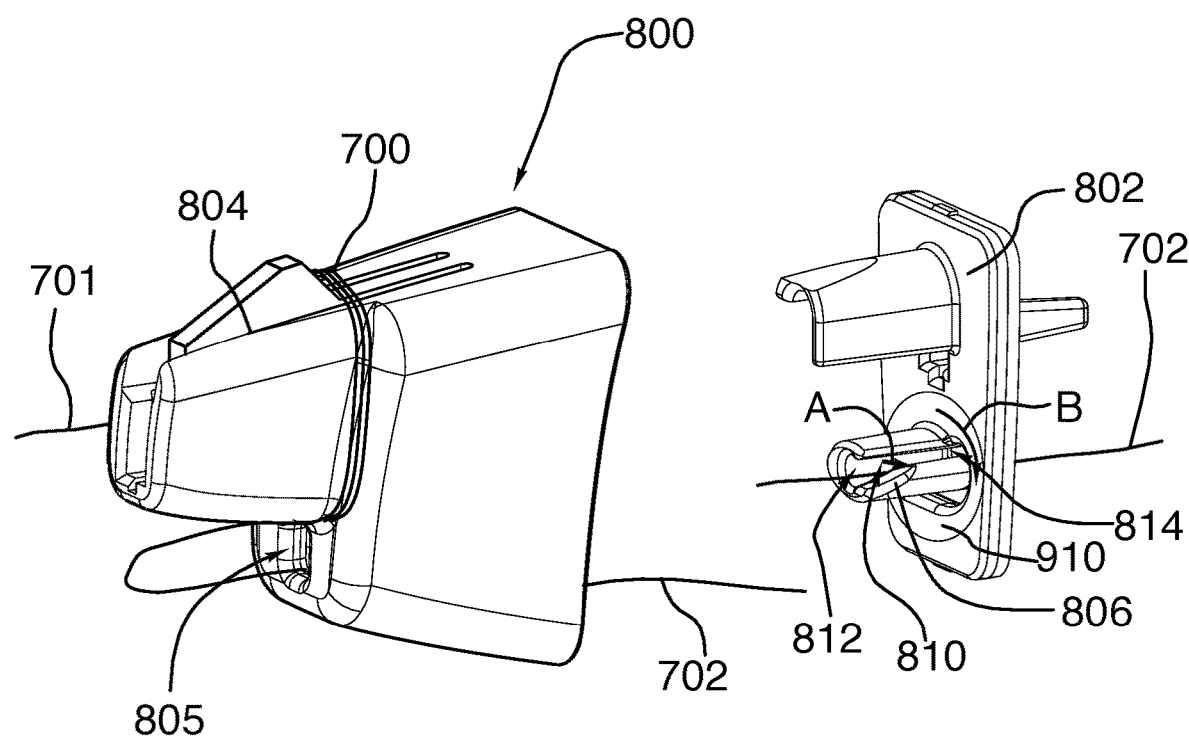
Figure 22F:
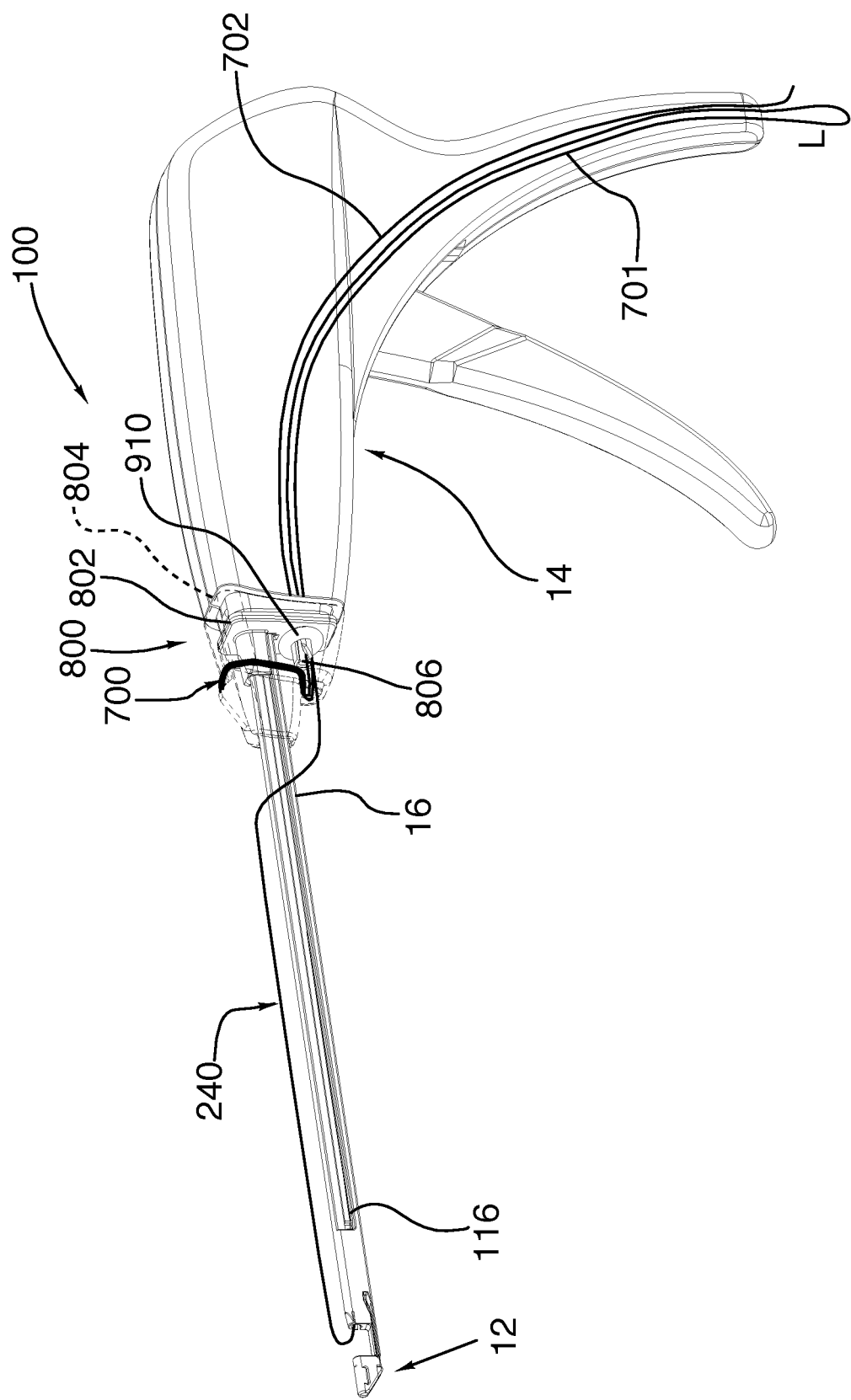

This is further illustrated in FIG. 22e, where the suture 240 is guided laterally outwards (as shown by directional arrow A) such that it exits from the longitudinally extending slot 814). The suture 240 may then be guided in a circular motion (as shown by directional arrow B) through the slot 816 such that it is positioned between the projection 806 and the O-ring 910. The resilient O-ring 910 substantially holds or restrains the second portion 702 of the suture 240 by applying a force to maintain tension on it. Specifically, the O-ring functions to maintain tension on the second portion 702 of the suture by frictionally engaging it. In addition to holding the second portion 702, the suture retaining element such as O-ring 910 can hold one or more other portions of the suture 240, such as the service loop L of the suture first portion 701. In one such example, the service loop L of the first portion 701 may be passed through the O-ring together with the second portion 702 in the manner described above. Once passed through the O-ring, both the service loop L of the first portion 701 and the second portion 702 may be routed through the device proximal portion 14, for example through tubing as shown in FIG. 22f. In one such example, the O-ring functions to keep the service loop L taut to allow one end of suture portion 701 to remain coupled to the needle 116 housed within the device shaft 16. In a specific example, the suture portion 701 is coupled to the needle tip via a knot formed at the end of the suture portion 701. The O-ring helps to keep the suture portion 701 taut to retain the knot within a slot within the needle tip.

Features for Controlled Deployment of a Partially Pre-Tied Knot

In one broad, embodiments of the present invention provide a means to allow for a controlled deployment of a partially or fully pre-tied knot. As a feature of this broad aspect, a knot slider is provided that is coupled to the shaft/handle of the device via a releasable coupling. As a further feature of this broad aspect, a means is provided to prevent the partially or fully pre-tied knot from sliding until a predetermined force is applied to the releasable coupling.

Figure 22G:
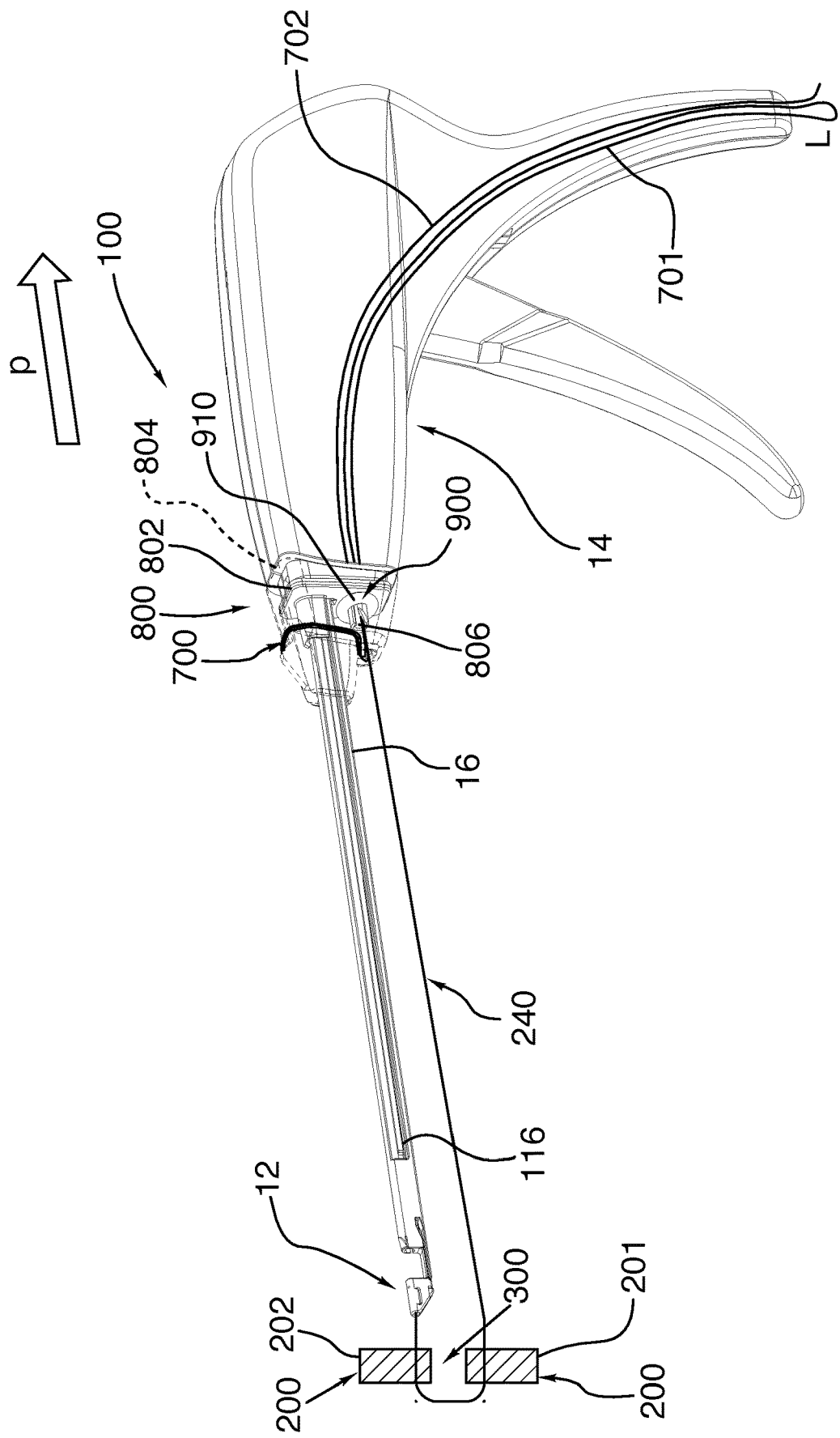
Figure 22I:
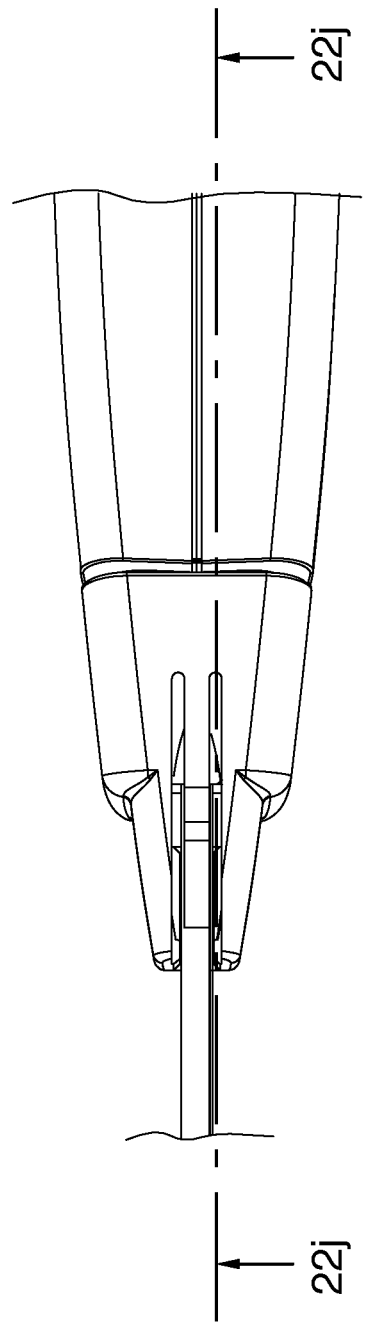
Figure 22J:
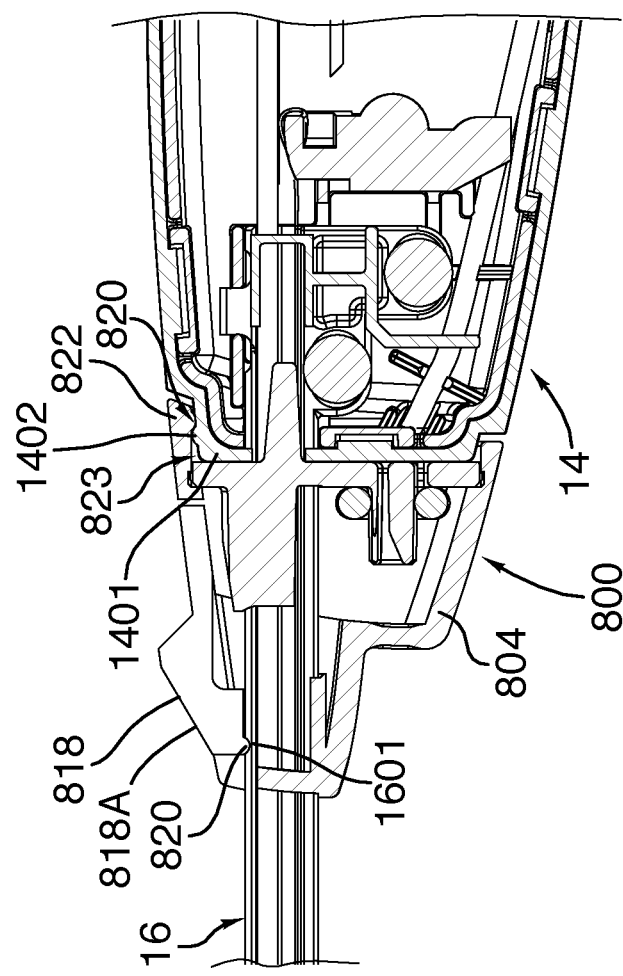

Feature for Releasably Coupling Knot Slider
Detachable Coupling Using a Projection on the Arm In one specific example, the shaft 16 of the proximal portion 14 comprises a notch or a recess 1601, as shown in FIG. 22j, which co-operatively engages with a projection 820 on the knot slider 800. In one example, a projection 820 is formed on the flexible arm 818 of the outer slider body 804, which co-operatively engages with recess 1601 in order to detachably couple the knot slider 800 to the shaft 16. In some embodiments, the projection 820 may be formed at any other suitable location on the knot slider 800. In other embodiments, a projection may be formed on the shaft 16 that may engage a recess within the knot slider 800. Alternatively, any other engagement mechanism may be provided that allows the knot slider 800 to be detachably coupled to the device 100.

Detachable Coupling Using Projections on the Slider and Device Proximal Portion

In one specific example, as shown in FIGS. 22i and 22j, the projection 820' may be formed within a portion 822 of the outer slider body 804 that defines a hollow cavity 823. Portion 822 of the knot slider 800 is then mounted onto a raised segment 1401 of the device proximal portion 14. In other words, the raised segment 1401 of the device proximal portion 14 is received within the hollow cavity 823 defined by the knot slider 800. In one example, the raised segment 1401 is formed onto a handle body forming a part of the device proximal portion 14. An additional projection 1402 is formed on the raised portion 1401. When the knot slider 800 is mounted onto the raised portion 1401, the projection 1402 of the device proximal portion and projection 820' of the knot slider form a snap-fit engagement for detachably coupling the slider 800 to the device proximal portion 14. This may help ensure that the knot slider 800 remains in its proximal position during shipment and/or handling of the device and during use, until such as time as is desired for the knot slider 800 to be released from its proximal position.

Passive Coupling Between the Knot Slider and the Device Proximal Portion

Figure 22K:
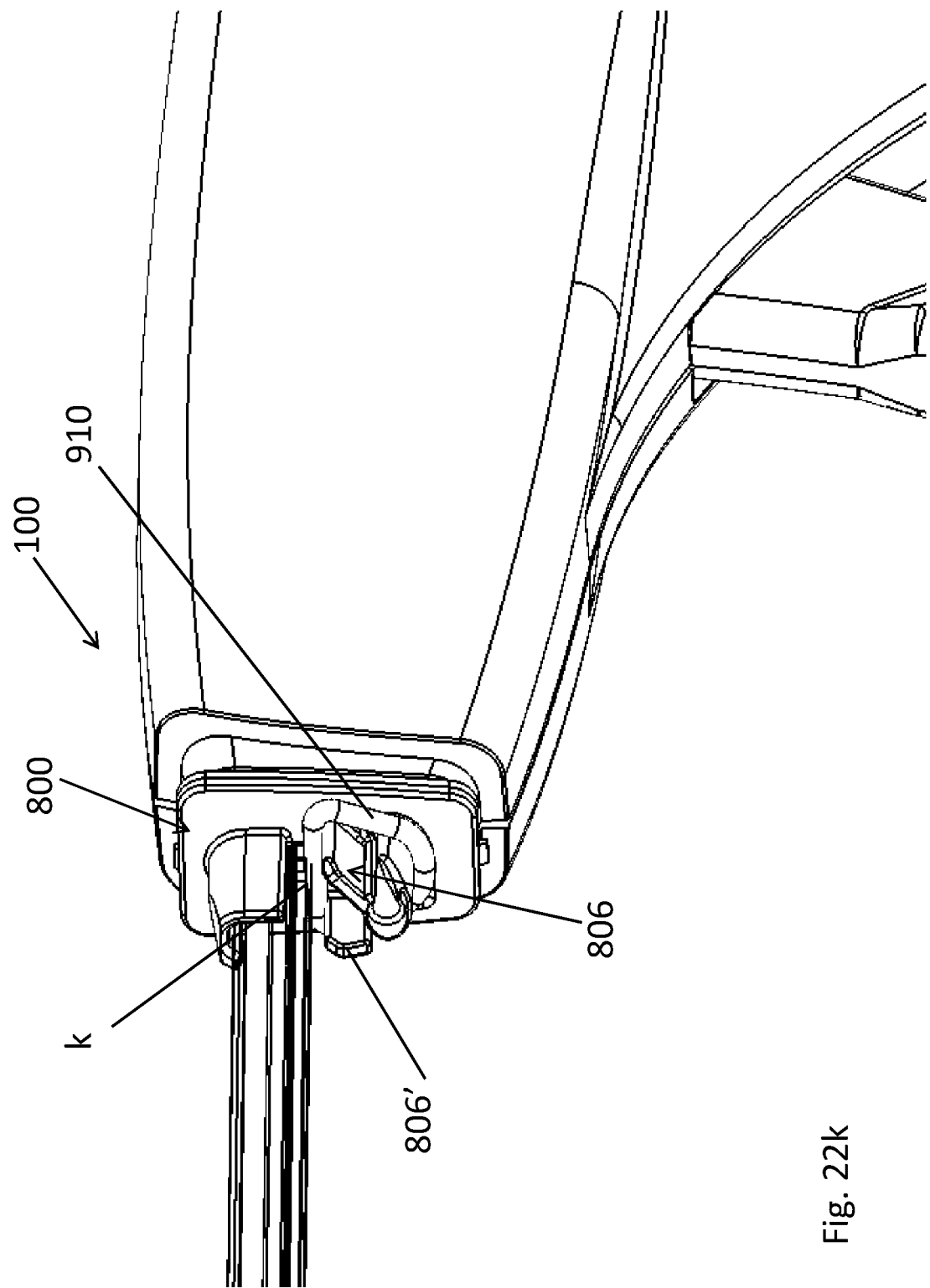

In one specific example as shown in FIG. 22k, the knot slider 800 is passively coupled to the shaft 16 of the device 100. The O-ring 910 is mounted onto the projection 806 and an additional projection 806', as shown. The shaft 16 presses into O-ring to deflect the O-ring. Thus, there is contact between the O-ring and the shaft 16. The knot slider 800 is passively coupled to shaft 16 via interference or frictional engagement between the O-ring 910 and shaft 16. The frictional engagement between the O-ring and shaft 16 is sufficient to prevent premature deployment or disengagement of the knot slider 800 from the shaft 16.

Features for Deploying a Partially Pre-Tied Knot Distal to the Device

In another broad aspect, embodiments of the present invention provide features for deploying a partially pre-tied knot distally off of the device. As a feature of this broad aspect, embodiments of the present invention provide a means to prevent loops of the partially pre-tied knot from getting caught within the device (for example within a tissue receiving gap of the device) prior to deployment. As an example of this feature, a knot slider is provided that is detachably coupled to the device that slides to a distal position to cover the tissue-receiving gap, with the loops being released once the gap is covered to prevent the loops from being engaged within the gap. The knot slider prevents the loops from sliding off until it is in its distal position over the gap at which point the knot slider allows the loops to be deployed or released. In one particular example, the knot slider has a flexible arm that blocks/prevents the loops from sliding off until the slider is in its distal position over the tissue receiving gap, at which point the arm can bend into the tissue receiving gap allowing the loops to slide off the knot slider. In a further example, the arm and the knot slider have tapers to facilitate sliding of the suture.

Stopping Mechanism for Positioning Knot Slider in its Distal Position
Stopping Mechanism Comprises a Tail Hook on the Knot Slider As the knot slider 800 translates distally along the shaft 16, a stopping mechanism may be provided to allow the knot slider 800 to be positioned over the tissue receiving gap 10. In this distal position, Since, the knot slider 800 covers the tissue receiving gap 10 in this distal position, it prevents the loops 700 from being released within the tissue receiving gap 10 and getting stuck therein. In one embodiment, the knot slider 800 comprises a tail hook 824. In a specific example, the tail hook 824 is a part of the inner slider body 802. The tail hook 824 is operable to slide along a recess or groove 1603 that runs along a portion of the shaft 16, as shown in FIG. 23b (i). When the tail hook 824 reaches the end of the recess or groove 1603, further distal translation of the knot slider 800 is impeded. The tail hook 824 abuts against or engages a portion of the shaft 16, allowing the knot slider 800 be positioned in its distal position over the tissue receiving gap 10. The tail hook 824 stops the knot slider 800 in the correct position so the flexible arm 818 is lined up with/adjacent the tissue gap 10, so that it can be deflected into the tissue receiving gap 10 when tension is applied to the suture 240, to allow the loops 700 to be released. Furthermore, the tail hook 824 may additionally prevent the knot slider 800 from falling off the shaft 16.

Stopping Mechanism Comprises a Snap

In other embodiments, alternative means of stopping distal translation of the knot slider may be provided. In one example, a snap or snap arm may be provided instead of a tail hook to allow the knot slider 800 to stop in the desired distal position. The snap may be actively biased towards the shaft and may comprise an engaging feature that clips or grabs onto the shaft with a biasing force. As the knot slider 800 translates distally along the shaft, the snap rides along the shaft until it reaches the tissue receiving gap and is deflected therein (or snaps into the tissue gap) because of the bias. As a result, the snap abuts/stops against the proximal face of the distal tip 12. In one particular example, two snaps or snap arms may be provided to mitigate the risk of one of the snaps interfering with the taut segment 703a of suture portion 701 that is running across the tissue receiving gap 10. This allows at least one of the snaps to be deflected into the tissue receiving gap 10 to stop the knot slider 800 in its desired distal position.

Features Allowing Loops to be Released

A Deflectable Flexible Arm

As described hereinabove, the loops 700 are held in place by the arm 818 which prevents them from sliding off. The flexible arm 818 has been positioned against and rests against the shaft 16 until the knot slider 800 is in its distal position. During the time that the arm 818 is in its initial position 818A, it cannot bend inwards due to hindrance created by the shaft 16. However, when the knot slider is in its distal position, the inward motion of the flexible arm 818 is no longer blocked by the shaft 16, as the flexible arm 818 is now positioned adjacent the tissue receiving gap 10. Therefore, as the device 100 is pulled, continued tension on the suture 240 causes the flexible arm 818 to bend or deflect inwards into the tissue receiving gap 10 into its second or bent position 818B, as shown in FIG. 23b(ii). The loops 700 are no longer substantially blocked by the arm 818 and are free to slide distally off the arm 818. In one example as shown, the arm 818 of the knot slider 800 is angled or tapered, which facilitates the removal of the loops 700 by allowing them to slide along the tapered surfaces of the arm 818. In a specific example, as shown, the arm 818 is of substantially a triangular shape comprising both a distal taper and a proximal taper. In some embodiments, the arm 818 may be actively biased and once the arm 818 is located adjacent the tissue receiving gap 10, in the absence of any obstruction/hindrance created by the shaft 16, the arm 818 moves inwards towards its biased position such that it is positioned within the tissue receiving gap 10. In some embodiments, as the arm 818 may be sized to allow the arm to deflect into its second position distal to the device distal tip 12. In other words, instead of the arm 818 being deflected into the tissue receiving gap 10, the arm 818 is deflected into the space distal to the device 100. In some embodiments, an automatic mechanism may be provided for the release of the loops 700. In one such example, the loops 700 may be released when the user presses a button. Alternatively, in some embodiments, the loops 700 may be released by an additional squeeze of a trigger, such as a third squeeze of the trigger.

Taper on the Knot Slider

Figure 23A:
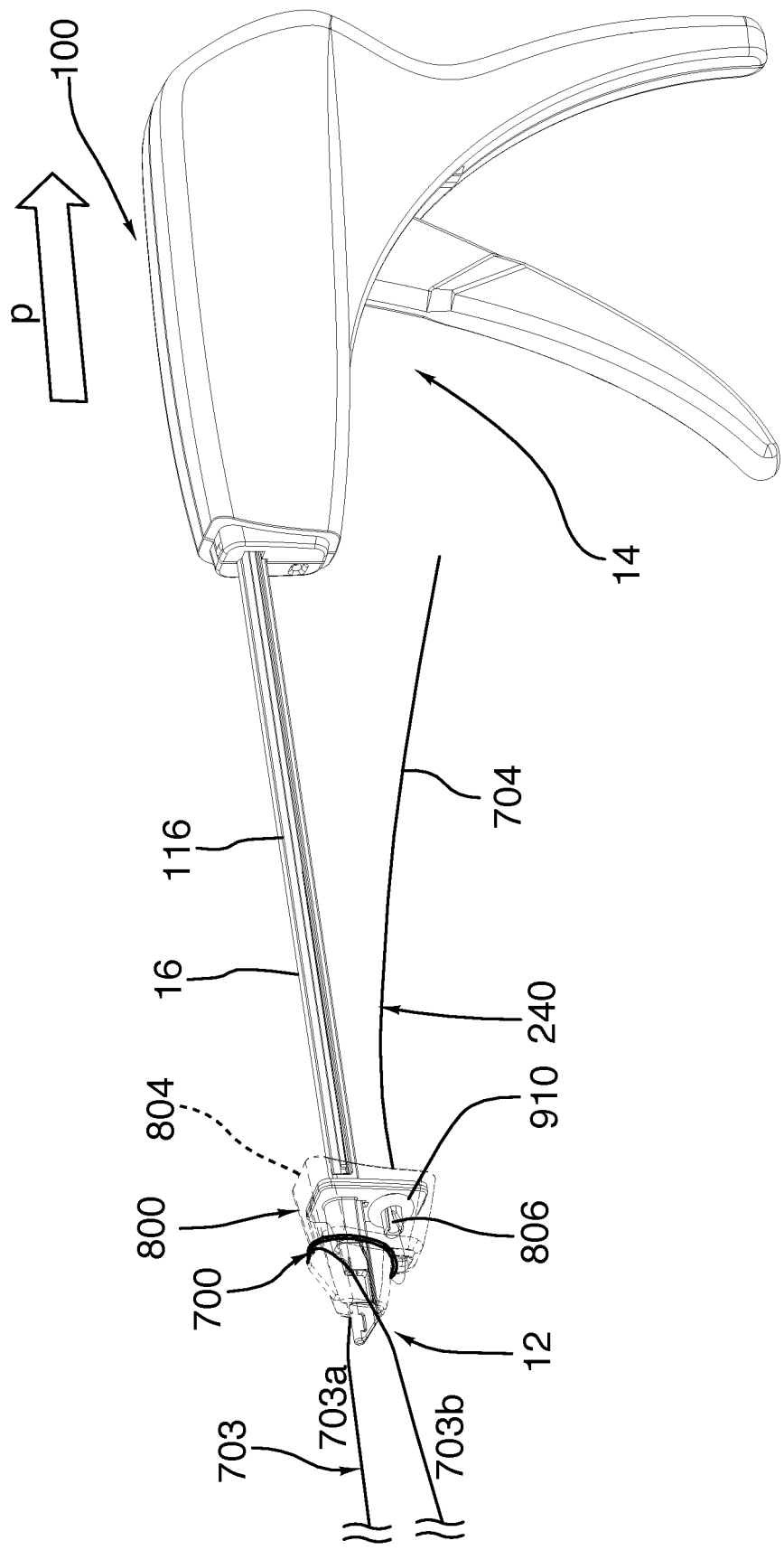

Additionally, in some embodiments, the knot slider 800 along a portion thereof is also angled and tapers down towards its distal end, In other words, the knot slider 800 reduces in diameter from its proximal end to its distal end. In some embodiments, the knot slider 800 may comprise a downward step between tapered portions thereof. Since, the loops 700 are wrapped around the knot slider 800 and thus constrict around it, the downward taper of the knot slider 800 may allow the loops 700 to be released/slide off with relative ease. Furthermore, the downward taper of the knot slider 800 may prevent the loops 700 from getting caught on (or gripping/binding to) the knot slider 800 and thus may allow the loops 700 to be released. In some embodiments, the distal direction is defined as the direction along the longitudinal axis of the device 100 away from the user, and the proximal direction is defined as the direction along the longitudinal axis of the device towards the user. Additionally the top of the knot slider 800 is defined as the side of the knot slider 800 where the arm 818 is positioned, whereas the bottom of the knot slider 800 is defined as the opposing side. In some embodiments, when the loops are installed on the knot slider 800, the loops 700 may not be vertical/perpendicular with respect to the shaft 16 when viewed from the side, as shown in FIG. 23a. The loops 700 may be oriented at an angle from the vertical or perpendicular as shown. The bottom portion of the loops is defined as the portion of the loops 700 that is in contact with the bottom of the knot slider 800 and the top portion of the loops is defined as the portion of the loops 700 in contact with the top portion of the knot slider 800. In some embodiments, if the bottom portion of the loops 700 is positioned proximally to the top portion; as tension is applied to the loops 700 to release the loops 700, the top portion starts to move and the loops may grip/bind on the knot slider 800 and not come off. Thus, in some embodiments, the loops 700 may be oriented such that the portion of the bottom portion of the loops 700 at the bottom of the knot slider 800 is positioned distal to the top portion of the loops 700 at the top of the knot slider 800.

Alternatives

Needle Spanning the Tissue Receiving Gap

In some embodiments, means may be provided to allow the needle 116 to span across the tissue receiving gap 10, prior to deploying the partially pre-tied knot. In one particular example, the device 100 is withdrawn to deploy the partially pre-tied knot. As the device 100 is withdrawn, the suture loops 700 of the pre-tied knot first slide distally along shaft 16, and then along the needle 116 spanning across the tissue receiving gap 10. The loops 700 then may slide onto the distal tip 12 and are subsequently released distal to the device 100. Additional features may be provided to facilitate translation of the suture loops 700 at the transition between the needle 116 and the distal tip 12.

Tubing to Cover the Tissue Receiving Gap

In some embodiments, the device 100 may be provided with a sheath or tubing that is positioned around the shaft 16. Prior to deploying the partially pre-tied knot, the sheath or tubing may be advanced such that it spans across or covers the tissue receiving gap 10. Similar to embodiments discussed above, in one particular example, the device may be withdrawn to release/deploy the loops 700 of the partially pre-tied knot. The loops 700 of may slide distally along the shaft 16 until they reach the sheath or tubing spanning across the tissue receiving gap 10. The loops 700 may then slide along the sheath or tubing and onto the distal tip 12. The loops 700 may then be released distal to the device distal tip 12. In one specific example, the sheath or tubing may comprise clear tubing.

Manipulating the Device Distal Tip

Retracting the Device Distal Tip

In some embodiments, the distal tip 12 of the device 100 may be retracted to close the tissue receiving gap 10, to enable the loops 700 of the partially pre-tied knot to be released without being caught within the tissue receiving gap 10. Thus, in one example, when the device 100 is retracted to release the loops 700, the loops 700 may slide distally along the shaft 16 and then along the distal tip 12 that has eliminated/closed the tissue receiving gap 10. The loops may then be released distal to the device distal tip 12.

Swivel the Device Distal Tip

In alternate embodiments, the distal tip 12 of the device 100 may be pivotally coupled to the shaft 16 and may be pivoted or swiveled with respect to the shaft 16, prior to deploying/releasing the pre-tied knot. Thus, the distal tip 12 may be pivoted (or rotated) away from the path of the loops 700. The loops 700 may then be released and may slide distally along the shaft 16 without being caught within the tissue receiving gap 10.

Each of these embodiments are described in greater detail hereinbelow with reference to the device in use.

In some embodiments, a device 100 may be provided for passing suture that contains features for managing suture as described herein below wither reference to FIGS. 28*a-h* and FIGS. 29*a-9e*.

Features for Suture Management

In one broad aspect, the device of the present invention comprises features for suture management. By means of introduction, certain features have been incorporated into the device for preventing damage to the suture, while other features have been incorporated into the device for routing the suture. Still furthermore, features are provided to prevent the device from jamming.

In some embodiments, the present invention provides a structure/feature to allow suture to be routed without being constrained. As an example of this, embodiments of the present invention provide a slot.

In some embodiments, the present invention provides a means to limit damage to the suture while the suture is being manipulated. As an example of this, embodiments of the present invention provide a spacing/gap to allow suture to pass freely without fraying. In another example, embodiments of the present invention provide surface modifications such as cut-outs to prevent damage to the suture such as fraying.

In some embodiments, the present invention provides a means to prevent the device from jamming or locking. As an example of this, embodiments of the present invention provide a spacing/gap for the suture to prevent the suture from binding the device mechanism. In another example, embodiments of the present invention provide surface modifications such as cut-outs to provide space for the suture to prevent the suture from binding the device mechanism.

Example 1

The various features described above will be discussed with reference to usage of the device as shown in FIGS. 28*a*-28*h*. Certain features of the device related to suture management may be described with respect to one or more stages of a medical procedure (i.e. the same features may be discussed more than once, if they play a role at more than one stage of the procedure).

A device 100 is disclosed for passing a suture 240 through a region of tissue. Device 100 comprises a device proximal portion 14 comprising a shaft 16 that is coupled to a device distal tip portion having a distal tip 12. The device 100 further comprises a suture moving assembly 2822 housed within the device 100 for moving a suture 240 between the device proximal portion 14 and the distal tip 12. The suture moving assembly 2822 comprises a needle 116 within which a stylet 2819 is positioned. The stylet 2819 and the needle 116 are housed within chamber or channel 16B defined by the shaft 16. A suture 240 (comprising an enlarged portion such as a knot 250) is held at one end within the needle 116, with the knot 250 being retained within the needle and the stylet 2819 being positioned proximal to the knot 250.

Figure 28A:
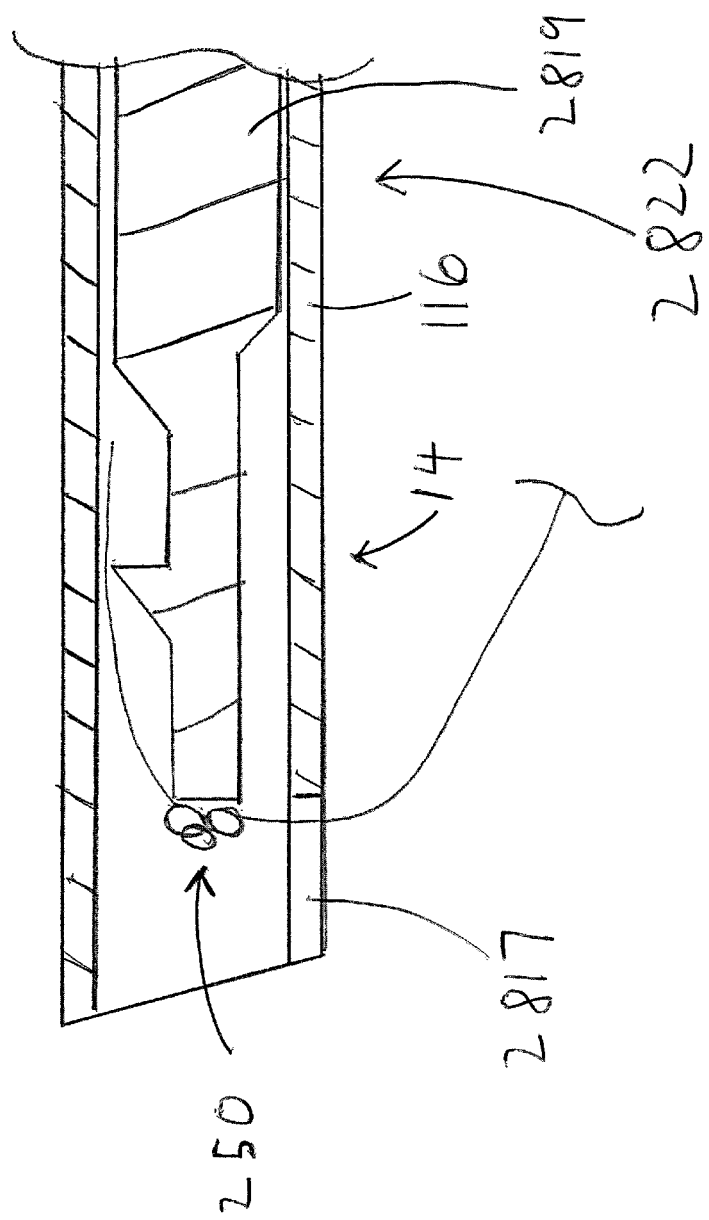

Features Used, for Example, During Initial Passing of Suture Distally through Tissue Features for Facilitating Routing of the Suture In some embodiments, the device 100 described comprises a structure/feature to allow the suture 240 to be routed in a manner limiting constraint of the suture. In one specific example, the feature for facilitating routing of the suture 240 comprises a slot. The suture 240 is guided through a slot 2817 to the exterior of the needle and exists through as similar slot 2817' formed within the shaft 16 as shown in FIG. 28*b*. The needle slot 2817 and the shaft slot 2817' are 90 degrees out of rotation with respect to each other as shown in FIGS. 28*a* and 28*b*. In other words, the needle slot 2817 and the shaft slot 2817' are radially offset from one another. The enlarged portion of the suture 240, such as a knot 250 is unable to pass through the slot 2817 within the needle, thus maintaining the position of the enlarged portion of the suture within the needle lumen. The slot 2817 within the needle may be positioned proximal and, for example, adjacent to, a distal end of the needle 116.

In one example, slots 2817 and 2817' are designed to route the suture 240 towards the exterior of the shaft 16, so that the suture 240 does not interfere with forward translation of the suture moving assembly 2822 thus substantially minimizing damage to the suture 240. Thus, in the specific embodiment shown, the risk of suture 240 getting frayed or chaffed is substantially reduced as the needle/stylet assembly is advanced distally to pass the suture 240 through a segment of tissue (positioned within tissue receiving gap 2810) and into the suture holder. In some embodiments, the slot 2817 is provided with a blunt face, which may further minimize the risk of damage to suture 240 as it is routed through the slot. Furthermore, the slot 2817 also may help prevent damage to the suture 240 by preventing the suture 240 from being routed across a sharp end point of the needle 116. Additionally, the slot 2817 minimizes damage to the suture 240 resulting from pinching which prevents the device 100 from jamming or locking. Slot 2817' of the shaft 16 works in conjunction with the needle slot 2817 to perform a similar function including reducing the risk of device failure due to binding/locking of the device. In some embodiments as shown in FIG. 28*a*, the suture may be held in frictional contact between the stylet 319 and needle 116.

In some embodiments, the slot 2817 may offer additional advantages. In one specific example, since the suture 240 is located in the slot 2817 behind a bevel end face of the needle 116, the slot 2817 of the needle allows tension to be applied to the suture 240 while enabling the knot 250 to remain within the needle (when it is pulled against the inner wall of the needle 116). In the absence of a slot 2817, the suture 240 may exit the needle 116 as tension is applied to the suture 240. In other words, in the absence of the slot 2817, tension may cause the suture 240 to be pulled out of the needle 116. Thus, the needle slot 2817 allows the suture 240 to be maintained within the needle slot 2817 such that the suture position remains substantially fixed relative to the needle 116 when the needle 116 is advanced towards the trap 2816 (i.e. during deployment). In such embodiments, the suture, while retained within needle 116, may or may not be substantially coupled directly thereto. This may additionally help minimize the risk of suture 240 getting damaged or interfering with the suture moving assembly (i.e. locking/binding the device mechanism) as it is advanced.

In some alternative embodiments, a slot is present only in the shaft and not in the needle or vice versa.

Gap or Spacing for Suture Management

Figure 28C:
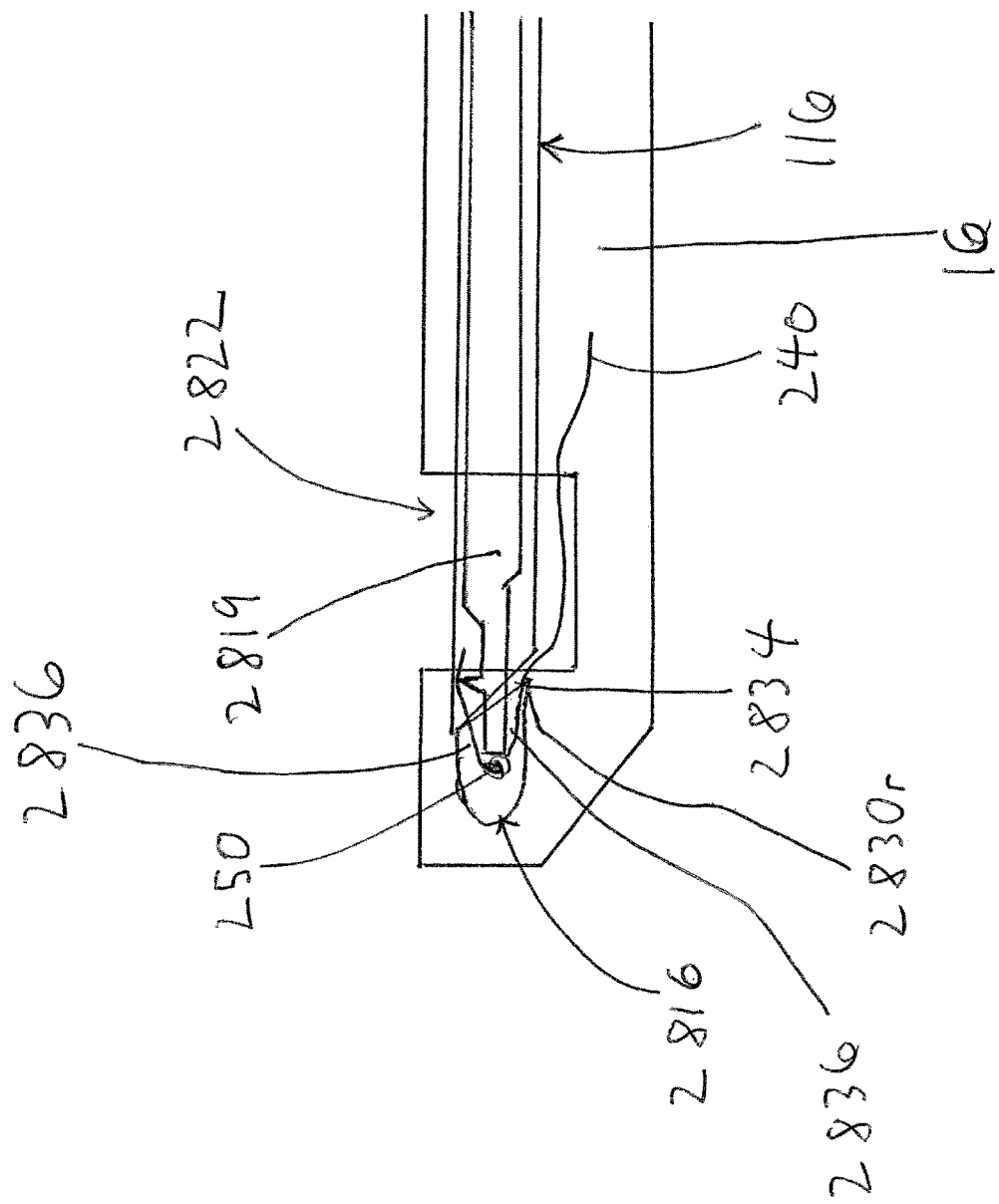

In order to pass the suture 240 through the tissue, the device 100 is positioned such that a first segment of tissue is received within the tissue receiving gap. The suture moving assembly 2822 (comprising needle 116, stylet 2819 and suture 240 operably coupled thereto) is then translated distally, such that it passes through the first segment of tissue until the needle 116 abuts a suture holder such as the trap 2816, as illustrated in FIG. 28c. The stylet 2819 is then advanced further to deposit the suture knot 250 and thus suture 240 within the trap 2816 as shown in FIG. 28d, whereas the needle 116 cannot be advanced further due to interference by the trap 2816. The trap 2816 may comprise features, as described previously, to capture the suture 240. The stylet 2819 is now positioned within the trap 2816.

Gap or Spacing Provided Between the Needle Distal End Face and the Trap Proximal End Face In one specific example, as shown in FIGS. 28c and 28d, a gap or spacing 2834 is provided between the distal end face of the needle and the proximal end face of the trap for suture clearance. The suture 240 is routed through the gap or spacing 2834 substantially without being damaged or frayed. In other words, as the stylet 2819 is advanced, the suture 240 is translating relative to the needle 116 and the trap 2816. By having a gap or spacing 2834 between needle 116 and trap 2816, the suture 240 is substantially free to move.

Figure 28F:
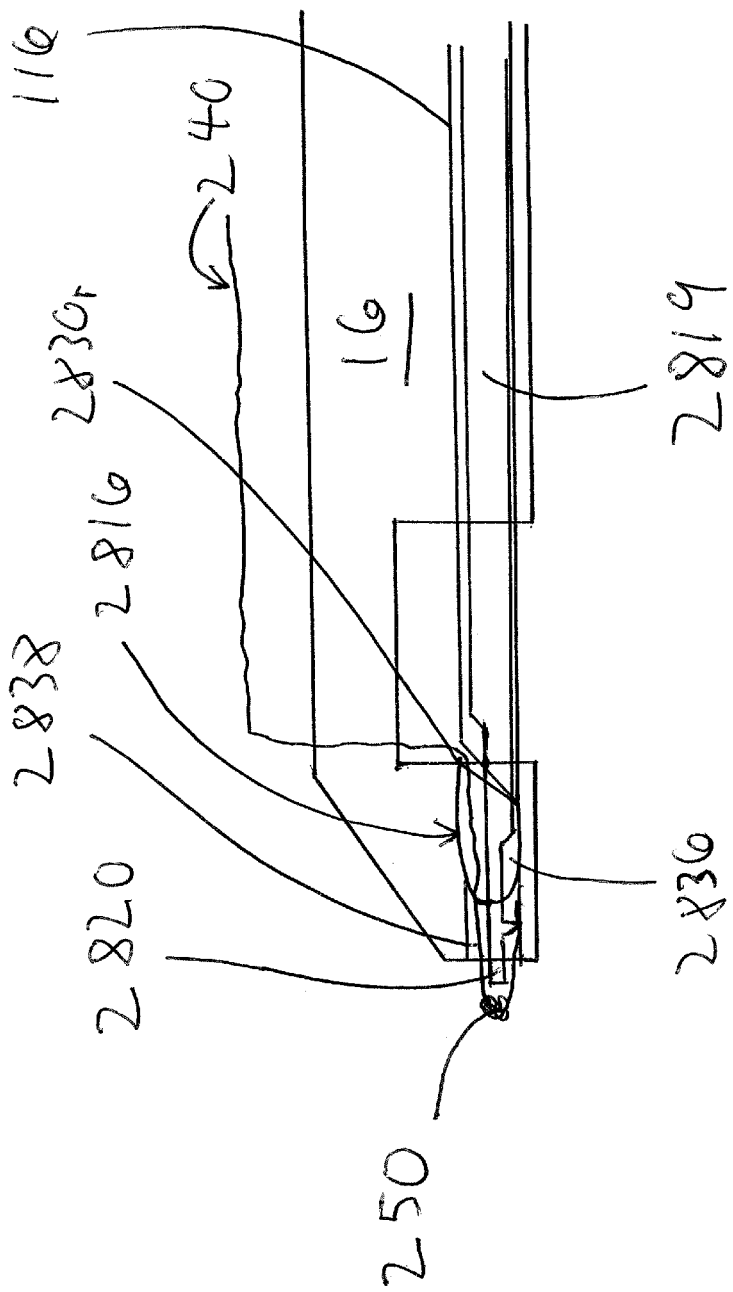
Figure 289:
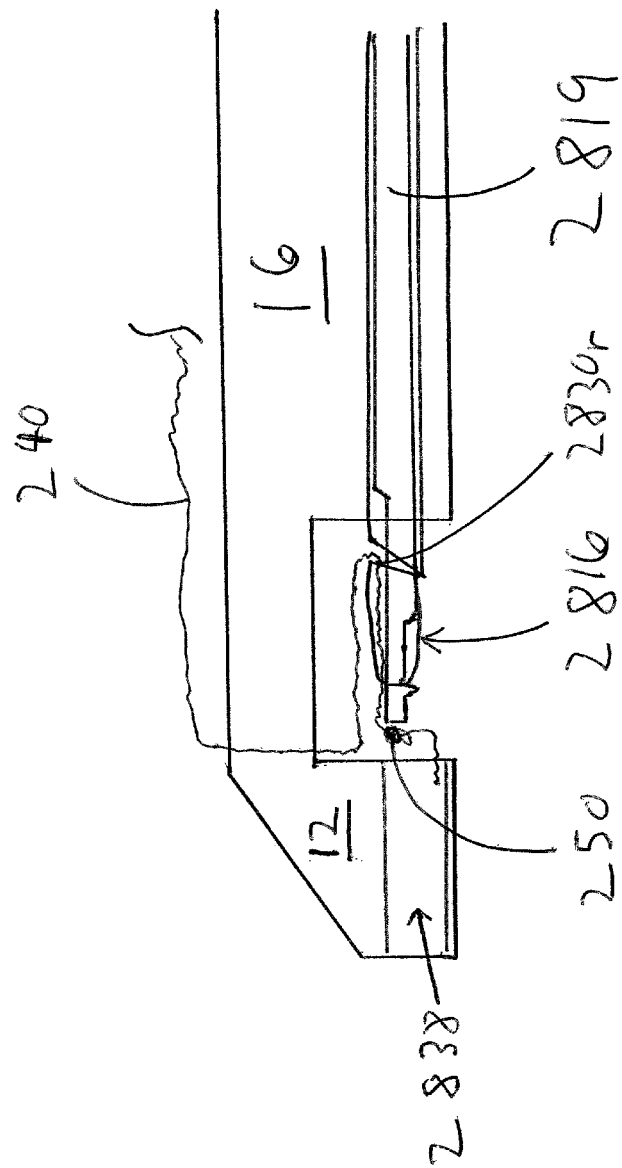

In one specific example as shown, the gap or spacing 2834 is created by providing a mismatch between the distal end face of the needle 116 and the proximal end face of the trap 2816, as shown in FIGS. 28c and 28d. More specifically, the gap or spacing 2834 is created by providing diverging angles on the trap face and needle face. In one example, a chamfer is additionally provided on the trap edge. In one specific example, the gap or spacing 2834 is created by providing a relief cut-out 2830r. The relief cut-out 2830r provides a passage between the trap 2816 and the needle 116, and prevents the suture 240 from getting frayed or chaffed due to suture 240 being pinched between the trap 2816 and the needle 116 as shown in FIGS. 28d and 28f. Thus, the relief cut-out 2830r helps minimize damage to the suture 240. By minimizing the risk of suture 240 being pinched the relief cut-out may also prevent the device 100 from getting locked/jammed.

Advantages of the Gap/Spacing in Preventing Damage to Suture

As shown in FIGS. 28c and 28d, the gap or spacing 2834 formed between the distal end face of the needle 116 and the proximal end face of the trap 2816, provides sufficient clearance to prevent suture 240 from becoming pinched between the needle 116 and the trap 2816, which may help prevent chafing or fraying or severing of the suture 240.

Advantages of the Gap/Spacing in Preventing Binding/Jamming of the Device

Additionally, the gap or spacing 2834 prevents jamming/locking of the device by preventing pinching of the suture 240. In other words, in some embodiments, the gap or spacing 2834 allows for improved routing of suture 240 which may substantially reduce the risk of failure of device 100. More specifically, the gap or spacing 2834 between the needle 116 and the trap 2816 may help prevent the suture moving assembly 2822 (which includes the needle 116 and the stylet 2819) or any of the moving components within device 100 from binding or jamming due to the suture 240 getting caught therebetween.

Gap or Spacing Provided Between the Stylet and the Trap

Furthermore, the suture moving assembly 2822 (or a part thereof) may also comprise features to substantially minimize damage to the suture 240. In one specific example, as illustrated in FIGS. 28c-28d, the stylet 2819 has a reduced cross-section along a distal portion thereof (also discussed previously and shown in FIGS. 7a-7e). When the stylet 2819 is positioned within the trap 2816 to deposit the suture 240 within the trap 2816, a gap or spacing 2836 forms between the distal portion of the stylet 2819 having the reduced cross-section and an inner wall of the trap 2816. In other words there is a clearance for the suture 240 adjacent to the stylet 2819. In some embodiments, the gap or space 2836 may be provided in the form of symmetric clearance as shown in FIG. 28d(ii) where the stylet 2819 has a reduced cross-section substantially along its outer periphery. In other embodiments, the gap or spacing 2836 may be provided in the form an asymmetric clearance as shown in FIG. 28d(i), where a portion of the stylet 2819 periphery has a reduced cross-section.

Advantages of the Gap/Spacing

In operation, as the stylet 2819 translates out of the needle 116 and into the trap 2816, the suture 240 is advanced with it as the knot 250 is pushed by the stylet 2819. Having clearance or gap/spacing 2836 substantially adjacent to the stylet 2819 allows the suture 240 to slide inside the trap 2816 without pinching or binding and allows the stylet 2819 to deposit the suture knot 250 within the trap 2816 such that it is coupled thereto. In other words, the gap or spacing 2836 allows the suture 240 to travel. Thus, the gap or spacing 2836 substantially prevents fraying of the suture 240 as it is routed between the trap 2816 and the stylet 2819 as the stylet 2819 is advanced. Furthermore, the gap or spacing 2836 also prevents the device from jamming by preventing the suture from being pinched or caught between the stylet 2819 and the trap 2816. The stylet 2819 is then withdrawn from the distal tip 12 to the shaft 16. The clearance of gap/spacing 2836 may also aid withdrawal of the stylet 2819, by preventing damage to the suture 240 and by preventing jamming of the device as the stylet 2819 is withdrawn. In one specific example, a minimal amount of clearance is provided between the trap 2816 and the interior of the distal tip 12, sufficient to provide the advantages described above while minimizing the risk of suture 240 being caught between trap 2816 and the interior of distal tip 12.

Surface Modifications for Suture Management

After, the stylet 3019 has been withdrawn from the distal tip 12 to the shaft 16, the device 100 is re-positioned to pass suture 240 through a second segment of tissue. As shown in FIG. 28e, as the device 100 is rotated for example by 180 degrees, the suture 240 is pulled towards the axis of rotation of the device, for example, along the longitudinally extending neck 15 of the device 100. In some embodiments, as discussed previously, in order to prevent the suture 240 from being caught and from chafing, a relief cut-out 2830r (this feature is more clearly illustrated in FIG. 28e) is provided within the trap 2816 of the suture moving assembly 3022. In some embodiments, the relief cut-out 2830r is provided at the location where suture 240 is pulled and positioned when leaving the distal tip 12, thus substantially preventing the suture 240 from being damaged. More specifically, in some embodiments, the relief cut-out 2830r is provided within the trap 2816 towards the rotational axis of the device 100, as shown in FIG. 28e. In other words, the relief cut-out 2830r is provided within the trap 2816 at a location facing or adjacent the neck 15, as shown in the drawings, and prevents the suture 240 from being frayed or cut against a sharp corner or edge of the trap 2816, as it is routed away from the distal tip 12. In addition, cut-out 2830r allows additional room for suture routing, thereby reducing the risk of the suture causing the device to jam or lock-up.

Features Used During Withdrawal of Suture Proximally through Tissue

Features in the Distal Portion

Gap or Spacing for Suture Management

Gaps/Spacings Between the Stylet, Needle and the Trap

As shown in FIG. 28f, the stylet 2819 having a stylet tip 2820, is then re-advanced distally a second time, such that is passes through a second segment of tissue towards the distal tip 12. On the second advancement of the stylet 2819, substantially all of the stylet tip 2820 passes through the trap 2816 to couple the trap 2816 thereto. The gap or space 2836 between the stylet 2819 and trap 2816, as well as gap 2834 between needle end face and trap 2816 (both gaps shown previously) may additionally help limit or prevent damage to the suture 240 as the stylet 2819 is advanced. The gap 2834 is further enhanced by the cut-out 2830r, to ensure that the suture 240 is not damaged or constrained as the needle 116 and the stylet 2819 are advanced. As a result, the risk of the device 100 binding/jamming may be reduced. Additionally, in order to accommodate the stylet tip 2820 within the trap 2816, the knot 250 (and thus suture 240) advances distally with the stylet tip 2820 as the stylet tip 2820 passes through the trap 2816. The gap or space 2836 (shown and discussed above) allows the knot 250 and the suture 240 to be advanced distally substantially without being pinched or bound. The gap or space 2836 may also substantially prevent the suture 240 from being damaged minimizing chafing or fraying of suture 240.

Gap or Spacing Formed Distal to the Trap

Additionally as shown in FIG. 28f, a space or gap may be provided distal to the trap 2816 within the distal tip 12 in order to accommodate the knot 250. In one specific example, the space or gap may be provided in the form of a channel 2838, which is more readily visualized in FIG. 28g. The channel 2838 is provided between the suture moving assembly 2822 (i.e. trap 2816 of the suture moving assembly 2822) and a wall of the distal tip 12 that defines chamber 12B. The channel is of a sufficient length to ensure that the knot 250 can advance a sufficient distance in front of the stylet 2819. In other words, the channel 2838 allows the knot 250 to advance a distance substantially equal to the length of the stylet tip 2820. The channel 2838 may help prevent the knot 250 from falling to the side of the stylet 2819. The channel 2838 allows suture 240 to be drawn distally through the trap 2816, minimizing pinching of the suture 240 by the stylet tip 2820 as it passes through the trap 2816. This may help minimize risk of failure of device 100. More specifically, the dimensions of channel 2838 may help prevent binding of the device mechanism as the stylet 2819, trap 2816 and suture knot 250 are withdrawn back through the distal tip by avoiding suture 240 getting caught there-between. The gap or space 2836 between the stylet and trap 3106, as well as gap 2834 between needle end face and trap 2816 may additionally help prevent damage to the suture as the stylet is withdrawn. Furthermore, the channel 2838 (specifically, the length thereof) also prevents the stylet 2819 from becoming inadvertently coupled to a distal face of the device distal tip 12.

Surface Modification for Suture Management

Additional features may be provided within the device 100 to further aid in minimizing damage to the suture 240 as the trap 2816 and thus suture knot 250 are withdrawn using the stylet 2819 through the second segment of tissue towards the proximal portion 14. As shown in FIG. 28g, the suture 240 bends at about 180 degrees around the trap 2816 as the trap 2816 (and thus suture 240) is withdrawn through the second segment of tissue upon retraction of the needle 116 and the stylet 2819. Thus the suture 240 makes a sharp bend around the face of the trap 2816. A relief or cut-out may be provided within the trap 2816 such as cut-out 2830r (as discussed previously). The cut-out 2830r may provide a substantially blunt edge in order to minimize abrasion or cutting of the suture 240 against a sharp edge of the trap 2816.

Features in the Proximal Portion

Gap or Spacing for Suture Management

Counter-Bore Formed within the Device Proximal Portion

As the trap 2816 is withdrawn into shaft 16 of the proximal housing (as discussed previously), the suture 240 may double back or fold onto itself. As discussed above, a gap or spacing 2830p may be provided in the form of a counter-bore 2832, between the exterior of the trap 2816 and interior of the shaft 16 to accommodate the suture 240. Additionally, the counter-bore 2832 may also provide sufficient room/space to allow the knot 250 to be positioned adjacent the stylet and the trap 2816.

More specifically, the knot 250 may become positioned around the stylet tip 2820 and may become lodged against the trap 2816, as the stylet 2819 is withdrawn. As the stylet is withdrawn, tension is applied to the suture 240 to pull it through the tissue, which is resisted by the knot 250 as it in unable to go back (move proximally) through the trap 2816 (For example, between fingers of the trap 2816). Thus, being in tension but being unable to pass back through the trap, the knot 250 may become positioned beside the stylet 2819. As a result, a spacing or gap (such as counter-bore 2832) is provided within the shaft 16 to accommodate the knot 250 beside the stylet 2819, while the needle/trap/stylet are retracted out of the tissue receiving gap 2810. Thus, the counter-bore 2832 provides sufficient space to substantially prevent damage to suture 240 and may additionally prevent the device 100 from failing (e.g. due to binding of the mechanism due to the suture 240 being pinched, for example between the trap and/or stylet and the interior of the shaft 16).

Thus, some embodiments of the present invention provide a means to substantially prevent the device 100 from failing. More specifically, some embodiments of the present invention provide a means to prevent suture 240 from getting pinched between various components, in order to prevent the device mechanism from binding (or in other words in order to prevent the moveable components of the device from getting jammed).

Features for Facilitating Routing of the Suture

Furthermore, in some embodiments the device 100 comprises features to allow suture 240 to be routed within the proximal portion or housing 14 to prevent the suture 240 from getting entangled or damaged. In one such embodiment, as discussed previously and shown in FIG. 22g, the suture 240 comprises a first portion forming a post having a service loop, and longitudinally opposed second portion forming a locker. In one example, the service loop of the post and the locker may be relatively long and may stored within a handle of the device proximal portion 14, in order to minimize the risk of suture 240 tangling. However, the locker and post may be stored such that the suture 240 can be deployed with relative ease during use. In a specific example of this embodiment, suture routing tubes are provided within the handle, and the first and second portions of the suture 240 are individually routed through one of the tubes and housed therein. In alternate embodiments, the suture 240 may be routed through a spool payout mechanism. In still other embodiments, the first and second portions of the suture 240 may be guided through clips or separate channels within the proximal portion 14 to prevent the suture from getting entangled.

Example 2

Alternative suture management features will now be discussed with reference to an alternative embodiment of a suture passing device. In this alternative embodiment, the device incorporates a 'suture passing assembly' 2922 which may, for example, include any of the following: needle 116, stylet 2919, and/or a suture holder 2916, etc. In other words, in this alternative embodiment, there may or may not be a stylet, and suture holder 2916 may be passed both ways through the tissue (i.e. proximally through the tissue and then back distally).

In one specific example, the elongate member may comprise a combination of the stylet 2919 and the needle 116. In another example, the elongate member forming the suture moving assembly 2922 may comprise a needle 116, without a stylet. In some embodiments, the suture moving assembly 2922 may be operable to pass suture 240 between shaft 16 and the distal tip 12 (distally or proximally), to pass suture 240 through tissue. In other embodiments, the suture moving assembly 2922 may be operable to pass a suture holder 2916, with suture 240 coupled or secured thereto, between the shaft 16 and distal tip 12 (distally or proximally). In some embodiments, the suture moving assembly 2922 may be operable to first draw suture 240 between the distal tip 12 and the shaft 16 proximally through a first segment of tissue and then pass suture 240 (with or without a suture holder 2916) distally through a second segment of tissue.

As discussed above with respect to Example 1, the various features will be identified with reference to the movement of suture 240 using the embodiment of device 100 shown in FIG. 29.

Figure 29A:
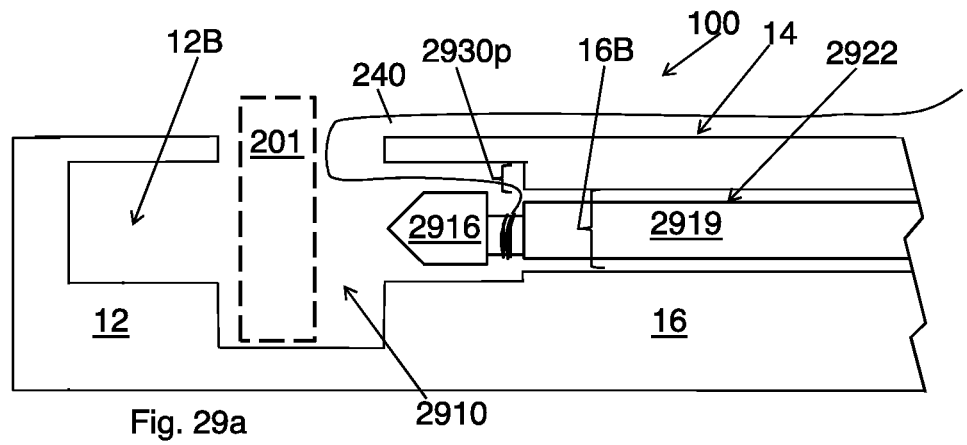
FIGS. 29*a*-29*e* illustrate a device and method in accordance with another embodiment of the present invention.

Features Used, for Example, During Initial Passing of Suture Distally through Tissue
A Gap or Spacing for Suture Management
A Gap or Spacing Formed within the Proximal Shaft In one example, as shown in FIG. 29*a*, a device 100 is disclosed for passing a suture 240 through a region of tissue. Device 100 comprises a device proximal portion 14 comprising a shaft 16 that is coupled to a device distal tip portion having a distal tip 12. The device 100 further comprises a suture moving assembly 2922 housed within the device 100 for moving a suture 240 between the device proximal portion 14 and the distal tip 12. A part of the suture moving assembly 2922 may be housed within the device proximal portion 14 (for example within a lumen or chamber 16B defined by shaft 16 of the proximal portion 14) and a part of the suture moving assembly 2922 may at least partially be receivable within the distal tip 12 (for example within a chamber 12B defined by the distal tip 12). The suture 240 may be operably coupled to one or more components of the suture moving assembly 2922. In some embodiments of the present invention, the chamber 16B within the shaft 16 (of the device proximal portion 14) and chamber 12B within the distal tip 12, each include a spacing or gap (formed between components of suture moving assembly 2922 and an inner wall of either shaft 16 or distal tip 12, respectively) to allow the suture 240 to be passed substantially without being damaged. In some embodiments, the width of chamber 16B may vary along the length of the shaft 16. Thus, while chamber 16B in FIG. 29*a* is shown as referring to the narrower, proximal portion of the shaft lumen, it also refers to the wider, more distal portion of the shaft lumen as shown, for example, in FIG. 29*d*.

Figure 29B:
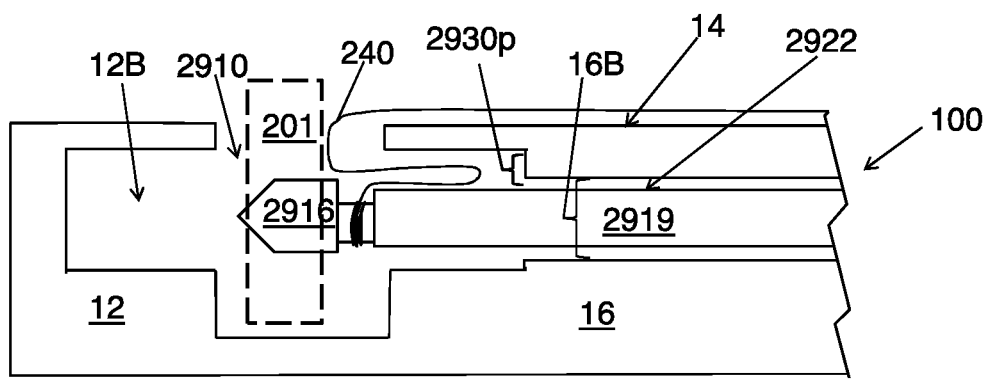

In one embodiment, the device 100 is positioned within tissue such that a first segment of tissue 201 is received within the tissue receiving gap 2910. As shown in FIG. 29*b*, when the suture moving assembly 2922 is housed within shaft 16, a (minimal) gap or spacing forms between an outer surface of the suture moving assembly 2922 and an inner wall of the shaft 16. In the specific example shown, the gap or spacing is denoted by reference numeral 2930*p*. Gap 2930*p* may, in some embodiments, comprise a counter-bore or offset recess.

Advantages of the Gap/Spacing in Preventing Damage to Suture

As shown in FIG. 29*b*, the gap or spacing 2930*p* between suture moving assembly 2922 and shaft 16, provides sufficient room to prevent suture 240 from getting pinched between the suture moving assembly 2922 (as it is advanced) and the shaft 16, for example by folding onto itself as shown in FIG. 29*b*, and thus may substantially prevent pinching of the suture which can lead to chafing, fraying or other damage to the suture.

Advantages of the Gap/Spacing in Preventing Binding/Jamming of the Device

Additionally, the gap or spacing 2930*p* substantially prevents (or minimizes the risk of) jamming/locking of the device by preventing pinching of the suture. In other words, in some embodiments, the gap or spacing 2930*p* allows for improved routing of suture 240 which may substantially reduce the risk of failure of device 100. More specifically, the gap or spacing 2930*p* may help prevent the suture moving assembly 2922 or any of the moving components within device 100 from binding or jamming due to the suture 240. In other words, the gap or spacing 2930*p* prevents the suture moving assembly 2922 from locking due to the suture 240 getting caught between the suture moving assembly 2922 and the shaft 16, thus interfering with its advancement.

A Gap or Spacing Formed within the Distal Tip

Figure 29C:
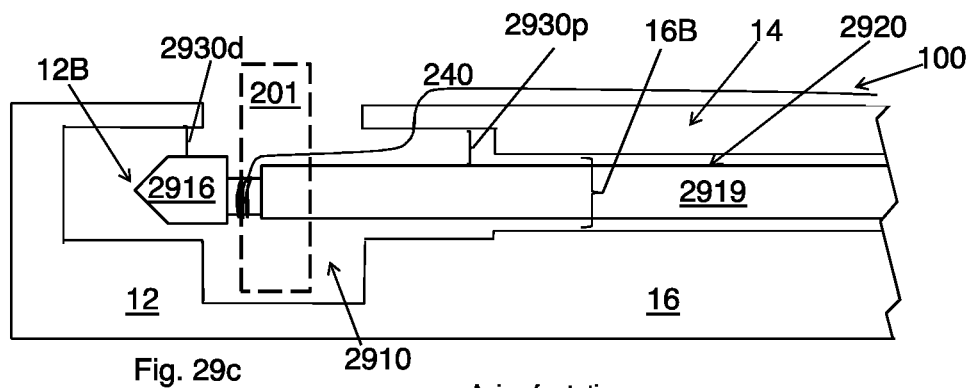

Similar to the gap or spacing 2930*p* present within chamber 16B of shaft 16 of the proximal housing 14, chamber 12B defined by the distal tip 12 may also define a spacing or gap, denoted by 2930*d* in FIG. 29*c*. The suture moving assembly 2922 is advanced distally to pass suture 240 through a segment of tissue, and advanced further towards the distal tip 12, to couple the suture 240 thereto. In the embodiments as shown in FIG. 29*c*, the suture moving assembly 2922 is advanced until a portion of the assembly 2922 is received within the device distal tip 12. In one specific example, a suture holder 2916 of the suture moving assembly 2922 is positioned within chamber 12B of the distal housing. A gap 2930*d* is formed between the outer diameter of the suture holder 2916 and inner walls of distal tip 12 defining chamber 12B. The gap 2930*d* allows the suture 240 to be routed so that it is not pinched or caught between a portion of the distal tip 12 and the suture moving assembly 2922. In some examples, the suture moving assembly is rotated to couple the suture holder 2916 to the distal tip 12, and an additional relief or gap may be provided which may allow the suture holder 2916 to be coupled to the distal tip 12 substantially without damaging the suture 240. After the suture holder 2916 has been deposited at the distal tip 12 (in those embodiments that function in this manner), the stylet 2919, or other elongate member, is then withdrawn proximally and received within the proximal portion 14. The gap 2930*d* may also help minimize damage to the suture as the elongate member is withdrawn proximally. It should be noted that the drawings are not drawn to scale and, as such, gap 2930d may, in some embodiments, be sufficiently large so as to allow sufficient space for manipulation of the various components described herein while limiting/preventing suture 240 from being constrained or damaged. For example, in some embodiments, gap 2930d is suitably dimensioned so as to prevent suture 240 from being maneuvered into position between components of suture moving assembly 2922 and the inner wall of distal tip 12.

Features Used During Withdrawal of Suture Proximally through Tissue

Surface Modifications for Suture Management

Figure 29D:
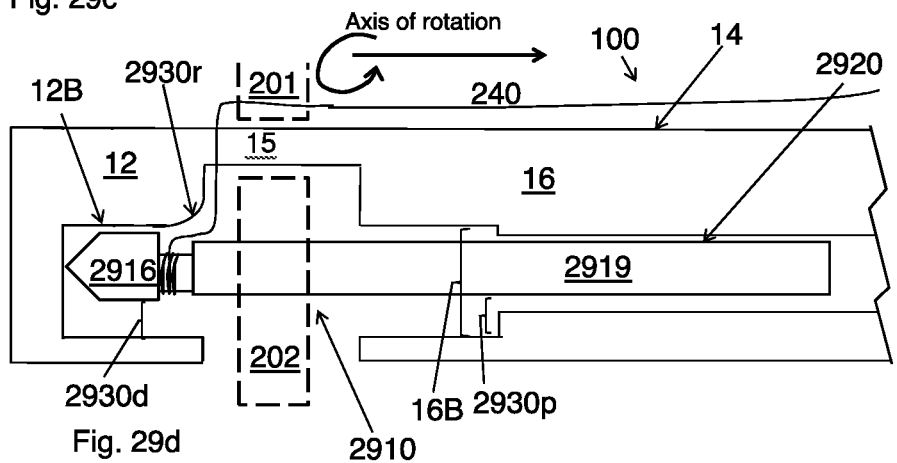

In some embodiments, device 100 may be repositioned as shown in FIG. 29d, so that a second segment of tissue 202 is received within the tissue receiving gap 2910. In one example, device 100 is rotated pulling suture 240 towards the axis of rotation of the device. In the example shown, the suture 240 is pulled towards the neck 15. In order to prevent the suture 240 from getting caught and chafing a relief cut-out 2930r may be provided. The relief 2930r may be formed within the distal tip 12 adjacent the neck 15 (as shown). Alternatively, or in addition, a cut-out may be present within a part of the suture moving assembly 2922, such as within the suture holder 2916. The relief cut-out 2930r prevents or limits the suture 240 from being frayed or cut by a sharp corner or edge of the distal tip 12 and/or a corner of the part of the suture moving assembly 2922, such as suture holder 2916.

After the device 100 (with the suture holder 2916 coupled to the distal tip 12) has been rotated along its axis to receive the second segment 202 of tissue within the tissue receiving gap 2910, components of the suture moving assembly 2922 are re-advanced towards the distal tip 12 to retrieve the suture. As these components enter the distal tip 12 for the second time there may be risk of damage to the suture, such as fraying, or risk of the device being jammed/locked due to pinching of suture 240. The spacing or gap 2930d within the distal tip 12, as well as any cut-outs present, for example in the distal tip and/or the suture holder, may help minimize the risk of damage to the suture 240 and/or failure of device 100.

The suture moving assembly 2922 is then withdrawn so that the suture 240 is now drawn/passed from the device distal tip 12, through the second segment 202 of tissue, to the device proximal portion 14. The spacing or gap 2930d (described earlier) as well as the relief cut-outs, such as cut-out 2930r, may additionally help prevent damage to the suture and reduce the risk of the device 100 jamming as the suture moving assembly 2922 is withdrawn proximally.

In other words, gap 2930d, as well as any relief cut-outs or other surface modifications, help mitigate the risk of suture damage and/or device failure both when the suture moving assembly enters the distal tip as well as when it is retracted along with the suture.

Gap or Spacing for Suture Management

Figure 29E:
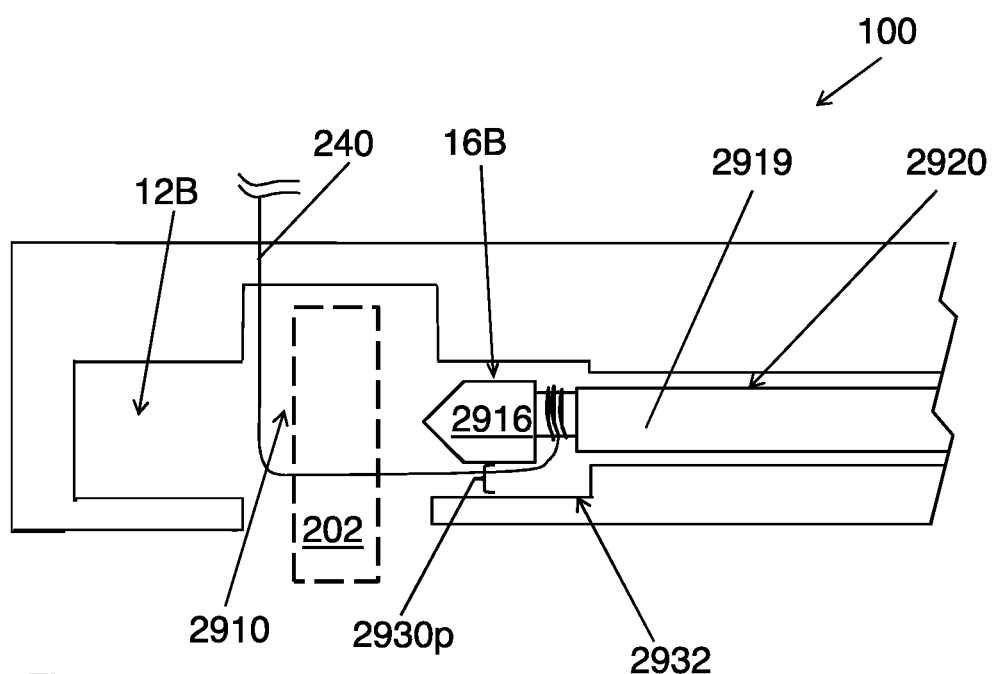

As the suture moving assembly 2922 is pulled back into shaft 16 of the proximal housing, spacing is provided to accommodate the suture 240 beside the suture moving assembly 2922. As described previously, a gap or spacing 2930p is provided within the proximal shaft 16, which provides sufficient space to substantially minimize chafing or fraying of the suture 240. In one specific example, the spacing 2930p is in the form of a counter-bore 2932, as shown in FIG. 29e. The counter-bore 2032 provides sufficient room within the shaft 16 to prevent the suture 240 from being pinched between a part of the suture moving assembly 2922 (as it is retracted) and the shaft 16.

Alternative Embodiment of a Device for Passing Suture

Figure 20A:
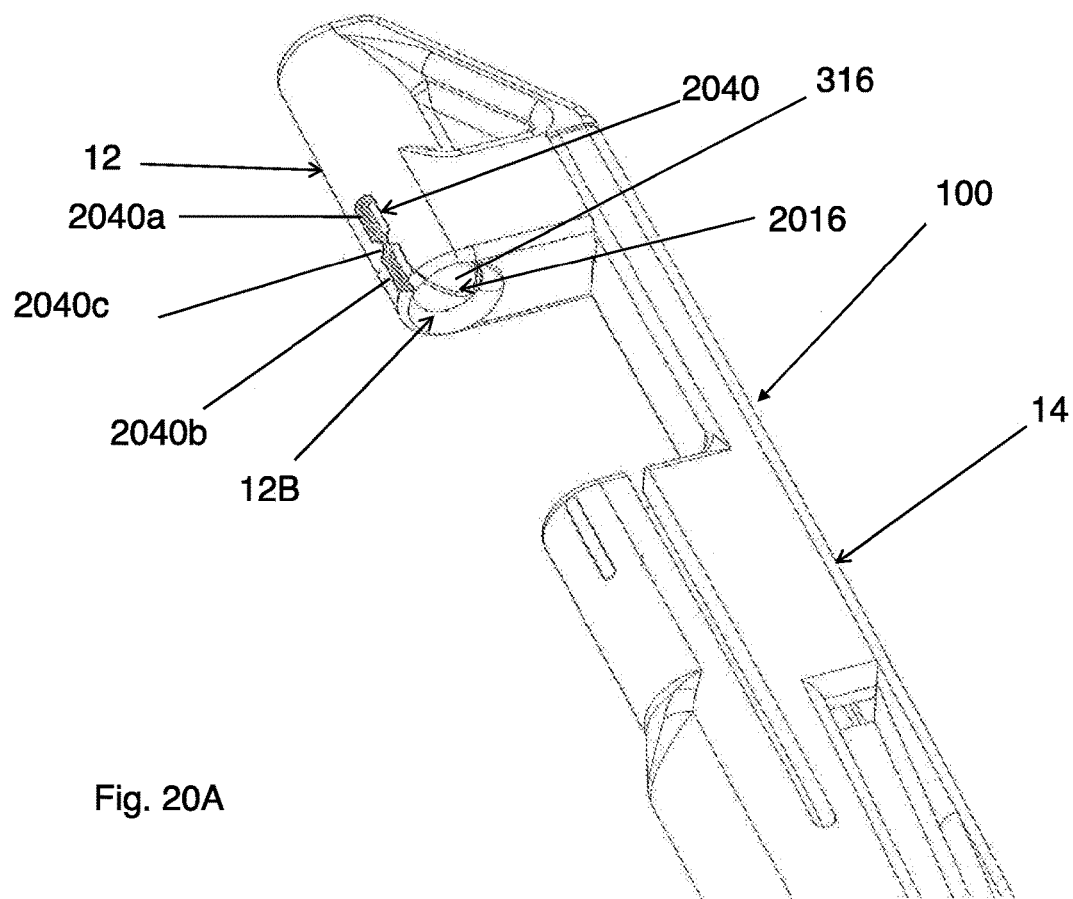
FIGS. 20*a*-20*e* illustrate a device and method in accordance with another alternate embodiment of the present invention.

In an alternative embodiment as shown in FIG. 20A, a device 100 is provided that is similar to the embodiments discussed above. The distal tip 12 has receiving chamber 12B for receiving and holding a suture holder such as a trap 2016 therein. The distal tip 12 comprises a slot 2040 axially disposed along an outer surface thereof. Slot 2040 is formed from two substantially rectangular slots 2040a and 2040b, with slot 2040b being positioned distal to slot 2040a. The two slots 2040a, 2040b are spaced apart by a pair of inwardly directed tabs 2040c that extend into the slot 2040. In one example, the tabs 2040c comprise a resilient material.

Figure 20B:
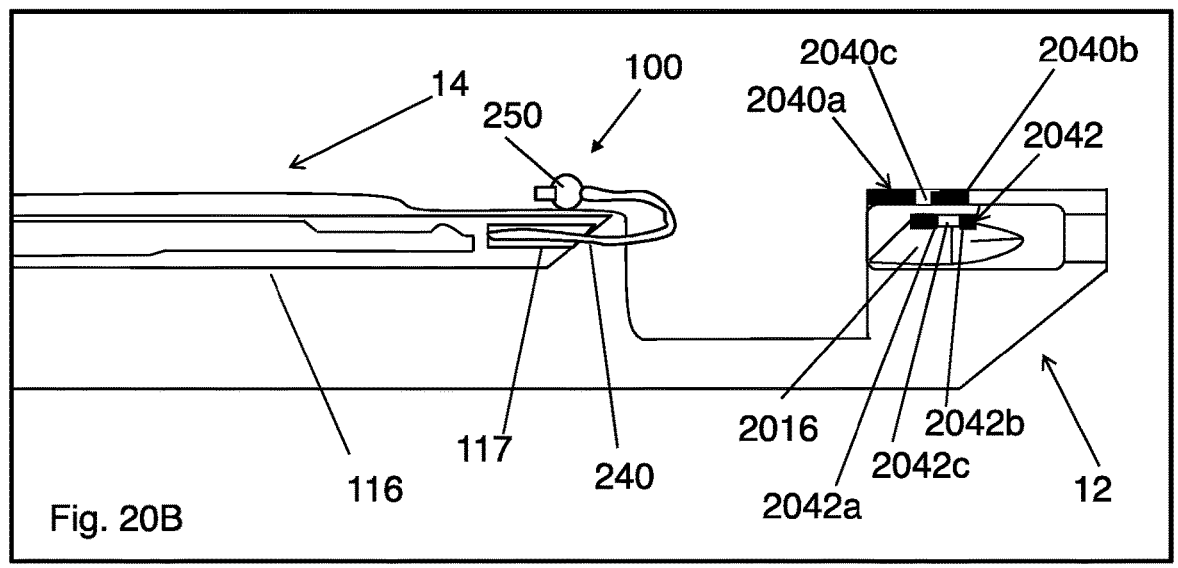
Figure 20C:
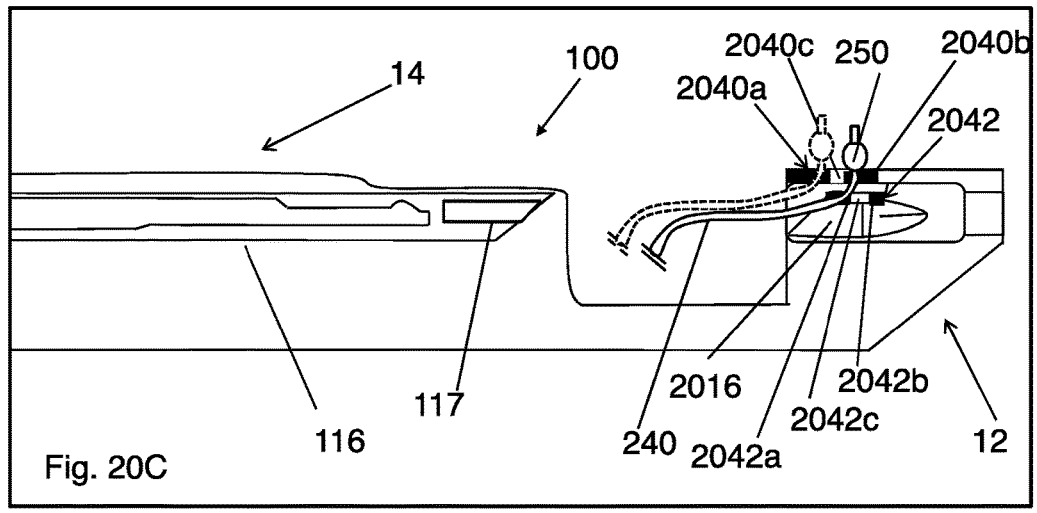
Figure 20D:
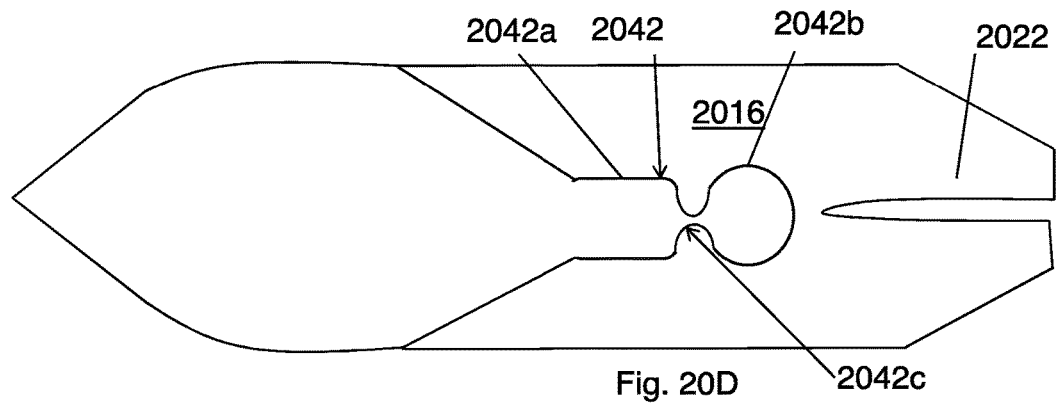

Similarly, the trap 2016 also comprises a slot 2042 that is axially disposed along its outer surface, as shown in FIGS. 20B, 20C and 20D. Trap 2016 comprises a pair of inwardly directed tabs 2042c that extend into the slot 2042. The tabs 2042c can be formed from a resilient material and can deform when sufficient force is applied. Trap 2016 is held within the chamber 12B of the distal tip 12 such that slots 2042 and 2040 are aligned with each other. The slots 2042 and 2040 are positioned such that tabs 2042c, 2040c are offset from each other. Tabs 2042c of the trap 2016 are positioned distal to tabs 2040c of the distal tip 12 such that clearance is provided to pass/route a suture 240 through the slot 2042 and into slot 2040b. An alternative method of use of the device is described with respect to the embodiment shown in FIG. 20A and is described herein below.

Method of Use

Hybrid Method

Device 100, in accordance with an embodiment of the present invention can be used to repair tissue defects. Thus, according to another aspect of the present invention there is provided a method of treating a defect in a tissue. The method is effected by passing a portion of a suture through a first region of the tissue positioned around the defect and coupling a suture portion to a suture holder. The suture holder is then retrieved through a second region of the tissue which is across the defect from the first region thereby forming a knotable loop. The loop can then be tied to close the defect.

Use of device 100 in repairing a tissue defect is described in greater detail below with reference to FIGS. 2a-3d. The tissue defect repaired by the present device can be, for example, a tear in annulus fibrosus tissue or a defect formed in the annulus fibrosus as part of a discectomy procedure. Tissues that may be treated using embodiments of the present invention include, but are not limited to: annulus fibrosus tissue of an intervertebral disc, meniscal tissue of the knee, muscle tissue, ligaments, tendons or other tissues of the shoulder or other soft tissues within a patient's body, for example tissues that are amenable to arthroscopic treatment or are amenable to suturing. In one specific example of a method of treating a defect within the meniscus, the defect may non-limitingly include delamination or tears of the meniscus (as mentioned previously) and a method of the present invention may be useful to reverse the delamination, or secure/contain the tear.

Other applications of a method of the present invention may include treatment of a defect, such as a tear within a ligament, a defect within percutaneous tissue, or a defect within the outer surface of tissue such as skin. Still further examples of a method of the present invention may include use within surgical procedures or in vessel repair, shoulder or hip repair.

For example, when treating a defect in the annulus fibrosus tissue of an intervertebral disc, device 100 is inserted at the site of the defect 300, as illustrated in FIG. 2a.

In some embodiments, the device 100 is sized and configured to be usable through a surgical portal that may be placed at the treatment site as part of a discectomy or other surgical procedure. The device 100 is inserted through defect 300 such that tissue 200 is received within tissue receiving gap 10. Distal tip 12 is inserted through the defect and positioned within substantially within the nucleus pulposus while proximal portion 14 is positioned substantially outside the annulus fibrosus with neck portion 15 of device 100 positioned through the defect. A suture passing member (e.g. stylet 319) is initially positioned within proximal portion 14 on a proximal side 200a of tissue 200 and a suture holder 316 coupled to distal tip 12 is positioned on a distal side of the tissue 200b. In one example, tissue on a first side of the defect 300, which may be referred to herein as a "first segment" 201 of tissue, is positioned within the tissue receiving gap 10, as illustrated in FIG. 2a. Activation of trigger 218 (shown in FIGS. 1a-b) translates stylet 319 from the proximal side 200a to the distal side 200b through the tissue at tissue region or site P1. As is illustrated in FIG. 2b, a tissue puncturing member such as needle 116 can be used to penetrate tissue 200 at puncture site P1 prior to advancing stylet 319. Alternatively, needle 116 and stylet 319 can be advanced together. Needle 116 may create a desired first puncture through puncture site P1. The puncture is created through a first location within the first segment of tissue 201 at some distance from the defect 300 on a first side of the defect 300.

When device 100 is positioned within tissue 200 as described above, it may be angled such that the amount of tissue between defect 300 and puncture site P1 (the 'bite depth') is maximized. This helps to maximize the distance (from defect 300) at which the suture 240 is passed through the tissue, thereby reducing the likelihood of suture 240 tearing through the tissue when tension is applied to suture 240. Such angling can also be used to pass suture 240 through tissues that are thicker or are better capable of holding the suture (such as more fibrous tissue for example) than tissues adjacent to defect 300. In some examples, the suture 240 is passed through tissues that may be preferable, in that they are better able to retain or support the suture 240.

Figure 2D:
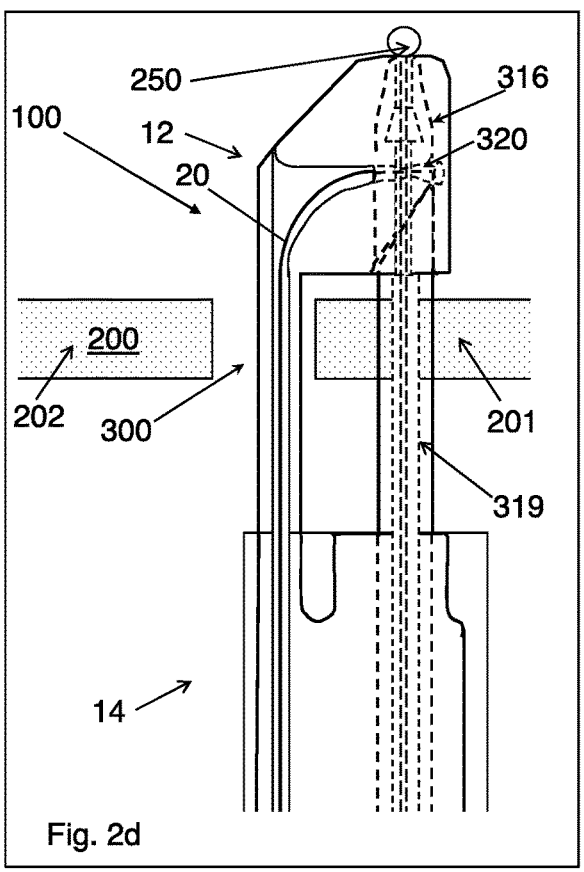
Figure 2E:
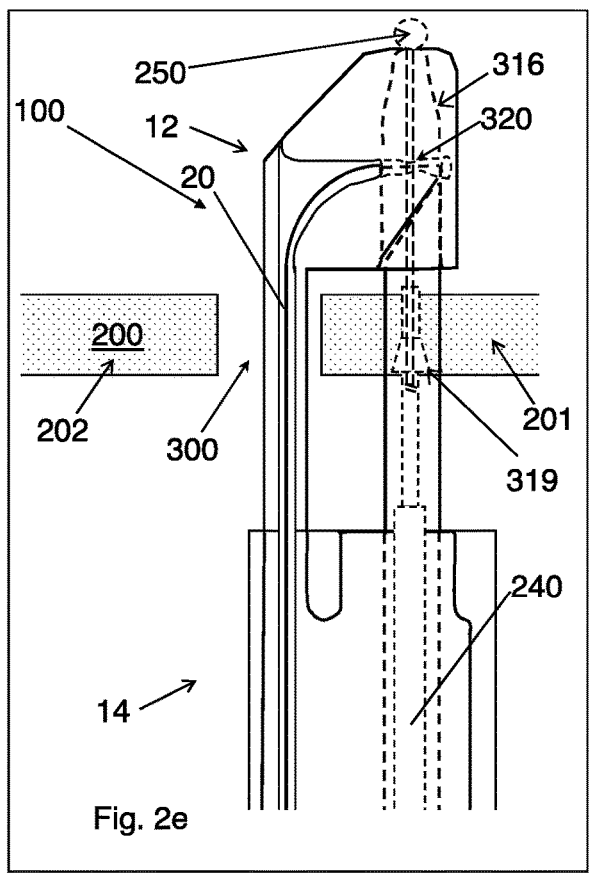
Figure 2F:
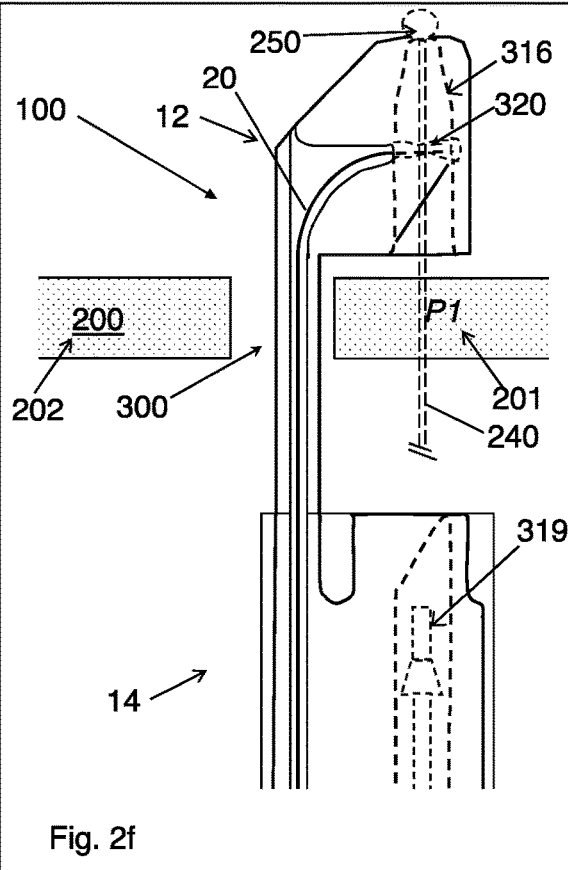
Figure 3A:
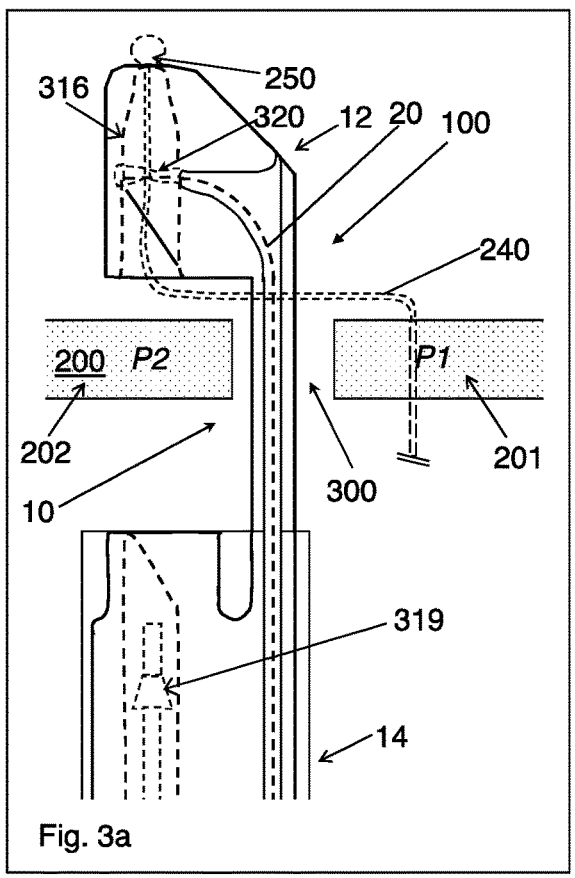
FIGS. 3a-3d illustrate further steps of a method in accordance with an embodiment of the present invention.

Once the knot 250 is retained by suture holder 316 as shown in FIG. 2d, stylet 319 is retracted, leaving the knot 250 coupled to the suture holder 316 at the distal tip 12 (see FIGS. 2e and 2f). Device 100 can then be repositioned such that region P2 of tissue 200 (across defect 300) is positioned within tissue receiving gap 10.

Figure 3B:
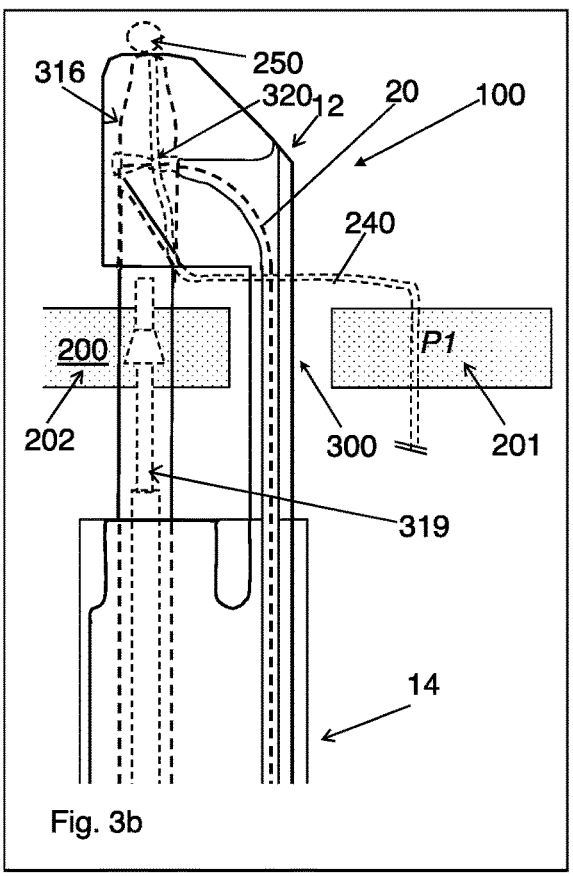

As shown in FIG. 2c, needle 116 and stylet 319 can be advanced together following puncturing through P1 to abut and stop against a proximal face of suture holder 316, positioned at distal tip 12. In one specific example, as mentioned above the suture holder 316 includes a trap 416 with a bevel at its proximal end face and the needle 116 may also be beveled at its distal end, to allow engagement with the beveled end face of trap 416. In some examples, there may be a partial interaction between the beveled end face of trap 416 and the beveled distal end of needle 116. In other words, the trap and the needle may meet only along a portion of their end faces. In one such embodiment, the partial interaction between needle 116 and trap 416 allows a channel or gap 334 to form there-between as shown in FIG. 3b. This allows for a portion of suture 240 to be passed through channel or gap 334 to help prevent suture 240 from being cut, frayed or severed. The interaction between the needle 116 and trap 416, in some embodiments, may be sufficient to prevent the suture knot 250 from inadvertently escaping through the channel 334. In another example, there may be a complete end to end interaction between the beveled end face of the trap and the beveled distal end of the needle 116. In other words trap 416 and needle 116 may meet substantially along their entire end faces.

In one example, stylet 319 advancing the suture knot 250, is advanced distally through suture holder 316 such that suture knot 250 is coupled to, or engages, the suture retaining element of suture holder 316. The distal end of stylet 319 pushes the suture knot 250 into suture holder 316, allowing suture knot 250 to be positioned on the distal side of tissue 200. Suture holder 316 allows substantially one way travel of the suture knot 250, i.e. suture holder 316 allows the suture knot 250 to pass substantially distally through the suture holder 316 (for example through an opening at the distal end of the suture holder 316) while impeding or preventing the knot 250 from being retracted through the same opening once it is passed therethrough.

As illustrated and discussed in greater detail below, the stylet 319 pushes the knot 250 through the suture holder 316 such that it exits through an opening on the distal side of the suture holder 316. A distal portion of stylet 319 is received within the suture holder 316 without being permanently coupled or secured thereto; in other words, the stylet is received in a manner whereby the stylet 319 is free to retract independently from the suture holder 316. In a particular embodiment, the suture holder 316 comprises a resilient material which allows movement of the stylet 319 into suture holder 316 and allows the knot 250 to be pushed through the suture holder 316 such that it is retained on the distal side of the suture holder 316.

Once the knot 250 is retained by suture holder 316 as shown in FIG. 2d, stylet 319 is retracted, leaving the knot 250 coupled to the suture holder 316 at the distal tip 12 (see FIGS. 2e and 2f). Device 100 can then be repositioned such that region P2 of the second segment of tissue 202 (across defect 300) is positioned within tissue receiving gap 10. In one specific example, as shown in FIG. 3a, the device 100 is rotated about 180 degrees to position the device 100 at region P2 on the opposing side of the defect 300. In some such embodiments, the device is rotated approximately 180 degrees prior to passing the suture through region P2. Device 100 can also be repositioned such that the suture holder 316 is retracted through a second location through the first segment 201 of tissue on the same side of defect (P3).

Figure 3C:
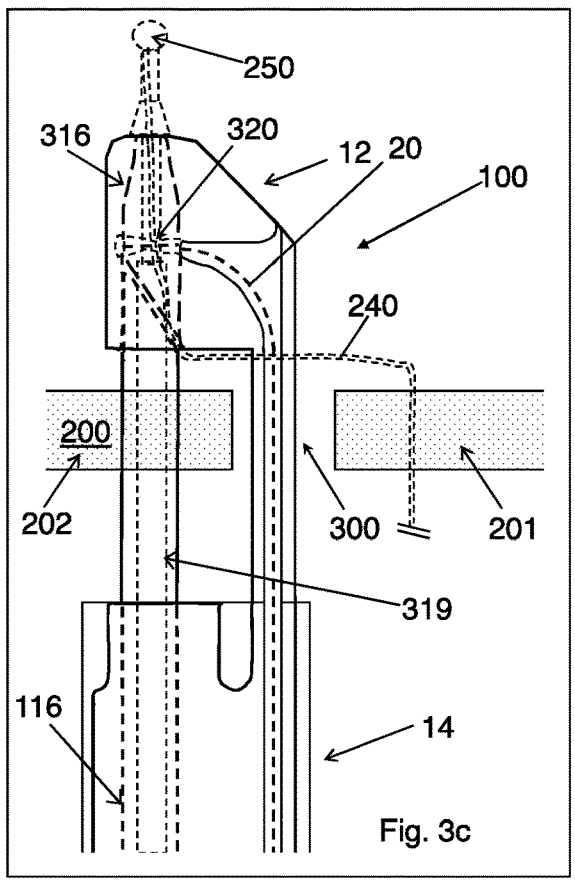
Figure 3D:
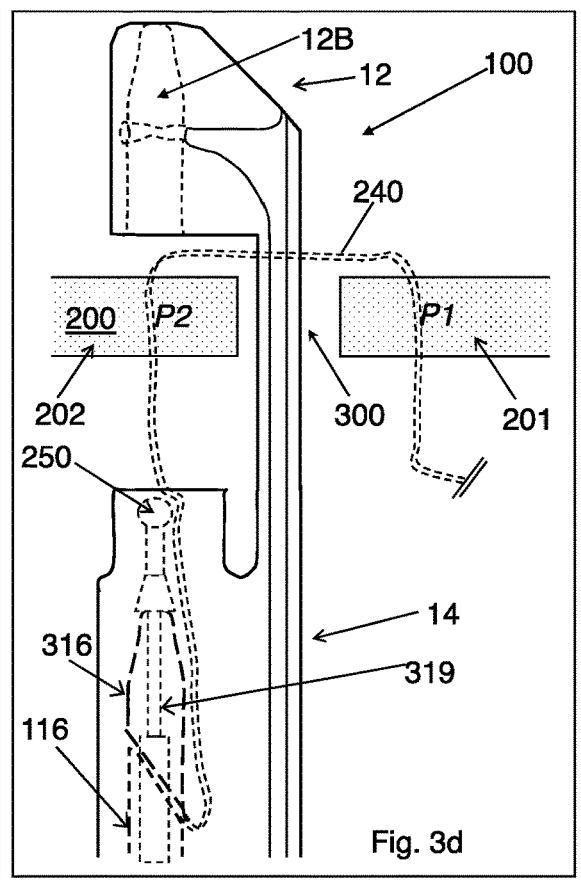

In order to retrieve suture holder 316, a suture holder retrieving element such as stylet 319 is then re-advanced through, for example, tissue site P2, along with a tissue puncturing element such as needle 116 or following puncturing of tissue 200 by needle 116. Once needle 116 is passed through tissue 200, it abuts against a surface of suture holder 316 which impedes further advancement of needle 116 as shown in FIG. 3b. Stylet 319 is then advanced further through suture holder 316 and engages suture holder 316, as illustrated in FIG. 3c. Suture holder 316 allows substantially one way travel of the stylet 319, relative to the suture holder 316, thereby allowing the stylet 319 to travel distally through suture holder 316, while substantially limiting or preventing proximal movement of stylet 319 there-through (once the stylet has been advanced beyond the portion of the suture holder configured to engage with the stylet). Stylet 319 is then retracted through the tissue site P2 (which is displaced across defect 300 from P1), for example on the second side 202 of the defect, but before stylet 319 is retracted, the suture holder is disengaged from distal tip 12 which allows it to be retracted along with stylet 319 as shown in FIG. 3d. The ends of suture 240 may be tied to allow for a substantially 360° suture loop to be placed around defect 300. In some examples, suture holder 316 is resilient and comprises a structure and/or material that provides both flexibility and elasticity, while having sufficient rigidity to allow the stylet 319 to remove the suture holder 316 from the distal tip 12 during retraction of the stylet 319. These properties of rigidity and flexibility may help prevent backward or proximal movement of the stylet 319 relative to the suture holder 316 as noted above.

Thus, when the stylet 319 is retracted through the tissue site P2, the suture holder 316 is retracted along with the stylet 319. This allows the suture knot 250 to be withdrawn proximally through tissue site P2 using the suture holder 316. In one embodiment, as shown in FIG. 3d, the suture holder is drawn from the distal side of the tissue 200 (for example, the internal surface of the tissue), to the proximal side of the tissue 200 (for example, the external surface of the tissue). Thus, the suture 240 has been passed through tissue sites P1 and P2 and across a region of tissue 200 or across tissue defect 300.

In some embodiments, the device may be rotated, for example by 90 degrees, prior to withdrawing the device from the tissue. In one particular example, if the device 100 had previously been rotated in a clockwise direction prior to passing suture 240 through the second segment of tissue, the device 100 may be rotated again approximately 90 degrees in a clockwise direction before withdrawing the device 100 from the tissue. Alternatively, if the device 100 had previously been rotated in a counter-clockwise direction prior to passing suture 240 through the second segment of tissue, the device 100 may be rotated approximately 90 degrees in a counter-clockwise direction before withdrawing the device 100 from the tissue. In other words, the device 100 may be rotated by about 90 degrees in the same direction as it was previously rotated before withdrawing the device 100 from the tissue. This may help to ensure that a portion of the device does not catch or snag a portion of suture 240 as the device is withdrawn from the patient's body. In other embodiments, device 100 may be retracted without rotation, taking care not to snag or grab the suture while retracting.

A closure knot 252 may then be provided to approximate tissue flanking the defect 300. In some examples, the closure knot 252 is provided as a pre-tied knot. In other examples, the closure knot 252 is formed by tying the ends of suture 240. The embodiments of a device and method described above may aid in approximation of a defect within the tissue and can be used for example to provide a suture loop that substantially completely encircles the defect. More specifically, defect 300 may then be treated by approximating the defect 300 by securing the suture strands that have been passed through both regions P1 and P2, on the first and opposing sides of the defect 300 using a closure knot. The closure knot may be formed during the procedure or may be in the form of a pre-tied knot that is tightened to approximate the tissue by bringing tissue on the first and second sides of the tissue together.

Figure 8A:
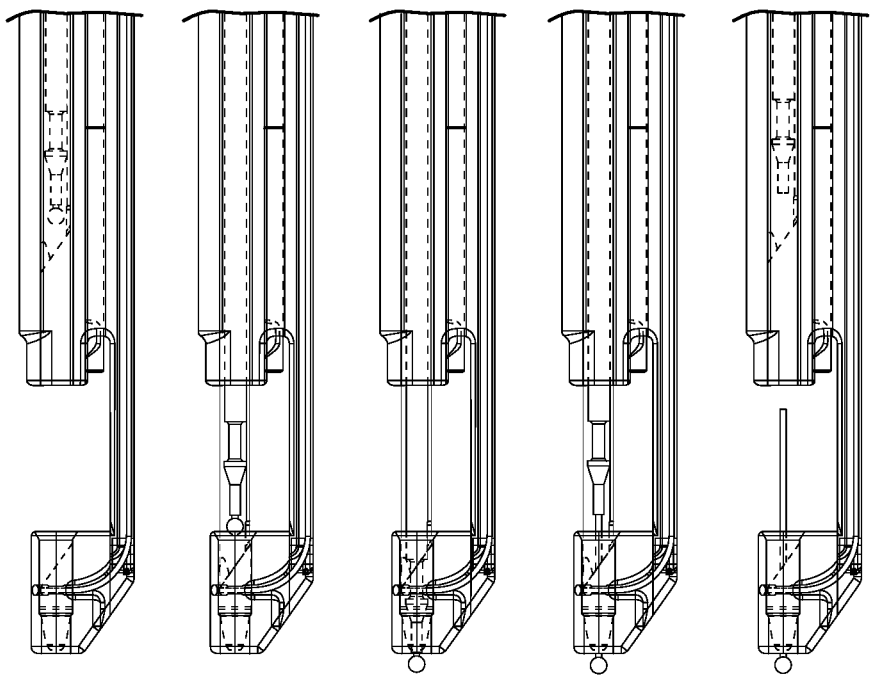
FIGS. 8a-8b illustrate steps of a method in accordance with an embodiment of the present invention.
Figure 8B:
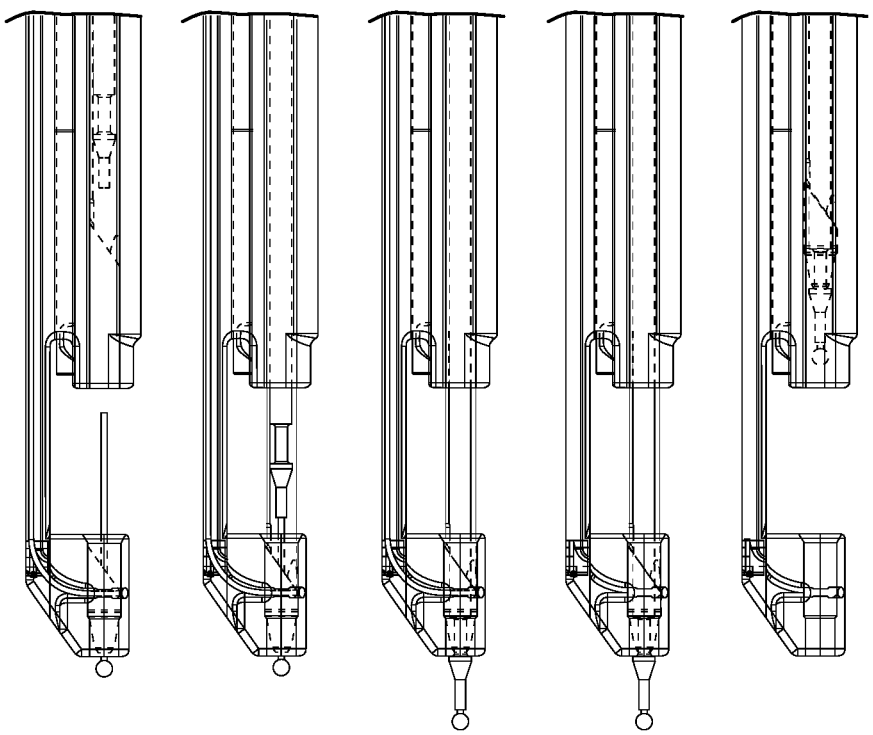

An overview of the specific embodiment of a method of the present invention, as described above, is illustrated in FIGS. 8a and 8b. FIG. 8a shows steps involved in depositing a suture knot at the distal tip, in accordance with a method of the present invention, the steps being shown in order from top to bottom. Initially, the device in its starting position is positioned at a desired tissue location. The needle then penetrates through the tissue (with the stylet and suture being housed within the needle). Thereafter, the stylet advances and pushes suture knot through the trap. The stylet and needle then retract from tissue and suture end such as suture knot remains through the trap. FIG. 8b shows steps involved in retrieving the trap from the distal tip, the steps being shown in order from top to bottom. The surgeon then repositions the device for second needle stick. The needle penetrates tissue (the stylet being housed within needle). Then the stylet advances until its tip is captured by the trap. The retention wire is then retracted from the trap. The needle, trap, stylet and suture then retract from tissue.

In accordance with various embodiments of methods described herein above, one or more of the steps may be automated.

Although one embodiment of a method is described herein above, which involves passing a portion of a suture through a tissue site on one side of the defect to couple the suture portion to a suture holder, and retrieving the suture holder through an opposing side of the defect, alternative embodiments for practicing the invention exist. Certain alternatives are described herein, but other alternatives are possible as well.

In one alternate embodiment, the method of the present invention may comprise initially passing the suture holder (with a portion of a suture detachably coupled thereto) through a first tissue site on one side of the defect, and subsequently retrieving the suture portion through a second tissue site an opposing side of the defect, i.e. reversing the order described above.

In another alternate embodiment, the method of the present invention may comprise retrieving a portion of a suture for example from a device distal tip placed on a distal side of the tissue, passing the suture through a first tissue site such that it is passed from a distal side of the tissue to the proximal side of the tissue, and capturing it within a suture holder (e.g. within the device proximal portion). The method may further comprise passing the suture holder through a second tissue site, such that it is passed from the proximal side of the tissue to the distal side of the tissue and coupling the suture holder to the device distal tip. In one example, this may allow for an internal knot to be placed within the tissue.

In another alternate embodiment, the method of the present invention may comprise passing a portion of the a suture through a soft tissue on one side of the defect and coupling the suture portion to a suture holder comprising a suture anchor, whereby the suture anchor is then retrieved through an opposing side of the defect.

Method of Dropping or Deploying a Suture Knot in Accordance with Various Embodiments of the Present Invention
Method of Deploying a Suture Knot Disposed on an Elongate Member Using a Suture Retaining Member As described hereinabove, in some embodiments a device 100 may be provided for deploying a partially or fully pre-tied knot with the device additionally comprising a suture retaining component 900 for retaining a portion of the suture as shown in FIGS. 21a-e. In some embodiments of the present invention as discussed earlier with respect to FIGS. 2 and 3, the device 100 may be used to deploy a closure knot after the suture has been passed through for example, first and second segments of tissue on both sides of a defect, in order to re-approximate tissue on both sides of the defect 300. In other words, a device may be used to deploy a knot to substantially re-approximate the defect 300 by bringing together the first and second tissue segments around the defect 300. The embodiments of a device and method described above may aid in approximation of a defect within the tissue and can be used for example to provide a 360 degree suture loop, i.e. a suture loop that substantially completely circumscribes the defect.

Figure 21B:
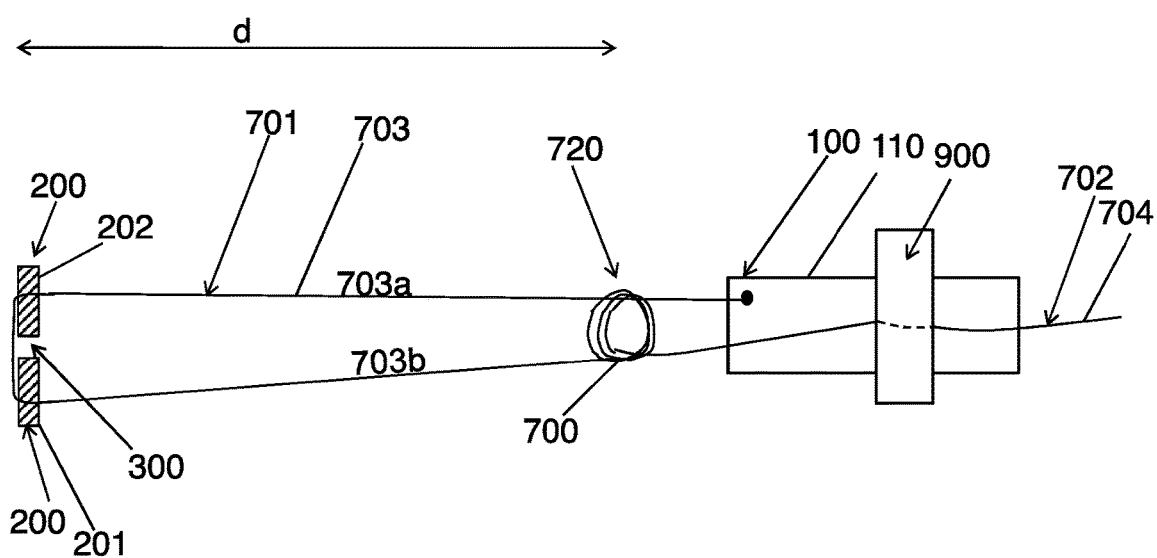

During use, the device 100 is withdrawn proximally along with segment 703a of the post 703 coupled thereto until the suture 240 is taut, thus placing the suture 240 in tension. Since the system is in tension, as the device 100 (and thus segment 703a of the post 703) is pulled or retracted further, the loops 700 fall or release distally off the device 100 and segment 703a of the post 703 is pulled proximally through the loops 700. In other words, the loops 700 are deployed or released over segment 703a of the post 703. When the loops are positioned over the post 703, they form a knot 720 (FIG. 21b). As shown in FIG. 21b, the loops are deployed at a distance d from the tissue 200. The distance by which the device 100 is withdrawn proximally is substantially equivalent to the distance the loops 700 are displaced distally. More specifically, the suture 240 is routed such that segment 703a of the post 703 extends from the distal end of the device 100 to tissue 200, and the post passes through tissue 200 with segment 703b extending proximally from tissue 200 back towards loops 700 to which it is integrally coupled. As a result, the proximally directed force applied to segment 703a of the post 703 results in a distally directed force being applied to segment 703b of the post 703 which translates to a distally directed force applied against the loops 700, thus pulling them off the device 100 and onto the post 703.

Figure 21C:
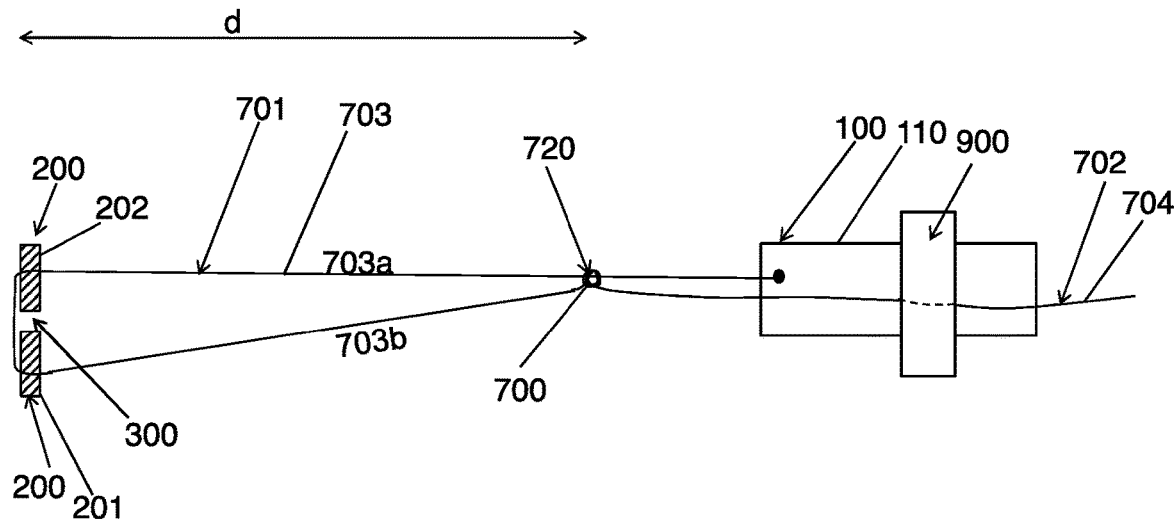

The device 100 is then retracted further while the second portion 702 of the suture 240 forming the locker 704 is held by the retaining or tensioning element 900. In other words, the retaining or tensioning element 900 provides resistance to movement by, for example, providing a frictional force $F_f$ (not shown in the drawings) against the locker 704, thus preventing the locker 704 from slipping. As shown in FIG. 21c, as the device 100 is pulled/retracted, the device 100 (and thus segment 703a of the post 703) is withdrawn proximally with respect to the tissue 200 while the loops 700 of the knot 720 substantially collapse or cinch around the post 703. In some embodiments, the knot 720 is cinched substantially at distance d (not necessarily the same as the distance 'd' in FIG. 21b above) from the tissue 200 in proximity to a distal end of the device 100. In some embodiments, the position of the knot 720 with respect to tissue 200 remains unchanged as the knot 720 is being collapsed or cinched. Thus, in some embodiments, as described herein, allow the retaining or tensioning element 900 to retain or maintain tension on the second portion 702 of the suture strand 240 (such as a locker 704) while the knot 720 is being cinched or collapsed.

Thus, in some embodiments, the device includes a means (such as the retaining or tensioning element 900) for limiting/preventing motion of one portion of the suture strand 240, such as a second portion 702 of the suture strand 240, relative to another portion of the suture strand, such as a part of the first portion 701 of the suture strand, during at least a part of the knot deployment procedure. For example, the device may limit motion of the second portion 702 relative to a part of the first portion 701 that is affixed to the device 100, while the knot 720 is collapsed. More specifically, the retaining or tensioning element 900 may limit movement of the locker 704 relative to a part of the segment 703a of the post 703 that is coupled to the device 100. In other words, the retaining or tensioning element 900 prevents motion of the second portion 702 of the suture strand 240 relative to the device 100. In some embodiments, the means for limiting/preventing motion (such as the retaining element 900) may apply a frictional force and/or maintain tension on a portion of the suture 240. Retaining second portion 702 within retaining element 900 may also be understood to allow motion of parts of suture portion 701 relative to the retained suture portion 702. Put differently, if suture portion 702 would not be retained but would rather be free to move, then it would move at the same rate as other parts of the suture and there would therefore be no relative motion between those suture portions; limiting motion of portion 702, however, allows other parts of the suture to move relative to portion 702. Thus, retaining suture portion 702 within retaining element 900 may function to either enable or prevent/limit relative motion between the suture portions, depending on which portions of suture are examined.

Figure 21D:
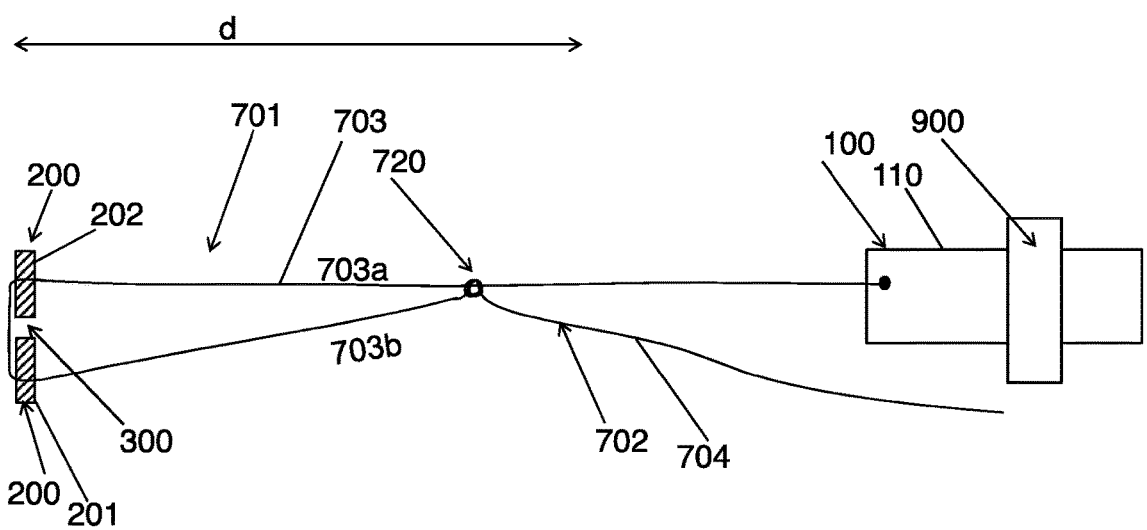
Figure 21E:
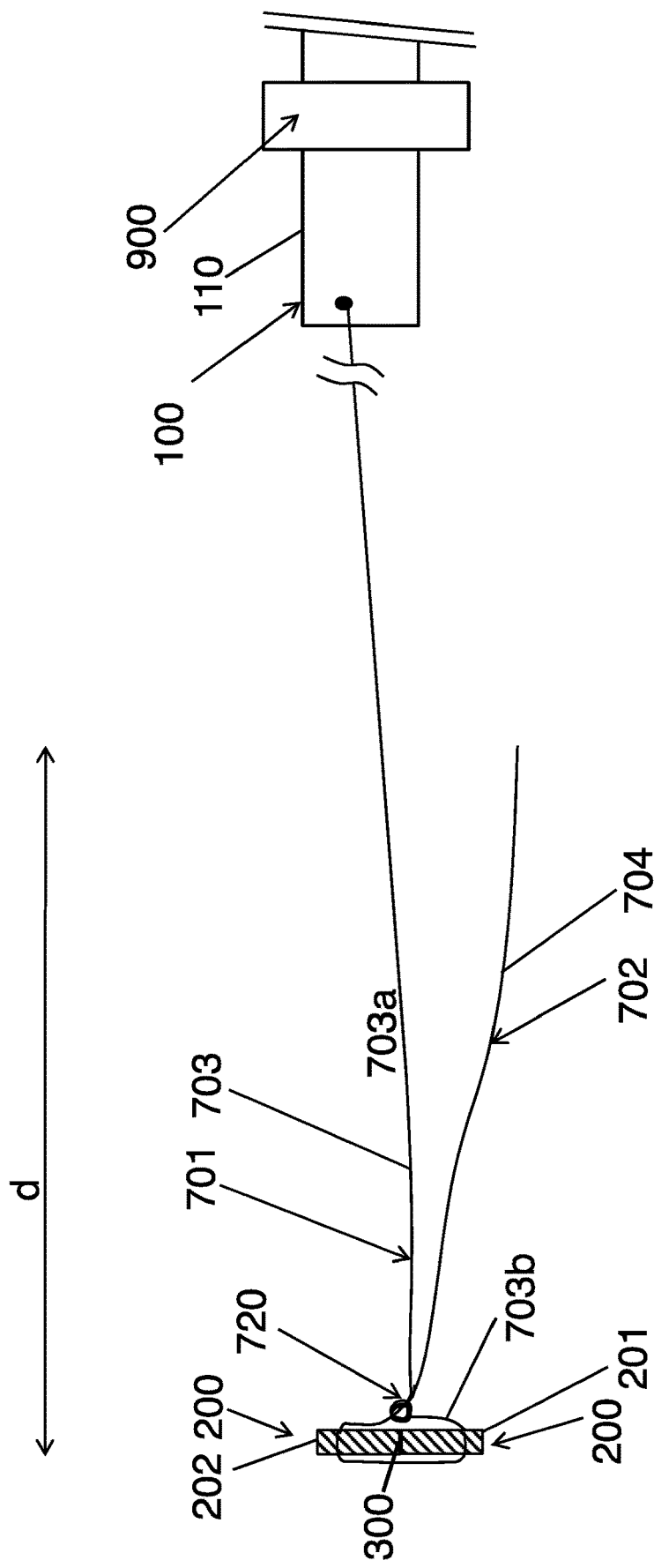

As the knot 720 is cinched or collapsed, the device 100 is withdrawn or retracted further, relative to tissue 200. As shown in FIG. 21d, when further collapsing the knot 720 requires a force that is greater than the force $F_f$ applied by the tensioning or retaining element 900 to the locker 704, the knot 720 begins to translate or slide distally along the post 703 (thus allowing the device 100 to be withdrawn) and the locker 704 is released from the tensioning or retaining element 900. Some embodiments allow the locker 704 to be automatically released or withdrawn from the retaining element 900, for example when the knot is sliding, to avoid premature locking, excessive tightening or cinching of the knot 720. Releasing the locker 704, allows the locker 704 and the portion of post 703 affixed to device 100 to move relative to one another. In some embodiments, as shown in FIG. 21e, the device 100 is withdrawn until the knot 720 slides to rest substantially adjacent/against tissue 200. This allows, for example, the suture 240 to place tension on the first and second segments 201, 202 of the tissue 200, in order to approximate the defect 300.

Thus in one broad aspect, embodiments of the present invention comprise a device having one or more features for: a) retaining/restraining a portion of the suture strand while tension is applied to another portion of the suture strand to cinch the knot; and b) releasing the portion of suture strand prior to the knot being locked or excessively tightened or cinched. In some embodiments, the suture as a whole is still retained by the device at a different location along the suture length. In order words, the particular portion of suture that was retained by the retaining feature of the device may be released such that it is free to move, while other portions of the suture strand may remain coupled to/retained by the device. It should be understood that the term "release" (and its cognates) may comprise an active or passive act of releasing (or a combination of the two), allowing/enabling, for example, relative motion between two portions of the suture strand. Thus, "releasing the one portion of suture strand" may thereby allow the one portion of suture strand (for example, locker 704) to move relative to another portion of the suture strand (for example a part of segment 703a of the post 703 that is coupled to the device 100).

Method of Deploying a Partially or Fully Pre-Tied Knot that is Indirectly Coupled the Device As discussed above with respect to FIGS. 22a-f, a device may be provided to deploy a pre-tied knot after the suture 240 has been passed through both first and second segments 201, 202 of tissue 200 (for example around a defect 300), in order to bring the tissue segments together. The device 100 of FIGS. 22a-f comprises a pre-tied knot in terms of loops 700 that are indirectly coupled to the device shaft 16. The loops 700 are disposed onto a knot slider 800 that is mounted on the device shaft 16. After suture has been passed through the first and second segments of tissue 201, 202, a slight reduction can be observed in the amount of suture present in service loop L within the proximal portion or proximal housing 14, as shown in FIG. 22g. The device 100 may then be withdrawn proximally and pulled away from the patient (the proximal direction is shown by arrow p). The suture within the service loop L is initially held by the force of friction $F_f$ applied by the O-ring on the service loop L. The force $F_f$ that is applied by the O-ring on the service loop L is less than the force required to decouple the knot slider 800 from the shaft 16. In the embodiment where the knot slider 800 is passively coupled to the shaft 16 as shown in FIG. 22k, the force $F_f$ that is applied by the O-ring is less than the force of frictional engagement between the O-ring 910 and the shaft 16. As the device is pulled proximally the suture portion 701 is placed in tension applying a force $F_A$ to the suture in the service loop L. Once the force $F_A$ exceeds the force $F_f$ applied by the O-ring, the service loop L is pulled out of engagement with the O-ring. The service loop L slips out from between the O-ring 910 and the projection 806, as shown in FIG. 22h. Thus, as the device 100 is drawn back the excess suture, i.e. the segment of suture portion 701 forming the service loop L is deployed or pulled out from the proximal housing 14.

As the device 100 is withdrawn or retracted further, the excess suture from the service loop L is also consequently withdrawn. Once the excess suture has been withdrawn, the slack in suture portion 701 has been removed and the suture portion 701 is placed in tension. As the device 100 is further retracted, the taut suture portion 701 places tension on the loops 700 wrapped around the knot slider 800. In other words, as the suture portion 701 is placed in tension, force is applied to the loops 700 formed around the knot slider 800, thus applying a force $F_B$ (not shown in the drawings) on the knot slider 800. Force $F_B$ is sufficient to disengage the knot slider 800 from the shaft 16 or any other part of the proximal portion 14 or device 100 to which it is detachably coupled.

Thus, when a sufficient force $F_B$ is applied on the knot slider 800 as tension is placed on the suture 240, the projection 820 of knot slider 800 will move out of engagement from projection 1402 of the device proximal portion. The knot slider 800 is decoupled from the device proximal portion 14 and, as the device 100 is retracted/pulled, it slides distally along the shaft 16. The tail hook 824 of the knot slider slides along the recess or groove 1603 of the shaft 16 until it reaches the end of the groove 1603. The tail hook abuts against or engages a portion of the shaft 16. As shown in FIG. 23a, the knot slider 800 is then positioned in its second configuration within the tissue receiving gap 10 of device 100. The knot slider 800 is positioned such that the flexible arm 818 is lined up with or adjacent the tissue receiving gap 10.

Thus, when the device 100 is withdrawn proximally as discussed above, continued tension on the suture 240 causes the flexible arm 818 to bend or deflect (from its initial position 818A which blocks the loops 700) inwardly into the tissue receiving gap 10 into its second position 818B to release the loops 700. The taper on the arm 818 may facilitate deployment of loops 700. Additionally the downward taper on the knot slider 800 may also facilitate removal of the loops 700. When the arm moves into the gap 10, the tension applied by the suture 240 to the top portion of the loops 700, allows deployment of the loops 700 off the knot slider 800. The tension on the top portion of the loops 700 will pull the top portion forward and since the bottom portion of the loops may already be distally ahead of the top portion, and positioned on a taper, the loops 700 may slip/slide off the knot slider 800 well with relative ease.

The remainder of the knot deployment method discussed herein below is in reference to the function of the retaining or tensioning element 900 which in this particular example comprises the o-ring 910 discussed previously. With respect to FIGS. 21a-e and further illustrated in FIGS. 23a and 23b, in some embodiments, suture portion 701 forms a post 703 and suture portion 702 forms a locker 704 with post 703 comprising segments 703a and 703b. Once the knot slider 800 is in its second or distal position, the device has been withdrawn such that suture portion 701 (703) is in tension. The device 100 is then pulled further in a proximal direction, such that the loops 700 of the partially pre-tied knot are released as shown in FIG. 23b.

In further detail, in some embodiments the post 703 is routed such that segment 703a of the post 703 runs distally from the device distal tip 12 to the second segment 202 of tissue 200. The post 703 then passes through the second segment 202, along the opposite side/face of the tissue 200 and through the first segment 201 of the tissue 200. Post segment 703b then runs proximally from the first segment 201 of tissue 200 to the loops 700. Thus, when the device 100 (and thus segment 703a of the post 703) is retracted/pulled proximally while the locker 704 (of suture portion 702) is held by the O-ring 910, segment 703b of the post 703 exerts a "pulling" force on the loops 700 distally, allowing them to be deployed or released onto the post 703 in proximity to the device distal tip 12. The positioning of the knot slider 800 within the tissue receiving gap 10 prevents the loops 700 from being released within the tissue receiving gap 10. This prevents the loops from being deployed onto neck 15 of the device and collapsing or cinching thereon as they are tightened. Since the knot slider 800 is positioned within the tissue receiving gap 10, when the device is retracted/pulled, the loops 700 are deployed distally off the knot slider 800 onto the first portion 701 of the suture 240 that is coupled to the device 100, i.e. the post segment 703a. Thus, the loops 700 are deployed distally onto the post segment 703a forming a knot 720 while tension is maintained on the locker by the O-ring 910. In one example, the loops 700 are deployed at a distance d from the tissue 200, as shown in FIG. 23b.

With further proximal movement of the device 100, the O-ring further functions to tension the suture 240 to aid in collapsing the loops 700 of the knot 720. As device 100 is retracted, a segment 703a of the post 703 is withdrawn proximally while tension is maintained on the locker 704 by the O-ring 910. The proximal movement of segment 703a of the post 703, while locker 704 is retained, applies a force $F_C$ (not shown in the drawings) to suture 240 forming loops 700, causing the loops 700 to collapse from a first diameter to a second smaller diameter, thus collapsing the knot 720 around the post 703. The force $F_C$ applied to the suture to collapse the knot 720 is less than the $F_f$ applied by O-ring 910 to the locker 704. Thus, the retaining or tensioning element such as the O-ring 910 retains and/or restrains a second portion 702 (forming the locker 704) of the suture 240 while tension is applied to the first portion 701 (forming the post 703) of the suture 240 to cinch or partially cinch the knot 720.

Figure 23C:
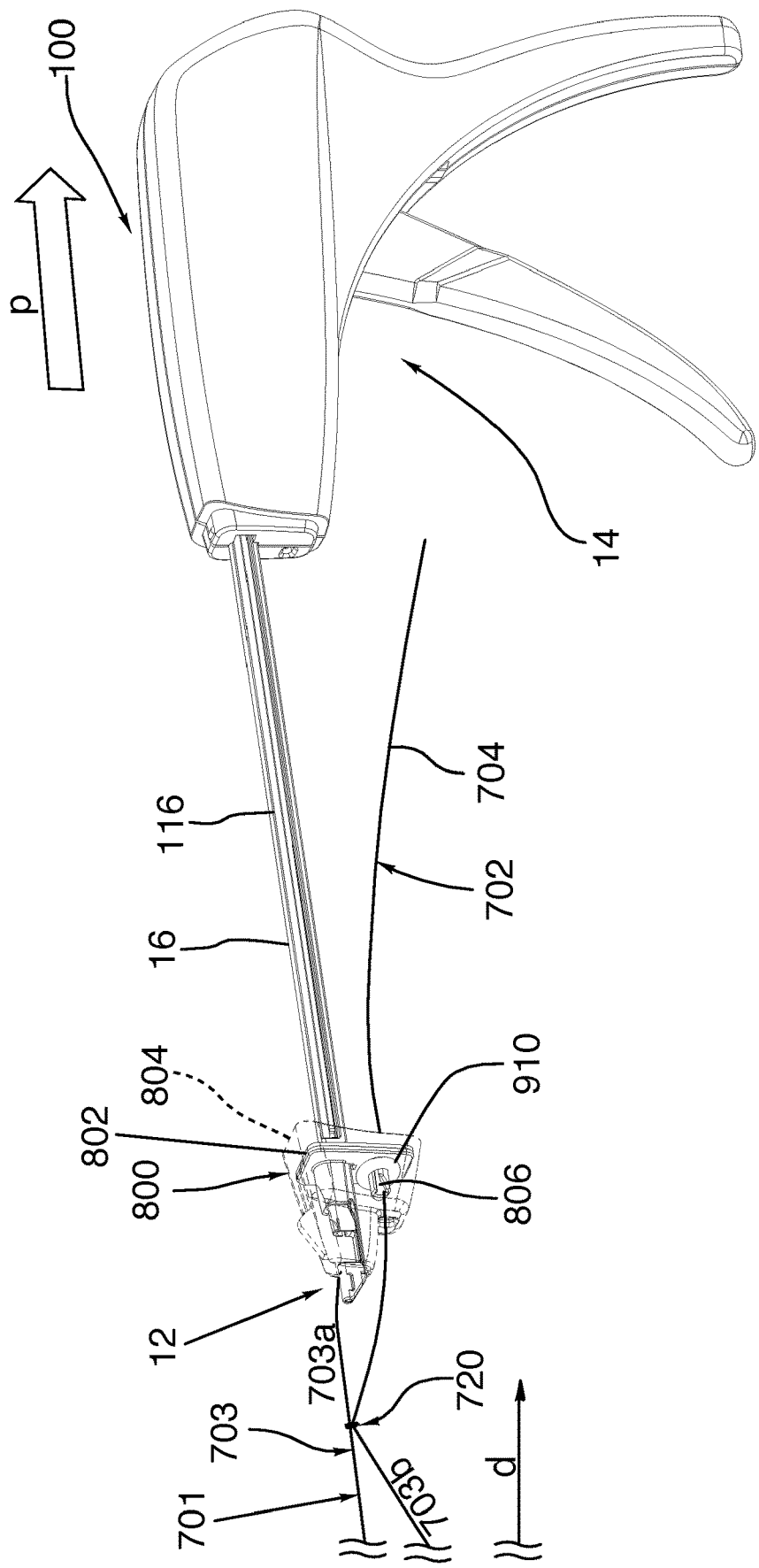

More specifically, the O-ring 910 provides resistance against movement of the locker 704, preventing the locker 704 from moving which assists in collapsing the knot 720. In other words, the O-ring 910 applies a retention force such as a force of friction $F_f$ against the locker 704 while the post 703 is tensioned. The knot 720 collapses until the force to further collapse the knot is greater than the force/tension applied by the O-ring on the locker 704. The knot 720 is collapsed distal to the device 100 in proximity to the device distal tip 12, as shown in FIG. 23c. As the device 100 is pulled the knot 720 remains substantially stationary with respect to tissue 200 with the device 100 moving proximally relative to tissue 200. An increase in length of suture is observed proximal to the knot 720 between the knot 720 and the device distal tip 12 due to the decrease in length 1 of the loops 700 as they collapse. The O-ring 910 places sufficient tension on the locker 704 to allow the knot 720 to collapse, but the tension is less than the force required to lock the knot 720.

Figure 23D:
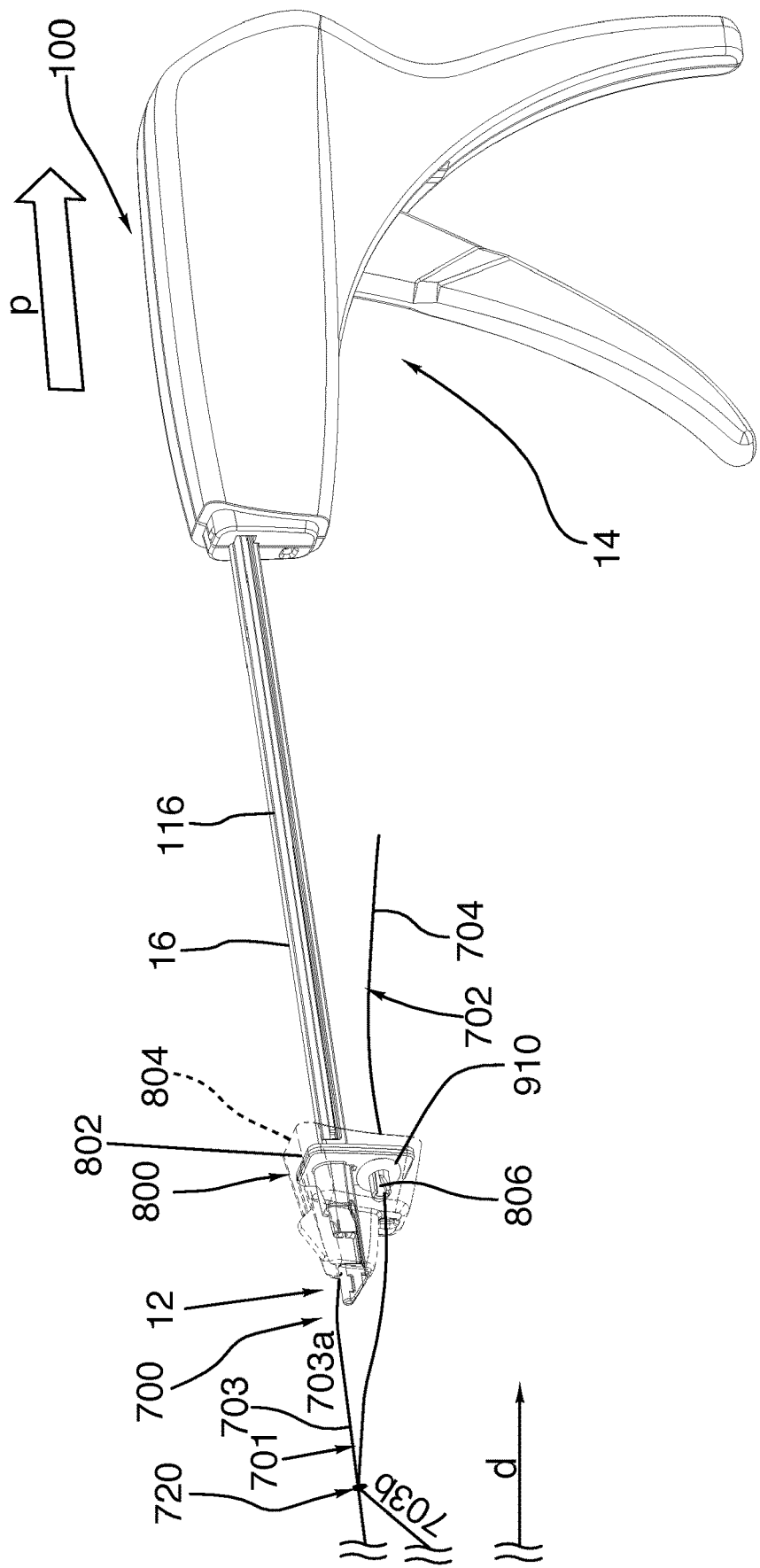
Figure 23E:
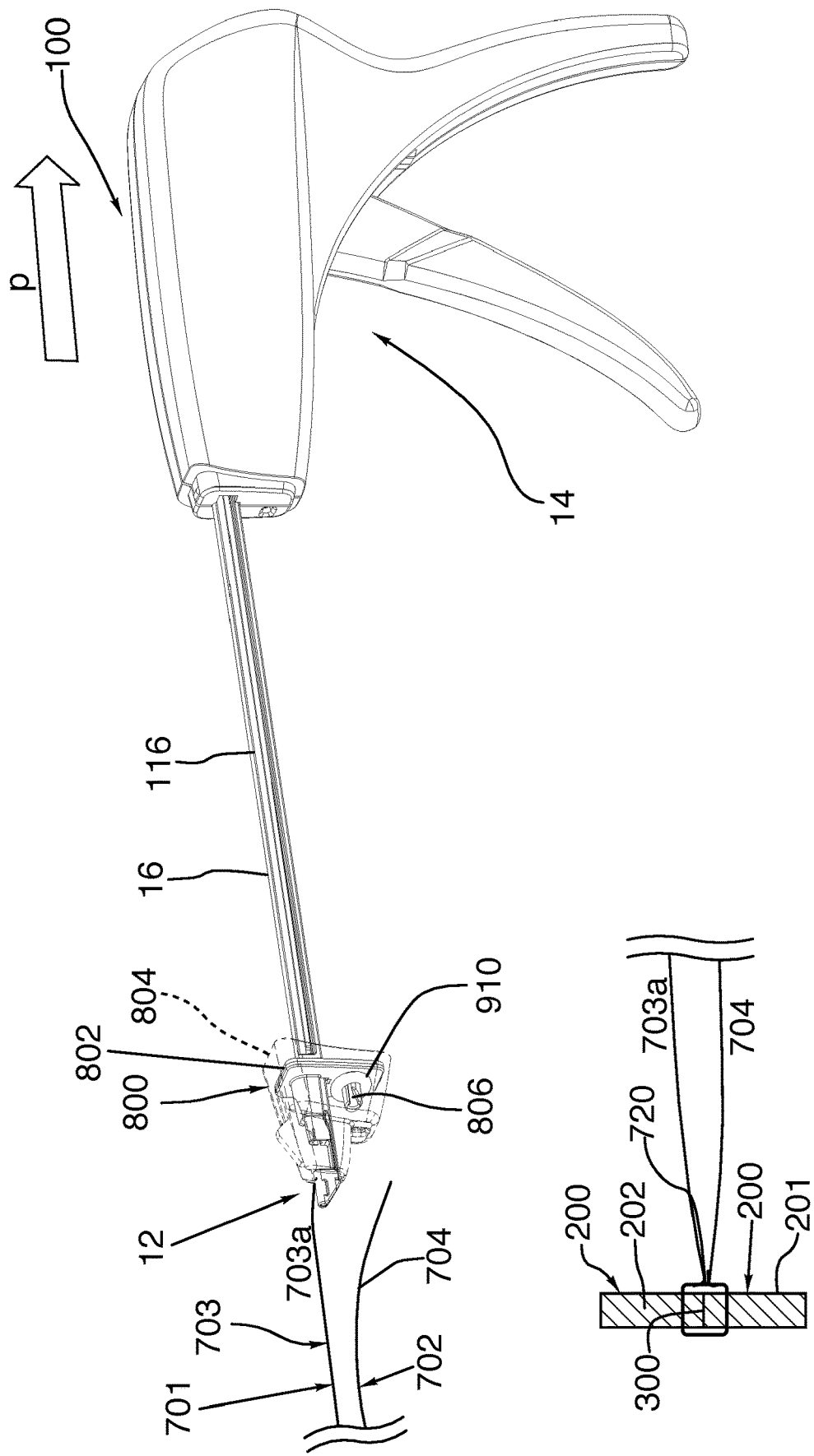

Once the knot 720 has been collapsed, additional force is required to tighten or lock the knot 720. The device 100 is further retracted proximally, thereby retracting/pulling post segment 703a and applying a force $F_C$ on the loops 700. When the force $F_C$ is greater than the force $F_f$ applied by the O-ring 910 on the locker 704, the locker 704 is released and the collapsed loops 700, and thus knot 720, slide distally along the post 703 as shown in FIG. 23d. In other words, the applied suture tension is greater than the frictional force applied by the O-ring. This causes the locker 704 to move distally relative to the O-ring 910 causing the locker 704 to slide relative to the O-ring 910. Thus, the retaining or tensioning element such as the O-ring 910 releases the second portion 702 (forming the locker 704) prior to the knot 720 being locked or excessively tightened or cinched. More specifically, some embodiments allow for retaining the locker 704 of the suture 240 while the knot is being cinched while allowing the locker 704 to be automatically released or withdrawn from the retaining or tensioning element, for example when the knot is sliding, to avoid premature locking, excessive tightening or cinching of the knot 720. In specific example, when the knot 720 begins to slide, the locker 704 is no longer held in frictional contact with the O-ring 910 and may slip out completely from the O-ring. In other examples, the locker 704 may be free to slide or translate distally relative to the O-ring 910 but is held by the O-ring 910 during the procedure. When the O-ring releases the locker 704 it allows relative movement between the locker 704 and the part of segment 703a of the post 703 that is coupled to the device 100. The loops 700 continue to travel distally along the post 703 until they are in proximity to the tissue 200, as shown in FIG. 23e.

Additional force may be applied to the locker 704 and/or the post 703 in order to further tighten and/or lock the knot 720 for example in order to approximate the defect 300. Furthermore, the locker 704 and the post 703 may be used to create additional knots in order to further secure the knot 720. In one specific example, the additional knots are half-hitches. In a particular embodiment, four half-hitches are created. In another example, the additional knot is an overhand knot or surgeon's knot. In one specific example, the additional knot is a double-overhand knot where either the post or the locker may be pulled to lock the knot. Alternatively both the post and the locker may be pulled simultaneously in order to lock the knot. In one specific example, the knot 720 is sliding locking knot. In one specific example the knot 720 is a Dines knot.

Alternative Embodiment of a Method of Deploying a Pre-Tied Knot Using a Device Comprising a Retaining or Tensioning Element in the Form of a Spring Member An alternative embodiment of a method of deploying a pre-tied knot as shown in FIG. 24. In operation, the device 100 is withdrawn to deploy the loops 700 distally off the device 100 at a distance from tissue 200. The loops 700 are displaced distally substantially by the same distance that the device 100 (and thus segment 703a of the post) has travelled proximally. After the loops 700 have been deployed forming a knot such as a Dines knot 720, the device 100 is pulled proximally, withdrawing the post segment 703a coupled thereto while the locker 704 is retained by the resilient member 912. In some embodiments, as force is applied to the post 703, the Dines knot 720 collapses distal to the device 100 in proximity to the device at substantially the same distance from the tissue 200 at which the loops 700 have been deployed. The Dines knot 720 collapses until the force applied to the post 703 to further collapse the knot is greater than the retention force applied by resilient member 912 on the locker 704. At this point the knot 720 begins to slide towards the tissue and the loop Y of the locker 704 slips out of engagement with the resilient member 912. Thus, although the resilient member 912 retains the locker 704 while tension is being applied to the post 703 to collapse or cinch the knot 720, it releases the locker 704 as the knot 720 begins to slide, prior to the knot being locked or excessively tightened or cinched. The device 100 continues to be pulled until the knot 720 slides to a position substantially adjacent the tissue. The knot 720 may then be locked by applying a force to the locker 704 and/or the post 703.

In an alternate embodiment as described above with respect to the description of the device, the retaining or tensioning element 900 for holding the second portion 702 of the suture such as the locker 704, may includes two interlocking mechanical pieces. The first mechanical piece interacts with the second mechanical piece (i.e. the two pieces are co-operatively engaged with each other). The suture 240 is passed through tissue as discussed previously for embodiments described herein above. The device 100 is then withdrawn proximally to deploy loops 700 onto the post 703 forming a knot 720. The device 100 is further pulled proximally to collapse the knot 720 until such time that the force required to further collapse the knot 720 is greater than the holding force of the two mechanical pieces. Thus, similar to embodiments described above, the retaining or tensioning element 900 retains the second portion 702 of the suture 240 while tension is applied to the first portion 701 of the suture to cinch the knot 720 but allows the second portion 702 to be released or withdrawn, for example automatically, when the knot is sliding to avoid premature locking or excessive tightening or cinching of the knot 720. An example of this comprises a first resilient member coupled to the locker 704, the first resilient member being coupled to a second resilient member that is attached to the device body similar to the example shown in FIG. 24.

Alternative Methods for Deploying the Loops of a Pre-Tied Knot are Described Further Herein Below with Respect to FIGS. 25-27.

Figure 25A:
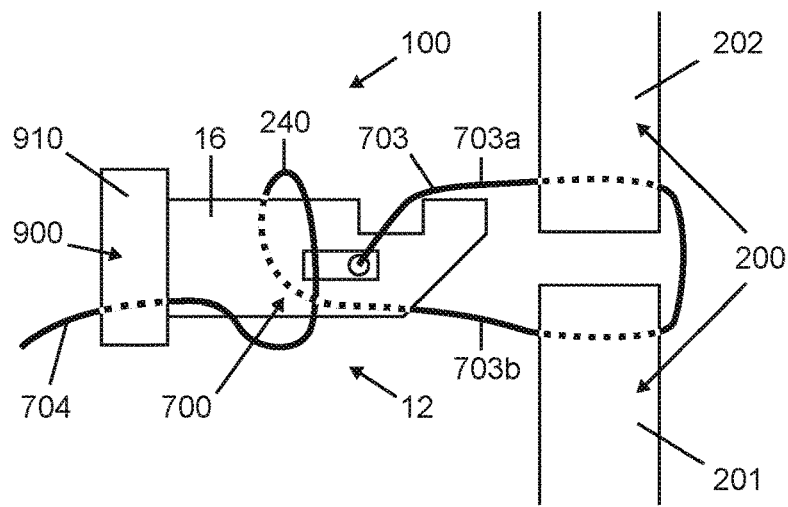
FIGS. 25*a*-25*e* illustrate a device and method in accordance with another embodiment of the present invention.
Figure 25B:
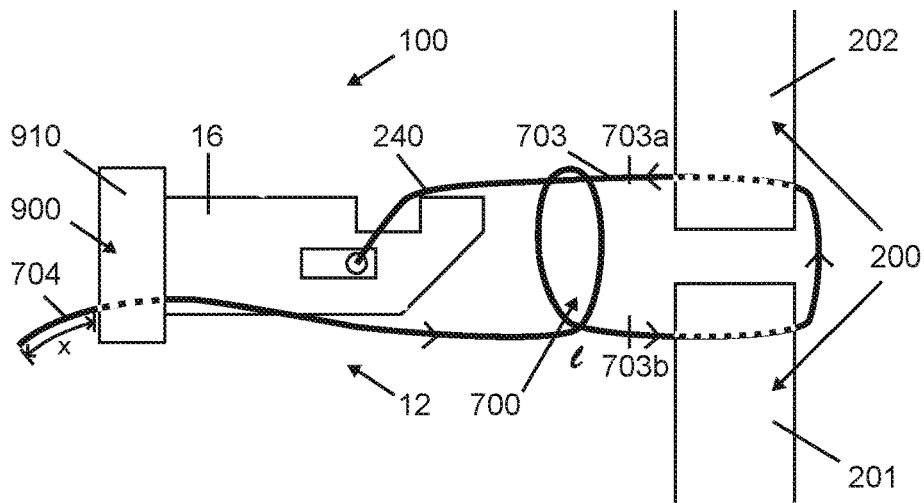

In some embodiments as shown in FIG. 25a, the loops 700 of a partially or fully pre-tied knot are formed onto a portion of the shaft 16. The loops 700 are formed distal to a retaining or tensioning element 900 mounted on the device shaft 16. In one example, the retaining or tensioning element comprises an O-ring 910. As discussed previously herein above, the first portion 701 of the suture 240 extending from the loops 700 forms the post 703 with the post comprising segments 703a and 703b. Whereas the second portion 702, extending from the loops 700, forms the locker 704. Similar to embodiments discussed previously, the device 100 is used to pass suture through the tissue 200. The suture 240 is passed through both first and second segments of tissue, 201, 202 and the device is then withdrawn proximally enabling the loops 700 of the partially pre-tied knot to be deployed or released over the post 703 as shown in FIG. 25b, forming a knot 720 at a distance from the tissue 200. Since the post 703 is connected to the device, extends distally, through the tissue and back proximally to the loops 700, as post segment 703a is retracted/pulled proximally, post segment 703b is pulled distally and pulls loops 700 distally off the device to form the knot 720. The length of a portion of the suture 240 forming the loops 700 is denoted as l.

Figure 25C:
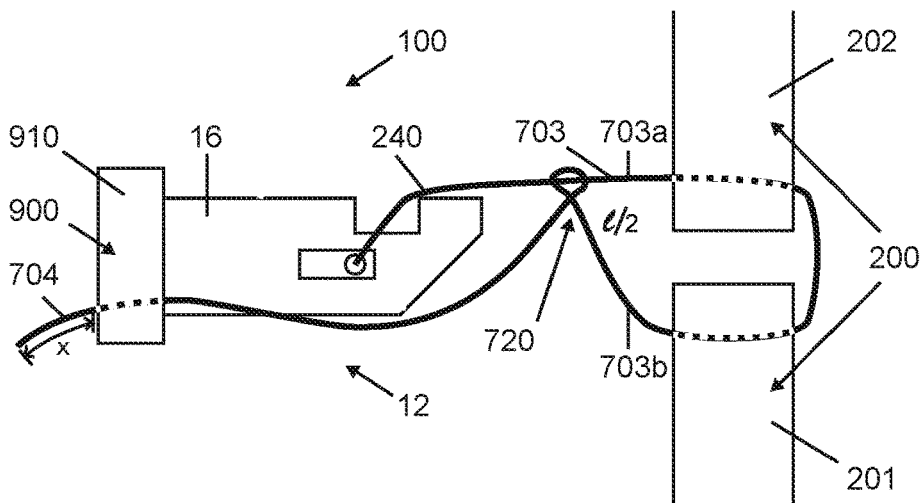
Figure 25D:
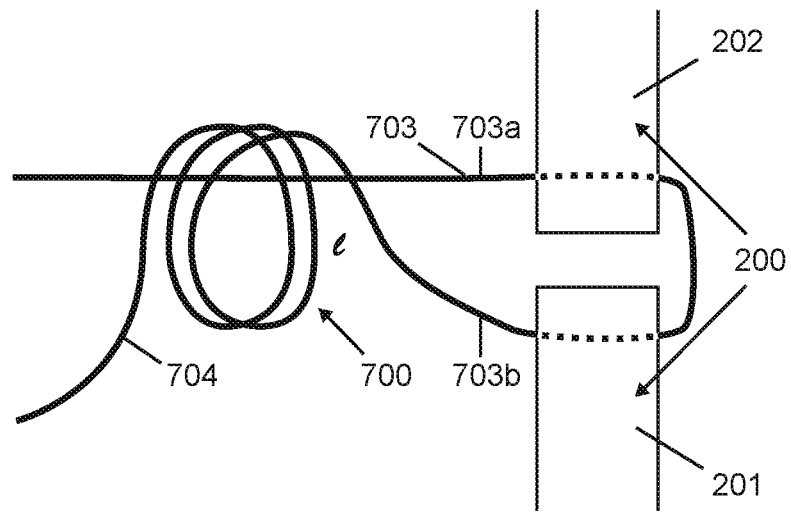
Figure 25E:
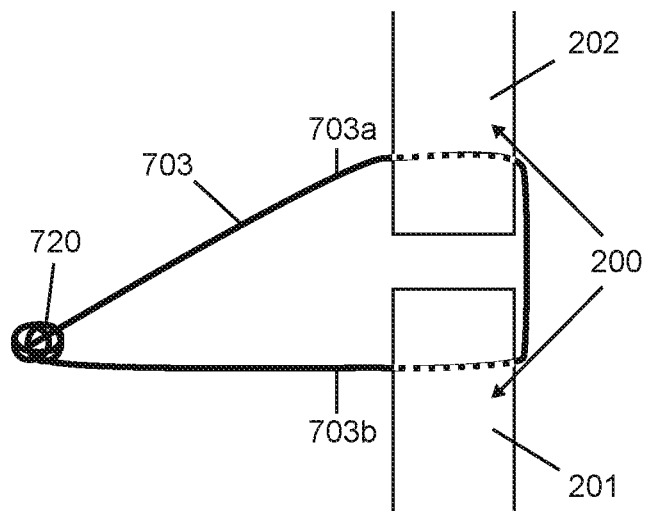

As the device is withdrawn further, post segment 703*a* is pulled, tensioning the post 703, while the retaining or tensioning element 900 in the form of the O-ring 910 restrains locker 704. The O-ring frictionally engages the locker 704 allowing the tension in the post 703 to collapse the loops 700 and thus knot 720. More specifically, as post segment 703*a* is pulled proximally relative to the tissue 200, an increase in length is observed in each of post segment 703*a* and the locker 704. The increase in length is seen proximal to the knot 720 between the knot 720 and the device distal tip 12 and is substantially a result of the decrease in diameter or length l of the loops 700. As shown in FIG. 25*c*, the extra suture 240 now seen in the post segment 703*a* and locker 704, proximal to the collapsed knot 720, is altogether substantially equal to the length of l of the suture originally forming loops 700 and is denoted by ½ for each of 703*a* and 704. Thus, in summation, as the device 100 is pulled proximally, it collapses the loops 700, thus partially cinching the knot 720 (also shown in FIGS. 25*d*, 25*e*). The knot 720 is collapsed distal, and substantially adjacent, to the distal tip of the device 100. The loops 700 continue to collapse until the O-ring 910 no longer resists movement of the locker 704

Figures 26A, 26B:
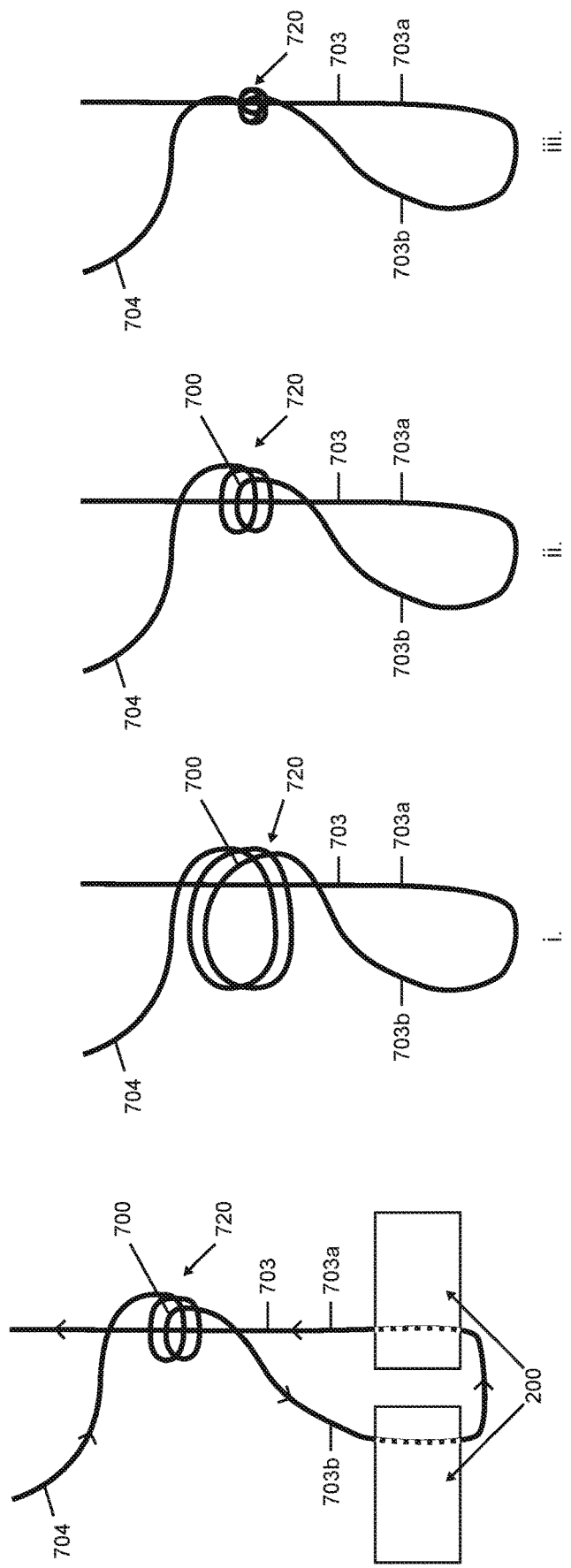
FIGS. 26*a*-26*b* illustrate a device and method in accordance with another embodiment of the present invention.

The mechanism involved in collapsing the knot is further described in FIGS. 26*a* and 26*b*. As the device 100 is retracted, the post segment 703*a* is retracted along with it. The force with which the post segment 703*a* is retracted is denoted as $F_v$ (not shown). The force that is applied by the O-ring to retain the locker 704 is denoted as $F_f$. As the post segment 703*a* is retracted/pulled proximally, it results in a force $F_v$ being applied on the knot 720 which is less than the force of friction $F_f$ applied by the retaining or tensioning element 900 on the locker 704. This allows the post 703 to collapse the knot 720, as shown in FIG. 26*a* and FIG. 26*b*. As the knot is collapsed, greater and greater forces are required to tighten the knot, and eventually $F_v$ applied by the post 703 is greater than $F_f$ applied by the retaining or tensioning element 900. The locker 704 is then released from the retaining or tensioning element 900 and knot 720 slides distally along the post 703. The device 100 is retracted/pulled/withdrawn until the knot 720 slides to a position substantially adjacent the tissue. Thus, similar to embodiments described above, the retaining or tensioning element 900 retains the locker 704 while tension is applied to the post 703 to cinch the knot 720 but allows the locker 704 to be released or withdrawn, for example automatically, when the knot is sliding to avoid premature locking or excessive tightening or cinching of the knot 720. As the knot is 720 is slid to a position adjacent the tissue 200, the tension in the suture 240 allows the first and second segments 701, 702 of tissue to be approximated for example, to close a defect within the tissue. The knot 720 may be tightened by pulling the locker 704 and/or the post 703. Additional knots may be formed on top of the knot 720 in order to further secure the knot 720.

Figure 27A:
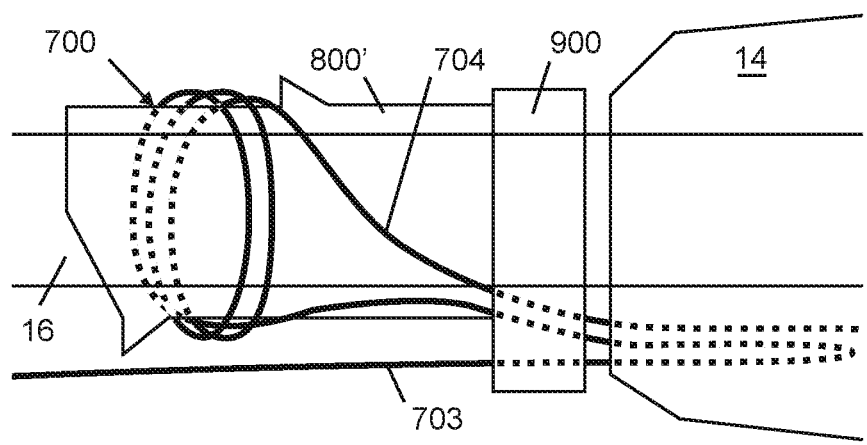
FIGS. 27*a*-27*d* illustrate a device and method in accordance with still another embodiment of the present invention.
Figure 27B:
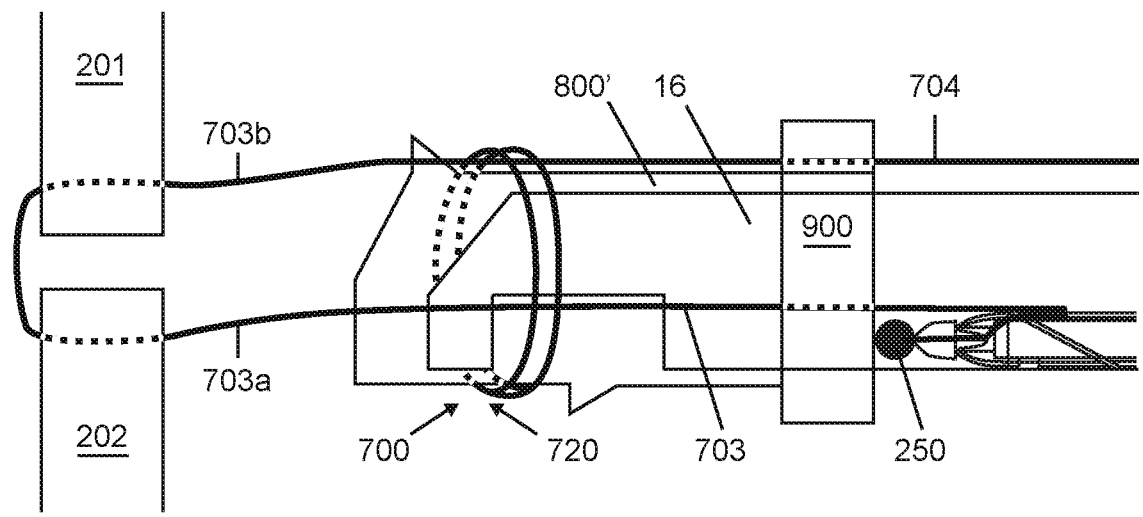
Figure 27C:
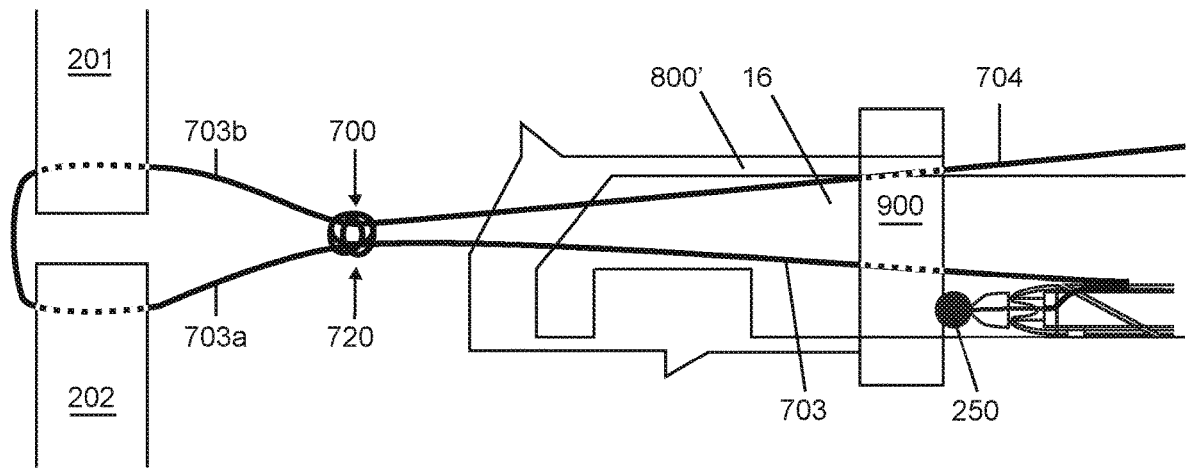
Figure 27D:
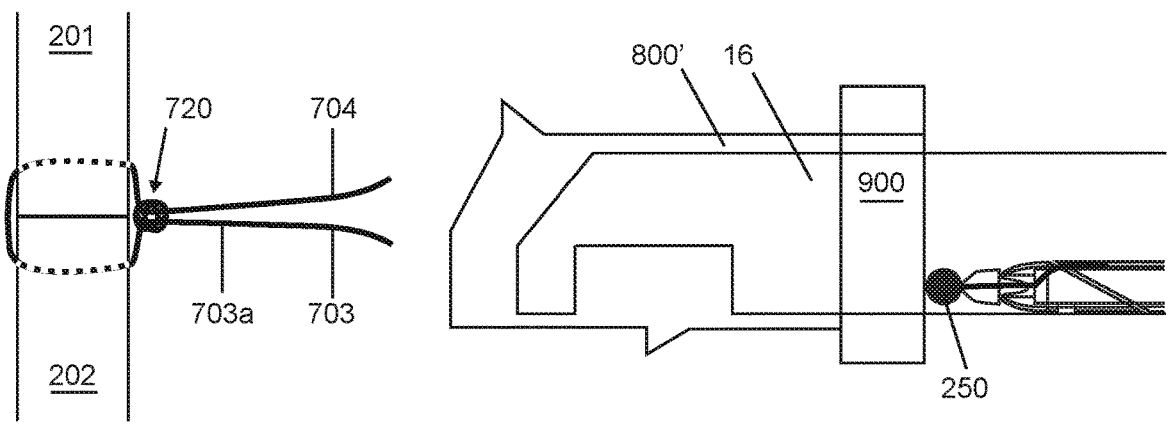

Similar to embodiments described above, another embodiment is shown in FIG. 27*a*, where loops 700 of the partial knot are positioned over or stored around a portion of the device 100, such as a component of the shaft 16 or a component mounted on the shaft 16, such as a slider 800'. The first and second portions of the suture 240 extending from the loops 700 are routed under a retaining or tensioning element or tensioner 900 positioned on the device shaft 16, proximal to the loops 700 and may be stored within the device proximal portion 14 such as within the handle of the device 100. The first and second ends of the suture 240 form the post 703 and locker 704 respectively with the post 703 comprising segments 703*a* and 703*b*. The device 100 may be used to pass suture through first and second segments 201, 202 of tissue 200 around a defect 300, similar to embodiments discussed previously. The device 100 is then retracted/pulled/withdrawn such that the loops 700 of the partial knot are positioned over/about the post, completing or forming the knot 720 as shown in FIG. 27*b*. In a particular example, the component onto which loops 700 are mounted, such as slider 800', slides until it is positioned at a distal end of the device, with the loops 700 now being positioned over the post 703, forming the knot 720. The device 100 is pulled further so that the loops are deployed off the distal end of the device 100 onto the post 703 distal to the device 100. As described previously, when the device is withdrawn further, the post segment 703*a* is pulled, resulting in post 703 applying a force on the knot 720 while the retaining or tensioning element 900 maintains tension or pulls on the locker 704 to cinch knot. This allows cinching or collapsing of the knot 720, as shown in FIG. 27*c*. As the device is further retracted, the force applied by the post 703 is eventually greater than the force $F_f$ applied by the tensioning or retaining element 900 on the locker 704. The locker 704 is released and the knot 720 begins to slide down towards the tissue 200. Thus, similar to embodiments described above, the retaining or tensioning element 900 retains the locker 704 while the knot 720 is being cinched while allowing the locker 704 to be released or withdrawn from the retaining element when the knot is sliding to avoid premature locking or excessive tightening or cinching of the knot 720. The locker may be pulled fully through the tensioning or retaining element. As the knot 720 slides towards the tissue 200, suture 240 places tension on the first and second segments 201, 202 of tissue 200, in order to approximate the defect 300 as shown in FIG. 27*d*. In one particular example, a suture knot 250 that may be coupled to the suture (to assist in passing the suture) may remain in the device shaft 16 while the post 703 is separated from the instrument.

Method of Use of Various Depth Selection and Interlock Mechanisms

Method of Use of Device 100 with Respect to the Manual Needle Release Button and Manual Depth Selector as Described Herein Above Manual Needle Release Button As described above, the stylet is advanced beyond the needle by various amounts during the course of a procedure. Various interlock and depth selection features (which allow the stylet 319 to decouple from the needle 116, to advance to various distances) can be embodied in various ways as described previously. The specific embodiment of the manual needle release button is described further in terms of the operation of the device. The details of the mechanism of device 100 is described further with reference to FIG. 1*a*. The trigger 218 has a geared portion 220 that co-operatively engages with a gear rack 434 of the stylet hub 430 that is able to slide within the chamber 140 defined by the handle of device 100. The trigger 218 is coupled to a biasing mechanism such as a spring biased mechanism. When the trigger 218 is in a neutral position, the spring is held against the bias. As the trigger is actuated (also shown in FIG. 4*a*), the geared portion 220 of the trigger 218 advances the gear rack 434 which further exerts a force against the spring bias. The stylet hub 430 translates distally with the gear rack 434 causing the needle hub 130 (that is coupled to the stylet hub 430 by button 600 in its initial position 600A), to translate distally with respect to the handle chamber. Additionally, needle 116 is advanced with the needle hub 130.

The needle functions as a tissue puncturing member and in one example, advancement of needle 116 allows needle 116 to puncture tissue 200 at site P1. As mentioned previously, in the illustrated embodiment of FIG. 2b, the stylet 319 is housed within the needle 116 and is also passed through the tissue 200 at site P1. The stylet 319 functions as a suture passing member and the suture 240 having a knot 250 is passed through the tissue using the stylet 319. The suture knot 250 is positioned adjacent the stylet tip and is carried distally by the stylet tip as it is advanced. As the needle 116 is advanced further it abuts against a proximal face of the suture holder 316 at the distal tip 12 and the trigger 218 cannot be actuated further as shown by FIG. 2c. The needle release button 600 is then depressed (to position 600B, as shown in FIG. 4b), allowing the needle hub 130 to disengage from the stylet hub 430. This allows the trigger 218 to be depressed further and the stylet hub 430 to translate distally with respect to the needle hub 130. This allows the stylet hub 430 to be advanced distally such that the stylet 319 is received within the suture holder 316 to deposit the suture knot 250 therein.

With reference to FIG. 2d, stylet 319 is advanced distally, to a predetermined distance required to deposit the suture knot 250, such that the knot 250 is coupled to the suture holder 316. The suture holder 316 comprises a suture retaining component for retaining the suture knot 250. FIGS. 4a-4g illustrate the operation of device 100 with respect to selective advancement of the stylet 319 with respect to the needle 116 to allow a suture 240 to be passed through a first segment of tissue 201. In accordance with a method of the present invention (discussed above) the device 100 is then repositioned to then allow suture 240 to be passed through a second segment of tissue 202 as shown in FIGS. 3a-3d. The trigger 218 may be re-actuated to re-advance until needle 116 abuts the suture holder 316 (FIG. 3b). Similar to the mechanism described above, the needle release button 600 may be depressed again to position 600B to remove the obstruction from interference block 601 to allow the stylet hub 430 to advance. The stylet 319 is then advanced distally, further than the predetermined distance required to deposit the suture knot 250, such that the stylet 319 is coupled to the suture holder 316 to retract the suture holder 316 with the stylet 319 (FIGS. 3c-3d). Thus, as can be seen in FIGS. 2d and 3c, in this specific embodiment of the present invention, the stylet 319, upon a first actuation of the trigger, is initially advanced a certain distance to deposit the suture portion such as knot 250 through the suture holder 316 (FIG. 2d). Further, upon a second actuation of the trigger (after repositioning the device on the other side of the defect), the stylet 319 is subsequently advanced a greater distance to capture the suture holder 316 (FIG. 3c). In order to allow for varying the distance to which a stylet 319 is advanced when the trigger 218 is actuated, certain embodiments of the present invention provide a depth selection mechanism (depth selector) 500, as shown in FIGS. 5a, 5b and 6a-e.

Manual Depth Selector

The mechanism of the device 100 is now described with reference to the depth selector 500. FIGS. 5a-5e illustrate operation of device 100 using the depth selector 500 (also referred to as the depth selection or adjustment mechanism) to advance the stylet 319 through a first region of tissue to deposit the knot 250 within the suture holder 316 such that the stylet 319 functions as a suture passing member. Additionally FIGS. 6a-6h illustrate operation of device 100 using the depth selector 500 to advance the stylet 319 further to retrieve the suture holder 316 through a second region of tissue 200, such that the stylet functions as a suture holder retrieving member. As mentioned with respect to an embodiment of a device of the present invention, FIGS. 5a and 5b illustrate the depth selector 500 is in its first/initial or starting position or depth setting 500A and illustrate the starting and final (after trigger actuation) locations of the depth selection or adjustment mechanism 500 with respect to the handle housing. In accordance with the method, prior to actuation of the trigger 218, the device may be position at a defect 300 as shown in FIGS. 2a-2d, to receive a first segment of tissue 201 the tissue receiving gap 10 so that suture 240 may be passed through tissue adjacent the puncture site P1. With reference now to FIG. 5d, the depth selector 500 is initially its first position or initial depth setting 500A and is positioned such that the tab T is positioned adjacent the stylet hub proximal portion 432. Thus, the tab T is positioned distal to the stylet hub proximal portion 432. As the trigger is actuated to advance needle 116 and stylet 319, the needle release button 600 is depressed as discussed above, The button 600 moves from its initial position 600A to 600B (Not shown) to allow the stylet 319 to travel further than needle 116. At initial depth setting 500A, the tab T is positioned or contained between the distal surface of the stylet hub proximal portion 432 and the needle hub 130, and prevents the stylet hub proximal portion 432 from being further advanced to be positioned flush with the needle hub 130. Thus, travel of the stylet hub 430 distally within the handle chamber 140 is limited due to the interference created by the tab T, resulting in the stylet hub proximal portion 432, being positioned at a distance Y2 (FIG. 5b) from the distal end of the handle chamber 140. This allows the stylet 319 to extend into the suture holder 316 (for example, trap 416) so that only the distal portion of the stylet and thus the suture knot 250 is passed through the suture holder 316, as shown in FIG. 2d. Thus, allowing the stylet 319 to function as a suture passing member. The stylet 319 does not couple to suture holder 316 and is free to travel back when the trigger 218 is released.

FIG. 5e illustrates the step described above with respect to FIGS. 2e and 2f, whereby the trigger 218 is released, allowing the stylet 319 to retract while leaving the suture knot 250 engaged with the trap 416 at the distal tip 12. After depositing the suture knot 250 through tissue site P1, when the trigger 218 is retracted it allows the stylet hub 430 to translate proximally, and further retraction of the trigger 218 allows the needle release button 600 to move back to its first or original position 600A to re-engage the needle hub 130 to the stylet hub 430, as shown in FIG. 5e. In further detail, as the trigger is released, the stylet hub 430 translates proximally and spring 605 returns to its uncompressed state allowing the needle hub 130 to be spaced at its nominal distance with respect to the stylet hub proximal portion 432. In other words, in FIG. 5e, the needle hub 130 and the stylet hub 430 both return to substantially the same position they occupied in FIG. 5c prior to trigger actuation). Previously, the button 600 had been kept in the depressed position 600B by the stylet hub 430 pressing against it. As the stylet hub is retracted, it no longer presses on the button 600. The stylet 319 may then re-engage the needle 116 with button 600 moving to its first position 600A (as the spring 603 in the spring loaded button 600 recoils back to its uncompressed state), and both the stylet and needle 116 may then be automatically retracted together to their initial positions within proximal portion 14.

In accordance with FIG. 3a, the device 100 may be rotated and the position of the device 100 adjusted to allow suture 240 to be drawn through a second segment of tissue on the other side of the defect 300. For example, in order to substantially seal the defect 300, the suture 240 may be passed through tissue adjacent the puncture site P2. The depth selector may now be set to its second position or depth setting 500B as shown in FIG. 6a (also depicted in FIGS. 4c and 4e).

Figure 6B:
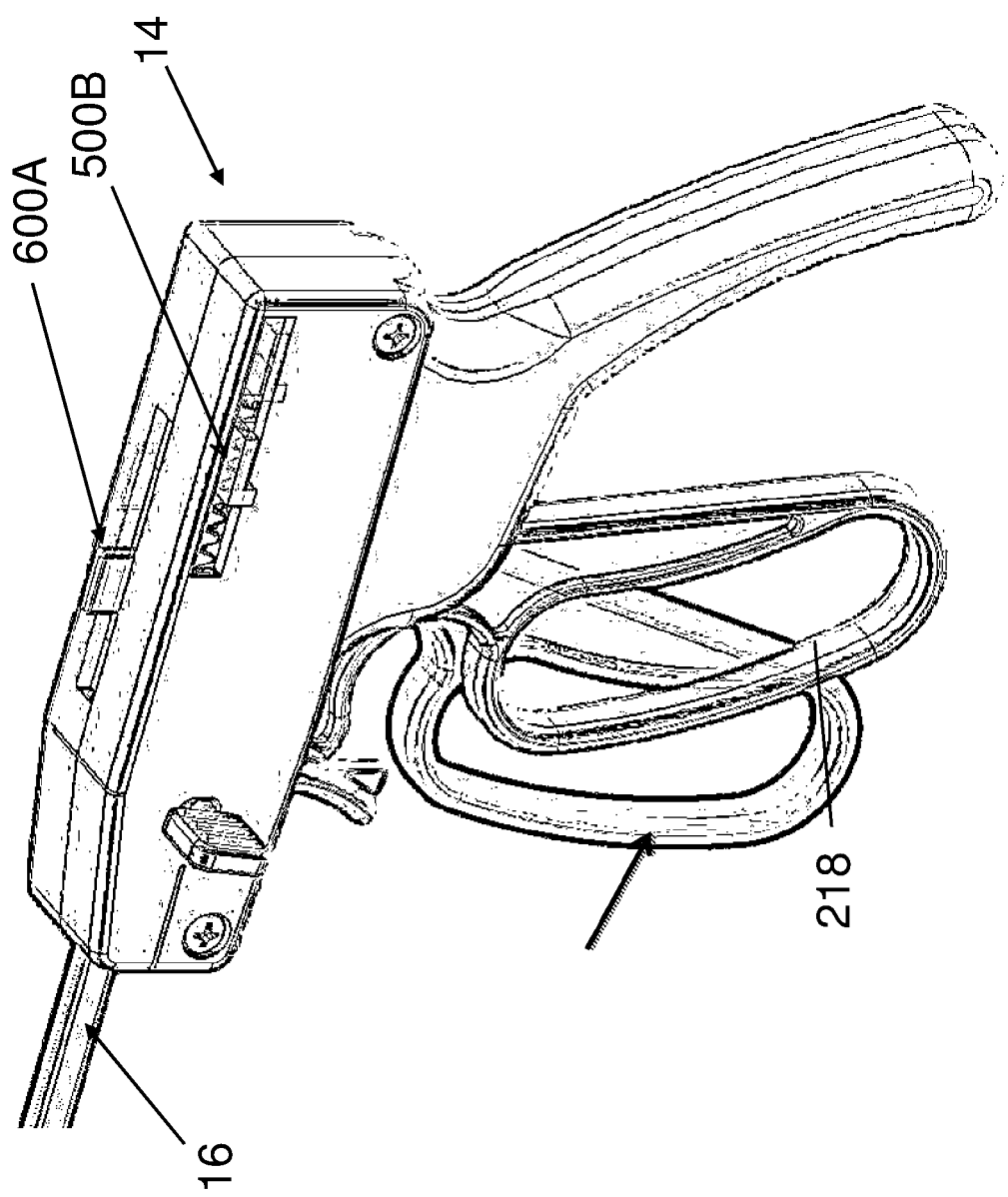
Figure 6C:
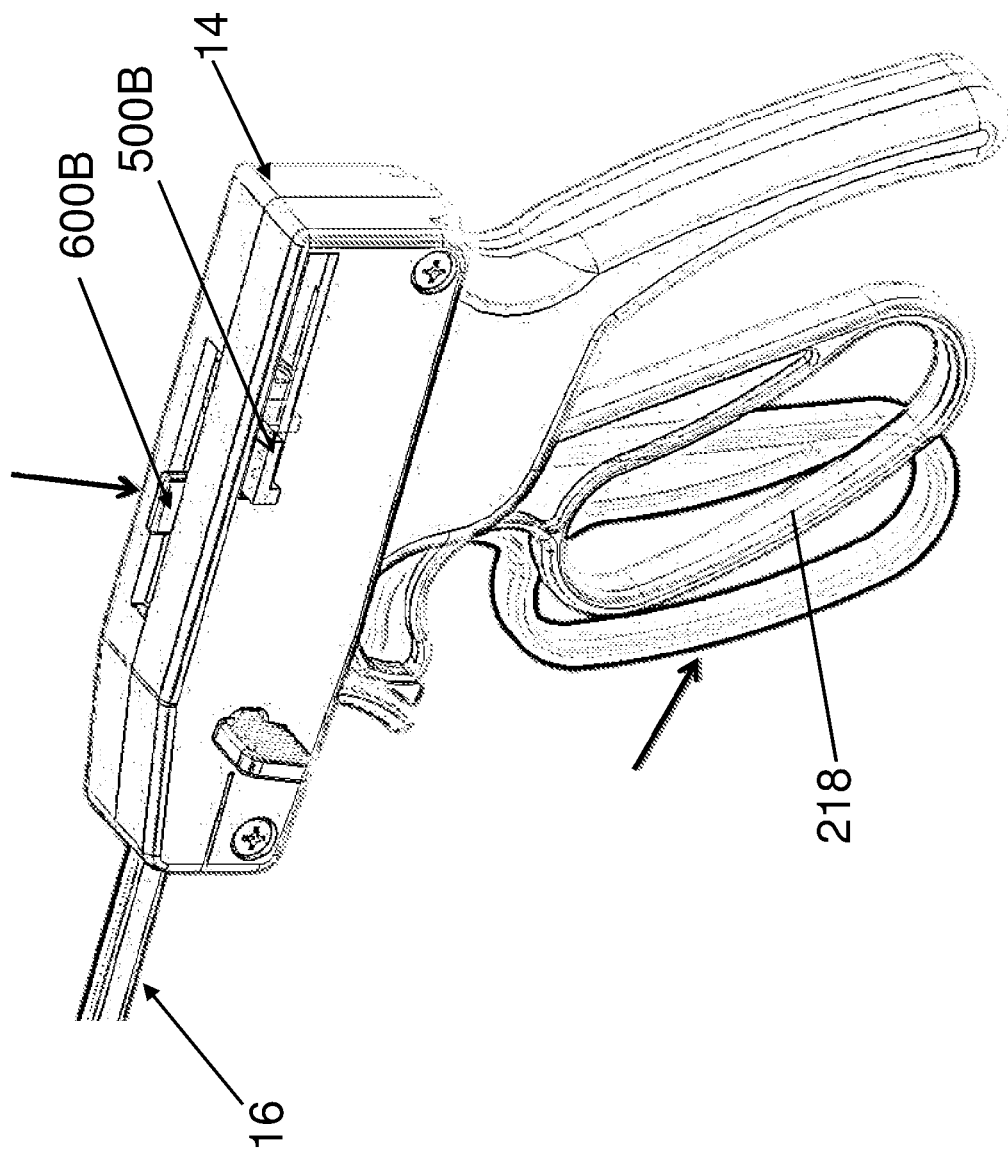
Figure 6D:
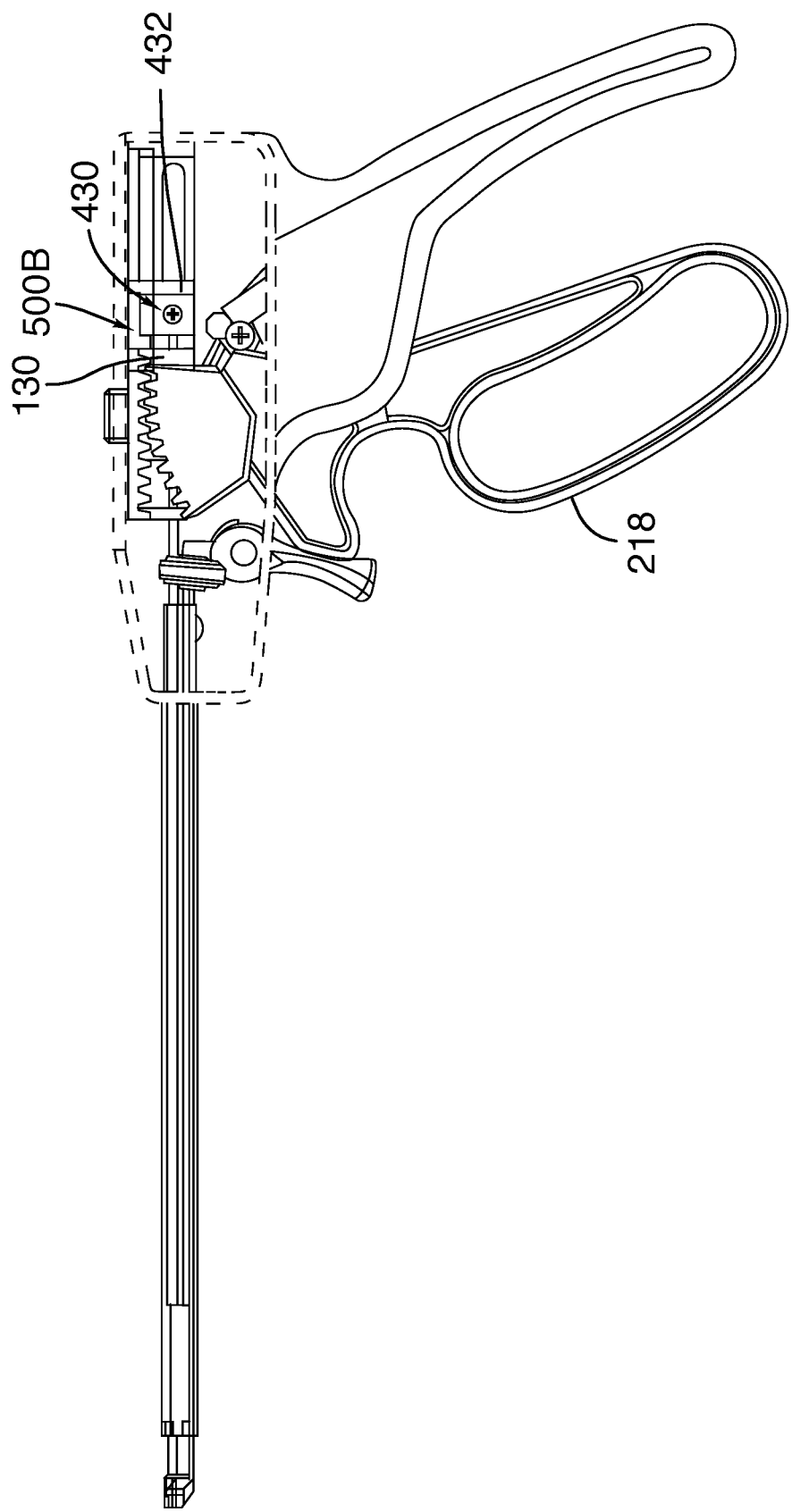
Figure 6E:
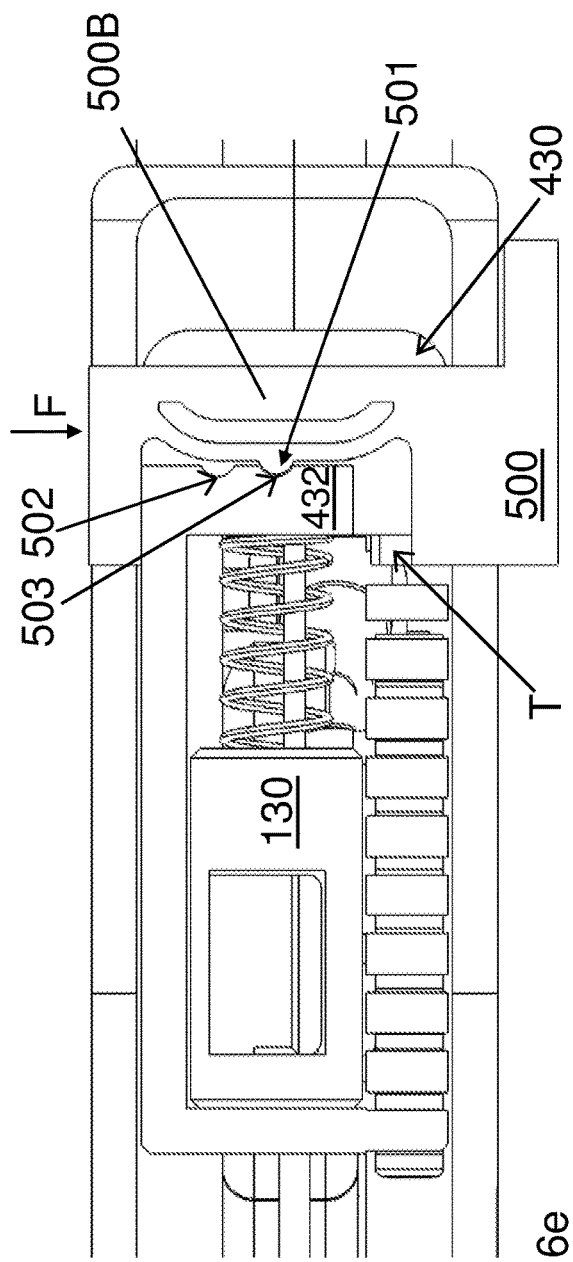

With reference to FIG. 6b, the trigger is actuated to allow the stylet 319 and the needle 116 to be re-advanced from their initial positions such that the needle 116 punctures tissue at puncture site P2 on the other side of the defect. As outlined previously, the needle 116 is advanced until it abuts against the suture holder 316 at the distal tip 12. The needle release button 600 is then depressed, as shown in FIG. 6c, so that it moves from its first position 600A to its second position 600B. This decouples the stylet 319 from the needle 116, allowing the stylet to advance into the suture holder 316 at the device distal tip 12 to engage the suture holder 316, as shown in FIG. 6d and as described previously with reference to FIG. 3c. Thus, allowing the stylet 319 to function as a suture holder retrieving member. Actuation of the depth selector 500 to its second depth setting 500B, as shown in FIG. 6a, allows the stylet 319 to advance to a second distal position (e.g. a second predetermined distal position) which is further distally, relative to the position described above with reference to FIGS. 2d and 5b and which allows stylet 319 to engage or couple to suture holder 316.

Figure 6F:
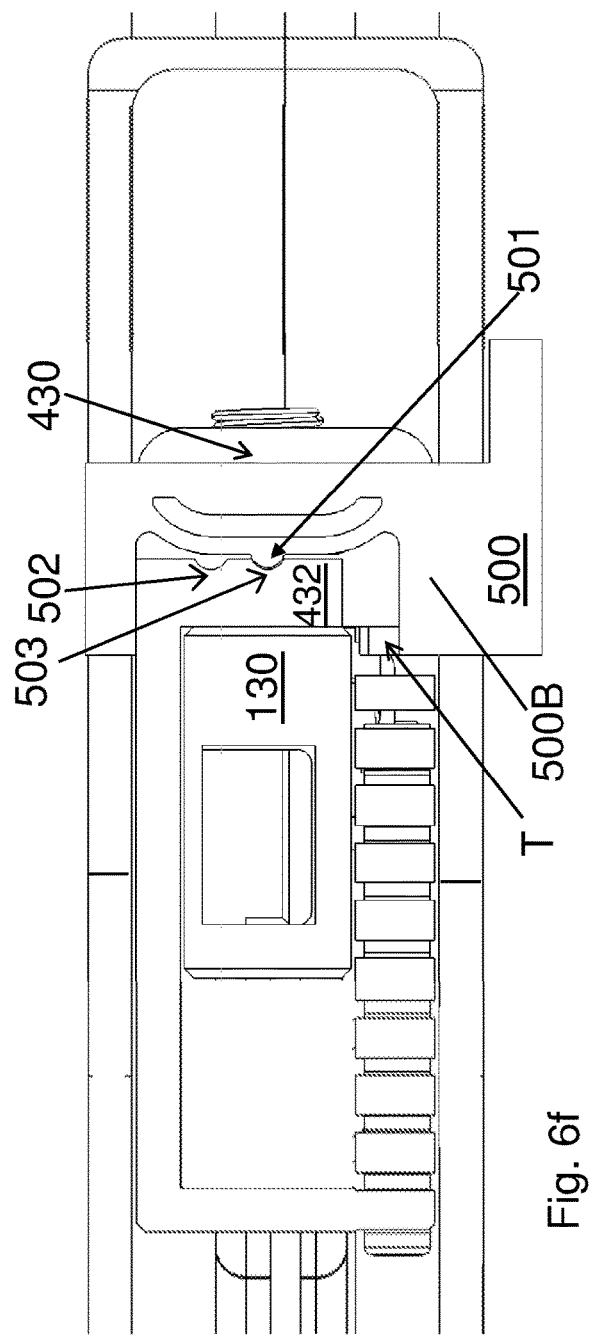
Figure 6G:
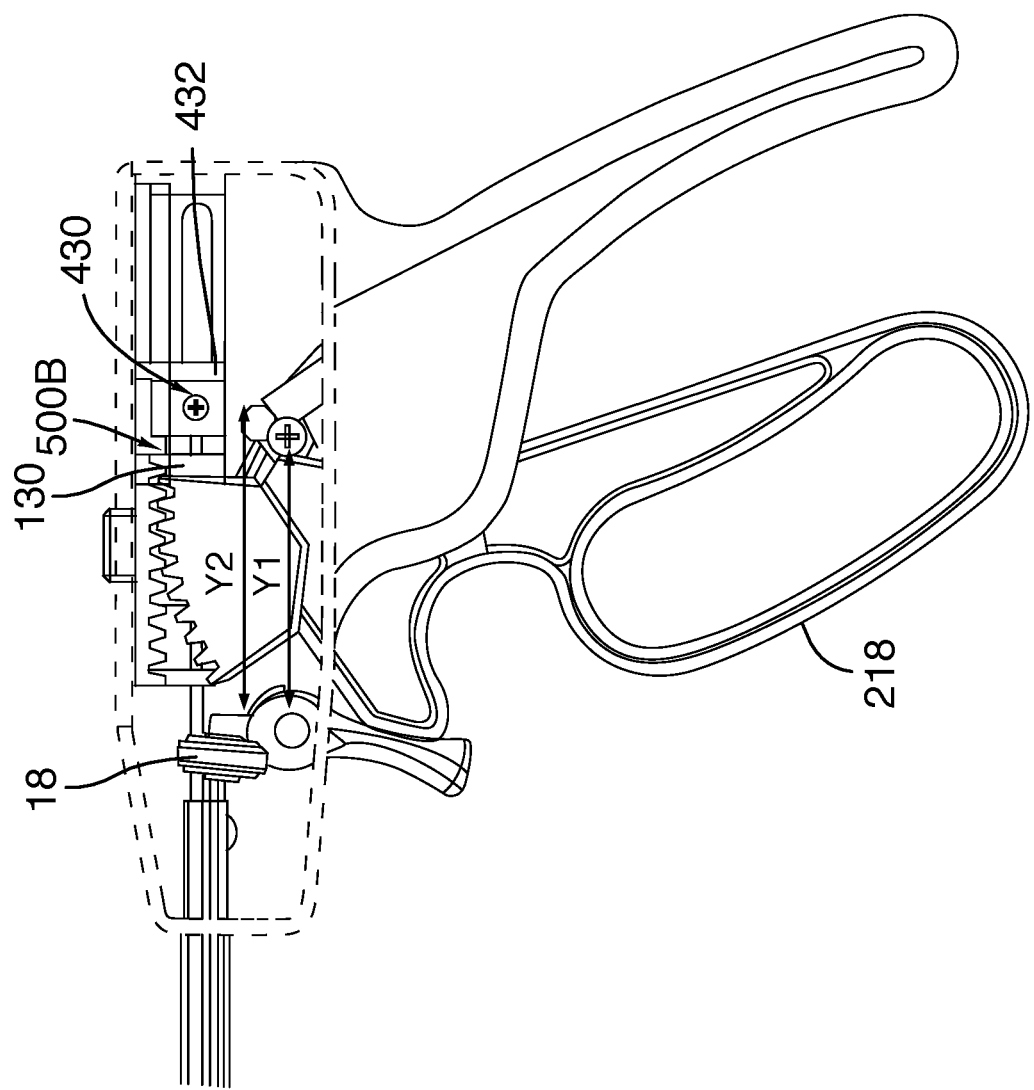
Figure 6M:
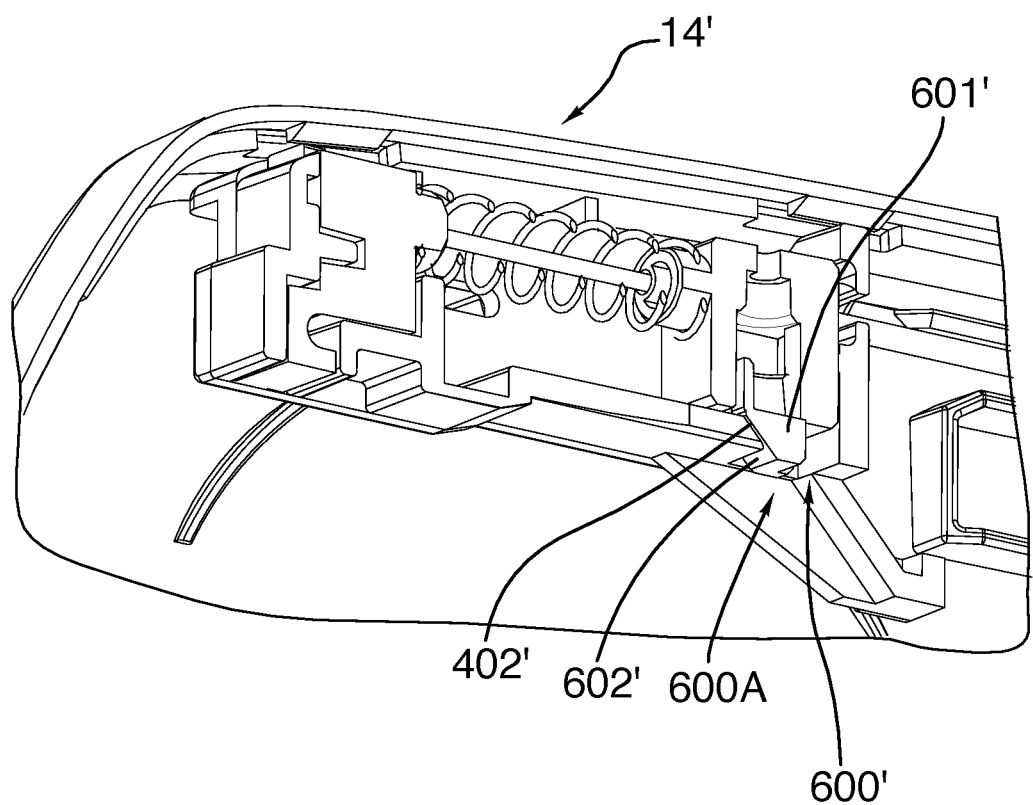
FIGS. 6m-6x illustrate a device and method in accordance with yet another alternative embodiment of the present invention.

As shown in FIG. 6e, the depth selector 500 may be moved into its second position by applying a transversally directed force F against the depth selector 500, thereby moving the projection 501 of the depth selector into the second indentation 503 within the stylet hub, which allows the depth selector to remain in its second position 500B (until a counter force is applied to move it back to its first position). With reference now to FIG. 6e, when the depth setting 500B of depth selector 500 is in its second position the tab T of the depth selector 500 is no longer located between the distal surface of the stylet hub proximal portion 432 and needle hub 130. In this position, the depth selector tab T does not interfere with the advancement of the stylet hub 430 relative to the needle hub 130. In other words, the tab T is located external to the travel path of stylet hub 430. As the stylet hub 430 is advanced within the handle chamber 140 relative to the needle hub 130, the distance the stylet hub 430 travels distally is not limited by the depth selector 500. In an alternative embodiment, during the second trigger actuation as the stylet 319 is advanced a second time, the distance the stylet hub 430 travels may also be limited by the depth selector 500. This allows the stylet hub proximal portion 432 to be positioned flush against the proximal surface of the needle hub 130, i.e. the stylet hub proximal portion 432 travels maximally with respect to the needle hub 130 within the handle chamber 140, as shown in FIG. 6f. Thus, as illustrated in FIG. 6g, using the second depth setting 500B results in the stylet hub proximal portion 432 being positioned at a closer distance Y1 from the distal end of the handle chamber 140, compared to distance Y2 using the first depth setting 500A. This enables further advancement of the stylet which allows the stylet 319 to extend into the suture holder 316 (such as trap 416) so that it engages the suture holder 316 as shown in FIG. 3c.

With reference now to FIG. 6h, when the trigger 218 is released, the biasing mechanism coupled to trigger 218, such as the spring-biased mechanism, automatically urges the gear rack 434 of the stylet hub 430 to translate proximally within the handle chamber 140. The stylet 319 is then retracted when the trigger 218 is released, allowing the suture holder 316 to be retracted along with the stylet 319 (as previously discussed with respect to FIG. 3d).

As noted above with respect to FIG. 3d, the distal tip 12 of device 100 defines a receiving chamber 12B. The receiving chamber 12B receives the suture holder 316 therein. The suture holder 316 comprises an engagement feature for releasably coupling the suture holder 316 to the distal tip 12. In one specific example of this, the suture holder 316 is initially secured within the receiving chamber using a wire 20 that engages the suture holder 316. The wire 20 may be attached to a wire stop 18, shown in FIG. 6h. The wire 20 may be removed by pulling the wire stop 18, to allow disengagement of the suture holder 316 with the receiving chamber 12B. This allows retraction of the suture holder 316, upon release of the trigger 218 (FIG. 6h).

Method of Use of an Automatic Needle Release Button with an Automatic Depth Selector Having a Mechanism for Generating an Audible Feedback as Described Herein Above.

Automatic Depth Selector with a Mechanism for Generating an Audible Feedback

Figure 6N:
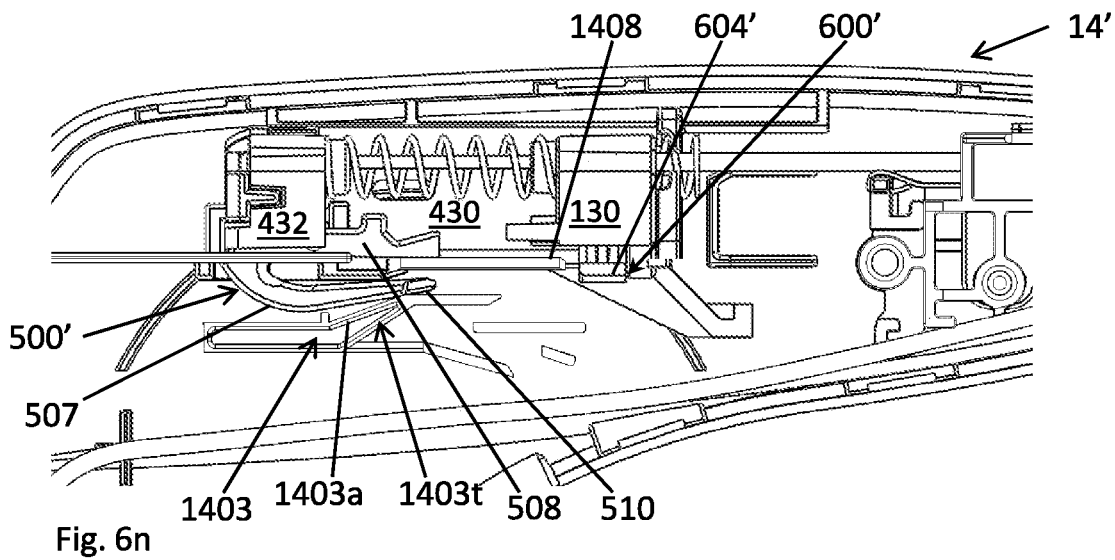

An alternative embodiment of the depth selector 500' is described with references to FIGS. 6m-6x that comprises an additional mechanism for generating audible feedback indicating when the translation of the stylet 319 to each of its respective first and second translation distances is complete. During the first actuation of the trigger, the stylet hub proximal portion 432 translates distally, allowing the depth selector 500' coupled thereto to translate distally. As shown in FIG. 6n, the lower arm 507 of the depth selector 500' is deflectable and flexes as tab 510 rides up along an upper surface 1403a of the control rib 1403 (which includes a tapered section 1403t). Thus, the lower arm 507 moves from its un-deflected position into its deflected position. Contrary to this, the upper arm 508 may not flex and remains in its initial position. In one example, the upper arm 508 is in contact with the stylet hub proximal portion 432 which limits the upward movement of arm 508.

Figure 6O:
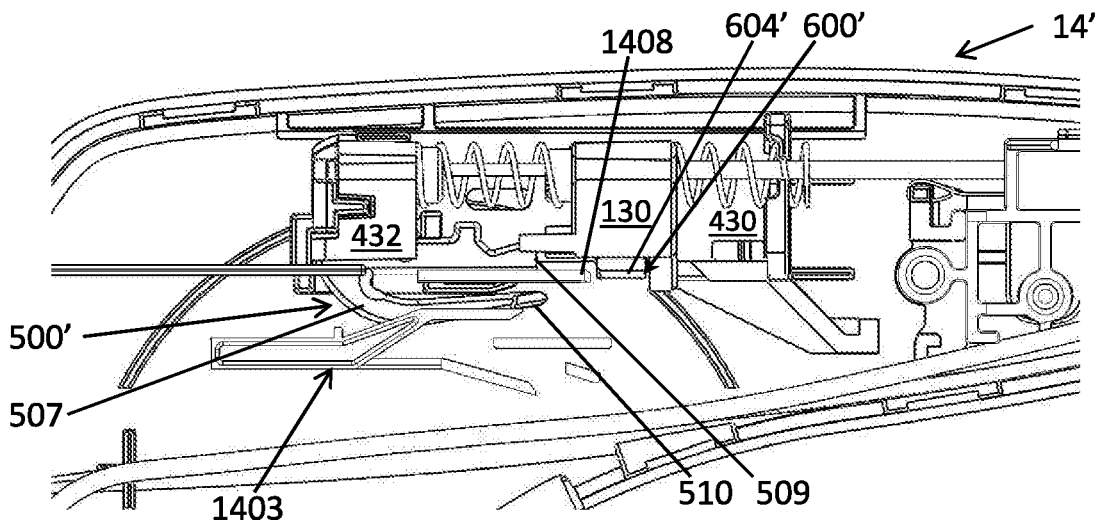
Figure 6P:
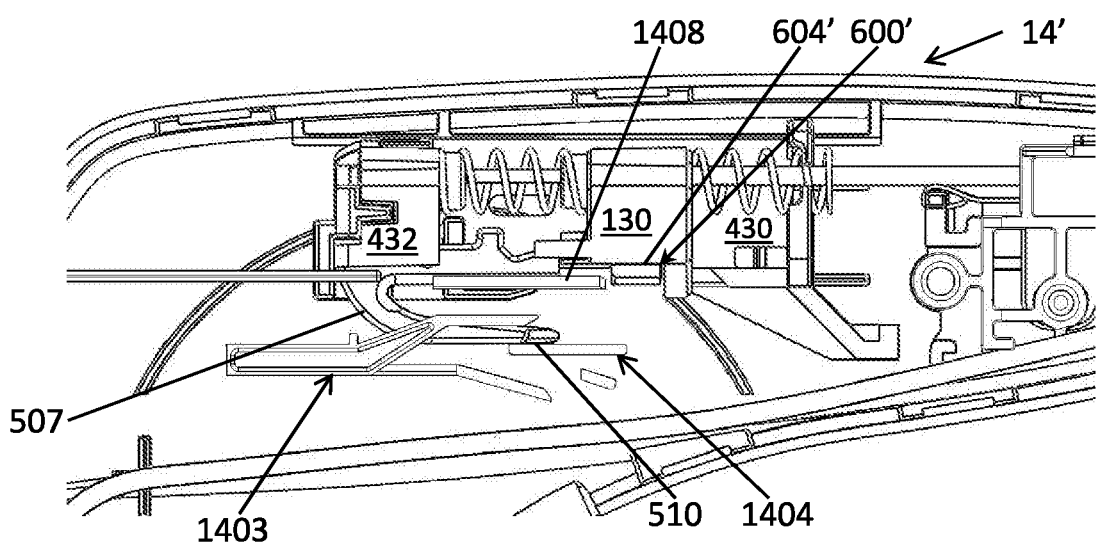
Figure 6Q:
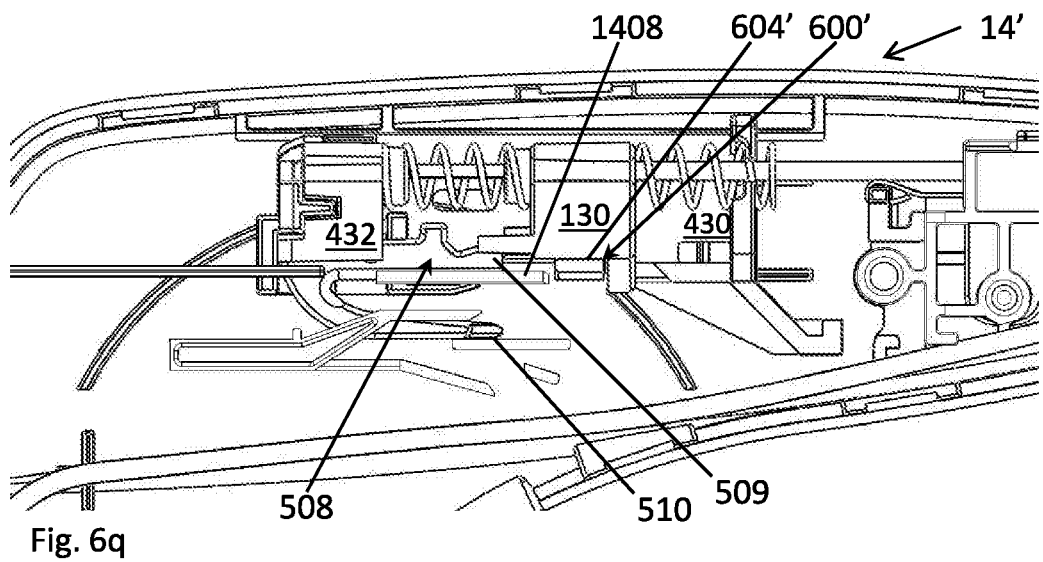
Figure 6R:
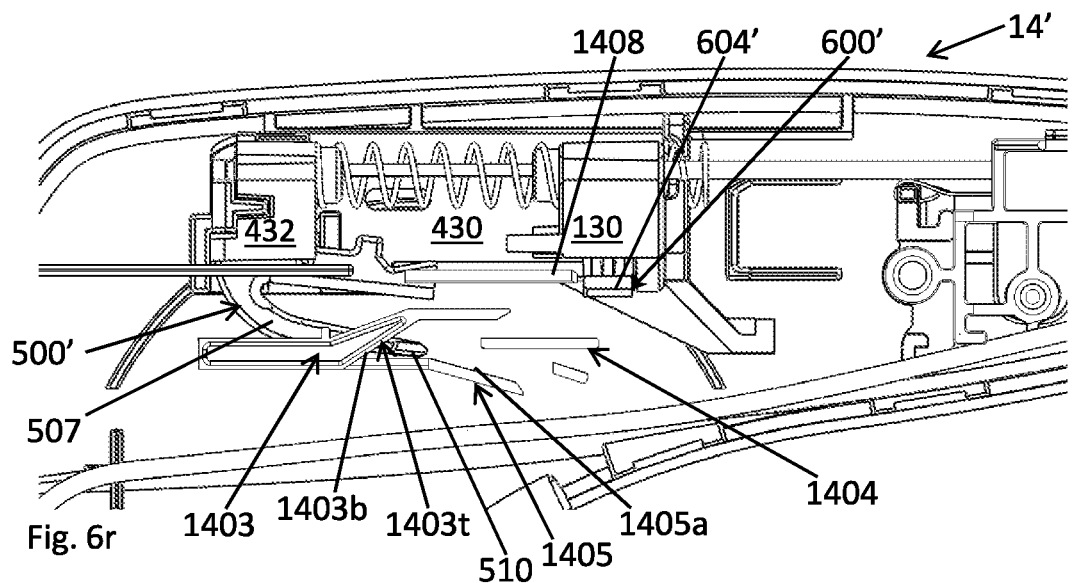
Figure 6S:
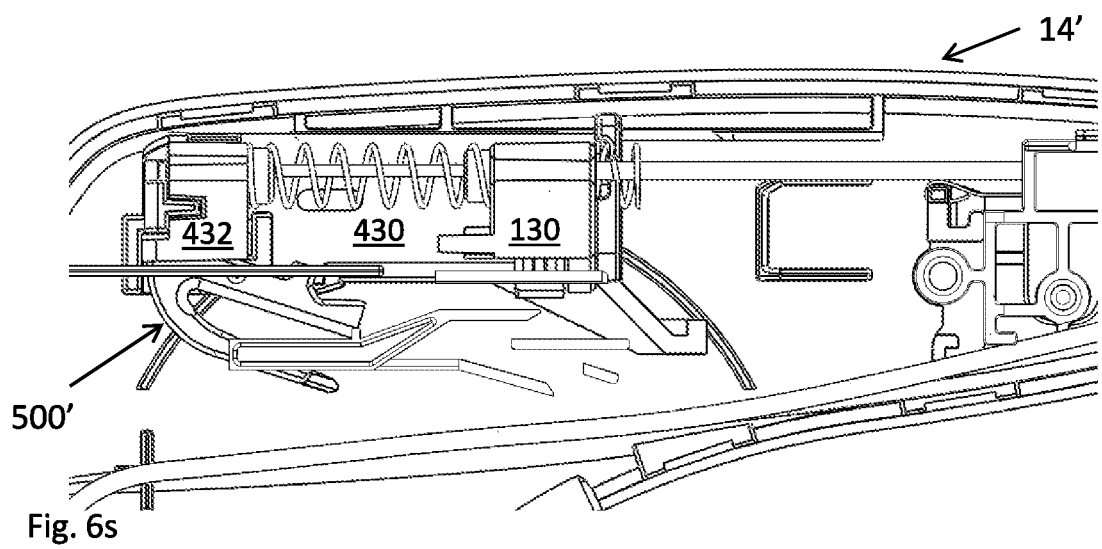

As the stylet hub proximal portion 432 and the depth selector 500' are advanced further, the tab 510 on the lower arm 507 reaches the end of the control rib 1403 just prior to the stop 509 contacting the needle hub 130, as shown in FIG. 6o. As the tab 510 on the lower arm 507 advances past the end of the control rib 1403, the arm 507 springs back to its un-deflected initial position as shown in FIG. 6p. As it deflects back to its initial position it collides with click rib 1404, thus making a "click" sound. The "click" sound indicates that the translation of the suture passing element, such as the stylet 319 to its desired translation distance is complete. For example, the "click" may indicate that the stylet 319 has been advanced to a distance to allow the stylet to deposit a suture through a suture holder. As shown in FIG. 6q (in which the components are in positions similar to those shown in FIG. 6p), the stop 509 on the upper arm 508 touches the needle hub 130 and thus limits further forward or distal translation of the stylet hub proximal portion 432. As the trigger is released as shown in FIG. 6r, the stylet hub 430 retracts proximally towards its initial/starting position. As the depth selector 500' is retracted with the stylet hub 430, tab 510 of the lower arm 507 slides along and past the proximal end of the click rib 1404, and is then guided along an upper surface 1405a of control rib 1405. The tab 510 of the lower arm 507 then engages with the control rib 1403 pivoting the depth selector 500' downwards. A lower surface 1403b of the control rib 1403 along the tapered section 1403t may additionally guide/force the tab 510 of the lower arm 507 down, thus guiding/forcing the depth selector 500' to deflect or pivot into its second position. Once the stylet hub 430 has been fully retracted upon release of the trigger, as shown in FIG. 6s, the depth selector 500' is now in its second position and is ready for the second actuation of the trigger. The depth selector 500' has been rotated downwards such that it will not contact the needle hub 130, and will not impede/limit the movement of the stylet hub 430.

Figure 6T:
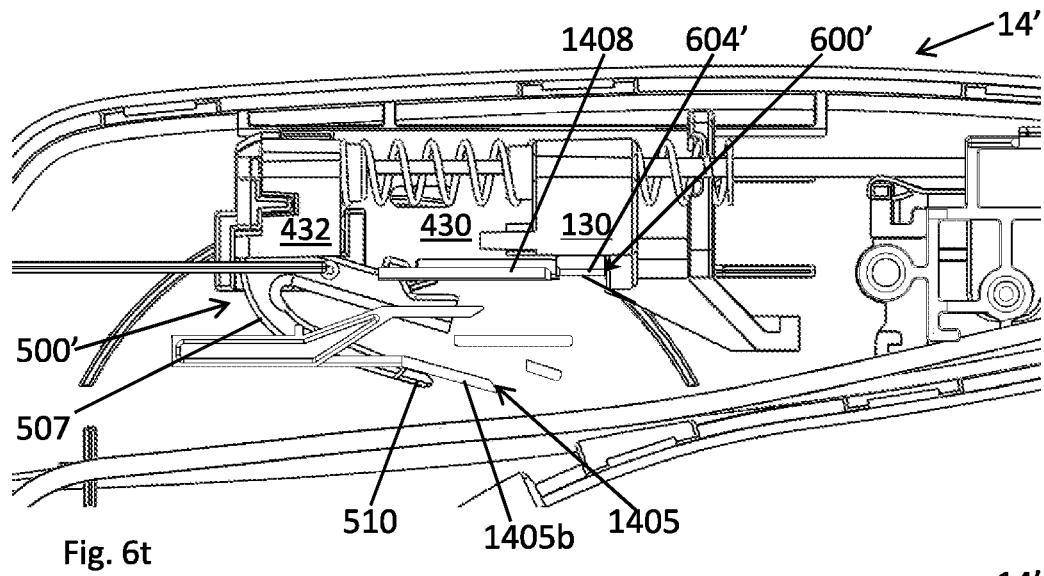
Figure 6U:
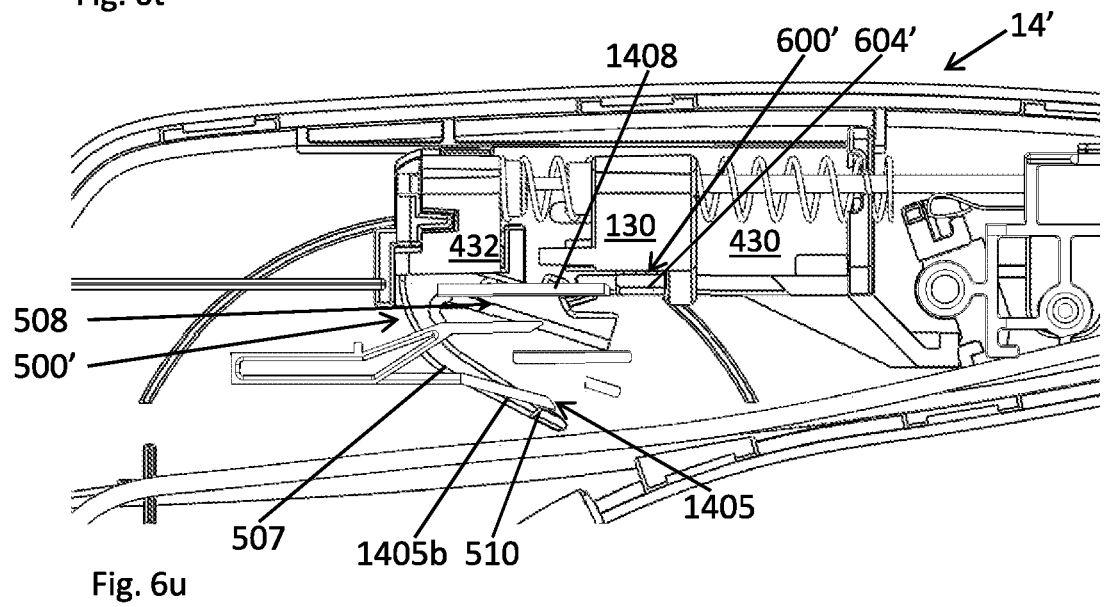
Figure 6V:
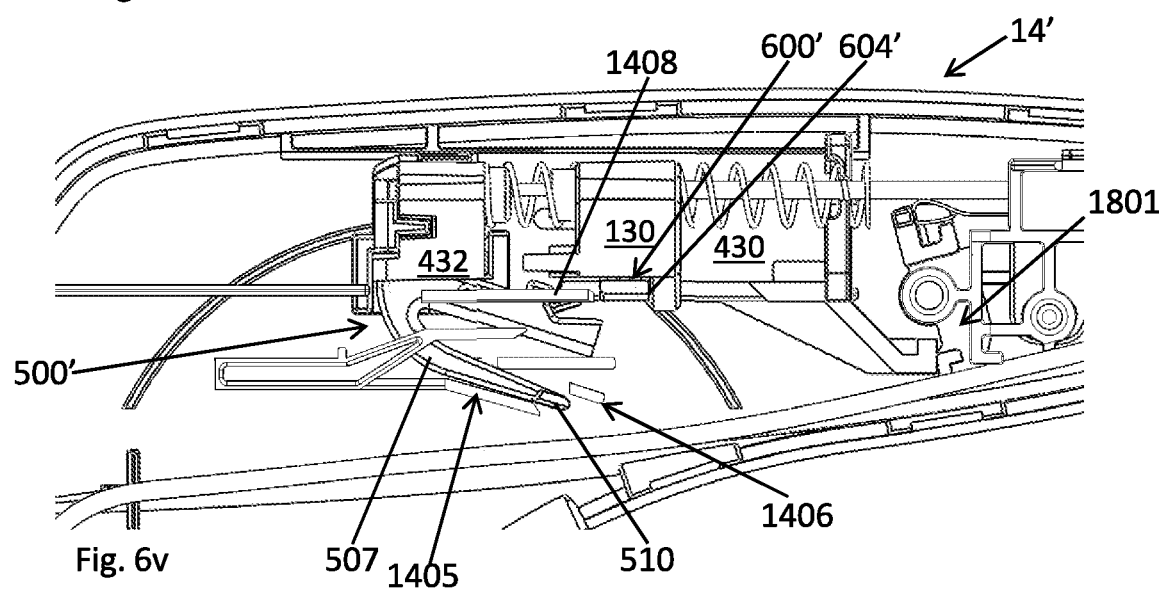
Figure 6W:
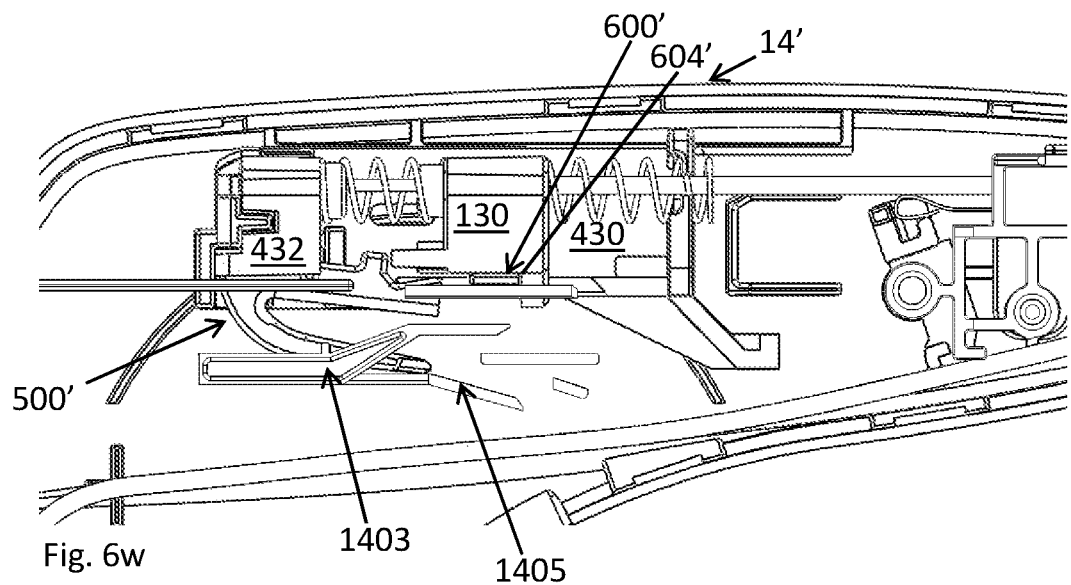
Figure 6X:
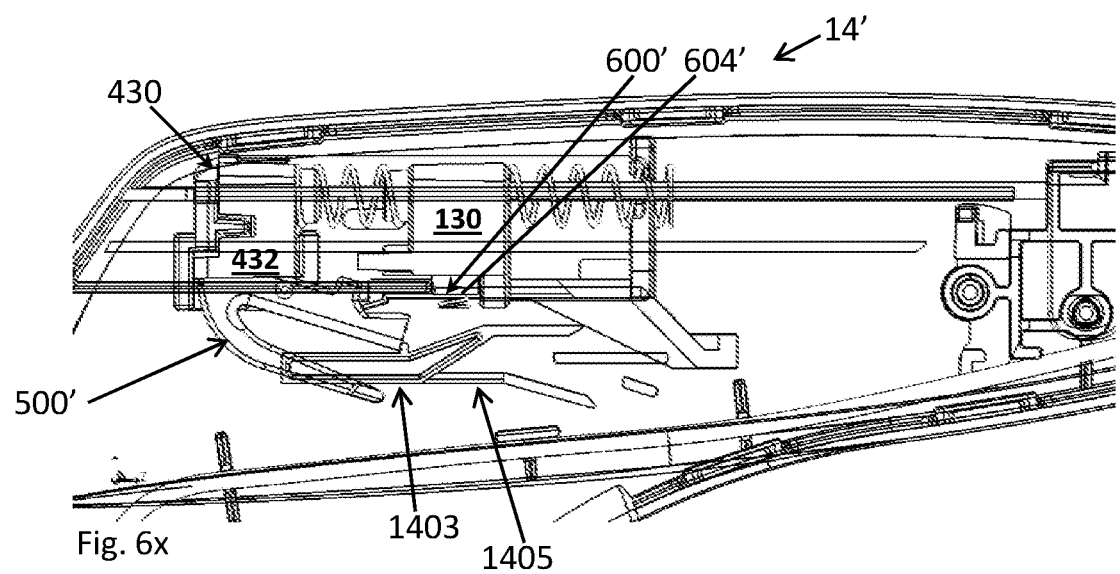

As the trigger is actuated again to advance the stylet hub 430, the depth selector 500' remains in its second position as shown in FIG. 6t with tab 510 of lower arm 507 translated distally until it abuts against or engages the lower surface 1405b of the guide or control rib 1405. As tab 510 of the lower arm 507 rides down/along the a tapered portion of the lower surface 1405b of the control rib 1405, the lower arm 507 flexes, whereas the upper arm 508 cannot flex and remains in its position as shown in FIG. 6u. The position of the upper arm 508 is maintained by contact with the stylet hub 430. As the lower arm 507 flexes the upper and lower arms 508, 507 are pushed apart from each other. As tab 510 of the lower arm 507 reaches the end of the control rib 1405, the lower arm 507 springs back to its un-deflected position and collides with the click rib 1406 making a "click" sound, as shown in FIG. 6v. The "click" sound indicates that the translation of the suture holder retrieving member, such as the stylet 319, to its desired translation distance, is complete. In such an embodiment, the arm 507 and rib 1406 may be understood to be components of a feature for providing an indication that the suture passing member has been advanced by a desired amount. For example, the "click" indicates that the stylet 319 has been advanced to a distance to allow it to engage with the suture holder, which will allow the stylet 318 to withdraw the suture holder along with it when it is retracted. As shown in FIG. 6v, during the second actuation of the trigger, the depth selector 500' does not contact needle hub 130, allowing further translation of the stylet hub 430, which in turn allows the stylet to be advanced further for engaging with the suture holder. The translation of the stylet hub 430 is limited by a wire puller 1801 also shown in FIG. 6v. The trigger is then released allowing the stylet hub 430 to retract, allowing depth selector 500' to retract therewith. As illustrated in FIGS. 6w and 6x, the depth selector 500' is guided by control ribs 1405 and 1403 as it is retracted, allowing it to pivot back to its second position.

Method of Use of an Automatic Needle Release Button Along with the Depth Selector Described Presently Above.

During the first actuation of the trigger, as the stylet hub 430 translates distally, it allows the needle hub 130 to translate distally to the position shown in FIG. 6n. The ramp 402' of the stylet hub 430 engages ramp 602' of the button 600' that is coupled to the needle hub 130 as shown in FIG. 6n(i), pushing the needle hub 130 distally. The hook 604' of the button 600' is now positioned past the tab 1408 as shown in FIG. 6n(ii).

As the trigger is actuated further, the needle coupled to the needle hub 130 may encounter tissue resistance. In some embodiments, resistance may be observed as the needle abuts against the suture holder at the distal end of the device. This causes the ramp 402' on the stylet hub 430 to depress the ramp 602' on the needle hub 130 as shown in FIG. 6o(i). As tab 1408 is no longer preventing the hook 604' of the needle release button 600' from retracting, the needle release button 600' moves to its depressed or second position 600B', illustrated in FIGS. 6o(i) and 6o(ii). The stylet hub 430 and the needle hub 130 disengage from each other and are no longer operationally coupled. This allows the stylet hub 430 to advance relative to the needle hub 130 as shown in FIGS. 6o, 6p and 6q while keeping the needle release button 600' in its depressed position 600B'. This is further illustrated in FIGS. 6q(i) and 6q(ii) by the translation of ramp 402' of the stylet hub 430 past the needle release button 600 and the needle hub 130. In some embodiments, this may allow the stylet to be translated to deposit a suture within the suture holder at the distal tip of the device. The trigger is then released allowing the stylet hub 430 to retract or translate proximally. As shown in FIGS. 6r, 6r(i) and 6r(ii), as the stylet hub 430 is retracted it no longer depresses the needle release button 600' allowing it to return to its nominal position 600A. The needle hub 130 and the stylet hub 430 are coupled once again. As shown in FIGS. 6s, 6s(i) and 6s(ii), the stylet hub 430 and the needle hub 130 then translate further proximally. During this proximal translation, hook 604' of the needle release button 600' rides below tab 1408 of the housing 14' as shown in FIG. 6s(ii) and the button 600' remains in its nominal position 600A.

Upon second actuation of the trigger, the stylet hub 430 is then re-advanced The interaction between ramp 402' of the stylet hub 430 and ramp 602' of the needle release button 600' (that is coupled to the needle hub 130), allows or forces the stylet hub 430 and the needle hub 130 to advance together. Hook 604' of the needle release button 600' rides below the tab 1408 until it is advanced beyond the tab 1408. As shown in FIGS. 6t, 6t(i) and 6t(ii), once the hook 604' is positioned past the tab 1408, further actuation of the trigger causes the stylet hub 430 to depress the needle release button 600' into its second or depressed position 600B'. In some embodiments, this is a result of the needle encountering resistance and not being able to advance. This causes the needle hub 130 to be decoupled from the stylet hub 430, allowing the stylet hub 430 to advance relative to the needle hub 130. As the trigger is actuated further, the stylet hub 430 advances further relative to the needle hub 130, as shown previously in FIGS. 6u and 6v and is further illustrated in FIGS. 6v(i), and 6v(ii). In one particular embodiment, the stylet hub 430 is advanced to allow the stylet to engage the suture holder at the distal tip to allow the suture holder to be retracted with the stylet. As the trigger is then released the stylet hub 430 and the needle 130 retract together as a unit. The needle release button 600' remains in its depressed position 600B' and hook 604' of the needle release button 600' rides above the tab 1408 as shown in FIG. 6w and further illustrated in FIGS. 6w(i) and 6w(ii). When the trigger is fully released, the stylet hub 430 and needle hub 130 have been retracted proximally as shown in FIG. 6x, and the stylet withdraws the suture holder proximally as it is retracted. The needle release button 600' remains in its depressed or second position 600B'.

In some of the embodiments described above with respect to FIGS. 6m-6x, the springs illustrated in the figures are shown in their uncompressed state but as would be known to one skilled in the art the springs will be compressed between the respective components.

Alternative Embodiment for Passing Suture to Distal Tip and Capturing the Suture Using the Suture Trap In accordance with an alternative embodiment of the present invention, a method is disclosed for passing suture, the method comprising passing suture from the device proximal portion to the distal tip to be held therein, and capturing the suture using the suture holder while retrieving the suture holder from the distal tip. In operation, the device 100 is positioned within a region of tissue having a defect. The device is positioned such that a first segment of tissue is positioned within a tissue receiving gap 10 of the device 100. The suture 240 may be held within a needle 116 for example within a notch 117 as shown in FIG. 20B, and the needle 116 may then be advanced to pass the suture 240 through the first segment of tissue. A stylet 319 may additionally be housed within the needle and may be used in conjunction with the needle 116 to slide the suture 240 into the trap 2016. In one example, the stylet 319 may be advanced distally further than the needle 116 to pass the suture 240 through both slot 2040a of the distal tip 12 and slot 2042a of the trap 2016, as shown in dashed outline in FIG. 20C. The stylet 319 may then be translated further such that it pushes the suture 240 through the resilient tab 2040c of the distal tip 12. The needle 116 and the stylet 319 may then be retracted. The suture 240 is held within slot 2040b within the distal tip 12 and knot 250 rests against an outer surface of the distal tip 12. The knot may be larger than the opening defined by slot 2040b to help prevent the suture 240 from disengaging from the distal tip 12. The suture 240 is held between the two sets of tabs 2040c and 2042c as shown in FIG. 20C. Alternatively, the needle 116 may be sized to be received within the trap 2016 and may be used to push the suture 240 through tabs 2040c into slot 2040b of distal tip 12, with the suture 240 being routed through a notch within the needle.

Figure 20E:
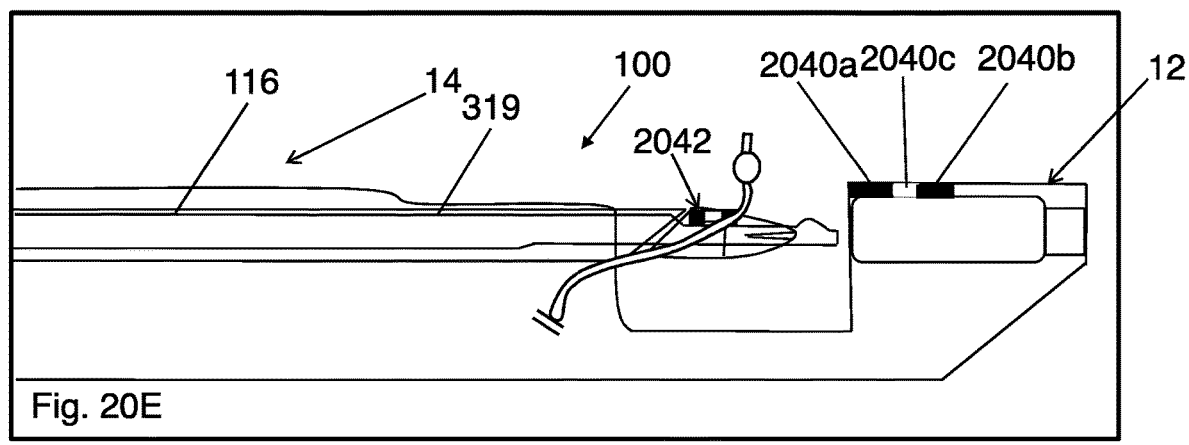

The device 100 may then be repositioned such that the second segment of tissue is received within the tissue receiving gap 10. The needle 116 and a stylet 319 housed within the needle 116 may both be advanced through the second segment of tissue. The needle 116 may be translated longitudinally until it abuts against the trap 2016. The stylet 319 may then advanced further through the trap 2016 such that it engages the trap 2016. The suture 240 at this point is held between the two sets of tabs 2040c and 2042c. The suture 240 is positioned distal to tab 2040c and proximal to tab 2042c. The stylet 319 is then retracted allowing the trap 2016 to be pulled along with it. As the trap 2016 is retracted, the movement of the trap 2016 relative to the distal tip 12 causes the suture 240 to pass through the second set of tabs 2042c and into the slot 2042b of the trap 2016. The stylet 319 and thus the 2016 is retracted further the suture 240 disengages or slips/squeezes through the first set of tabs 2040c and moves into slot 2040a. Thus suture 240 is now held or captured within slot 2042b of the trap 2016 and has been disengaged from the distal tip 12, as shown in FIG. 20E. The stylet 319, trap 2016 and thus suture 240 are then withdrawn further through the second segment of tissue. Thus, the suture 340 has been passed through both the first and second segment of tissue around the defect. The defect may be approximated by deploying a knot to tighten and tie the two ends of the suture. In other embodiments, slot 2040 of the device distal tip may not comprise a pair of tabs 2040c. In one such embodiment the suture 240 is passed from the device proximal portion to the distal tip 12 through the first segment of tissue as described previously. The suture 240 is coupled to the distal tip 12 by passing suture 240 through the pair of tabs 2042c of the trap 2016 using the stylet 319, wherein trap 2016 is coupled to the distal tip 12. The trap 2016 can then be disengaged from the distal tip 12 and retracted using the stylet 319 to pass suture 240 through the second segment of tissue as previously described.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of treating a defect in the annulus fibrosus tissue of an intervertebral disc, the defect comprising a tissue opening, the method comprising: passing a portion of a suture through a first edge region of the tissue opening; retrieving the suture portion through a second edge region of the tissue opening; deploying a knot; and approximating the first edge region of the tissue and the second edge region of the tissue, wherein the suture loop substantially completely circumscribes the defect, and wherein a surface of the first edge region mates with a surface of the second edge region, and whereby when the surface of the first edge region mates with the surface of the second region the defect is closed.

2. The method of claim 1, wherein the knot is a partially pre-tied knot.

3. The method of claim 1, wherein the step of deploying the knot comprises releasing loops of suture over an end of the suture forming a knot.

4. The method of claim 1, wherein the portion of the suture is passed through a first and second puncture.

5. The method of claim 4, wherein each of the first and second puncture is spaced apart from the edge of the tissue opening.

6. The method of claim 1, wherein a first portion of the suture forms a post and the second portion of the suture forms a locker.

7. The method of claim 6, wherein a partially pre-tied knot is deployed onto the post of the suture forming a knot.

8. The method of claim 7, wherein the knot is a Dines knot.

9. The method of claim 7, wherein the locker is held in tension as the knot is deployed.

10. The method of claim 1, further comprising the step of creating an additional knot for further securing the knot.

11. The method of claim 10, wherein the additional knot is half-hitches.

12. The method of claim 10, wherein the additional knot is an overhand knot or surgeon's knot.

13. A method of treating a defect in the annulus fibrosus tissue of an intervertebral disc, the method comprising:
passing a portion of a suture through tissue at a first location, from a proximal side of the tissue to a distal side of the tissue;
retrieving the portion of a suture through tissue at a second location thereby passing the suture portion to the proximal side of the tissue and causing the suture to traverse a segment along the distal side of the tissue;

deploying a knot; and approximating the distal side of the tissue by tightening the suture traversing the segment along the distal side of the tissue; and approximating the proximal side of the tissue by tightening the knot on the proximal side of the tissue;

wherein the suture substantially completely encircles the defect.

14. The method of claim 13, wherein the suture encircling the defect forms a 360 degree suture loop.

15. The method of claim 13, wherein the tissue on each side of the defect mates along the proximal side of the tissue and the distal side of the tissue.

\* \* \* \* \*